(12) United States Patent
Voelker et al.

(10) Patent No.: US 10,280,430 B2
(45) Date of Patent: *May 7, 2019

(54) NUCLEIC ACID CONSTRUCTS AND METHODS FOR PRODUCING ALTERED SEED OIL COMPOSITIONS

(71) Applicant: Monsanto Technology LLC, St. Louis, MO (US)

(72) Inventors: Toni Voelker, Davis, CA (US); JoAnne J. Fillatti, Davis, CA (US); Neal A. Bringe, St. Charles, MO (US); Tim Ulmasov, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 132 days.

This patent is subject to a terminal disclaimer.

(21) Appl. No.: 14/317,592

(22) Filed: Jun. 27, 2014

(65) Prior Publication Data

US 2014/0310836 A1  Oct. 16, 2014

Related U.S. Application Data

(60) Division of application No. 12/320,043, filed on Jan. 15, 2009, now Pat. No. 8,802,922, which is a continuation of application No. 11/379,328, filed on Mar. 16, 2006, now Pat. No. 7,566,813, and a continuation-in-part of application No. 10/508,401, filed as application No. PCT/US03/08610 on Mar. 21, 2003, now abandoned, said application No. 11/376,328 is a continuation-in-part of application No. 10/669,888, filed on Sep. 25, 2003, now abandoned, which is a continuation-in-part of application No. 10/393,347, filed on Mar. 21, 2003, now Pat. No. 7,601,888, said application No. 11/376,328 is a continuation-in-part of application No. 10/688,240, filed on Oct. 17, 2003, now abandoned, which is a continuation-in-part of application No. 10/393,347, filed on Mar. 21, 2003, now Pat. No. 7,601,888.

(60) Provisional application No. 60/772,614, filed on Feb. 13, 2006, provisional application No. 60/781,519, filed on Mar. 10, 2006, provisional application No. 60/365,794, filed on Mar. 21, 2002, provisional application No. 60/390,185, filed on Jun. 21, 2002.

(51) Int. Cl.
| | |
|---|---|
| *A01H 1/00* | (2006.01) |
| *C12N 15/82* | (2006.01) |
| *A01H 5/10* | (2018.01) |
| *A23D 9/00* | (2006.01) |
| *C10L 1/02* | (2006.01) |
| *C11B 1/00* | (2006.01) |
| *C12N 9/02* | (2006.01) |
| *A23K 10/30* | (2016.01) |
| *A23K 20/147* | (2016.01) |
| *A23K 20/158* | (2016.01) |

(52) U.S. Cl.
CPC .......... *C12N 15/8247* (2013.01); *A01H 5/10* (2013.01); *A23D 9/00* (2013.01); *A23K 10/30* (2016.05); *A23K 20/147* (2016.05); *A23K 20/158* (2016.05); *C10L 1/026* (2013.01); *C11B 1/00* (2013.01); *C12N 9/0083* (2013.01); *C12N 15/8216* (2013.01); *C12N 15/8218* (2013.01); *C12N 15/8237* (2013.01); *Y02E 50/13* (2013.01)

(58) Field of Classification Search
CPC ....................................................... A01H 1/00
USPC ....................................................... 800/281
See application file for complete search history.

(56) References Cited

U.S. PATENT DOCUMENTS

| | | |
|---|---|---|
| 4,557,734 A | 12/1985 | Schwab et al. |
| 5,454,842 A | 10/1995 | Poirier et al. |
| 5,475,099 A | 12/1995 | Knauf et al. |
| 5,500,361 A | 3/1996 | Kinney |
| 5,516,980 A | 5/1996 | Fehr et al. |
| 5,627,061 A | 5/1997 | Barry et al. |
| 5,633,435 A | 5/1997 | Barry et al. |
| 5,714,670 A | 2/1998 | Fehr et al. |
| 5,723,595 A | 3/1998 | Thompson et al. |
| 5,723,761 A | 3/1998 | Voelker et al. |
| 5,750,845 A | 5/1998 | Fehr et al. |
| 5,850,026 A | 12/1998 | Debonte et al. |

(Continued)

FOREIGN PATENT DOCUMENTS

| | | |
|---|---|---|
| EP | 0 959 133 A1 | 11/1999 |
| JP | 2002-517201 A | 6/2002 |

(Continued)

OTHER PUBLICATIONS

Smith et al 2000, Nature, 407:319-320.*
Liu et al. Genbank Accession No. AJ271842).*
Buhr et al. 2002, The Plant Journal 30:155-163.*
Liu et al. Genbank Accession No. AJ271842, 2000.*
Bosher et al. 1999 Genetics 153:1245-1256.*

(Continued)

*Primary Examiner* — Li Zheng

(74) *Attorney, Agent, or Firm* — Chunping Li; Arnold & Porter Kaye Scholer

(57) ABSTRACT

The present invention is in the field of plant genetics and provides recombinant nucleic acid molecules, constructs, and other agents associated with the coordinate manipulation of multiple genes in the fatty acid synthesis pathway. In particular, the agents of the present invention are associated with the simultaneous enhanced expression of certain genes in the fatty acid synthesis pathway and suppressed expression of certain other genes in the same pathway. Also provided are plants incorporating such agents, and in particular plants incorporating such constructs where the plants exhibit altered seed oil compositions.

19 Claims, 24 Drawing Sheets

Specification includes a Sequence Listing.

(56) References Cited

U.S. PATENT DOCUMENTS

| | | | |
|---|---|---|---|
| 5,888,947 A | 3/1999 | Lambert et al. | |
| 5,891,203 A | 4/1999 | Ball et al. | |
| 5,955,329 A | 9/1999 | Yuan et al. | |
| 5,955,650 A | 9/1999 | Hitz | |
| 6,013,114 A | 1/2000 | Hille et al. | |
| 6,022,577 A | 2/2000 | Chrysam et al. | |
| 6,133,509 A | 10/2000 | Fehr et al. | |
| 6,150,512 A | 11/2000 | Yuan | |
| 6,331,664 B1 | 12/2001 | Rubin-Wilson et al. | |
| 6,369,296 B1 | 4/2002 | Ratcliff et al. | |
| 6,372,965 B1 | 4/2002 | Lightner et al. | |
| 6,380,462 B1 | 4/2002 | Kridl | |
| 6,426,448 B1 | 7/2002 | Booth et al. | |
| 6,444,876 B1 | 9/2002 | Lassner et al. | |
| 6,506,559 B1 | 1/2003 | Fire et al. | |
| 6,573,099 B2 | 6/2003 | Graham | |
| 6,822,141 B2 | 11/2004 | Lardizabal et al. | |
| 6,949,698 B2 | 9/2005 | Booth, Jr. et al. | |
| 7,067,722 B2 | 6/2006 | Fillatti | |
| 7,166,771 B2 | 1/2007 | Eenennaam et al. | |
| 7,566,813 B2 * | 7/2009 | Voelker | A01H 5/10 800/278 |
| 7,601,888 B2 * | 10/2009 | Fillatti | A23D 9/00 800/278 |
| 8,524,680 B2 * | 9/2013 | Brown | C12N 15/111 514/44 A |
| 8,802,922 B2 * | 8/2014 | Voelker | A01H 5/10 536/24.5 |
| 2002/0034814 A1 | 3/2002 | Atabekov et al. | |
| 2003/0049835 A1 | 3/2003 | Helliwell et al. | |
| 2003/0135882 A1 | 7/2003 | Metzlaff et al. | |
| 2003/0172399 A1 | 9/2003 | Fillatti | |
| 2004/0006792 A1 | 1/2004 | Fillatti et al. | |
| 2004/0107460 A1 | 6/2004 | Fillatti et al. | |
| 2004/0126845 A1 | 7/2004 | Eenennaam et al. | |
| 2005/0034190 A9 | 2/2005 | Fillatti et al. | |
| 2006/0080750 A1 | 4/2006 | Fillatti et al. | |
| 2006/0206963 A1 | 9/2006 | Voelker et al. | |
| 2007/0074305 A1 | 3/2007 | Eenennaam et al. | |
| 2008/0222756 A1 | 9/2008 | Fillatti et al. | |
| 2009/0119805 A1 | 5/2009 | Fillatti et al. | |
| 2009/0151029 A1 | 6/2009 | Voelker et al. | |

FOREIGN PATENT DOCUMENTS

| | | |
|---|---|---|
| JP | 2002-519051 A | 7/2002 |
| JP | 2005-530506 A | 10/2005 |
| JP | 2005-530507 A | 10/2005 |
| WO | WO 94/10189 A1 | 5/1994 |
| WO | WO 94/11516 A1 | 5/1994 |
| WO | WO 96/06936 A2 | 3/1996 |
| WO | WO 93/11245 A1 | 6/1996 |
| WO | WO 97/40698 A1 | 11/1997 |
| WO | WO 98/05770 A2 | 2/1998 |
| WO | WO 98/30083 A1 | 7/1998 |
| WO | WO 98/46776 A2 | 10/1998 |
| WO | WO 98/53083 A1 | 11/1998 |
| WO | WO 98/56239 A2 | 12/1998 |
| WO | WO 99/15682 A2 | 4/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 99/63096 A2 | 12/1999 |
| WO | WO 99/64579 A2 | 12/1999 |
| WO | WO 00/01713 A2 | 1/2000 |
| WO | WO 00/07432 A1 | 2/2000 |
| WO | WO 00/18880 A2 | 4/2000 |
| WO | WO 00/44895 A1 | 8/2000 |
| WO | WO 00/44914 | 8/2000 |
| WO | WO 00/68374 A1 | 11/2000 |
| WO | WO 01/11061 A2 | 2/2001 |
| WO | WO 01/14538 A2 | 3/2001 |
| WO | WO 01/34822 A2 | 5/2001 |
| WO | WO 01/35726 A1 | 5/2001 |
| WO | WO 01/36598 A1 | 5/2001 |
| WO | WO 01/70949 A1 | 9/2001 |
| WO | WO 01/79499 A1 | 10/2001 |
| WO | WO 02/04581 A1 | 1/2002 |
| WO | WO 02/10365 A2 | 2/2002 |
| WO | WO 02/15675 A1 | 2/2002 |
| WO | WO 02/059336 A2 | 8/2002 |
| WO | WO 02/081711 A1 | 10/2002 |
| WO | WO 02/088301 A2 | 11/2002 |
| WO | WO 03/080802 A2 | 10/2003 |
| WO | WO 04/000871 A2 | 12/2003 |
| WO | WO 04/001000 A2 | 12/2003 |
| WO | WO 04/001001 A2 | 12/2003 |
| WO | WO 2005/030982 A2 | 4/2005 |
| WO | WO 2005/079389 A2 | 9/2005 |
| WO | WO 2007/095243 A2 | 8/2007 |
| WO | WO 2011/005998 A1 | 1/2011 |

OTHER PUBLICATIONS

Extended European Search Report dated Mar. 11, 2015, in European Patent Application No. 14196149.0.

Hamilton et al., "A Species of Small Antisense RNA in Post-transcriptional Gene Silencing in Plants," Science, 286:950-952 (1999).

Dehesh et al., "KAS IV: a 3-ketoacyl-ACP Synthase from Cuphea sp. is a Medium Chain Specific Condensing Enzyme," The Plant Journal, 15(3):383-390 (1998).

Cromwell, "Soybean Meal—An Exceptional Protein Source," Soybean Meal InfoCenter, pp. 1-15 (2012) <http://www.soymeal.org/ReviewPapers/SBMExceptionalProteinSource.pdf>.

Heuzé et al., Soybean meal, Feedipedia, a programme by INRA, CIRAD, AFZ and FAO, pp. 1-6 (2015) <http://www.feedipedia.org/node/674>.

Soybean, Feed Industry Guide, 1$^{st}$ Edition, pp. 1-47 (2010).

Heppard et al., "Developmental and Growth Temperature Regulation of Two Different Microsomal ω-6 Desaturase Genes in Soybeans," Plant Physiol. 110:311-319 (1996).

Bennett et al., "Inhibition of Vascular Smooth Muscle Cell Proliferation in vitro and in vivo by C-myc Antisense Oligodeoxynucleotides," J. Clin. Invest., 93:820-828 (1994).

Bosher et al. , "RNA Interference Can Target Pre-mRNA: Consequences for Gene Expression in a Caenorhabditis elegans Operon," Genetics, 153:1245-1256 (1999).

Bouchon et al., "Oil Distribution in Fried Potatoes Monitored by Infrared Microspectroscopy," Journal of Food Science, 66(7):918-923 (2001).

Burch-Smith et al., "Applications and advantages of virus-induced gene silencing for gene function studies in plants," The Plant Journal, 39:734-746 (2004).

Buhr et al., "Ribozyme Termination of RNA Transcripts Down-Regulate Seed Fatty Acid Genes in Transgenic Soybean," The Plant Journal, 30(2):155-163 (2002).

Byrum et al., "Alteration of the omega-3 fatty acid desaturase gene is associated with reduced linolenic acid in the A5 soybean genotype," Theor. Appl. Genet., 94:356-359 (1997).

Cartea et al., "Comparison of Sense and Antisense Methodologies for Modifying the Fatty Acid Composition of Arabidopsis thaliana Oilseed," Plant Science, 136:181-194 (1998).

Chapman et al., "Transgenic cotton plants with increased seed oleic acid content," JAOCS, 78:941-947 (2001).

Chuang et al., "Specific and Heritable Genetic Interference by Double-Stranded Rna in Arabidopsis thaliana," PNAS, 97(9):4985-4990 (2000).

Clark-Walker et al., "Location of Transcriptional Control Signals and Transfer RNA Sequences in Torulopsis glabrata Mitochondrial DNA," EMBO, 4(2):465-473 (1985).

Cogoni et al., "Post-Transcriptional Gene Silencing Across Kingdoms," Curr. Opin. Gen. & Devel., 10(6):638-643 (2000).

Colliver et al., "Differential modification of flavonoid and isoflavonoid biosynthesis with an antisense chalcone synthase construct in transgenic Lotus corniculatus," Plant Mol. Biol., 35:509-522 (1997).

(56) References Cited

OTHER PUBLICATIONS

Crossway et al., "Integration of Foreign DNA Following Microinjection of Tobacco Mesophyll Protoplasts," *Mol. Gen. Genet.*, 202(2):179-185 (1986).
Database EM_GSS 'Online! EMBL Heidelberg, Germany; AC AL071390, May 29, 1999, Genoscope: "*Drosophila melanogaster* genome surface sequence TET3 end of BAC: BACR32M05," XP002163063, Abstract.
Database EMPLN 'Online! EMBL Heidelberg, Germany; AC/ID AC004705, May 21, 1998, Lin X et al.: "Sequence and analysis of chromosome 2 of the plant *Arabidopsis thaliana*" XP002163064, Abstract.
Database EM_GSS 'Online! EMBL Heidelberg, Germany; AC AL105179, Jul. 26, 1999, Genoscope: "*Drosophila melanogaster* genome survey sequence T7 end of BAC: BACN13A12" XP002163065, Abstract.
Database EM-NEW 'Online! EMBL Heidelberg, Germany; AC/ID AB022220, Jan. 15, 1999, Sato S. et al.: "*Arabidopsis thaliana* genomic DNA, chromosome 3, P1 clone: MLN21" XP002163066, Abstract.
Database EM_GSS 'Online! EMBL Heidelberg, Germany; AC AL069706, May 29, 1999, Genoscope: "*Drosophila melanogaster* genome survey sequence T7 end of BAC: BACR29B23" XP002163067, Abstract.
Database EM_GSS 'Online! EMBL Heidelberg, Germany; AC AL063932, May 29, 1999, Genoscope; "*Drosophila melanogaster* genome survey sequence TET3 end of BAC: BACR8010" XP002163068, Abstract.
Database EM_GSS 'Online! EMBL Heidelberg, Germany; AC AL108811, Jul. 26, 1999, Genoscope: "*Drosophila melanogaster* genome survey sequence SP6 end of BAC BACN37D10" XP002163069, Abstract.
Database EM_NEW 'Online! EMBL Heidelberg, Germany; AC/ID AB026636, May 7, 1999, Sato S. et al.: "*Arabidopsis thaliana* genomic DNA, chromosome 3, TAC clone: K14A17," XP002163070, Abstract.
Database EMEST_PLN 'Online! EMBL Heidelberg, Germany; AC/ID AW297948, Feb. 8, 2000, Shoemaker R. et al.: "Public soybean EST project," XP002163071, Abstract.
Database EMPLN 'Online! EMBL Heidelberg, Germany; AC AL161581, Mar. 15, 2000, Weichselgartner M. et al.: "*Arabidopsis thaliana* chromosome 4, contig fragment No. 77," XP002163072, Abstract.
Daun et al., "Effect of Frost Damage on the Quality of Canola (*B. napus*)," JAOCS, 62(4):715-719 (1985).
DeLuca, "Molecular characterization of secondary metabolic pathways," *AgBiotech News and Information*, 5(6):225N-229N (1993).
Dörmann et al., "Accumulation of Palmitate in *Arabidopsis* Mediated by the Acyl-Acyl Carrier Protein Thioesterase FATB1," *Plant Physiology*, 123:637-643 (2000).
Duffield et al., "U.S. Biodiesel Development: New Markets for Conventional and Genetically Modified Agricultural Products," *Economic Research Service USDA*, pp. 1-31 (1998).
Dunn et al., "Recent Advances in the Development of Alternative Diesel Fuel from Vegetable Oils and Animal Fats," *Recent Res. Devel. in Oil Chem.*, 1:31-56 (1997).
Erhan et al., "Lubricant Basestocks from Vegetable Oils," *Industrial Crops and Products*, 11:277-282 (2000).
European Search Report dated May 4, 2011, in European Patent Application No. 10195208.
Fehr et al., "Breeding for fatty acid composition of soybean oil," VII World Soybean Research Conference, IV International Soybean Processing and Utilization Conference, III Congresso Mondial de Soja (Brazilian Soybean Congress) Proceedings, Feb. 29-Mar. 5, 2004, pp. 815-821.
Fire et al., "Potent and Specific Genetic Interference by Double-Stranded RNA in *Caenorhabditis elegans*," *Nature*, 391:806-811 (1998).
Gryson et al., "Detection of DNA During the Refining of Soybean Oil," *JAOCS* 79(2):171-174 (2002).

Halpin et al., "Enabling Technologies for Manipulating Multiple Genes on Complex Pathways," *Plant Molecular Biology*, 47:295-310 (2001).
Hamada et al., "Modification of Fatty Acid Composition by Over- and Antisense-Expression of a Microsomal ω-3 Fatty Acid Desaturase Gene in Transgenic Tobacco," *Transgenic Research*, 5(2):115-121 (1996).
Hamilton et al., "A Transgene with Repeated DNA Causes High Frequency, Post-Transcriptional Suppression of ACC-Oxidase Gene Expression in Tomato," *The Plant Journal*, 15(6):737-746 (1998).
Hannon, "RNA Interference," *Nature*, 418:244-251 (2002).
Helliwell et al., "High-throughput vectors for efficient gene silencing in plants," *Functional Plant Biology*, 29:1217-1225 (2002).
International Preliminary Examination Report dated Dec. 6, 2001, in International Patent Application No. PCT/US00/22613.
International Preliminary Examination Report dated Jul. 27, 2004, in International Patent Application No. PCT/US03/19437.
International Search Report dated Nov. 13, 2003, in International Patent Application No. PCT/US03/08610.
International Search Report dated Jul. 12, 2005, in International Patent Application No. PCT/US04/31605.
International Search Report dated Apr. 9, 2004, in International Patent Application No. PCT/US03/19445.
International Search Report dated Jun. 21, 2004, in International Patent Application No. PCT/US03/019437.
International Search Report dated Apr. 26, 2001, in International Patent Application No. PCT/US00/22613.
International Search Report dated Jul. 12, 2007, in International Patent Application No. PCT/US07/003823.
Jaworski et al., "Industrial oils from transgenic plants," *Current Opinion in Plant Biology*, 6:178-184 (2003).
Kandimalla et al., "Design, biochemical, biophysical and biological properties of cooperative antisense oligonucleotides," *Nucleic Acids Research*, 23(17):3578-3584 (1995).
Kinney et al., "Designer oils: the high oleic acid soybean," *Genetic Modification in the Food Industry*, Chapter 10, pp. 193-213 (1998).
Kinney, "Plants as industrial chemical factories—new oils from genetically engineered soybeans," *Fett/Lipid*, 100(4-5):173-176 (1998).
Kusaba, "RNA Interference in Crop Plants," *Current Opinion in Biotechnology*, 15:139-143 (2004).
Lang et al., "Preparation and characterization of bio-diesels from various bio-oils," *Bioresource Technology*, 80:53-62 (2001).
Lee et al., "Antisense Expression of the CK2 α-Subunit Gene in *Arabidopsis*. Effects on Light-Regulated Gene Expression and Plant Growth," *Plant Physiology*, 119:989-1000 (1999).
Levin et al., "Methods of Double-Stranded RNA-Mediated Gene Inactivation in *Arabidopsis* and Their Use to Define an Essential Gene in Methionine Biosynthesis," *Plant Mol. Biol.*, 44(6):759-775 (2000).
Lewin, "How Did Interrupted Genes Evolve?," *Genes*, $2^{nd}$ Edition, pp. 333-337 (2009).
Martin et al., "A comparison of Oleic Acid Metabolism n the Soybean (*Glycine max* [L.] Merr.) Genotypes Williams and A5, a mutant with decreased linoleic acid in the seed," *Plant Phys.*, 61:41-44 (1986).
Martinez-Rivas et al., "Oxygen-independent temperature regulation of the microsomal oleate desaturase (FAD2) activity in developing sunflower (*Helianthus annuus*) seeds," *Physiologia Plantarum*, 117:179-185 (2003).
Matzke et al., "RNA-Based Silencing Strategies in Plants," *Curr. Opin. Gen. & Devel.*, 11(2):221-227 (2001).
McCormick et al, "Effect of Humidity on Heavy-Duty Transient Emissions from Diesel and Natural Gas Engines at High Altitude," *Journal of the Air & Waste Management Association*, 47:784-791 (1997).
Meister et al., "Sequence-specific inhibition of microRNA- and siRNA-induced RNA silencing," *RNA*, 10(3):544-550 (2004).
Mensink et al., "Effect of Dietary Fatty Acids on Serum Lipids and Lipoproteins: A Meta-Analysis of 27 Trials," *Arteriosclerosis and Thrombosis*, 12(8):911-919 (1992).
Montgomery et al., "RNA as a Target of Double-Stranded RNA-Mediated Genetic Interference in *Caenorhabditis elegans*," *Proc. Natl. Acad. Sci. USA*, 95(96):15502-15507 (1998).

(56) References Cited

OTHER PUBLICATIONS

Mroczka et al., "An Intron Sense Suppression Construct Targeting Soybean FAD2-1 Requires a Double-Stranded RNA-Producing Inverted Repeat T-DNA Insert," *Plant Physiology*, 153(2):882-891 (2010).
Napoli et al., "Introduction of a Chimeric Chalcone Synthase Gene into Petunia Results in Reversible Co-Suppression of Homologous Genes in trans," *The Plant Cell*, 2:279-289 (1990).
Neff et al., "Odor Significance of Undersirable Degradation Compounds in Heated Triolein and Trilinolein," *JAOCS*, 77(12):1303-1313 (2000).
Ngo et al., "Double-stranded RNA induces mRNA degradation in *Trypanosoma brucei*," *Proc. Natl. Acad. Sci. USA*, 95:14687-14692 (1998).
Okuley et al.,"*Arabidopsis* FAD2 Gene Encodes the Enzyme that is Essential for Polyunsaturated Lipid Synthesis," *The Plant Cell*, 6:147-158 (1994).
Padgette et al., *Crop Sci.*, "Development, Identification, and Characterization of a Glyphosate-Tolerant Soybean Line," 35:1451-1461 (1995).
Parrish et al., "Functional Anatomy of a dsRNA Trigger: Differential Requirement for the Two Trigger Strands in RNA Interference," *Molecular Cell*, 6:1077-7087 (2000).
Pauli et al., "Detection of DNA in soybean oil," *Z Lebensm Unters Forsch A*, 207:264-267 (1998).
Peele et al., "Silencing of a meristematic gene using geminivirus-derived vectors," *The Plant Journal*, 27(4):357-366 (2001).
Pokorny, "Flavor Chemistry of Deep Fat Frying in Oil," *Flavor Chemistry of Lipid Foods* (eds. Min & Smouse), Chapter 7, pp. 113-155, American Oil Chem. Soc., Champaign, IL (1989).
Qing, Thesis entitled "The Isolation and Characterisation of Fatty Acid Desaturase Genes in Cotton," University of Sydney, Australia, pp. ii-iv, 24-26, 121-123, 142, 167-168, 172-174, 179-181 (1998).
Sharma et al., "In Silico Identification and Comparative Genomics of Candidate Genes Involved in Biosynthesis and Accumulation of Seed Oil in Plants," *Comparative and Functional Genomics*, 2012:1-14 (2012).
Sharp, "RNAi and Double-Strand RNA," *Genes & Development*, 13:139-141 (1999).
Sharp, "RNA Interference—2001," *Genes & Development*, 15:485-490 (2001).
Singh et al., "Transgenic expression of a delta 12-epoxygenase gene in *Arabidopsis* seeds inhibits accumulation of linoleic acid," *Planta*, 212:872-879 (2001).
Singh et al., "Metabolic engineering of new fatty acids in plants," *Current Opinion in Plant Biology*, 8:197-203 (2005).
Smith et al., "Total silencing by intron-spliced hairpin RNAs," *Nature*, 407:319-320 (2000).
Stam et al., "Post-transcriptional silencing of chalcone synthase in *Petunia* by inverted transgene repeats," *The Plant Journal*, 12(1):63-82 (1997).
Stam et al., "The Silence of Genes in Transgenic Plants," *Annals of Botany*, 79:3-12 (1997).
Stoutjeskijk et al., "hpRNA-Mediated Targeting of the *Arabidopsis* FAD 2 Gene Gives Highly Efficient and Stable Silencing," *Plant Physiology*, 129:1723-1731 (2002).
Supplemental European Search Report completed on Jun. 29, 2005, in European Patent Application No. 03711656.3.
Supplementary European Search Report completed on Nov. 7, 2006, in European Patent Application No. 04 78 5109.
Supplementary Partial European Search Report completed on Jan. 8, 2007, in European Patent Application No. 03 76 1158.
Sweetlove et al., "Starch metabolism in tubers of transgenic potato (*Solanum tuberosum*) with increased ADPglucose pyrophosphorylase," *Biochemical Journal*, 320:493-498 (1996).
Thomas et al., "Size constraints for targeting post-transcriptional gene silencing and for RNA-directed methylation in *Nicotiana benthamiana* using a potato virus X vector," *The Plant Journal*, 25(4):417-25 (2001).
Timmons et al., "Relationships Among Dietary Roasted Soybeans, Milk Components, and Spontaneous Oxidized Flavor of Milk," *Journal of Diary Science*, 84(11):2440-2449 (2001).
Toborek et al., "Unsaturated Fatty Acids Selectively Induce an Inflammatory Environment in Human Endothelial Cells," *American Journal of Clinical Nutrition*, 75:119-125 (2002).
van der Krol et al., "Flavonoid Genes in Petunia: Addition of a Limited Number of Gene Copies May Lead to a Suppression of Gene Expression," *The Plant Cell*, 2:291-299 (1990).
Voelker et al., "Variations in the Biosynthesis of Seed-Storage Lipids," *Annu Rev Plant Physiol Plant Mol Biol*, 52:335-361 (2001).
Wagner et al., "RNAi trigger fragment truncation attenuates soybean FAD2-1 transcript suppression and yields intermediate oil phenotypes," *Plant Biotechnology Journal*, 2010:1-8 (2010).
Warner et al., "Effect of Oleic and Linoleic Acids on the Production of Deep-Fried Odor in Heated Triolein and Trilinolein," *Journal of Agricultural Food Chemical*, 49:899-905 (2001).
Waterhouse, P.M. et al., "Virus Resistance and Gene Silencing in Plants Can be Induced by Simultaneous Expression of Sense and Antisense RNA," *Proc. Natl. Acad. Sci. USA*, 95:13959-13964 (1998).
Wesley et al., "Construct Design for Efficient, Effective and High-Throughput Gene Silencing in Plants," *The Plant Journal*, 27(6):581-590 (2001).
Yu et al., "RNA interference by expression of short-interfering RNAs and hairpin RNAs in mammalian cells," *Proc. Natl. Acad. Sci.*, 99(9):6047-6052 (2002).

* cited by examiner

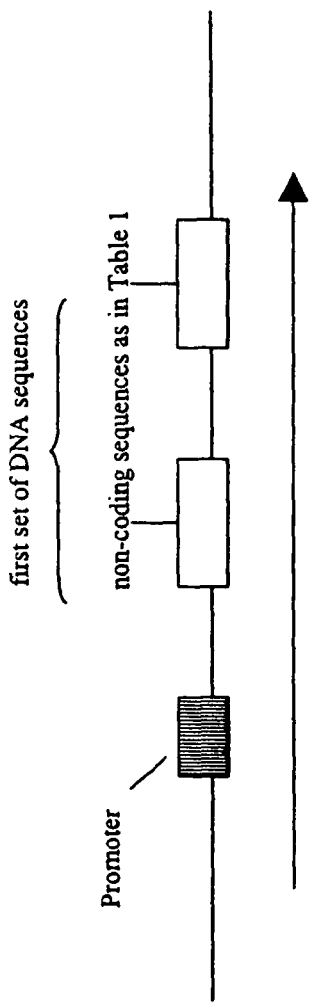
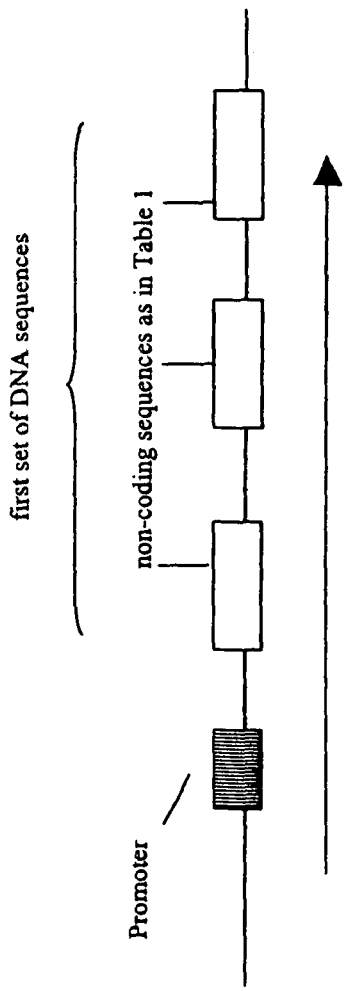
Figure 5(a)
Figure 5(b)

SEQUENCE LISTING

<160> NUMBER OF SEQ ID NOS: 62

<210> SEQ ID NO 1
<211> LENGTH: 420
<212> TYPE: DNA
<213> ORGANISM: Glycine max
<220> FEATURE:
<223> OTHER INFORMATION: FAD2-1A intron 1

<400> SEQUENCE: 1

```
gtaaattaaa ttgtgcctgc acctcgggat atttcatgtg gggttcatca tatttgttga      60
ggaaaagaaa ctcccgaaat tgaattatgc atttatatat cctttttcat ttctagattt     120
cctgaaggct taggtgtagg cacctagcta gtagctacaa tatcagcact tctctctatt     180
gataaacaat tggctgtaat gccgcagtag aggacgatca caacatttcg tgctggttac     240
tttttgtttt atggtcatga tttcactctc tctaatctct ccattcattt tgtagttgtc     300
attatcttta gatttttcac tacctggttt aaaattgagg gattgtagtt ctgttggtac     360
atattacaca ttcagcaaaa caactgaaac tcaactgaac ttgtttatac tttgacacag     420
```

<210> SEQ ID NO 2
<211> LENGTH: 405
<212> TYPE: DNA
<213> ORGANISM: Glycine max
<220> FEATURE:
<223> OTHER INFORMATION: FAD2-1B intron 1

<400> SEQUENCE: 2

```
gtatgatgct aaattaaatt gtgcctgcac cccaggatat ttcatgtggg attcatcatt      60
tattgaggaa aactctccaa attgaatcgt gcatttatat ttttttttcca tttctagatt     120 tcttgaaggc ttatggtata ggcacctaca attatcagca cttctctcta ttgataaaca     180
attggctgta ataccacagt agagaacgat cacaacattt tgtgctggtt acctttttgtt     240 ttatggtcat gatttcactc tctctaatct gtcacttccc tccattcatt ttgtacttct     300 catattttc acttcctggt tgaaaattgt agttctcttg gtacatacta gtattagaca     360
```

```
ttcagcaaca acaactgaac tgaacttctt tatactttga cacag            405
```

<210> SEQ ID NO 3
<211> LENGTH: 1704
<212> TYPE: DNA
<213> ORGANISM: Glycine max
<220> FEATURE:
<223> OTHER INFORMATION: FAD2-1B promoter

<400> SEQUENCE: 3

```
actatagggc acgcgtggtc gacggcccgg gctggtcctc ggtgtgactc agcccaagt     60
gacgccaacc aaacgcgtcc taactaaggt gtagaagaaa cagatagtat ataagtatac   120
catataagag gagagtgagt ggagaagcac ttctcctttt tttttctctg ttgaaattga   180
aagtgttttc cgggaaataa ataaaataaa ttaaaatctt acacactcta ggtaggtact   240
tctaatttaa tccacacttt gactctatat atgttttaaa aataattata atgcgtactt   300
acttcctcat tatactaaat ttaacatcga tgattttatt ttctgtttct cttctttcca   360
cctacataca tcccaaaatt tagggtgcaa ttttaagttt attaacacat gttttagct    420
gcatgctgcc tttgtgtgtg ctcaccaaat tgcattcttc tctttatatg ttgtatttga   480
atttcacac catatgtaaa caagattacg tacgtgtcca tgatcaaata caaatgctgt    540
cttatactgg caattttgata aacagccgtc cattttttct ttttctcttt aactatatat  600
gctctagaat ctctgaagat tcctctgcca tcgaatttct ttcttggtaa caacgtcgtc   660
gttatgttat tattttattc tattttttatt ttatcatata tatttcttat tttgttcgaa  720
gtatgtcata ttttgatcgt gacaattaga ttgtcatgta ggagtaggaa tatcacttta   780
aaacattgat tagtctgtag gcaatattgt cttctttttc ctcctttatt aatatatttt   840
gtcgaagttt taccacaagg ttgattcgct tttttttgtcc ctttctcttg ttctttttac  900
ctcaggtatt ttagtctttc atggattata agatcactga gaagtgtatg catgtaatac   960
taagcaccat agctgttctg cttgaattta tttgtgtgta aattgtaatg tttcagcgtt   1020
ggctttccct gtagctgcta caatggtact gtatatctat tttttgcatt gttttcattt   1080
tttcttttac ttaatcttca ttgctttgaa attaataaaa caatataata tagttttgaac  1140
tttgaactat tgcctattca tgtaattaac ttattcactg actcttattg tttttctggt   1200
agaattcatt ttaaattgaa ggataaatta agaggcaata cttgtaaatt gacctgtcat   1260
aattacacag gaccctgttt tgtgcctttt tgtctctgtc tttggttttg catgttagcc   1320
tcacacagat atttagtagt tgttctgcat acaagcctca cacgtatact aaaccagtgg   1380
acctcaaagt catggcctta cacctattgc atgcgagtct gtgacacaac ccctggtttc   1440
catattgcaa tgtgctacgc cgtcgtcctt gtttgtttcc atatgtatat tgataccatc   1500
aaattattat atcatttata tggtctggac cattacgtgt actctttatg acatgtaatt   1560
gagttttta attaaaaaaa tcaatgaaat ttaactacgt agcatcatat agagataatt    1620
gactagaaat tgatgacttt attctttcct aatcatattt tcttgtattg atagccccgc   1680
tgtccctttt aaactcccga gaga                                          1704
```

<210> SEQ ID NO 4
<211> LENGTH: 4497
<212> TYPE: DNA
<213> ORGANISM: Glycine max
<220> FEATURE:
<223> OTHER INFORMATION: FAD2-1A genomic clone

```
<400> SEQUENCE: 4
cttgcttggt aacaacgtcg tcaagttatt attttgttct tttttttttt atcatatttc        60
ttattttgtt ccaagtatgt catattttga tccatcttga caagtagatt gtcatgtagg       120
aataggaata tcactttaaa ttttaaagca ttgattagtc tgtaggcaat attgtcttct       180
tcttcctcct tattaatatt ttttattctg ccttcaatca ccagttatgg gagatggatg       240
taatactaaa taccatagtt gttctgcttg aagtttagtt gtatagttgt tctgcttgaa       300
gtttagttgt gtgtaatgtt tcagcgttgg cttccctgt aactgctaca atggtactga        360
atatatattt tttgcattgt tcatttttt cttttactta atcttcattg ctttgaaatt        420
aataaaacaa aagaaggac cgaatagttt gaagtttgaa ctattgccta ttcatgtaac        480
ttattcaccc aatcttatat agttttctg gtagagatca ttttaaattg aaggatataa        540
attaagagga aatacttgta tgtgatgtgt ggcaatttgg aagatcatgc gtagagagtt      600
taatggcagg ttttgcaaat tgacctgtag tcataattac actgggccct ctcggagttt      660
tgtgcctttt tgttgtcgct gtgtttggtt ctgcatgtta gcctcacaca gatatttagt      720
agttgttgtt ctgcatataa gcctcacacg tatactaaac gagtgaacct caaaatcatg      780
gccttacacc tattgagtga aattaatgaa cagtgcatgt gagtatgtga ctgtgacaca      840 accccggtt tcatattgc aatgtgctac tgtggtgatt aaccttgcta cactgtcgtc        900
cttgtttgtt tccttatgta tattgatacc ataaattatt actagtatat cattttatat      960
tgtccatacc attacgtgtt tatagtctct ttatgacatg taattgaatt ttttaattat     1020
aaaaaataat aaaacttaat tacgtactat aagagatgc tcttgactag aattgtgatc      1080
tcctagtttc ctaaccatat actaatattt gcttgtattg atagcccctc cgttcccaag     1140
agtataaaac tgcatcgaat aatacaagcc actaggcatg gtaaattaaa ttgtgcctgc     1200
acctcgggat atttcatgtg gggttcatca tatttgttga ggaaaagaaa ctcccgaaat     1260
tgaattatgc atttatatat ccttttttcat ttctagattt cctgaaggct taggtgtagg    1320
cacctagcta gtagctacaa tatcagcact tctctctatt gataaacaat tggctgtaat     1380
gccgcagtag aggacgatca caacatttcg tgctggttac tttttgtttt atggtcatga     1440
tttcactctc tctaatctct ccattcattt tgtagttgtc attatcttta gattttttcac    1500 tacctggttt aaaattgagg gattgtagtt ctgttggtac atattacaca ttcagcaaaa     1560
caactgaaac tcaactgaac ttgtttatac tttgacacag ggtctagcaa aggaaacaac     1620
aatgggaggt agaggtcgtg tggcaaagtg gaagttcaag ggaagaagcc tctctcaagg     1680
gttccaaaca caaagccacc attcactgtt ggccaactca agaaagcaat tccaccacac     1740
tgctttcagc gctccctcct cacttcattc tcctatgttg tttatgacct tcatttgcc     1800 ttcattttct acattgccac cacctacttc cacctccttc ctcaaccctt ttccctcatt     1860
gcatggccaa tctattgggt tctccaaggt tgccttctca ctggtgtgtg ggtgattgct     1920
cacgagtgtg gtcaccatgc cttcagcaag taccaatggg ttgatgatgt tgtgggtttg     1980
acccttcact caacacttt agtcccttat ttctcatgga aaataagcca tcgccgccat     2040
cactccaaca caggttccct tgaccgtgat gaagtgtttg tcccaaaacc aaaatccaaa     2100
gttgcatggt tttccaagta cttaaacaac cctctaggaa gggctgtttc tcttctcgtc     2160
acactcacaa tagggtggcc tatgtattta gccttcaatg tctctggtag accctatgat    2220
agttttgcaa gccactacca cccctatgct cccatatatt ctaaccgtga gaggcttctg    2280
atctatgtct ctgatgttgc tttgtttct gtgacttact ctctctaccg tgttgcaacc     2340
```

```
ctgaaagggt tggtttggct gctatgtgtt tatggggtgc ctttgctcat tgtgaacggt    2400
tttcttgtga ctatcacata tttgcagcac acacactttg ccttgcctca ttacgattca    2460
tcagaatggg actggctgaa gggagctttg gcaactatgg acagagatta tgggattctg    2520
aacaaggtgt tcatcacat aactgatact catgtggctc accatctctt ctctacaatg    2580
ccacattacc atgcaatgga ggcaaccaat gcaatcaagc caatattggg tgagtactac    2640
caatttgatg acacaccatt ttacaaggca ctgtggagag aagcgagaga gtgcctctat    2700
gtggagccag atgaaggaac atccgagaag ggcgtgtatt ggtacaggaa caagtattga    2760
tggagcaacc aatgggccat agtgggagtt atggaagttt tgtcatgtat tagtacataa    2820
ttagtagaat gttataaata agtggatttg ccgcgtaatg actttgtgtg tattgtgaaa    2880
cagcttgttg cgatcatggt tataatgtaa aaataattct ggtattaatt acatgtggaa    2940
agtgttctgc ttatagcttt ctgcctaaaa tgcacgctgc acgggacaat atcattggta    3000
atttttttaa aatctgaatt gaggctactc ataatactat ccataggaca tcaaagacat    3060
gttgcattga ctttaagcag aggttcatct agaggattac tgcataggct tgaactacaa    3120
gtaatttaag ggacgagagc aactttagct ctaccacgtc gttttacaag gttattaaaa    3180
tcaaattgat cttattaaaa ctgaaaattt gtaataaaat gctattgaaa aattaaaata    3240
tagcaaacac ctaaattgga ctgatttta gattcaaatt taataattaa tctaaattaa    3300 acttaaatt tataatatat gtcttgtaat atatcaagtt ttttttttta ttattgagtt    3360
tggaaacata taataaggaa cattagttaa tattgataat ccactaagat cgacttagta    3420
ttacagtatt tggatgattt gtatgagata ttcaaacttc actcttatca taatagagac    3480
aaaagttaat actgatggtg gagaaaaaaa aatgttattg ggagcatatg gtaagataag    3540
acggataaaa atatgctgca gcctggagag ctaatgtatt ttttggtgaa gttttcaagt    3600
gacaactatt catgatgaga acacaataat attttctact tacctatccc acataaaata    3660
ctgattttaa taatgatgat aaataatgat taaaatattt gattctttgt taagagaaat    3720
aaggaaaaca taaatattct catggaaaaa tcagcttgta ggagtagaaa ctttctgatt    3780 ataatttta tcaagtttaa ttcattcttt taatttat tattagtacaa aatcattctc    3840 ttgaatttag agatgtatgt tgtagcttaa tagtaatttt ttattttat aataaaattc    3900 aagcagtcaa atttcatcca aataatcgtg ttcgtgggtg taagtcagtt attccttctt    3960
atcttaatat acacgcaaag gaaaaaataa aaataaaatt cgaggaagcg cagcagcagc    4020
tgataccacg ttggttgacg aaactgataa aaagcgctgt cattgtgtct ttgtttgatc    4080
atcttcacaa tcacatctcc agaacacaaa gaagagtgac ccttcttctt gttattccac    4140
ttgcgttagg tttctacttt cttctctctc tctctctctc tcttcattcc tcattttcc     4200 ctcaaacaat caatcaattt tcattcagat tcgtaaattt ctcgattaga tcacggggtt    4260
aggtctccca ctttatcttt tcccaagcct ttctctttcc cccttccct gtctgccca     4320 taaaattcag gatcggaaac gaactgggtt cttgaatttc actctagatt ttgacaaatt    4380
cgaagtgtgc atgcactgat gcgacccact cccccttttt tgcattaaac aattatgaat    4440
tgaggttttt cttgcgatca tcattgcttg aattgaatca tattaggttt agattct       4497
```

<210> SEQ ID NO 5
<211> LENGTH: 206
<212> TYPE: DNA
<213> ORGANISM: Glycine max
<220> FEATURE:

<223> OTHER INFORMATION: FAD2-1A 3'UTR

<400> SEQUENCE: 5

```
tggagcaacc aatgggccat agtgggagtt atggaagttt tgtcatgtat agtacataa      60
ttagtagaat gttataaata agtggatttg ccgcgtaatg actttgtgtg tattgtgaaa    120
cagcttgttg cgatcatggt tataatgtaa aaataattct ggtattaatt acatgtggaa    180
agtgttctgc ttatagcttt ctgcct                                          206
```

<210> SEQ ID NO 6
<211> LENGTH: 125
<212> TYPE: DNA
<213> ORGANISM: Glycine max
<220> FEATURE:
<223> OTHER INFORMATION: FAD2-1A 5'UTR

<400> SEQUENCE: 6

```
ccatatacta atatttgctt gtattgatag cccctccgtt cccaagagta taaaactgca     60
tcgaataata caagccacta ggcatgggtc tagcaaagga acaacaatg ggaggtagag     120
gtcgt                                                                125
```

<210> SEQ ID NO 7
<211> LENGTH: 191
<212> TYPE: DNA
<213> ORGANISM: Glycine max
<220> FEATURE:
<223> OTHER INFORMATION: FAD3-1A intron 1

<400> SEQUENCE: 7

```
gtaataattt ttgtgtttct tactcttttt ttttttttt tgtttatgat atgaatctca      60
cacattgttc tgttatgtca tttcttcttc atttggcttt agacaactta aatttgagat    120
ctttattatg tttttgctta tatggtaaag tgattcttca ttatttcatt cttcattgat    180
tgaattgaac a                                                          191
```

<210> SEQ ID NO 8
<211> LENGTH: 346
<212> TYPE: DNA
<213> ORGANISM: Glycine max
<220> FEATURE:
<223> OTHER INFORMATION: FAD3-1A intron 2

<400> SEQUENCE: 8

```
ttagttcata ctggcttttt tgtttgttca tttgtcattg aaaaaaaatc ttttgttgat     60
tcaattattt ttatagtgtg tttggaagcc cgtttgagaa aataagaaat cgcatctgga    120
atgtgaaagt tataactatt tagcttcatc tgtcgttgca agttctttta ttggttaaat    180
ttttatagcg tgctaggaaa cccattcgag aaaataagaa atcacatctg gaatgtgaaa    240
gttataactg ttagcttctg agtaaacgtg gaaaaccac attttggatt tggaaccaaa    300
ttttatttga taaatgacaa ccaaattgat tttgatggat tttgca                   346
```

<210> SEQ ID NO 9
<211> LENGTH: 142
<212> TYPE: DNA
<213> ORGANISM: Glycine max
<220> FEATURE:
<223> OTHER INFORMATION: FAD3-1A intron 3A

<400> SEQUENCE: 9

```
gtatgtgatt aattgcttct cctatagttg ttcttgattc aattacattt tatttatttg     60
```
gtaggtccaa gaaaaaaggg aatctttatg cttcctgagg ctgttcttga acatggctct      120
tttttatgtg tcattatctt ag                                              142

<210> SEQ ID NO 10
<211> LENGTH: 1228
<212> TYPE: DNA
<213> ORGANISM: Glycine max
<220> FEATURE:
<223> OTHER INFORMATION: FAD3-1A intron 4

<400> SEQUENCE: 10
taacaaaaat aaatagaaaa tagtgggtga acacttaaat gcgagatagt aatacctaaa       60 aaagaaaaa aatataggta taataaataa tataactttc aaaataaaaa gaaatcatag      120
agtctagcgt agtgtttgga gtgaaatgat gttcacctac cattactcaa agattttgtt      180 gtgtcccta gttcattctt attattttac atatcttact tgaaaagact ttttaattat      240
tcattgagat cttaaagtga ctgttaaatt aaaataaaaa acaagtttgt taaaacttca      300
aataaataag agtgaaggga gtgtcatttg tcttctttct tttattgcgt tattaatcac      360
gtttctcttc tcttttttt ttttcttctc tgctttccac ccattatcaa gttcatgtga      420
agcagtggcg gatctatgta aatgagtggg gggcaattgc acccacaaga ttttattttt      480
tatttgtaca ggaataataa aataaaactt tgcccccata aaaataaat attttttctt      540 aaaataatgc aaaataaata taagaaataa aaagagaata aattattatt aattttatta      600
ttttgtactt tttatttagt ttttttagcg gttagatttt ttttcatga cattatgtaa      660 tcttttaaaa gcatgtaata ttttttatttt gtgaaaataa atataaatga tcatattagt      720
ctcagaatgt ataaactaat aataatttta tcactaaaag aaattctaat ttagtccata      780
aataagtaaa acaagtgaca attatatttt atatttactt aatgtgaaat aatacttgaa      840
cattataata aaacttaatg acaggagata ttacatagtg ccataaagat atttttaaaaa      900 ataaaatcat taatacactg tactactata taatattcga tatatatttt taacatgatt      960
ctcaatagaa aaattgtatt gattatattt tattagacat gaatttacaa gccccgtttt     1020
tcatttatag ctcttacctg tgatctattg ttttgcttcg ctgttttgtt tggtcaaggg     1080
acttagatgt cacaatatta atactagaag taaatatttta tgaaaacatg taccttacct     1140
caacaaagaa agtgtggtaa gtggcaacac acgtgttgca ttttttggccc agcaataaca     1200 cgtgtttttg tggtgtacta aaatggac                                        1228

<210> SEQ ID NO 11
<211> LENGTH: 625
<212> TYPE: DNA
<213> ORGANISM: Glycine max
<220> FEATURE:
<223> OTHER INFORMATION: FAD3-1A intron 5

<400> SEQUENCE: 11
gtacatttta ttgcttattc acctaaaaac aatacaatta gtacatttgt tttatctctt       60
ggaagttagt cattttcagt tgcatgattc taatgctctc tccattctta aatcatgttt      120
tcacacccac ttcatttaaa ataagaacgt gggtgttatt taatttcta ttcactaaca      180 tgagaaatta acttatttca agtaataatt ttaaaatatt tttatgctat tatttttatta     240 caaataatta tgtatattaa gtttattgat tttataataa ttatattaaa attatatcga      300 tattaattttt tgattcactg atagtgtttt atattgttag tactgtgcat ttattttaaa     360

```
attggcataa ataatatatg taaccagctc actatactat actgggagct tggtggtgaa    420
aggggttccc aaccctcctt tctaggtgta catgctttga tacttctggt accttcttat    480
atcaatataa attatatttt gctgataaaa aaacatggtt aaccattaaa ttcttttttt    540
aaaaaaaaaa ctgtatctaa actttgtatt attaaaaga agtctgagat taacaataaa    600
ctaacactca tttggattca ctgca                                         625
```

<210> SEQ ID NO 12
<211> LENGTH: 98
<212> TYPE: DNA
<213> ORGANISM: Glycine max
<220> FEATURE:
<223> OTHER INFORMATION: FAD3-1A intron 3B

<400> SEQUENCE: 12

```
ggtgagtgat ttttttgactt ggaagacaac aacacattat tattataata tggttcaaaa    60
caatgacttt ttctttatga tgtgaactcc attttttta                            98
```

<210> SEQ ID NO 13
<211> LENGTH: 115
<212> TYPE: DNA
<213> ORGANISM: Glycine max
<220> FEATURE:
<223> OTHER INFORMATION: FAD3-1A intron 3C

<400> SEQUENCE: 13

```
ggtaactaaa ttactcctac attgttactt ttcctcctt tttttttatta tttcaattct     60 ccaattggaa atttgaaata gttaccataa ttatgtaatt gtttgatcat gtgca         115
```

<210> SEQ ID NO 14
<211> LENGTH: 1037
<212> TYPE: DNA
<213> ORGANISM: Glycine max
<220> FEATURE:
<223> OTHER INFORMATION: Fad3-1C intron 4

<400> SEQUENCE: 14

```
gtaacaaaaa taaatagaaa atagtgagtg aacacttaaa tgttagatac taccttcttc     60 ttctttttt tttttttttt gaggttaatg ctagataata gctagaaaga gaaagaaaga    120
caaatatagg taaaaataaa taatataacc tgggaagaag aaaacataaa aaagaaata    180 atagagtcta cgtaatgttt ggattttga gtgaaatggt gttcacctac cattactcaa    240
agattctgtt gtctacgtag tgtttggact ttggagtgaa atggtgttca cctaccatta    300
ctcagattct gttgtgtccc ttagttactg tcttatattc ttagggtata ttcttttattt    360 tacatccttt tcacatctta cttgaaaaga ttttaattat tcattgaaat attaacgtga    420
cagttaaatt aaaataataa aaaattcgtt aaaacttcaa ataaataaga gtgaaaggat    480 catcatttt cttctttctt ttattgcgtt attaatcatg cttctcttct ttttttttctt    540 cgctttccac ccatatcaaa ttcatgtgaa gtatgagaaa atcacgattc aatgggaaagc    600 tacaggaacy ttttttgttt tgtttttata atcggaatta attatactc cattttttca    660 caataaatgt tacttagtgc cttaaagata atatttgaaa aattaaaaaa attattaata    720
cactgtacta ctatataata tttgacatat atttaacatg attttctatt gaaaatttgt    780
atttattatt ttttaatcaa aacccataag gcattaattt acaagaccca ttttcatt     840 atagctttac ctgtgatcat ttatagcttt aagggactta gatgttacaa tcttaattac    900
aagtaaatat ttatgaaaaa catgtgtctt accccttaac cttacctcaa caaagaaagt    960
```

```
gtgataagtg gcaacacacg tgttgctttt ttggcccagc aataacacgt gtttttgtgg   1020
tgtacaaaaa tggacag                                                  1037

<210> SEQ ID NO 15
<211> LENGTH: 4010
<212> TYPE: DNA
<213> ORGANISM: Glycine max
<220> FEATURE:
<223> OTHER INFORMATION: partial FAD3-1A genomic clone

<400> SEQUENCE: 15
acaaagcctt tagcctatgc tgccaataat ggataccaac aaaagggttc ttcttttgat     60
tttgatccta gcgctcctcc accgtttaag attgcagaaa tcagagcttc aataccaaaa    120
cattgctggg tcaagaatcc atggagatcc ctcagttatg ttctcaggga tgtgcttgta    180
attgctgcat tggtggctgc agcaattcac ttcgacaact ggcttctctg ctaatctat     240 tgccccattc aaggcacaat gttctgggct ctctttgttc ttggacatga ttggtaataa    300 ttttgtgtt tcttactctt tttttttttt ttttgtttat gatatgaatc tcacacattg    360
ttctgttatg tcatttcttc ttcatttggc tttagacaac ttaaatttga gatctttatt    420 atgttttgc ttatatggta aagtgattct tcattatttc attcttcatt gattgaattg    480
aacagtggcc atgaagcttt tcagatagcc cctttgctga atagcctggt gggacacatc    540
ttgcattcct caattcttgt gccataccat ggatggttag ttcatactgg ctttttgtt    600 tgttcatttg tcattgaaaa aaaatctttt gttgattcaa ttattttat agtgtgtttg    660 gaagcccgtt tgagaaaata gaaatcgca tctggaatgt gaaagttata actatttagc    720
ttcatctgtc gttgcaagtt cttttattgg ttaaattttt atagcgtgct aggaaaccca    780
ttcgagaaaa taagaaatca catctggaat gtgaaagtta taactgttag cttctgagta    840
aacgtggaaa aaccacattt tggatttgga accaaatttt atttgataaa tgacaaccaa    900
attgattttg atggattttg caggagaatt agccacagaa ctcaccatga aaccatgga    960 cacattgaga aggatgagtc atgggttcca gtatgtgatt aattgcttct cctatagttg   1020
ttcttgattc aattacattt tatttatttg gtaggtccaa gaaaaaggg aatctttatg   1080 cttcctgagg ctgttcttga acatggctct tttttatgtg tcattatctt agttaacaga   1140
gaagatttac aagaatctag acagcatgac aagactcatt agattcactg tgccatttcc   1200
atgtttgtgt atccaatta tttggtgagt gattttttga cttggaagac aacaacacat   1260
tattattata atatggttca aaacaatgac ttttttcttta tgatgtgaac tccattttt    1320 agttttcaag aagccccgga aaggaaggct ctcacttcaa tccctacagc aatctgtttc   1380
cacccagtga gagaaaagga atagcaatat caacactgtg ttgggctacc atgttttctc   1440
tgcttatcta tctctcattc attaactagt ccacttctag tgctcaagct ctatggaatt   1500
ccatattggg taactaaatt actcctacat tgttactttt tcctcctttt ttttattatt   1560
tcaattctcc aattggaaat ttgaaatagt taccataatt atgtaattgt ttgatcatgt   1620
gcagatgttt gttatgtggc tggactttgt cacatacttg catcaccatg gtcaccacca   1680
gaaactgcct tggtaccgcg gcaaggtaac aaaaataaat agaaaatagt gggtgaacac   1740
ttaaatgcga gatagtaata cctaaaaaaa gaaaaaaata taggtataat aaataatata   1800
actttcaaaa taaaagaaa tcatagagtc tagcgtagtg tttggagtga atgatgttc    1860 acctaccatt actcaaagat tttgttgtgt cccttagttc attcttatta ttttacatat   1920
```

```
cttacttgaa aagactttt  aattattcat  tgagatctta  aagtgactgt  taaattaaaa    1980
taaaaaacaa gtttgttaaa acttcaaata  aataagagtg  aagggagtgt  catttgtctt    2040
cttttctttta ttgcgttatt aatcacgttt ctcttctctt  tttttttttt  cttctctgct    2100
ttccacccat tatcaagttc  atgtgaagca  gtggcggatc  tatgtaaatg  agtgggggggc   2160
aattgcaccc acaagatttt  atttttttatt tgtacaggaa  taataaaata  aaactttgcc    2220
cccataaaaa ataaatattt  tttcttaaaa  taatgcaaaa  taaatataag  aaataaaaag    2280
agaataaatt attattaatt  ttattatttt  gtacttttta  tttagttttt  ttagcggtta    2340
gattttttt tcatgacatt  atgtaatctt  ttaaaagcat  gtaatatttt  tattttgtga    2400
aaataaatat aaatgatcat  attagtctca  gaatgtataa  actaataata  attttatcac    2460
taaaagaaat tctaatttag  tccataaata  agtaaaacaa  gtgacaatta  tattttatat    2520
ttacttaatg tgaaataata  cttgaacatt  ataataaaac  ttaatgacag  gagatattac    2580
atagtgccat aaagatattt  taaaaaataa  aatcattaat  acactgtact  actatataat    2640
attcgatata tattttttaac atgattctca  atagaaaaat  tgtattgatt  atattttatt    2700
agacatgaat ttacaagccc  cgttttttcat ttatagctct  tacctgtgat  ctattgtttt    2760
gcttcgctgt ttttgttggt  caagggactt  agatgtcaca  atattaatac  tagaagtaaa    2820
tatttatgaa aacatgtacc  ttacctcaac  aaagaaagtg  tggtaagtgg  caacacacgt    2880
gttgcatttt tggcccagca  ataacacgtg  ttttgtggt   gtactaaaat  ggacaggaat    2940
ggagttattt aagaggtggc  ctcaccactg  tggatcgtga  ctatggttgg  atcaataaca    3000
ttcaccatga cattggcacc  catgttatcc  accatcttt   cccccaaatt  cctcattatc    3060
acctcgttga agcggtacat  tttattgctt  attcacctaa  aaacaataca  attagtacat    3120
ttgttttatc tcttggaagt  tagtcatttt  cagttgcatg  attctaatgc  tctctccatt    3180
cttaaatcat gttttcacac  ccacttcatt  taaaataaga  acgtgggtgt  tattttaatt    3240
tctattcact aacatgagaa  attaacttat  ttcaagtaat  aattttaaaa  tattttatg    3300
ctattatttt attacaaata  attatgtata  ttaagtttat  tgattttata  ataattatat    3360
taaaattata tcgatattaa  ttttttgattc actgatagtg  ttttatattg  ttagtactgt    3420
gcatttattt taaaattggc  ataaataata  tatgtaacca  gctcactata  ctatactggg    3480
agcttggtgg tgaaaggggt  tcccaaccct  cctttctagg  tgtacatgct  ttgatacttc    3540
tggtaccttc ttatatcaat  ataaattata  ttttgctgat  aaaaaaacat  ggttaaccat    3600
taaattcttt ttttaaaaaa  aaactgtat   ctaaactttg  tattattaaa  agaagtctg    3660
agattaacaa taaactaaca  ctcatttgga  ttcactgcag  acacaagcag  caaaaccagt    3720
tcttggagat tactaccgtg  agccagaaag  atctgcgcca  ttaccatttc  atctaataaa    3780
gtatttaatt cagagtatga  gacaagacca  cttcgtaagt  gacactggag  atgttgttta    3840
ttatcagact gattctctgc  tcctccactc  gcaacgagac  tgagtttcaa  acttttggg    3900
ttattattta ttgattctag  ctactcaaat  tactttttt   ttaatgttat  gtttttgga    3960
gtttaacgtt ttctgaacaa  cttgcaaatt  acttgcatag  agagacatgg              4010
```

<210> SEQ ID NO 16
<211> LENGTH: 184
<212> TYPE: DNA
<213> ORGANISM: Glycine max
<220> FEATURE:
<223> OTHER INFORMATION: FAD3-1A 3'UTR

<400> SEQUENCE: 16

```
gtttcaaact ttttgggtta ttatttattg gattctagct actcaaatta ctttttttt     60 aatgttatgt tttttggagt ttaacgtttt ctgaacaact tgcaaattac ttgcatagag    120
agacatggaa tatttatttg aaattagtaa ggtagtaata ataaattttg aattgtcagt    180
ttca                                                                 184

<210> SEQ ID NO 17
<211> LENGTH: 143
<212> TYPE: DNA
<213> ORGANISM: Glycine max
<220> FEATURE:
<223> OTHER INFORMATION: FAD3-1A 5'UTR

<400> SEQUENCE: 17
tgcggttata taaatgcact atcccataag agtattttc gaagatttcc ttcttcctat      60
tctaggtttt tacgcaccac gtatccctga aaaagagag gaaccacact ctctaagcca    120
aagcaaaagc agcagcagca gca                                           143

<210> SEQ ID NO 18
<211> LENGTH: 2683
<212> TYPE: DNA
<213> ORGANISM: Glycine max
<220> FEATURE:
<223> OTHER INFORMATION: partial FAD3-1B genomic clone

<400> SEQUENCE: 18
gttcaagcac agcctctaca acatgttggt aatggtgcag ggaaagaaga tcaagcttat     60
tttgatccaa gtgctccacc acccttcaag attgcaaata tcagagcagc aattccaaaa   120
cattgctggg agaagaacac attgagatct ctgagttatg ttctgaggga tgtgttggta   180
gtgactgcat tggtagctgc agcaatcggc ttcaatagct ggttcttctg gccactctat   240
tggcctgcac aaggcacaat gttttgggca cttttttgttc ttggacatga ttggtaacta   300
attattatta caaattgtta tgttatgtta tgttatgttg ttgtgccttt ttctcagtga   360
tgctttagtc atttcatttc acttggttat gcatgattgt tcgttcatat gttctgtcat   420
ggtgagttct aatttgattg atgcatggaa cagtggtcat ggaagttttt caaacagtcc   480
tttgttgaac agcattgtgg gccacatctt gcactcttca attcttgtac cataccatgg   540
atggtcggtt ccttttagca actttttcatg ttcactttgt ccttaaattt tttttatgt    600 ttgttaaaaa atctttggtc tgatttaaca acctaaccat ttttacaact catggatttt   660
ttgcaggaga attagccaca ggactcacca tcagaaccat ggccatgttg agaaggatga   720
atcatgggtt ccggtattac tatgagtttg cttgattaat ttccacattt tttctttctt   780
cttaatttta atcagtggtt agatttggtt gtgttccgat agaagaaaag ggggtatcta   840
gagagatgtg aatttcatga agtggttcat gattatgtgt ctttatgcct ttatgtcagc   900
ttacagagaa agtttacaag aatctagaca acatgacaag aatgatgaga ttcactcttc   960
ctttccccat ctttgcatac ccctttatt tggtgagacc ctcttttcc agaatgacag    1020 cattatttta ctatatagta cctcaatttt tatattcta aaattttgaa ttcttgaaat   1080
tgaaaggaaa ggactttatt gggtctagca tctcactctc tctttgtgat atgaaccata   1140
tatttcagtg gagcagaagc cctggaaaag aaggctctca tttcaaccct tacagcaact   1200
tgttctctcc tggtgagaga agagatgtgc taacttcaac tctatgttgg ggcatcatgc   1260
tttctgtgct tctctatctt tccctcacaa tgggtccact ttttatgctc aagctctatg   1320
```

-continued

```
gggttcccta tttggtaatc tcactctcac actttcttta tacatcgcac gccagtgtgg    1380
gttatttgca acctacaccg aagtaatgcc ctataattaa tgaggttaac acatgtccaa    1440
gtccaatatt ttgttcactt atttgaactt gaacatgtgt agatcttcgt catgtggctg    1500
gatttcgtca cgtacttgca tcatcatggt tacaagcaga aactgccttg gtaccgtggc    1560
caggtatccc atttaacaca atttgtttca ttaacatttt aagagaattt ttttttcaaa    1620
atagttttcg aaattaagca ataccaagc aaattgttag atctacgctt gtacttgttt     1680
taaagtcaaa ttcatgacca aattgtcctc acaagtccaa accgtccact attttatttt    1740
cacctacttt atagcccaat ttgccatttg gttacttcag aaaagagaac cccatttgta    1800
gtaaatatat tatttatgaa ttatggtagt ttcaacataa aacatactta tgtgcagttt    1860
tgccatcctt caaaagaagg tagaaactta ctccatgtta ctctgtctat atgtaatttc    1920
acaggaatgg agttatctaa ggggtggtct tacaacagta gatcgcgact atggttggat    1980
caacaacatt caccatgaca ttggcaccca tgttatccat cacctttttcc ctcaaattcc    2040 acattatcat ttaatcgaag cggtattaat tctctatttc acaagaaatt attgtatgtc    2100
tgcctatgtg atctaagtca attttcacat aacacatgat caaactttct taattctttc    2160
ttctaaattg aaaagtgga ttatatgtca attgaaaatt ggtcaagacc acaaacatgt     2220
gatgatctcc caccttacat ataataattt ctcctattct acaatcaata atccttctat    2280
ggtcctgaat tgttcctttc tttttttcatt ttcttattct ttttgttgtc ccacaataga   2340
ctaaagcagc aaaggcagtg ctaggaaagt attatcgtga gcctcagaaa tctgggccat    2400
tgccacttca tctaataaag tacttgctcc acagcataag tcaggatcac ttcgttagcg    2460
actctggcga cattgtgtac taccagactg attcccagct ccacaaagat tcttggaccc    2520
agtccaacta aagttttttga tgctacattt acctatttca ctcttaaata ctatttccta   2580
tgtaatatgt aatttagaat atgttaccta ctcaaatcaa ttaggtgaca tgtataagct    2640
ttcataaatt atgctagaaa tgcacttact tttcaaagca tgc                      2683
```

```
<210> SEQ ID NO 19
<211> LENGTH: 160
<212> TYPE: DNA
<213> ORGANISM: Glycine max
<220> FEATURE:
<223> OTHER INFORMATION: FAD3-1B intron 1

<400> SEQUENCE: 19
gtaactaatt attattacaa attgttatgt tatgttatgt tatgttgttg tgccttttc      60 tcagtgatgc tttagtcatt tcatttcact tggttatgca tgattgttcg ttcatatgtt    120
ctgtcatggt gagttctaat ttgattgatg catggaacag                          160
```

```
<210> SEQ ID NO 20
<211> LENGTH: 119
<212> TYPE: DNA
<213> ORGANISM: Glycine max
<220> FEATURE:
<223> OTHER INFORMATION: FAD3-1B intron 2

<400> SEQUENCE: 20 gttccttta gcaacttttc atgttcactt tgtccttaaa tttttttta tgtttgttaa       60 aaaatctttg gtctgattta acaacctaac catttttaca actcatggat tttttgcag     119
```

```
<210> SEQ ID NO 21
<211> LENGTH: 166
```

<212> TYPE: DNA
<213> ORGANISM: Glycine max
<220> FEATURE:
<223> OTHER INFORMATION: FAD3-1B intron 3a

<400> SEQUENCE: 21
gtattactat gagtttgctt gattaatttc cacatttttt ctttcttctt aattttaatc        60
agtggttaga tttggttgtg ttccgataga agaaaagggg gtatctagag agatgtgaat       120
ttcatgaagt ggttcatgat tatgtgtctt tatgccttta tgtcag                      166

<210> SEQ ID NO 22
<211> LENGTH: 156
<212> TYPE: DNA
<213> ORGANISM: Glycine max
<220> FEATURE:
<223> OTHER INFORMATION: FAD3-1B intron 3b

<400> SEQUENCE: 22
gtgagaccct cttttccag aatgacagca ttattttact atatagtacc tcaatttta         60 tatttctaaa atttgaatt cttgaaattg aaaggaaagg actttattgg gtctagcatc       120
tcactctctc tttgtgatat gaaccatata tttcag                                156

<210> SEQ ID NO 23
<211> LENGTH: 148
<212> TYPE: DNA
<213> ORGANISM: Glycine max
<220> FEATURE:
<223> OTHER INFORMATION: FAD3-1B intron 3c

<400> SEQUENCE: 23
gtaatctcac tctcacactt tctttataca tcgcacgcca gtgtgggtta tttgcaacct       60
acaccgaagt aatgccctat aattaatgag gttaacacat gtccaagtcc aatattttgt      120
tcacttattt gaacttgaac atgtgtag                                         148

<210> SEQ ID NO 24
<211> LENGTH: 351
<212> TYPE: DNA
<213> ORGANISM: Glycine max
<220> FEATURE:
<223> OTHER INFORMATION: FAD3-1B intron 4

<400> SEQUENCE: 24
taacacaatt tgtttcatta acatttaag agaattttt tttcaaaata gttttcgaaa         60
ttaagcaaat accaagcaaa tgttagatc tacgcttgta cttgttttaa agtcaaattc       120
atgaccaaat tgtcctcaca agtccaaacc gtccactatt ttattttcac ctactttata     180
gcccaatttg ccatttggtt acttcagaaa agagaacccc atttgtagta aatatatat       240 ttatgaatta tggtagtttc aacataaaac atacttatgt gcagttttgc catccttcaa     300
aagaaggtag aaacttactc catgttactc tgtctatatg taatttcaca g              351

<210> SEQ ID NO 25
<211> LENGTH: 277
<212> TYPE: DNA
<213> ORGANISM: Glycine max
<220> FEATURE:
<223> OTHER INFORMATION: FAD3-1B intron 5

<400> SEQUENCE: 25
gtattaattc tctatttcac aagaaattat tgtatgtctg cctatgtgat ctaagtcaat       60

```
tttcacataa cacatgatca aactttctta attctttctt ctaaattgaa aaagtggatt    120
atatgtcaat tgaaaattgg tcaagaccac aaacatgtga tgatctccca ccttacatat    180
aataatttct cctattctac aatcaataat ccttctatgg tcctgaattg ttcctttctt    240
ttttcatttt cttattcttt tgttgtccc acaatag                              277

<210> SEQ ID NO 26
<211> LENGTH: 158
<212> TYPE: DNA
<213> ORGANISM: Glycine max
<220> FEATURE:
<223> OTHER INFORMATION: FAD3-1B 3'UTR

<400> SEQUENCE: 26
agtttttgat gctacattta cctatttcac tcttaaatac tatttcctat gtaatatgta     60
atttagaata tgttacctac tcaaatcaat taggtgacat gtataagctt tcataaatta    120
tgctagaaat gcacttactt ttcaaagcat gctatgtc                            158

<210> SEQ ID NO 27
<211> LENGTH: 83
<212> TYPE: DNA
<213> ORGANISM: Glycine max
<220> FEATURE:
<223> OTHER INFORMATION: FAD3-1B 5'UTR

<400> SEQUENCE: 27
tctaatacga ctcactatag ggcaagcagt ggtatcaacg cagagtacgc gggggtaaca     60
gagaaagaaa catttgagca aaa                                             83

<210> SEQ ID NO 28
<211> LENGTH: 4083
<212> TYPE: DNA
<213> ORGANISM: Glycine max
<220> FEATURE:
<223> OTHER INFORMATION: FATB-1 genomic clone

<400> SEQUENCE: 28
gggaaacaac aaggacgcaa aatgacacaa tagcccttct tccctgtttc cagcttttct     60
ccttctctct ctccatcttc ttcttcttct tcactcagtc aggtacgcaa acaaatctgc    120
tattcattca ttcattcctc tttctctctg atcgcaaact gcacctctac gctccactct    180
tctcattttc tcttcctttc tcgcttctca gatccaactc ctcagataac acaagaccaa    240
acccgctttt tctgcatttc tagactagac gttctaccgg agaaggttct cgattctttt    300
ctcttttaac tttattttta aataataat aatgagagct ggatgcgtct gttcgttgtg    360
aatttcgagg caatggggtt ctcatttccg ttacagttac agattgcatt gtctgctttc    420
ctcttctccc ttgtttcttt gccttgtctg attttcgtt tttatttctt acttttaatt    480
tttggggatg atattttttt ctgcattttt tcggtttgcg atgttttcag gattccgatt    540
ccgagtcaga tctgcgccgg cttatacgac gaatttgttc ttattcgcaa cttttcgctt    600
gattggcttg ttttacctct ggaatctcac acgtgatcaa ataagcctgc tatttagtt    660 gaagtagaat tgttctttta tcggaaagaa ttctatggat ctgttctgaa attggagcta    720
ctgtttcgag ttgctatttt tttagtagt attaagaaca gtttgcctt ttattttaca    780 ttttttttcct ttgcttttgc caaaagtttt tatgatcact ctcttctgtt tgtgatataa    840
ctgatgtgct gtgctgttat tatttgttat tggggtgaa gtataatttt ttgggtgaac    900
ttggagcatt tttagtccga ttgatttctc gatatcattt aaggctaagg ttgacctcta    960
```

```
ccacgcgttt gcgtttgatg ttttttccat tttttttta tctcatatct tttacagtgt    1020
ttgcctattt gcatttctct tctttatccc ctttctgtgg aaaggtggga gggaaaatgt    1080 atttttttt tctcttctaa cttgcgtata ttttgcatgc agcgaccttta gaaattcatt    1140 atggtggcaa cagctgctac ttcatcattt ttccctgtta cttcaccctc gccggactct    1200
ggtggagcag gcagcaaact tggtggtggg cctgcaaacc ttggaggact aaaatccaaa    1260
tctgcgtctt ctggtggctt gaaggcaaag gcgcaagccc cttcgaaaat taatggaacc    1320
acagttgtta catctaaaga aggcttcaag catgatgatg atctaccttc gcctcccccc    1380
agaactttta tcaaccagtt gcctgattgg agcatgcttc ttgctgctat cacaacaatt    1440
ttcttggccg ctgaaaagca gtggatgatg cttgattgga agccacggcg acctgacatg    1500
cttattgacc cctttgggat aggaaaaatt gttcaggatg gtcttgtgtt ccgtgaaaac    1560
ttttctatta gatcatatga gattggtgct gatcgtaccg catctataga aacagtaatg    1620
aaccatttgc aagtaagtcc gtcctcatac aagtgaatct ttatgatctt cagagatgag    1680
tatgctttga ctaagatagg gctgtttatt tagacactgt aattcaattt catatataga    1740
taatatcatt ctgttgttac ttttcatact atatttatat caactatttg cttaacaaca    1800
ggaaactgca cttaatcatg ttaaaagtgc tgggcttctt ggtgatggct ttggttccac    1860
gccagaaatg tgcaaaaaga acttgatatg ggtggttact cggatgcagg ttgtggtgga    1920
acgctatcct acatggttag tcatctagat tcaaccatta catgtgattt gcaatgtatc    1980
catgttaagc tgctatttct ctgtctattt tagtaatctt tatgaggaat gatcactcct    2040
aaatatattc atggtaatta ttgagactta attatgagaa ccaaaatgct ttggaaattt    2100
gtctgggatg aaaattgatt agatacacaa gctttataca tgatgaacta tgggaaacct    2160
tgtgcaacag agctattgat ctgtacaaga gatgtagtat agcattaatt acatgttatt    2220
agataaggtg acttatcctt gtttaattat tgtaaaaata gaagctgata ctatgtattc    2280
tttgcatttg ttttcttacc agttatatat accctctgtt ctgtttgagt actactagat    2340
gtataaagaa tgcaattatt ctgacttctt ggtgttgggt tgaagttaga taagctatta    2400
gtattattat ggttattcta aatctaatta tctgaaattg tgtgtctata tttgcttcag    2460
gggtgacata gttcaagtgg acactttggg ttctggatca gggaagaatg gtatgcgtcg    2520
tgattggctt ttacgtgact gcaaaactgg tgaaatcttg acaagagctt ccaggtagaa    2580
atcattctct gtaattttcc ttccccttc cttctgcttc aagcaaattt taagatgtgt    2640
atcttaatgt gcacgatgct gattggacac aattttaaat ctttcaaaca tttacaaaag    2700
ttatggaacc ctttctttc tctcttgaag atgcaaattt gtcacgactg aagtttgagg    2760
aaatcatttg aattttgcaa tgttaaaaaa gataatgaac tacatatttt gcaggcaaaa    2820
acctctaatt gaacaaactg aacattgtat cttagtttat ttatcagact ttatcatgtg    2880
tactgatgca tcaccttgga gcttgtaatg aattacatat tagcatttttc tgaactgtat    2940 gttatggttt tggtgatcta cagtgtttgg gtcatgatga ataagctgac acggaggctg    3000
tctaaaattc cagaagaagt cagacaggag ataggatctt atttttgtgga ttctgatcca    3060 attctagaag aggataacag aaaactgact aaacttgacg acaacacagc ggattatatt    3120
cgtaccggtt taagtgtatg tcaactagtt ttttttgtaat tgttgtcatt aatttctttt    3180
cttaaattat ttcagatgtt gctttctaat tagtttacat tatgtatctt cattcttcca    3240
gtctaggtgg agtgatctag atatcaatca gcatgtcaac aatgtgaagt acattgactg    3300
```

```
gattctggag gtatttttct gttcttgtat tctaatccac tgcagtcctt gttttgttgt    3360
taaccaaagg actgtccttt gattgtttgc agagtgctcc acagccaatc ttggagagtc    3420
atgagctttc ttccgtgact ttagagtata ggagggagtg tggtagggac agtgtgctgg    3480
attccctgac tgctgtatct ggggccgaca tgggcaatct agctcacagt ggacatgttg    3540
agtgcaagca tttgcttcga ctcgaaaatg gtgctgagat tgtgaggggc aggactgagt    3600
ggaggcccaa acctatgaac aacattggtg ttgtgaacca ggttccagca gaaagcacct    3660
aagattttga atggttaacg gttggagtt gcatcagtct ccttgctatg tttagactta     3720
ttctggcctc tggggagagt tttgcttgtg tctgtccaat caatctacat atctttatat    3780
ccttctaatt tgtgttactt tggtgggtaa gggggaaaag ctgcagtaaa cctcattctc    3840
tctttctgct gctccatatt tcatttcatc tctgattgcg ctactgctag gctgtcttca    3900
atatttaatt gcttgatcaa aatagctagg catgtatatt attattcttt tctcttggct    3960
caattaaaga tgcaatttc attgtgaaca cagcataact attattctta ttattttgt     4020 atagcctgta tgcacgaatg acttgtccat ccaatacaac cgtgattgta tgctccagct    4080
cag                                                                  4083

<210> SEQ ID NO 29
<211> LENGTH: 109
<212> TYPE: DNA
<213> ORGANISM: Glycine max
<220> FEATURE:
<223> OTHER INFORMATION: FATB-1 intron I

<400> SEQUENCE: 29
gtacgcaaac aaatctgcta ttcattcatt cattcctctt tctctctgat cgcaaactgc      60
acctctacgc tccactcttc tcatttctc ttcctttctc gcttctcag                  109

<210> SEQ ID NO 30
<211> LENGTH: 836
<212> TYPE: DNA
<213> ORGANISM: Glycine max
<220> FEATURE:
<223> OTHER INFORMATION: FATB-1 intron II

<400> SEQUENCE: 30
gttctcgatt cttttctctt ttaactttat ttttaaaata ataataatga gagctggatg      60
cgtctgttcg ttgtgaattt cgaggcaatg gggttctcat tttcgttaca gttacagatt     120
gcattgtctg ctttcctctt ctcccttgtt tctttgcctt gtctgatttt tcgtttttat     180
ttcttacttt taattttggg ggatggatat ttttctgca ttttttcggt ttgcgatgtt      240
ttcaggattc cgattccgag tcagatctgc gccggcttat acgacgaatt tgttcttatt     300 cgcaacttttt cgcttgattg gcttgtttta cctctggaat ctcacacgtg atcaaataag    360
cctgctattt tagttgaagt agaatttgtt ctttatcgga aagaattcta tggatctgtt     420
ctgaaattgg agctactgtt tcgagttgct attttttta gtagtattaa gaacaagttt      480 gcctttatt ttacattttt ttcctttgct tttgccaaaa gtttttatga tcactctctt      540
ctgtttgtga taactgat gtgctgtgct gttattattt gttatttggg gtgaagtata       600
attttttggg tgaacttgga gcatttttag tccgattgat ttctcgatat catttaaggc     660
taaggttgac ctctaccacg cgtttgcgtt tgatgttttt tccattttt ttttatctca      720 tatcttttac agtgttgcc tatttgcatt tctcttcttt atccccttc tgtggaaggt       780 gggagggaaa atgtatttt tttttctctt ctaacttgcg tatattttgc atgcag          836
```

<210> SEQ ID NO 31
<211> LENGTH: 169
<212> TYPE: DNA
<213> ORGANISM: Glycine max
<220> FEATURE:
<223> OTHER INFORMATION: FATB-1 intron III

<400> SEQUENCE: 31

```
gtaagtccgt cctcatacaa gtgaatcttt atgatcttca gagatgagta tgctttgact      60
aagatagggc tgtttattta gacactgtaa ttcaatttca tatatagata atatcattct     120
gttgttactt ttcatactat atttatatca actatttgct taacaacag                 169
```

<210> SEQ ID NO 32
<211> LENGTH: 525
<212> TYPE: DNA
<213> ORGANISM: Glycine max
<220> FEATURE:
<223> OTHER INFORMATION: FATB-1 intron IV

<400> SEQUENCE: 32

```
gttagtcatc tagattcaac cattacatgt gatttgcaat gtatccatgt taagctgcta      60
tttctctgtc tattttagta atctttatga ggaatgatca ctcctaaata tattcatggt     120
aattattgag acttaattat gagaaccaaa atgctttgga aatttgtctg ggatgaaaat     180
tgattagata cacaagcttt atacatgatg aactatggga aaccttgtgc aacagagcta     240
ttgatctgta caagagatgt agtatagcat taattacatg ttattagata aggtgactta     300
tccttgttta attattgtaa aaatagaagc tgatactatg tattctttgc atttgttttc     360
ttaccagtta tatataccct ctgttctgtt tgagtactac tagatgtata aagaatgcaa     420
ttattctgac ttcttggtgt tgggttgaag ttagataagc cattagtatt attatggtta     480
ttctaaatct aattatctga aattgtgtgt ctatatttgc ttcag                      525
```

<210> SEQ ID NO 33
<211> LENGTH: 389
<212> TYPE: DNA
<213> ORGANISM: Glycine max
<220> FEATURE:
<223> OTHER INFORMATION: FATB-1 intron V

<400> SEQUENCE: 33

```
gtagaaatca ttctctgtaa ttttccttcc cctttccttc tgcttcaagc aaatttttaag     60 atgtgtatct taatgtgcac gatgctgatt ggacacaatt ttaaatcttt caaacattta    120
caaaagttat ggaacccttt cttttctctc ttgaagatgc aaatttgtca cgactgaagt    180
ttgaggaaat catttgaatt ttgcaatgtt aaaaaagata atgaactaca tattttgcag    240
gcaaaaacct ctaattgaac aaactgaaca ttgtatctta gtttatttat cagactttat    300
catgtgtact gatgcatcac cttggagctt gtaatgaatt acatattagc attttctgaa    360
ctgtatgtta tggttttggt gatctacag                                        389
```

<210> SEQ ID NO 34
<211> LENGTH: 106
<212> TYPE: DNA
<213> ORGANISM: Glycine max
<220> FEATURE:
<223> OTHER INFORMATION: FATB-1 intron VI

<400> SEQUENCE: 34

```
tatgtcaact agttttttg taattgttgt cattaatttc ttttcttaaa ttatttcaga    60
tgttgctttc taattagttt acattatgta tcttcattct tccagt                 106

<210> SEQ ID NO 35
<211> LENGTH: 82
<212> TYPE: DNA
<213> ORGANISM: Glycine max
<220> FEATURE:
<223> OTHER INFORMATION: FATB-1 intron VII

<400> SEQUENCE: 35 gtattttct gttcttgtat tctaatccac tgcagtcctt gttttgttgt taaccaaagg   60
actgtccttt gattgtttgc ag                                            82

<210> SEQ ID NO 36
<211> LENGTH: 208
<212> TYPE: DNA
<213> ORGANISM: Glycine max
<220> FEATURE:
<223> OTHER INFORMATION: FATB-1 3'UTR

<400> SEQUENCE: 36
gatttgaaat ggttaacgat tggagttgca tcagtctcct tgctatgttt agacttattc   60
tggttccctg gggagagttt tgcttgtgtc tatccaatca atctacatgt ctttaaatat  120
atacaccttc taatttgtga tactttggtg ggtaaggggg aaaagcagca gtaaatctca  180
ttctcattgt aattaaaaaa aaaaaaaa                                     208

<210> SEQ ID NO 37
<211> LENGTH: 229
<212> TYPE: DNA
<213> ORGANISM: Glycine max
<220> FEATURE:
<223> OTHER INFORMATION: FATB-1 5'UTR

<400> SEQUENCE: 37
acaattacac tgtctctctc ttttccaaaa ttagggaaac aacaaggacg caaaatgaca   60
caatagccct tcttccctgt ttccagcttt tctccttctc tctctctcca tcttcttctt  120
cttcttcact cagtcagatc caactcctca gataacacaa gaccaaaccc gcttttctg  180 catttctaga ctagacgttc taccggagaa gcgaccttag aaattcatt              229

<210> SEQ ID NO 38
<211> LENGTH: 1398
<212> TYPE: DNA
<213> ORGANISM: Cuphea pulcherrima
<220> FEATURE:
<223> OTHER INFORMATION: KAS I gene

<400> SEQUENCE: 38
atgcattccc tccagtcacc ctcccttcgg gcctccccgc tcgacccctt ccgcccaaa    60 tcatccaccg tccgcccccct ccaccgagca tcaattccca acgtccgggc cgcttccccc 120
accgtctccg ctcccaagcg cgagaccgac cccaagaagc gcgtcgtgat caccggaatg  180
ggccttgtct ccgttttcgg ctccgacgtc gatgcgtact acgacaagct cctgtcaggc  240
gagagcggga tcggcccaat cgaccgcttc gacgcctcca gttccccac caggttcggc   300 ggccagattc gtggcttcaa ctccatggga tacattgacg gcaaaaacga caggcggctt  360
gatgattgcc ttcgctactg cattgtcgcc gggaagaagt ctcttgagga cgccgatctc  420
ggtgccgacc gcctctccaa gatcgacaag gagagagccg gagtgctggt gggacagga   480
```

```
atgggtggtc tgactgtctt ctctgacggg gttcaatctc ttatcgagaa gggtcaccgg    540
aaaatcaccc ctttcttcat ccctatgcc attacaaaca tggggtctgc cctgctcgct    600
attgaactcg gtctgatggg cccaaactat tcaatttcca ctgcatgtgc cacttccaac    660
tactgcttcc atgctgctgc taatcatatc cgccgtggtg aggctgatct tatgattgct    720
ggaggcactg aggccgcaat cattccaatt gggttgggag ctttgtggc ttgcagggct    780 ctgtctcaaa ggaacgatga ccctcagact gcctctaggc cctgggataa agaccgtgat    840
ggttttgtga tgggtgaagg tgctggagtg ttggtgctgg agagcttgga acatgcaatg    900
aaacgaggag cacctattat tgcagagtat ttgggaggtg caatcaactg tgatgcttat    960
cacatgactg acccaagggc tgatggtctc ggtgtctcct cttgcattga gagtagcctt   1020
gaagatgctg cgtctcacc tgaagaggtc aattacataa atgctcatgc gacttctact   1080
ctagctgggg atctcgccga gataaatgcc atcaagaagg ttttcaagaa cacaaaggat   1140
atcaaaatta atgcaactaa gtcaatgatc ggacactgtc ttggagcctc tggaggtctt   1200
gaagctatag cgactattaa gggaataaac accggctggc ttcatcccag cattaatcaa   1260
ttcaatcctg agccatccgt ggagttcgac actgttgcca acaagaagca gcaacacgaa   1320
gttaatgttg cgatctcgaa ttcatttgga ttcggaggcc acaactcagt cgtggctttc   1380
tcggctttca agccatga                                                 1398

<210> SEQ ID NO 39
<211> LENGTH: 1218
<212> TYPE: DNA
<213> ORGANISM: Cuphea pulcherrima

<400> SEQUENCE: 39
atgggtgtgg tgactcctct aggccatgac cctgatgttt tctacaataa tctgcttgat     60
ggaacgagtg gcataagcga gatagagacc tttgattgtg ctcaatttcc tacgagaatt    120
gctggagaga tcaagtcttt ctccacagat ggttgggtgg ccccgaagct ctctaagagg    180
atggacaagt tcatgctata catgctgacc gctggcaaga agcattaac agatggtgga    240 atcaccgaag atgtgatgaa agagctagat aaaagaaaat gcggagttct cattggctca    300
gcaatgggtg gaatgaaggt attcaatgat gccattgaag ccctaaggat ttcatataag    360
aagatgaatc ccttttgtgt acctttcgct accacaaata tggatcagc tatgcttgca    420 atggacttgg gatggatggg gcccaactac tcgatatcta ctgcttgtgc aacgagtaac    480
ttttgtataa tgaatgctgc gaaccatata atcagaggcg aagcagatgt gatgctttgc    540
gggggctcag atgcggtaat catacctatt ggtatgggag ttttgttgc atgccgagct    600 ttgtcccaga gaaattccga ccctactaaa gcttcaagac catgggacag taatcgtgat    660
ggatttgtta tgggggaagg agctggagtg ctactactag aggagttgga gcatgcaaag    720
aaaagaggtg cgactattta cgcagaattt ctaggtggaa gtttcacttg cgatgcctac    780
cacatgaccg agcctcaccc tgatggagct ggagtgattc tctgcataga gaaggctttg    840
gctcagtcag gagtctctag ggaagacgta aattacataa atgccatgc cacatccact    900 ccggctggag atatcaaaga gtaccaagct cttatccact gtttcggcca aaacagagag    960
ttaaaagtta attcaaccaa atcaatgatt ggtcaccttc tcggagcagc cggtggtgtg   1020
gaagcagttt cagtagttca ggcaataagg actgggtgga tccatccgaa tattaatttg   1080
gaaaacccag atgaaggcgt ggatacaaaa ttgctcgtgg gtcctaagaa ggagagactg   1140
```

```
aacgttaagg tcggtttgtc taattcattt gggtttggtg ggcacaactc gtccatactc    1200
ttcgcccctt acatctag                                                 1218

<210> SEQ ID NO 40
<211> LENGTH: 1191
<212> TYPE: DNA
<213> ORGANISM: Ricinus communis
<220> FEATURE:
<223> OTHER INFORMATION: delta-9 desaturase

<400> SEQUENCE: 40
atggctctca agctcaatcc tttcctttct caaacccaaa agttaccttc tttcgctctt      60
ccaccaatgg ccagtaccag atctcctaag ttctacatgg cctctaccct caagtctggt     120
tctaaggaag ttgagaatct caagaagcct tcatgcctc ctcgggaggt acatgttcag      180
gttacccatt ctatgccacc ccaaaagatt gagatcttta atccctaga caattgggct      240 gaggagaaca ttctggttca tctgaagcca gttgagaaat gttggcaacc gcaggatttt     300
ttgccagatc ccgcctctga tggatttgat gagcaagtca gggaactcag ggagagagca     360
aaggagattc ctgatgatta ttttgttgtt ttggttggag acatgataac ggaagaagcc     420
cttcccactt atcaaacaat gctgaatacc ttggatgag ttcgggatga acaggtgca       480 agtcctactt cttgggcaat ttggacaagg gcatggactg cggaagagaa tagacatggt     540
gacctcctca ataagtatct ctacctatct ggacgagtgg acatgaggca aattgagaag     600
acaattcaat atttgattgg ttcaggaatg gatccacgga cagaaaacag tccatacctt     660
gggttcatct acatcatt ccaggaaagg gcaaccttca tttctcatgg gaacactgcc       720
cgacaagcca agagcatgg agacataaag ttggctcaaa tatgtggtac aattgctgca      780
gatgagaagc gccatgagac agcctacaca aagatagtgg aaaaactctt tgagattgat     840
cctgatggaa ctgttttggc ttttgctgat atgatgagaa gaaaatttc tatgcctgca      900 cacttgatgt atgatggccg agatgataat cttttttgacc acttttcagc tgttgcgcag    960
cgtcttggag tctacacagc aaaggattat gcagatatat tggagttctt ggtgggcaga   1020
tggaaggtgg ataaactaac gggcctttca gctgagggac aaaaggctca ggactatgtt   1080
tgtcggttac ctccaagaat tagaaggctg aagagagag ctcaaggaag gcaaaggaa     1140 gcacccacca tgcctttcag ctggattttc gataggcaag tgaagctgta g           1191

<210> SEQ ID NO 41
<211> LENGTH: 1194
<212> TYPE: DNA
<213> ORGANISM: Simmondsia chinensis
<220> FEATURE:
<223> OTHER INFORMATION: delta-9 desaturase

<400> SEQUENCE: 41
atggcgttga agcttcacca cacggccttc aatccttcca tggcggttac ctcttcggga      60
cttcctcgat cgtatcacct cagatctcac cgcgttttca tggcttcttc tacaattgga    120
attacttcta aggagatacc caatgccaaa agcctcaca tgcctcctag agaagctcat     180
gtgcaaaaga cccattcaat gccgcctcaa aagattgaga ttttcaaatc cttggagggt    240
tgggctgagg agaatgtctt ggtgcatctt aaacctgtgg agaagtgttg gcaaccacaa    300
gattttctac ccgacccggc ctccgaggga tttatggatc aagtcaagga gttgagggaa    360
agaaccaaag aaatcccgga tgagtaccct gtggtgttgg ttggcgatat gatcactgaa    420
gaagctcttc cgacctacca gacgatgcta aacacgctcg atggagtacg tgatgagacg    480
```

```
ggtgccagcc ttacttcttg ggctatctgg acccgggcat ggaccgctga agagaatagg      540
cacggtgatc ttttgaacaa gtatctttac cttactggtc gagttgacat gaagcagata      600
gagaagacaa tccagtatct aatcggatct ggaatggacc ctcgaagtga aacaaccccc      660
tatctaggct tcatctacac ttccttccaa gagagagcaa ccttcatctc ccatggaaac      720
accgctaggc tcgccaaaga ccacggcgac tttcaactag cacaagtatg tggcatcatc      780
gctgcagatg agaagcgcca cgaaactgcc tacacaaaaa ttgtcgaaaa gctctttgaa      840
atcgacccag acggcgctgt tctagcacta gctgacatga tgagaaagaa ggtttccatg      900
ccagcccact taatgtatga tggcaaagat gacaatctct ttgagaacta ctcagccgtc      960
gctcaacaaa ttggagttta caccgcgaag gactacgctg acatcctcga cacctcgtt     1020 aatcgctgga agtcgagaa tttaatgggt ctgtctggcg agggacataa ggctcaagat     1080
ttcgtatgtg ggttggcccc gaggatcagg aaactcgggg agagagctca gtcgctaagc     1140
aaaccggtat ctcttgtccc cttcagctgg attttcaaca aggaattgaa ggtt           1194
```

```
<210> SEQ ID NO 42
<211> LENGTH: 2077
<212> TYPE: DNA
<213> ORGANISM: Artificial
<220> FEATURE:
<223> OTHER INFORMATION: FATB-2 cDNA Contig

<400> SEQUENCE: 42
```

```
gagggaaaca aggaagcgaa atgacacaat agtccttctt ccctgtttcc actttccagg       60
ttttctcctt ctcgtttgtt gagcgctttt ctctccctct ccctcttctt cactcagtca      120
gctgccgtag aaattcatta tggtggcaac agctgcaact tcatcatttt tccctgttac      180
ttcaccctcg ccggactctg gtggacatgc aaagttactc aaaataatcg ctggccctat      240
cacattattg ttaatattct tcccttcttt accttctact ttccgaatcc agaaaacacc      300
acaacaccac ccagaattgt tgggttccat tctcaaaaca gagaacaaga agaagaagaa      360
agagagagag tgaaaacggg aaaagcaaaa agttgtttct gtgattgatt ctctgcaacc      420
gaatcatcat cagccacttc ttcccgtttc atctctccca tttcttcttt tcttccgctc      480
tggttcagta aggcgaagag ggttaacgtt attcataatg gttgcaacag ccgctacggc      540
gtcgtttctt cccgtgcctt tgccagacgc tggaaaaggg aaaccaaga aactgggtgg      600 tggtggcggt ggcggtggcg gttctgtgaa cctcggagga ctcaaacaga aacaaggttt      660
gtgcggtggc ttgcaggtca aggcaaacgc acaagccct ccgaagaccg tggagaaggt      720
tgagaatgat ttgtcgtcgt cgtcctcgtc gatttcgcac gccccgagga ctttcatcaa      780
ccagttacct gactggagca tgcttctggc cgccatcacc accgtgttcc tggcggcgga      840
gaagcagtgg atgatgctgg attggaagcc gcggcgcccc gacatgctca ttgacccctt      900
tgggattggg aagatcgtgc aggatgggct tgtgttcagg cagaacttcc ccattaggtc      960
ctatgagatt ggcgccgata aaccgcgtc tatcgagact ttaatgaatc atttgcagga     1020
gactgcactt aatcatgtta agactgctgg gcttcttggt gatggatttg gttccacgcc     1080
tgaaatgtgc aaaagaacc tgatatgggt ggtgactaag atgcaggttg tggttgataa     1140
atatcccaca tggggtgatg ttgttcaagt agacacttgg gtatctgcat caggaagaa      1200 tggtatgtgt cgtgattggc ttgtgcgtga cgcgaaatct ggtgaaatct tgacaagagc     1260
ctccagtgtt tgggtcatga tgaataaagt gacaagaaga ctgtctaaaa ttcccgaaga     1320
```

| | |
|---|---|
| agtcagggca gagataagct cttatttttgt ggactctgct ccagttgtgc cagaggataa | 1380 |
| cagaaaacta accaaacttg atgaatccgc taatttcatt cgcactggtt taagtcccag | 1440 |
| atggaatgat ctagatgtga atcagcatgt taacaatgtg aagtatgttg ggtggattct | 1500 |
| ggagagtgct ccacagccac ttttggagag ccatgagctg tgtgccatga cattggagta | 1560 |
| caggagggag tgtggcagga acagtgtgct ggattccctc tctgatctct ctggtgctga | 1620 |
| tgtaggaaac ttggcagatg gtggattttt tgagtgcaag cacttgcttc gacttgatga | 1680 |
| tggtgctgag attgtgaggg gtaggactca atggaggccc aaacctttaa gcagcaactt | 1740 |
| tggtcatgtt ttgagtcagg ttccagttcc agcagaaagc acctgaatct tatcttattg | 1800 |
| attggcatca ctggaggagg agtggcataa attcatagag agctttgctt gttttttatca | 1860 |
| aatctacgta tcttaaaata tatataaaag aaagtgtgtt actttggcta aaaaagggga | 1920 |
| ggggaagtag aaagtaaaaa aaaaaaaaaa aatctcgctc tcatgatttt gtaattaaaa | 1980 |
| aatagctcct agcactactt tctcctacct gctccatttt ctgtttcact tatggttatg | 2040 |
| ctgctgcttg gtgtcatcaa tatttaattg tttcatc | 2077 |

<210> SEQ ID NO 43
<211> LENGTH: 4634
<212> TYPE: DNA
<213> ORGANISM: Glycine max

<400> SEQUENCE: 43

| | |
|---|---|
| ggaaacaagg aagcgaaatg acacaatagt ccttcttccc tgtttccact ttccaggttt | 60 |
| tctccttctc gtttgttgag cgcttttctc tccctctccc tcttcttcac tcagtcaggt | 120 |
| acgctaacaa atctgctatt caatcaattc ctctttctct ctgatctacg tacgtgtccg | 180 |
| caaactgcac ctccactctc cactcattcc atctaatctt cccttttcgc ttcagagatc | 240 |
| caactcctca tataattcaa gacaaaatcc cgcgttttct gcatttctag acgttctacc | 300 |
| ctacaaggtt ctcgattctt cttttttctt tttttttaga ctattattat tttaaaaaaa | 360 |
| taaaaataat aatgagagct ggatgcgtct gttcgttgtg aatttcgagg caatggggtt | 420 |
| ctgattttcg ttacagattg cattgtttgc tttcctcctc tccgtttttt ctttgccttg | 480 |
| ttttttatttt taattttggg gatgtttttcg gtcttgcctt tgtttctgca ttttttttttc | 540 |
| ggtttgcgat gttttcagat ctgcgctggc ttatacgacg aatttgttct tattcgtgac | 600 |
| tttccgcttg attgacctgt tttacctctg gaatctcaca cgtgatcaaa taaggctgct | 660 |
| attttagttg aagtagaatc tatacacact ttgtagcatt cttttttacga tcacttacac | 720 |
| gggtggtttt taatcaggct tttttttgtgg gggtataaac atcttcctcc tcgattcttt | 780 |
| ccgataaaag cttaattgga ttataggaag tgggaaacaa tgcgtgggag ctctttggtt | 840 |
| tgttttttcgt aggttaaact tgcaggttta agttctgaat caggagttcc aaatatagag | 900 |
| gctgggggca taaaaaaaga gaattctatg gatctgttct gaaattggag ccactgtttc | 960 |
| gagttgctat tttttttacta gtattaataa gaacaagttt gctttttatt ttacattttt | 1020 |
| tcccgtttct tttgccaaaa gtatttatga tcactctctt ctgtttgtga tattacttat | 1080 |
| aagtgctgtg ctgtaattat ttgttatttg gggtgaagta taattttttgg gtgaacttgg | 1140 |
| agcgttttta gttagattga tttctcgata tcatttaagg tttaggttga ccccttccac | 1200 |
| tcgtttgtgg ttgattgttt tttttttttt atctcttatc atttacagtg cttctttgcc | 1260 |
| tattttttttc attatcccct ttcgtgaaag gtaggagaag aaaaacaatg acttgcgtaa | 1320 |
| attttgcatg cagctgccgt agaaattcat tatggtggca acagctgcaa cttcatcatt | 1380 |

-continued

```
tttccctgtt acttcaccct cgccggactc tggtggacat gcaaagttac tcaaaataat    1440
cgctggccct atcacattat tgttaatatt cttcccttct ttaccttcta ctttccgaat    1500
ccagaaaaca ccacaacacc acccagaatt gttgggttcc attctcaaaa cagagaacaa    1560
gaagaagaag aaagagagag agtgaaaacg ggaaaagcaa aaagttgttt ctgtgattga    1620
ttctctgcaa ccgaatcatc atcagccact tcttcccgtt tcatctctcc catttcttct    1680
tttcttccgc tctggttcag taaggcgaag agggttaacg ttattcataa tggttgcaac    1740
agccgctacg gcgtcgtttc ttcccgtgcc tttgccagac gctggaaaag gaaacccaa    1800 gaaactgggt ggtggtggcg gtggcggtgg cggttctgtg aacctcggag gactcaaaca    1860
gaaacaaggt ttgtgcggtg gcttgcaggt caaggcaaac gcacaagccc ctccgaagac    1920
cgtggagaag gttgagaatg atttgtcgtc gtcgtcctcg tcgatttcgc acgcccgag    1980 gactttcatc aaccagttac ctgactggag catgcttctg gccgccatca ccaccgtgtt    2040
cctggcggcg gagaagcagt ggatgatgct ggattggaag ccgcggcgcc ccgacatgct    2100
cattgacccc tttgggattg ggaagatcgt gcaggatggg cttgtgttca ggcagaactt    2160
ccccattagg tcctatgaga ttggcgccga taaaaccgcg tctatcgaga ctttaatgaa    2220
tcatttgcag gtcagctttt gcaaaaaatt gctgagaatt gcattcagca atcacgataa    2280
atataacttt taataaatta ttatagaagt taagtaactt atcacgggtt gtcaacaaaa    2340
atttagagaa taattgcata ggacaaaact tacctacagt tcgtttgaca ttttttgtgt    2400 cgttttaaa tcaaaattaa aattttatct tggtaatttg cagattatta gatacaactc    2460
caatttcgat caaagaacaa tgccaaaaac acctatggaa tctaagtttt gtgcaattgc    2520
ttattgatga ttttattta ttgcctaaat tgtctgtttt ccaaacagga gactgcactt    2580
aatcatgtta agactgctgg gcttcttagt gatggatttg gttccacgct gaaatgtgca    2640
aaaagaacct gatatgggtg gtgactaaga tgcaggttgt ggttgataaa tatcccacat    2700
ggtaagttgg tgtgactaag aagaaccttt ttgatgtgtg aagaattgca aaggcgtcca    2760
tgctcagctg tgaaatcttc ttttgcctta ctcatcttta ctttgacttt atatagtatc    2820
tggttgaatt attttgtact tctgcatttg tttctgtcac ttgtgctttt ttgtttcaca    2880
aaattggtat gatagttagg aacttgggat taaaggcatg tttggaatat attgtgattg    2940
tgaattattt ttaaaaatat tttcactttt caaaatctat ctcatgaatc tgtaaaaata    3000
agaataaaaa ataaaactac tgtaatgtgt ataaaaaatt cttcttggat ggtaattgat    3060
ctgataagca catgcttttt acataatgaa ttatatgaag tcctttgcct taagtctgtt    3120
agactgggta tgagatatgg tagtaaattc ttttacatt ccgtacattt ttttgcatat    3180
ttctgtctta ttattgtaaa atgttggatg catatacagg ttttcaaaag aagcaactta    3240
taccatgtgc ccttttctgc attttggtct gttcgagaat aatctcttta gtaaattctg    3300
aatctgttca tctgaagttg agtgaatcta tatttgcttc aggggtgatg ttgttcaagt    3360
agacacttgg gtatctgcat cagggaagaa tggtatgtgt cgtgattggc ttgtgcgtga    3420
cgccaaatct ggtgaaatct tgacaagagc ctccaggtag atatcagttt caggaatcct    3480
ttttttctgt tgcctataga catgttttga agagttttc tgaatctgaa tgtttctctc    3540
tggtgatttg gcactgcttt taatctcacg aggctgtgtg aagttatcta ttatcatatt    3600
tactttctct taatacacca ctattgaaag gcaattcatt acagatttaa gcatacaaaa    3660
ttttgttgat gataattttt taatctacca acagtatcta atatcttctt aatttgttat    3720
```

| | |
|---|---:|
| taagtaccag ccttcaactt gtgtacatgt tgcaccttgg tgctacgaac ttataagcat | 3780 |
| tttctgattg gttgagtttg attttgattt tgatgttatg cagtgtttgg gtcatgatga | 3840 |
| ataaagtgac aagaagactg tctaaaattc ccgaagaagt cagggcagag ataagctctt | 3900 |
| attttgtgga ttctgctcca gttgtgccag aggataacag aaaactaacc aaacttgatg | 3960 |
| attcagctaa tttcattcgc actggtttaa gtcccagatg gaatgatcta gatgtgaatc | 4020 |
| agcatgttaa caatgtgaag tatgttgggt ggattctgga gagtgctcca cagccacttt | 4080 |
| tggagagcca tgagctgtgt gccatgacat tggagtacag gagggagtgt ggcaggaaca | 4140 |
| gtgtgctgga ttccctctct gatctctctg gtgctgatgt aggaaacttg gcagatggtg | 4200 |
| gattttttga gtgcaagcac ttgcttcgac ttgatgatgg tgctgagatt gtgaggggta | 4260 |
| ggactcaatg gaggcccaaa cctttaagca gcaactttgg tcatgttttg agtcaggttc | 4320 |
| cagttccagc agaaagcacc tgaatcttat cttattgatt ggcatcactg gaggaggagt | 4380 |
| ggcataaatt catagagagc tttgcttgtt tttatcaaat ctacgtatct taaaatatat | 4440 |
| ataaagaaa gtgtgttact ttggctaaaa aaggggaggg gaagtagaaa gtaaaaaaaa | 4500 |
| aaaaaaaaat ctcgctctca tgattttgta attaaaaaat agctcctagc actactttct | 4560 |
| cctacctgct ccatttttctg tttcacttat ggttatgctg ctgcttggtg tcatcaatat | 4620 |
| ttaattgttt catc | 4634 |

<210> SEQ ID NO 44
<211> LENGTH: 1215
<212> TYPE: DNA
<213> ORGANISM: Glycine max

<400> SEQUENCE: 44

| | |
|---|---:|
| gtacgctaac aaatctgcta ttcaatcaat tcctctttct ctctgatcta cgtacgtgtc | 60 |
| cgcaaactgc acctccactc tccactcatt ccatctaatc ttcccttttc gcttcagaga | 120 |
| tccaactcct catataattc aagacaaaat cccgcgtttt ctgcatttct agacgttcta | 180 |
| ccctacaagg ttctcgattc ttcttttttc ttttttttta gactattatt attttaaaaa | 240 |
| aataaaaata ataatgagag ctggatgcgt ctgttcgttg tgaatttcga ggcaatgggg | 300 |
| ttctgatttt cgttacagat tgcattgttt gctttcctcc tctccgtttt ttctttgcct | 360 |
| tgttttattt tttaattttg gggatgtttt cggtcttgcc tttgtttctg cattttttttt | 420 |
| tcggtttgcg atgttttcag atctgcgctg gcttatacga cgaatttgtt cttattcgtg | 480 |
| actttccgct tgattgacct gttttacctc tggaatctca cacgtgatca ataaggctg | 540 |
| ctattttagt tgaagtagaa tctatacaca ctttgtagca ttcttttttac gatcacttac | 600 |
| acgggtggtt tttaatcagg cttttttttgt ggggtataa acatcttcct cctcgattct | 660 |
| ttccgataaa agcttaattg gattatagga agtgggaaac aatgcgtggg agctctttgg | 720 |
| tttgtttttc gtaggttaaa cttgcaggtt taagttctga atcaggagtt ccaaatatag | 780 |
| aggctggggg cataaaaaaa gagaattcta tggatctgtt ctgaaattgg agccactgtt | 840 |
| tcgagttgct atttttttac tagtattaat aagaacaagt ttgcttttta ttttacattt | 900 |
| tttcccgttt cttttgccaa agtatttat gatcactctc ttctgtttgt gatattactt | 960 |
| ataagtgctg tgctgtaatt atttgttatt tggggtgaag tataattttt gggtgaactt | 1020 |
| ggagcgtttt tagttagatt gatttctcga tatcatttaa ggtttaggtt gacccccttcc | 1080 |
| actcgtttgt ggttgattgt tttttttttt ttatctctta tcatttacag tgcttctttg | 1140 |
| cctatttttt tcattatccc ctttcgtgaa aggtaggaga agaaaaacaa tgacttgcgt | 1200 |

```
aaattttgca tgcag                                                    1215
```

<210> SEQ ID NO 45
<211> LENGTH: 338
<212> TYPE: DNA
<213> ORGANISM: Glycine max

<400> SEQUENCE: 45

```
gtcagctttt gcaaaaaatt gctgagaatt gcattcagca atcacgataa atataacttt    60
taataaatta ttatagaagt taagtaactt atcacgggtt gtcaacaaaa atttagagaa   120
taattgcata ggacaaaact tacctacagt tcgtttgaca tttttttgtgt cgttttttaaa  180
tcaaaattaa aatttatct tggtaatttg cagattatta gatacaactc caatttcgat   240
caaagaacaa tgccaaaaac acctatggaa tctaagtttt gtgcaattgc ttattgatga   300
ttttatttta ttgcctaaat tgtctgtttt ccaaacag                           338
```

<210> SEQ ID NO 46
<211> LENGTH: 641
<212> TYPE: DNA
<213> ORGANISM: Glycine max

<400> SEQUENCE: 46

```
gtaagttggt gtgactaaga agaacctttt tgatgtgtga agaattgcaa aggcgtccat    60
gctcagctgt gaaatcttct tttgccttac tcatctttac tttgacttta tatagtatct   120
ggttgaatta ttttgtactt ctgcatttgt ttctgtcact tgtgctttt tgtttcacaa   180
aattggtatg atagttagga acttgggatt aaaggcatgt ttggaatata ttgtgattgt   240
gaattatttt taaaaatatt ttcacttttc aaaatctatc tcatgaatct gtaaaaataa   300
gaataaaaaa taaaactact gtaatgtgta taaaaaattc ttcttggatg gtaattgatc   360
tgataagcac atgcttttta cataatgaat tatatgaagt cctttgcctt aagtctgtta   420
gactgggtat gagatatggt agtaaattct ttttacattc cgtacatttt tttgcatatt   480
tctgtcttat tattgtaaaa tgttggatgc atatacaggt tttcaaaaga agcaacttat   540
accatgtgcc cttttctgca tttttggtctg ttcgagaata atctctttag taaattctga   600
atctgttcat ctgaagttga gtgaatctat atttgcttca g                       641
```

<210> SEQ ID NO 47
<211> LENGTH: 367
<212> TYPE: DNA
<213> ORGANISM: Glycine max

<400> SEQUENCE: 47

```
gtagatatca gtttcaggaa tcctttttt ctgttgccta tagacatgtt ttgaagagtt     60
tttctgaatc tgaatgtttc tctctggtga tttggcactg cttttaatct cacgaggctg   120
tgtgaagtta tctattatca tatttacttt ctccttaatac accactattg aaaggcaatt   180
cattacagat ttaagcatac aaaattttgt tgatgataat ttttaatcct accaacagta   240
tctaatatct tcttaattg ttattaagta ccagccttca acttgtgtac atgttgcacc   300
ttggtgctac gaacttataa gcattttctg attggttgag tttgattttg attttgatgt   360
tatgcag                                                             367
```

<210> SEQ ID NO 48
<211> LENGTH: 18
<212> TYPE: DNA

```
<213> ORGANISM: Artificial sequence
<220> FEATURE:
<223> OTHER INFORMATION: PCR primer

<400> SEQUENCE: 48
ctgtttccac tttccagg                                                  18

<210> SEQ ID NO 49
<211> LENGTH: 17
<212> TYPE: DNA
<213> ORGANISM: Artificial sequence
<220> FEATURE:
<223> OTHER INFORMATION: PCR primer

<400> SEQUENCE: 49
cttctcgttt gttgagc                                                   17

<210> SEQ ID NO 50
<211> LENGTH: 16
<212> TYPE: DNA
<213> ORGANISM: Artificial sequence
<220> FEATURE:
<223> OTHER INFORMATION: PCR primer

<400> SEQUENCE: 50
cagctgcaac ttcatc                                                    16

<210> SEQ ID NO 51
<211> LENGTH: 16
<212> TYPE: DNA
<213> ORGANISM: Artificial sequence
<220> FEATURE:
<223> OTHER INFORMATION: PCR primer

<400> SEQUENCE: 51
cttccccatt aggtcc                                                    16

<210> SEQ ID NO 52
<211> LENGTH: 18
<212> TYPE: DNA
<213> ORGANISM: Artificial sequence
<220> FEATURE:
<223> OTHER INFORMATION: PCR primer

<400> SEQUENCE: 52
cacttaatca tgttaaga                                                  18

<210> SEQ ID NO 53
<211> LENGTH: 17
<212> TYPE: DNA
<213> ORGANISM: Artificial sequence
<220> FEATURE:
<223> OTHER INFORMATION: PCR primer

<400> SEQUENCE: 53
gtcgtgattg gcttgtg                                                   17

<210> SEQ ID NO 54
<211> LENGTH: 17
<212> TYPE: DNA
<213> ORGANISM: Artificial sequence
<220> FEATURE:
<223> OTHER INFORMATION: PCR primer

<400> SEQUENCE: 54
ctctgctcca gttgtgc                                                   17
```

-continued

<210> SEQ ID NO 55
<211> LENGTH: 18
<212> TYPE: DNA
<213> ORGANISM: Artificial sequence
<220> FEATURE:
<223> OTHER INFORMATION: PCR primer

<400> SEQUENCE: 55
gcgagggtga agtaacag                                                 18

<210> SEQ ID NO 56
<211> LENGTH: 18
<212> TYPE: DNA
<213> ORGANISM: Artificial sequence
<220> FEATURE:
<223> OTHER INFORMATION: PCR primer

<400> SEQUENCE: 56
gcacaaacct tgtttctg                                                 18

<210> SEQ ID NO 57
<211> LENGTH: 17
<212> TYPE: DNA
<213> ORGANISM: Artificial sequence
<220> FEATURE:
<223> OTHER INFORMATION: PCR primer

<400> SEQUENCE: 57
caagaagccc agcagtc                                                  17

<210> SEQ ID NO 58
<211> LENGTH: 17
<212> TYPE: DNA
<213> ORGANISM: Artificial sequence
<220> FEATURE:
<223> OTHER INFORMATION: PCR primer

<400> SEQUENCE: 58
gatttcacca gatttcg                                                  17

<210> SEQ ID NO 59
<211> LENGTH: 17
<212> TYPE: DNA
<213> ORGANISM: Artificial sequence
<220> FEATURE:
<223> OTHER INFORMATION: PCR primer

<400> SEQUENCE: 59
gtgcgaatga aattagc                                                  17

<210> SEQ ID NO 60
<211> LENGTH: 17
<212> TYPE: DNA
<213> ORGANISM: Artificial sequence
<220> FEATURE:
<223> OTHER INFORMATION: PCR primer

<400> SEQUENCE: 60
ctttctgctg gaactgg                                                  17

<210> SEQ ID NO 61
<211> LENGTH: 97
<212> TYPE: DNA
<213> ORGANISM: Glycine max

```
<400> SEQUENCE: 61
aaaagatttc attcttcctc ttctaggtta ttacgcacca cccaccacgt atccctgaaa        60
agagagaaaa acacactaag ccaaagccaa agcagca                                97

<210> SEQ ID NO 62
<211> LENGTH: 159
<212> TYPE: DNA
<213> ORGANISM: Glycine max

<400> SEQUENCE: 62
gttatttatt ggattctagc tactcaaatt acttttttt taatgttacg tttttggagt        60
tttaacgttt tctgaacaac ttgcaaatta catgcataga gagacaggaa ttcatagtgg      120
gcctcaatgg aatatttatt tgaaattagt aaggtggta                            159
```

US 10,280,430 B2

NUCLEIC ACID CONSTRUCTS AND METHODS FOR PRODUCING ALTERED SEED OIL COMPOSITIONS

CROSS-REFERENCE TO RELATED APPLICATIONS

This application is a divisional application of U.S. application Ser. No. 12/320,043, filed Jan. 15, 2009, now U.S. Pat. No. 8,802,922, issued Aug. 12, 2014, which is a continuation of U.S. application Ser. No. 11/376,328, filed Mar. 16, 2006, now U.S. Pat. No. 7,566,813, issued Jul. 8, 2009, which is a continuation-in-part of U.S. application Ser. No. 10/669,888 filed Sep. 25, 2003, now abandoned; Ser. No. 10/668,240 filed on Sep. 24, 2003, now U.S. Pat. No. 7,166,771, issued Jan. 23, 2007; Ser. No. 10/393,347 filed Mar. 21, 2003, now U.S. Pat. No. 7,601,888, issued Oct. 13, 2009; Ser. No. 10/508,401 filed Mar. 25, 2005, now abandoned; and claims the benefit under 35 U.S.C. § 119(e) of U.S. Provisional Application Nos. 60/772,614, filed Feb. 13, 2006, and 60/781,519, filed Mar. 10, 2006. U.S. application Ser. No. 10/669,888, filed Sep. 25, 2003, now abandoned, is a continuation-in-part of U.S. application Ser. No. 10/393,347 filed Mar. 21, 2003, now U.S. Pat. No. 7,601,888, issued Oct. 13, 2009, which application claims the benefit under 35 U.S.C. § 119(e) of U.S. Provisional Application Nos. 60/365,794, filed Mar. 21, 2002, and 60/390,185, filed Jun. 21, 2002. U.S. application Ser. No. 10/668,240, filed on Sep. 24, 2003, now U.S. Pat. No. 7,166,771 issued Jan. 23, 2007, is a continuation-in-part of U.S. application Ser. No. 10/393, 347, filed Mar. 21, 2003, now U.S. Pat. No. 7,601,888, issued Oct. 13, 2009, which application claims the benefit under 35 U.S.C. § 119(e) of U.S. Provisional Application Nos. 60/365,794, filed Mar. 21, 2002, and 60/390,185, filed Jun. 21, 2002. U.S. application Ser. No. 10/508,401, filed Mar. 25, 2005, now abandoned, is a national phase continuation of PCT/US03/08610, filed Mar. 21, 2003, which claims the benefit of U.S. Provisional Application Nos. 60/365,794, filed Mar. 21, 2002, and 60/390,185, filed Jun. 21, 2002. The entirety of each of these applications is hereby incorporated by reference.

INCORPORATION OF SEQUENCE LISTING

A copy of the Sequence Listing in computer readable form of the sequence listing, containing the file named "SequenceListing.txt", which is 61,619 bytes in size (measured in Windows-XP) and which was recorded on Jun. 25, 2014, is herein incorporated by reference.

FIELD OF THE INVENTION

The present invention is directed to recombinant nucleic acid molecules, constructs, and other agents associated with the coordinate manipulation of multiple genes in the fatty acid synthesis pathway. In particular, the agents of the present invention are associated with the simultaneous enhanced expression of certain genes in the fatty acid synthesis pathway and suppressed expression of certain other genes in the same pathway. The present invention is also directed to plants incorporating such agents, and in particular to plants incorporating such constructs where the plants exhibit altered seed oil compositions.

BACKGROUND

Plant oils are used in a variety of applications. Novel vegetable oil compositions and improved approaches to obtain oil compositions, from biosynthetic or natural plant sources, are needed. Depending upon the intended oil use, various different fatty acid compositions are desired. Plants, especially species which synthesize large amounts of oils in seeds, are an important source of oils both for edible and industrial uses. Seed oils are composed almost entirely of triacylglycerols in which fatty acids are esterified to the three hydroxyl groups of glycerol.

Soybean oil typically contains about 16-20% saturated fatty acids: 13-16% palmitate and 3-4% stearate. See generally Gunstone et al., *The Lipid Handbook*, Chapman & Hall, London (1994). Soybean oils have been modified by various breeding methods to create benefits for specific markets. However, a soybean oil that is broadly beneficial to major soybean oil users such as consumers of salad oil, cooking oil and frying oil, and industrial markets such as biodiesel and biolube markets, is not available. Prior soybean oils were either too expensive or lacked an important food quality property such as oxidative stability, good fried food flavor or saturated fat content, or an important biodiesel property such as appropriate nitric oxide emissions or cold tolerance or cold flow.

Higher plants synthesize fatty acids via a common metabolic pathway—the fatty acid synthetase (FAS) pathway, which is located in the plastids. β-ketoacyl-ACP synthases are important rate-limiting enzymes in the FAS of plant cells and exist in several versions. β-ketoacyl-ACP synthase I catalyzes chain elongation to palmitoyl-ACP (C16:0), whereas β-ketoacyl-ACP synthase II catalyzes chain elongation to stearoyl-ACP (C18:0). β-ketoacyl-ACP synthase IV is a variant of β-ketoacyl-ACP synthase II, and can also catalyze chain elongation to 18:0-ACP. In soybean, the major products of FAS are 16:0-ACP and 18:0-ACP. The desaturation of 18:0-ACP to form 18:1-ACP is catalyzed by a plastid-localized soluble delta-9 desaturase (also referred to as "stearoyl-ACP desaturase"). See Voelker et al., 52 *Annu. Rev. Plant Physiol. Plant Mol. Biol.* 335-61 (2001).

The products of the plastidial FAS and delta-9 desaturase, 16:0-ACP, 18:0-ACP, and 18:1-ACP, are hydrolyzed by specific thioesterases (FAT). Plant thioesterases can be classified into two gene families based on sequence homology and substrate preference. The first family, FATA, includes long chain acyl-ACP thioesterases having activity primarily on 18:1-ACP. Enzymes of the second family, FATB, commonly utilize 16:0-ACP (palmitoyl-ACP), 18:0-ACP (stearoyl-ACP), and 18:1-ACP (oleoyl-ACP). Such thioesterases have an important role in determining chain length during de novo fatty acid biosynthesis in plants, and thus these enzymes are useful in the provision of various modifications of fatty acyl compositions, particularly with respect to the relative proportions of various fatty acyl groups that are present in seed storage oils.

The products of the FATA and FATB reactions, the free fatty acids, leave the plastids and are converted to their respective acyl-CoA esters. Acyl-CoAs are substrates for the lipid-biosynthesis pathway (Kennedy Pathway), which is located in the endoplasmic reticulum (ER). This pathway is responsible for membrane lipid formation as well as the biosynthesis of triacylglycerols, which constitute the seed oil. In the ER there are additional membrane-bound desaturases, which can further desaturate 18:1 to polyunsaturated fatty acids. A delta-12 desaturase (FAD2) catalyzes the insertion of a double bond into 18:1, forming linoleic acid (18:2). A delta-15 desaturase (FAD3) catalyzes the insertion of a double bond into 18:2, forming linolenic acid (18:3).

Many complex biochemical pathways have now been manipulated genetically, usually by suppression or over-expression of single genes. Further exploitation of the potential for plant genetic manipulation will require the coordinate manipulation of multiple genes in a pathway. A number of approaches have been used to combine transgenes in one plant—including sexual crossing, retransformation, co-transformation, and the use of linked transgenes. A chimeric transgene with linked partial gene sequences can be used to coordinately suppress numerous plant endogenous genes. Constructs modeled on viral polyproteins can be used to simultaneously introduce multiple coding genes into plant cells. For a review, see Halpin et al., *Plant Mol. Biol.* 47:295-310 (2001).

Thus, a desired plant phenotype may require the expression of one or more genes and the concurrent reduction of expression of another gene or genes. Thus, there exists a need to simultaneously over-express one or more genes and suppress, or down-regulate, the expression of a another gene or genes in plants using a single transgenic construct.

SUMMARY OF THE INVENTION

The present invention provides a recombinant nucleic acid molecule or molecules, which when introduced into a cell or organism are capable of suppressing, at least partially reducing, reducing, substantially reducing, or effectively eliminating the expression of at least one or more endogenous FAD2, FAD3, or FATB RNAs while at the same time coexpressing, simultaneously expressing, or coordinately producing one or more RNAs or proteins transcribed from a gene encoding beta-ketoacyl-ACP synthase I, beta-ketoacyl-ACP synthase IV, delta-9 desaturase, or CP4 EPSPS. The present invention also provides plant cells and plants transformed with the same nucleic acid molecule or molecules, and seeds, oil, and other products produced from the transformed plants.

Also provided by the present invention is a recombinant nucleic acid molecule comprising a first set of DNA sequences that is capable, when expressed in a host cell, of suppressing the endogenous expression of at least one, preferably two, genes selected from the group consisting of FAD2, FAD3, and FATB genes; and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, a delta-9 desaturase gene, and CP4 EPSPS.

Further provided by the present invention is a recombinant nucleic acid molecule comprising a first set of DNA sequences that is capable, when expressed in a host cell, of forming a dsRNA construct and suppressing the endogenous expression of at least one, preferably two, genes selected from the group consisting of FAD2, FAD3, and FATB genes, where the first set of DNA sequences comprises a first non-coding sequence that expresses a first RNA sequence that exhibits at least 90% identity to a non-coding region of a FAD2 gene, a first antisense sequence that expresses a first antisense RNA sequence capable of forming a double-stranded RNA molecule with the first RNA sequence, a second non-coding sequence that expresses a second RNA sequence that exhibits at least 90% identity to a non-coding region of a FATB gene, and a second antisense sequence that expresses a second antisense RNA sequence capable of forming a double-stranded RNA molecule with the second RNA sequence; and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, a delta-9 desaturase gene, and CP4 EPSPS.

The present invention provides methods of transforming plants with these recombinant nucleic acid molecules. The methods include a method of producing a transformed plant having seed with an increased oleic acid content, reduced saturated fatty acid content, and reduced polyunsaturated fatty acid content, comprising (A) transforming a plant cell with a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, a delta-9 desaturase gene, and CP4 EPSPS; and (B) growing the transformed plant, where the transformed plant produces seed with an increased oleic acid content, reduced saturated fatty acid content, and reduced polyunsaturated fatty acid content relative to seed from a plant having a similar genetic background but lacking the recombinant nucleic acid molecule.

Further provided are methods of transforming plant cells with the recombinant nucleic acid molecules. The methods include a method of altering the oil composition of a plant cell comprising (A) transforming a plant cell with a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, a delta-9 desaturase gene, and CP4 EPSPS; and (B) growing the plant cell under conditions where transcription of the first set of DNA sequences and the second set of DNA sequences is initiated, where the oil composition is altered relative to a plant cell with a similar genetic background but lacking the recombinant nucleic acid molecule.

The present invention also provides a transformed plant comprising a recombinant nucleic acid molecule which comprises a first set of DNA sequences that is capable, when expressed in a host cell, of suppressing the endogenous expression of at least one, preferably two, genes selected from the group consisting of FAD2, FAD3, and FATB genes, and a second set of DNA sequences that is capable, when expressed in a host cell, of increasing the endogenous expression of at least one gene selected from the group consisting of a beta-ketoacyl-ACP synthase I gene, a beta-ketoacyl-ACP synthase IV gene, a delta-9 desaturase gene, and CP4 EPSPS. Further provided by the present invention is a transformed soybean plant bearing seed, where the seed exhibits an oil composition which comprises 55 to 80% by weight oleic acid, 10 to 40% by weight linoleic acid, 6% or less by weight linolenic acid, and 2 to 8% by weight saturated fatty acids, and feedstock, plant parts, and seed derived from the plant. In another embodiment, the present invention provides a transformed soybean plant bearing seed, where the seed exhibits an oil composition which comprises about 65-80% oleic acid, about 3-8% saturates, and about 12-32% polyunsaturates. Also included is feedstock, plant parts, and seed derived from such plant. In another embodiment, the present invention provides a transformed soybean plant bearing seed, where the seed exhibits an oil composition which comprises about 65-80% oleic acid, about 2-3.5% saturates, and about 16.5-33% polyunsaturates. Also included is feedstock, plant parts, and seed derived from such plant.

The present invention provides a soybean seed exhibiting an oil composition comprising 55 to 80% by weight oleic acid, 10 to 40% by weight linoleic acid, 6% or less by weight linolenic acid, and 2 to 8% by weight saturated fatty acids, and also provides a soybean seed exhibiting an oil composition comprising 65 to 80% by weight oleic acid, 10 to 30% by weight linoleic acid, 6% or less by weight linolenic acid, and 2 to 8% by weight of saturated fatty acids. In another embodiment, the present invention provides a soybean seed exhibiting an oil composition comprising about 65-80% oleic acid, about 3-8% saturates, and about 12-32% polyunsaturates. In another embodiment, the present invention provides a soybean seed exhibiting an oil composition which comprises about 65-80% oleic acid, about 2-3.5% saturates, and about 16.5-33% polyunsaturates.

Also provided by the present invention are soyfoods comprising an oil composition which comprises 69 to 73% by weight oleic acid, 21 to 24% by weight linoleic acid, 0.5 to 3% by weight linolenic acid, and 2-3% by weight of saturated fatty acids.

The crude soybean oil provided by the present invention exhibits an oil composition comprising 55 to 80% by weight oleic acid, 10 to 40% by weight linoleic acid, 6% or less by weight linolenic acid, and 2 to 8% by weight saturated fatty acids. Another crude soybean oil provided by the present invention exhibits an oil composition comprising 65 to 80% by weight oleic acid, 10 to 30% by weight linoleic acid, 6% or less by weight linolenic acid, and 2 to 8% by weight of saturated fatty acids. In another embodiment, the crude soybean oil provided by the present invention exhibits an oil composition comprising about 65-80% oleic acid, about 3-8% saturates, and about 12-32% polyunsaturates. In another embodiment, the crude soybean oil provided by the present invention exhibits an oil composition comprising about 65-80% oleic acid, about 2-3.5% saturates, and about 16.5-33% polyunsaturates.

The present invention also provides a soybean seed exhibiting an oil composition comprising about 42% to about 85% by weight oleic acid and about 8% to about 1.5% by weight saturated fatty acids. In another embodiment, a soybean seed of the present invention exhibits an oil composition comprising about 42% to about 85% by weight oleic acid, about 8% to about 1.5% by weight saturated fatty acids, less than 35% by weight linolenic acid, wherein a combined amount of the oleic acid and the linolenic acid is about 65% to about 90% by weight of the total oil composition; and the seed has a recombinant nucleic acid molecule with a DNA sequence that has a fragment of FAD2-1 intron between about 50 and about 400 contiguous nucleotides in length, a FATB 3' UTR, and a FATB 5' UTR, a heterologous beta-ketoacyl-ACP synthase IV, and a heterologous delta-9 desaturase in a host cell.

A soybean seed of the present invention can exhibit an oil composition comprising about 50% to about 80% by weight oleic acid, about 8% to about 1.5% by weight saturated fatty acids, about 2% to about 45% by weight linoleic acid, about 4% to about 14% by weight linolenic acid, wherein a combined amount of the oleic acid and the linolenic acid is about 65% to about 90% by weight of the total oil composition, and the seed comprises recombinant nucleic acid molecule comprising a DNA sequence that comprises a fragment of FAD2-1 intron that is between about 50 and about 400 contiguous nucleotides in length, a FATB CTP coding region, and 42 contiguous nucleotides of a FATB 5' UTR. In another embodiment, a soybean seed can comprise a recombinant nucleic acid molecule comprising a DNA sequence that suppresses the endogenous expression of FAD2 and FATB, wherein the seed exhibits an oil composition comprising 46 to 75% by weight oleic acid, 1.5 to 8.5% by weight saturated fatty acids, 2.5 to 38% by weight linoleic acid, and 4.5 to 17.5% by weight linolenic acid.

The present invention also includes a method of reducing the amount of FAD2 gene suppression relative to the amount of FAD2 gene suppression obtained by expressing a dsRNAi construct having a recombinant FAD2 sequence consisting of an entire FAD2 intron or an entire FAD2 UTR by: i) expressing a recombinant FAD2 sequence in a plant cell, wherein the recombinant FAD2 sequence is derived from an endogenous FAD2 gene in a plant cell and the recombinant FAD2 sequence consists of a FAD2 intron fragment or a FAD2 UTR fragment; and ii) suppressing an endogenous FAD2 gene with the recombinant FAD2 sequence, wherein the amount of FAD2 gene suppression is less than the amount of gene expression obtained by expressing a dsRNAi construct having a recombinant FAD2 sequence consisting of the entire length of a FAD2 intron or the entire length of a FAD2 UTR.

Also provided by the present invention are methods of altering the oil composition of a plant cell by: transforming a plant cell with a recombinant FAD2 sequence derived from part of an endogenous FAD2 gene. The recombinant FAD2 sequence consists of a FAD2 intron fragment or a FAD2 UTR fragment; and growing the plant cell under conditions where transcription of the recombinant FAD2 sequence is initiated, whereby the oil composition is altered relative to a plant cell with a similar genetic background but lacking the recombinant FAD2 sequence. In another embodiment, a method of enhancing oleic acid content and reducing saturated fatty acid content in a plant seed by: i) shortening the length of a first recombinant FAD2 sequence until the amount of FAD2 gene suppression from a plant transformed with the first recombinant FAD2 sequence is at least partially reduced relative to the amount of FAD2 gene suppression in a plant cell comprising a similar genetic background and a second recombinant FAD2 sequence, where the second recombinant FAD2 sequence consists of more endogenous FAD2 sequence than the first recombinant FAD2 sequence; ii) expressing a recombinant FATB sequence capable of at least partially reducing FATB gene expression in a plant cell relative to the suppression of FATB in a plant cell with a similar genetic background but without the recombinant FATB sequence; iii) growing a plant with a recombinant nucleic acid molecule comprising the first recombinant FAD2 sequence and the recombinant FATB sequence; and iv) cultivating a plant that produces seed with a reduced saturated fatty acid content relative to seed from a plant having a similar genetic background but lacking the first recombinant FAD2 sequence and the recombinant FATB sequence.

In yet another embodiment, the present invention includes a method of producing a transformed plant having seed with a reduced saturated fatty acid content by: transforming a plant cell with a recombinant nucleic acid molecule which comprises a recombinant DNA sequence that suppresses the endogenous expression of FAD2 and FATB, where the recombinant DNA sequence has a nucleic acid sequence of recombinant FAD2 and recombinant FATB, wherein the FAD2 sequence consists of less than the entire sequence of a FAD2 intron; and growing the transformed plant, wherein the transformed plant produces seed with a reduced saturated fatty acid content relative to seed from a plant having a similar genetic background but lacking the recombinant DNA sequence.

In another embodiment, the present invention is directed to a method of modulating the fatty acid composition of oil from a seed of a temperate oilseed crop by isolating a genetic element of at least 40 nucleotides in length that is capable of suppressing the expression of an endogenous gene in the fatty acid synthesis pathway; generating more than one shortened fragment of the genetic element;
introducing each of the more than one shortened fragments into a plant cell of the temperate oilseed crop to produce transgenic plants; and selecting a transgenic plant comprising a shortened fragment of determined length and sequence that effects a desirable change in seed oil fatty acid composition.

The present invention also includes a soybean seed exhibiting an oil composition having a strongly reduced saturated fatty acid content and a moderately enhanced oleic acid content having a DNA sequence that suppresses endogenous expression of FAD2 in a plant cell, where the DNA sequence has a recombinant FAD2 sequence consisting of a FAD2 intron fragment. Another embodiment of the present invention is a nucleic acid molecule comprising a sequence of a FAD2-1A intron, where the FAD2-1A intron fragment is between about 60 to about 320 contiguous nucleotides. In an alternative embodiment, the present invention also includes a soybean seed having a first recombinant DNA sequence that suppresses the expression of endogenous soybean FAD2-1, comprising a soybean FAD2-1 intron, and a second recombinant DNA sequence that expresses increased levels of a gene selected from the group consisting of KASI, delta-9 desaturase, KASIV, and combinations thereof.

The present invention also includes a soybean plant cell of a soybean seed exhibiting a seed oil fatty acid composition comprising an oleic acid content of about 42% to about 85% by weight of the total fatty acids and a saturated fatty acid content of less than 8% by weight of the total fatty acids. Also included in the present invention is a soybean plant cell of a soybean seed exhibiting a seed oil fatty acid composition comprising an oleic acid content of about 42% to about 85% by weight of total fatty acids and a linolenic acid content of less than about 3% by weight of the total fatty acids.

The present invention also includes a nucleic acid molecule with a sequence of a FAD2-1A intron, where the FAD2-1A intron is between about 60 to about 320 contiguous nucleotides. Also included is a recombinant DNA construct comprising a fragment of soybean FAD2-1 intron that is between about 20 and about 420 contiguous nucleotides in length and a fragment of soybean FATB gene that is between about 40 and about 450 contiguous nucleotides in length. Another embodiment includes a recombinant nucleic acid molecule having a first DNA sequence that suppresses endogenous expression of soybean FAD2-1 and FATB, where the first recombinant DNA sequence includes a fragment of FAD2-1 intron that is between about 20 and about 420 contiguous nucleotides in length, a soybean FATB 3' UTR, and a soybean FATB 5' UTR or CTP coding area, and a second recombinant DNA sequence that increases the expression of at least one of the genes selected from the group consisting of beta-ketoacyl-ACP synthase IV and delta-9 desaturase.

The present invention also includes a non-blended soybean oil having a fatty acid composition comprising an oleic acid content of about 42% to about 85% by weight of the total fatty acids and a saturated fatty acid content of about 1.5% to about 8% by weight of the total fatty acids; a non-blended soybean oil having a fatty acid composition comprising an oleic acid content of from about 42% to about 85% by weight of the total fatty acids and a saturated fatty acid content of about 8% or less by weight of the total fatty acids; a non-blended soybean oil having a fatty acid composition comprising an oleic acid content of from about 42% to about 85% by weight of total fatty acids and a linolenic acid content of less than 3% by weight of the total fatty acids; and a non-blended soybean oil having a fatty acid composition comprising an oleic acid content of from about 42% to about 85% by weight of the total fatty acids, a saturated fatty acid content of about 8% or less by weight of the total fatty acids, and a linolenic acid content of about 1.5% or less by weight of the total fatty acids.

The present invention also includes a soybean meal derived from a soybean seed exhibiting a seed oil fatty acid composition comprising an oleic acid content of about 42% to about 85% by weight of the total fatty acids and a saturated fatty acid content of less than 8% by weight of the total fatty acids. Also included is a soybean meal derived from a soybean seed exhibiting a seed oil fatty acid composition comprising an oleic acid content of about 42% to about 85% by weight of total fatty acids and a linolenic acid content of less than about 3% by weight of the total fatty acids.

The present invention also includes a method of reducing the amount of FAD2 gene suppression relative to the amount of FAD2 gene suppression obtained by expressing a dsRNAi construct comprising a heterologous FAD2 sequence consisting of an entire FAD2 intron or an entire FAD2 UTR, the method by: i) expressing a heterologous FAD2 sequence in a plant cell, wherein the heterologous FAD2 sequence is derived from an endogenous FAD2 gene in a plant cell and consists of a FAD2 intron fragment or a FAD2 UTR fragment; and ii) suppressing an endogenous FAD2 gene with the heterologous FAD2 sequence, wherein the amount of FAD2 gene suppression is less than the amount of gene expression obtained by expressing a heterologous FAD2 sequence consisting of the entire length of a FAD2 intron or the entire length of a FAD2 UTR.

The present invention also includes a method of altering the oil composition of a plant cell by transforming a plant cell with a heterologous FAD2 sequence derived from part of an endogenous FAD2 gene, where the heterologous FAD2 sequence consists of a FAD2 intron fragment or a FAD2 UTR fragment; and growing the plant cell under conditions wherein transcription of the heterologous FAD2 sequence is initiated, whereby the oil composition is altered relative to a plant cell with a similar genetic background but lacking the heterologous FAD2 sequence.

The present invention also includes a method to enhance oleic acid content and reduce saturated fatty acid content in a plant seed comprising i) shortening the length of a first heterologous FAD2 sequence until the amount of FAD2 gene suppression from a plant transformed with the first heterologous FAD2 sequence is at least partially reduced relative to the amount of FAD2 gene suppression in a plant cell comprising a similar genetic background and a second heterologous FAD2 sequence, wherein the second heterologous FAD2 sequence consists of more endogenous FAD2 sequence than the first heterologous FAD2 sequence; ii) expressing a heterologous FATB sequence capable of at least partially reducing FATB gene expression in a plant cell relative to the suppression of FATB in a plant cell with a similar genetic background but without the heterologous FATB sequence; iii) growing a plant comprising a genome with the first heterologous FAD2 sequence and the heterologous FATB sequence; and iv) cultivating a plant that produces seed with a reduced saturated fatty acid content relative to seed from a plant having a similar genetic background but lacking the first heterologous FAD2 sequence and the heterologous FATB sequence.

The present invention also includes a method of modulating the fatty acid composition of oil from a seed of a temperate oilseed crop comprising, isolating a fragment of a genetic element of at least 40 nucleotides in length that is capable of suppressing the expression of an endogenous gene in the fatty acid synthesis pathway; introducing the genetic element into a plant cell of the temperate oilseed crop; producing a transgenic plant; and selecting a transgenic plant seed comprising the genetic element that modulates the fatty acid composition of oil from the seed.

In another embodiment, the present invention includes a cell of a soybean seed exhibiting a seed oil fatty acid composition comprising an oleic acid content of about 42% to about 85% by weight of the total fatty acids and a saturated fatty acid content of less than 8% by weight of the total fatty acids.

The present invention also includes a heterologous nucleic acid molecule comprising a fragment of soybean FAD2-1 intron that is between about 20 and about 420 contiguous nucleotides in length and a fragment of soybean FATB gene that is between about 40 and about 450 contiguous nucleotides in length. In another embodiment, the present invention is directed to a heterologous nucleic acid molecule comprising a nucleic acid sequence comprising a fragment of soybean FAD2-1 intron that is between about 20 and about 420 nucleotides in length, a fragment of a soybean FATB gene that is between about 40 to about 450 nucleotides in length, and a nucleic acid sequence that increases the expression of one or both of beta-ketoacyl-ACP synthase IV and delta-9 desaturase.

The present invention is also directed to a method for decreasing linolenic acid content of a soybean seed by i) introducing into a soybean cell a heterologous nucleic acid molecule comprising nucleic acid sequence from at least two members of a FAD3 gene family; ii) expressing a nucleic acid sequence from a FAD3 gene capable of at least partially reducing endogenous FAD3 gene expression in a plant cell; iii) growing a plant cell comprising a genome with the nucleic acid sequence from at least two members of the FAD3 gene family; and iv) cultivating the plant cell with a reduced linolenic acid content relative to a plant cell having a similar genetic background but lacking the at least two members of the FAD3 gene family. The present invention also includes a recombinant DNA construct with DNA fragments from at least two members of FAD3 gene family.

The present invention also includes a non-blended soybean oil having a fatty acid composition comprising an oleic acid content of from about 42% to about 85% by weight of the total fatty acids, a saturated fatty acid content of about 8% or less by weight of the total fatty acids, and a linolenic acid content of about 1.5% or less by weight of the total fatty acids.

BRIEF DESCRIPTION OF THE DRAWINGS

FIGS. 5(a)-(d) and 6(a)-(c) each depict illustrative configurations of a first set of DNA sequences.

DETAILED DESCRIPTION OF THE INVENTION

Description of the Nucleic Acid Sequences

Figure 1:
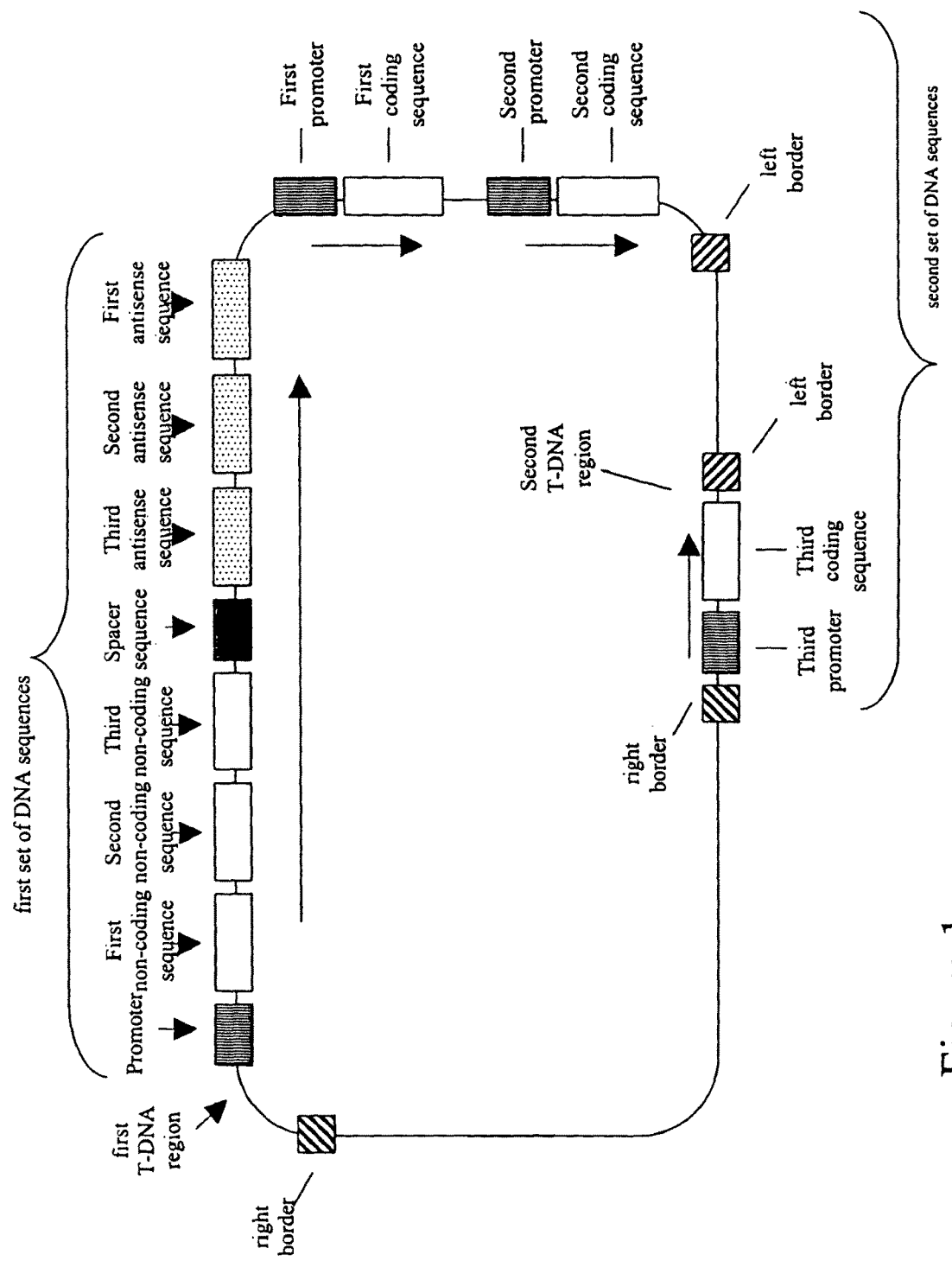
FIGS. 1-4 each depict exemplary nucleic acid molecule configurations.

SEQ ID NO: 1 is a nucleic acid sequence of a FAD2-1A intron 1.

SEQ ID NO: 2 is a nucleic acid sequence of a FAD2-1B intron 1.

SEQ ID NO: 3 is a nucleic acid sequence of a FAD2-1B promoter.

SEQ ID NO: 4 is a nucleic acid sequence of a FAD2-1A genomic clone.

SEQ ID NOs: 5 & 6 are nucleic acid sequences of a FAD2-1A 3' UTR and 5'UTR, respectively.

SEQ ID NOs: 7-13 are nucleic acid sequences of FAD3-1A introns 1, 2, 3A, 4, 5, 3B, and 3C, respectively.

SEQ ID NO: 14 is a nucleic acid sequence of a FAD3-1C intron 4.

SEQ ID NO: 15 is a nucleic acid sequence of a partial FAD3-1A genomic clone.

SEQ ID NOs: 16 & 17 are nucleic acid sequences of a FAD3-1A 3'UTR and 5'UTR, respectively.

SEQ ID NO: 18 is a nucleic acid sequence of a partial FAD3-1B genomic clone.

SEQ ID NOs: 19-25 are nucleic acid sequences of FAD3-1B introns 1, 2, 3A, 3B, 3C, 4, and 5, respectively.

SEQ ID NOs: 26 & 27 are nucleic acid sequences of a FAD3-1B 3'UTR and 5'UTR, respectively.

SEQ ID NO: 28 is a nucleic acid sequence of a FATB-1 genomic clone.

SEQ ID NO: 29-35 are nucleic acid sequences of FATB-1 introns I, II, III, IV, V, VI, and VII, respectively.

SEQ ID NOs: 36 & 37 are nucleic acid sequences of a FATB-1 3'UTR and 5'UTR, respectively.

SEQ ID NO: 38 is a nucleic acid sequence of a *Cuphea pulcherrima* KAS I gene.

SEQ ID NO: 39 is a nucleic acid sequence of a *Cuphea pulcherrima* KAS IV gene.

SEQ ID NOs: 40 & 41 are nucleic acid sequences of *Ricinus communis* and *Simmondsia chinensis* delta-9 desaturase genes, respectively.

SEQ ID NO: 42 is a nucleic acid sequence of a FATB-2 cDNA.

SEQ ID NO: 43 is a nucleic acid sequence of a FATB-2 genomic clone.

SEQ ID NOs: 44-47 are nucleic acid sequences of FATB-2 introns I, II, III, and IV respectively.

SEQ ID NOs: 48-60 are nucleic acid sequences of PCR primers.

SEQ ID NOs: 61 & 62 are nucleic acid sequences of soybean FAD3-1C 3'UTR and 5'UTR, respectively.

Definitions

"ACP" refers to an acyl carrier protein moiety. "Altered seed oil composition" refers to a seed oil composition from a transgenic or transformed plant of the invention which has altered or modified levels of the fatty acids therein, relative to a seed oil from a plant having a similar genetic background but that has not been transformed.

"Antisense suppression" refers to gene-specific silencing that is induced by the introduction of an antisense RNA molecule.

"Coexpression of more than one agent such as an mRNA or protein" refers to the simultaneous expression of an agent in overlapping time frames and in the same cell or tissue as another agent. "Coordinated expression of more than one agent" refers to the coexpression of more than one agent when the production of transcripts and proteins from such agents is carried out utilizing a shared or identical promoter.

"Complement" of a nucleic acid sequence refers to the complement of the sequence along its complete length.

"Cosuppression" is the reduction in expression levels, usually at the level of RNA, of a particular endogenous gene or gene family by the expression of a homologous sense construct that is capable of transcribing mRNA of the same strandedness as the transcript of the endogenous gene. Napoli et al., *Plant Cell* 2:279-289 (1990); van der Krol et al., *Plant Cell* 2:291-299 (1990).

"Crude soybean oil" refers to soybean oil that has been extracted from soybean seeds, but has not been refined, processed, or blended, although it may be degummed.

"CTP" refers to a chloroplastic transit peptide, encoded by the "chloroplastic transit peptide coding sequence".

When referring to proteins and nucleic acids herein, "derived" refers to either directly (for example, by looking at the sequence of a known protein or nucleic acid and preparing a protein or nucleic acid having a sequence similar, at least in part, to the sequence of the known protein or nucleic acid) or indirectly (for example, by obtaining a protein or nucleic acid from an organism which is related to a known protein or nucleic acid) obtaining a protein or nucleic acid from a known protein or nucleic acid. Other methods of "deriving" a protein or nucleic acid from a known protein or nucleic acid are known to one of skill in the art.

Double-stranded RNA ("dsRNA"), double-stranded RNA interference ("dsRNAi") and RNA interference ("RNAi") all refer to gene-specific silencing that is induced by the introduction of a construct capable of transcribing an at least partially double-stranded RNA molecule. A "dsRNA molecule" and an "RNAi molecule" both refer to a region of an RNA molecule containing segments with complementary nucleotide sequences and therefore can hybridize with each other and form double-stranded RNA. Such double-stranded RNA molecules are capable, when introduced into a cell or organism, of at least partially reducing the level of an mRNA species present in a cell or a cell of an organism. In addition, the dsRNA can be created after assembly in vivo of appropriate DNA fragments through illegitimate recombination and site-specific recombination as described in International Application No. PCT/US2005/004681, filed on Feb. 11, 2005, which is hereby incorporated by reference in its entirety.

"Exon" refers to the normal sense of the term as meaning a segment of nucleic acid molecules, usually DNA, that encodes part of or all of an expressed protein.

"Fatty acid" refers to free fatty acids and fatty acyl groups.

"Gene" refers to a nucleic acid sequence that encompasses a 5' promoter region associated with the expression of the gene product, any intron and exon regions and 3' or 5' untranslated regions associated with the expression of the gene product.

"Gene silencing" refers to the suppression of gene expression or down-regulation of gene expression.

A "gene family" is two or more genes in an organism which encode proteins that exhibit similar functional attributes, and a "gene family member" is any gene of the gene family found within the genetic material of the plant, e.g., a "FAD2 gene family member" is any FAD2 gene found within the genetic material of the plant. An example of two members of a gene family are FAD2-1 and FAD2-2. A gene family can be additionally classified by the similarity of the nucleic acid sequences. A gene, FAD2, for example, includes alleles at that locus. Preferably, a gene family member exhibits at least 60%, more preferably at least 70%, more preferably at least 80% nucleic acid sequence identity in the coding sequence portion of the gene.

"Heterologous" means not naturally occurring together.

A nucleic acid molecule is said to be "introduced" if it is inserted into a cell or organism as a result of human manipulation, no matter how indirect. Examples of introduced nucleic acid molecules include, but are not limited to, nucleic acids that have been introduced into cells via transformation, transfection, injection, and projection, and those that have been introduced into an organism via methods including, but not limited to, conjugation, endocytosis, and phagocytosis.

"Intron" refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein. An "intron dsRNA molecule" and an "intron RNAi molecule" both refer to a double-stranded RNA molecule capable, when introduced into a cell or organism, of at least partially reducing the level of an mRNA species present in a cell or a cell of an organism where the double-stranded RNA molecule exhibits sufficient identity to an intron of a gene present in the cell or organism to reduce the level of an mRNA containing that intron sequence.

A "low saturate" oil composition contains between 3.6 and 8 percent saturated fatty acids.

A "mid-oleic soybean seed" is a seed having between 50% and 85% oleic acid present in the oil composition of the seed.

A "low linolenic" oil composition contains less than about 3% linolenic acid by weight of the total fatty acids.

The term "non-coding" refers to sequences of nucleic acid molecules that do not encode part or all of an expressed protein. Non-coding sequences include but are not limited to introns, promoter regions, 3' untranslated regions (3'UTRs), and 5' untranslated regions (5'UTRs).

The term "oil composition" refers to levels of fatty acids.

A promoter that is "operably linked" to one or more nucleic acid sequences is capable of driving expression of one or more nucleic acid sequences, including multiple coding or non-coding nucleic acid sequences arranged in a polycistronic configuration.

"Physically linked" nucleic acid sequences are nucleic acid sequences that are found on a single nucleic acid molecule.

A "plant" includes reference to whole plants, plant organs (e.g., leaves, stems, roots, etc.), seeds, and plant cells and progeny of the same.

The term "plant cell" includes, without limitation, seed suspension cultures, embryos, meristematic regions, callus tissue, leaves, roots, shoots, gametophytes, sporophytes, pollen, and microspores.

"Plant promoters," include, without limitation, plant viral promoters, promoters derived from plants, and synthetic promoters capable of functioning in a plant cell to promote the expression of an mRNA.

A "polycistronic gene" or "polycistronic mRNA" is any gene or mRNA that contains transcribed nucleic acid sequences which correspond to nucleic acid sequences of more than one gene targeted for suppression or expression. It is understood that such polycistronic genes or mRNAs may contain sequences that correspond to introns, 5'UTRs, 3'UTRs, transit peptide encoding sequences, exons, or combinations thereof, and that a recombinant polycistronic gene or mRNA might, for example without limitation, contain sequences that correspond to one or more UTRs from one gene and one or more introns from a second gene.

A "seed-specific promoter" refers to a promoter that is active preferentially or exclusively in a seed. "Preferential activity" refers to promoter activity that is substantially greater in the seed than in other tissues, organs or organelles of the plant. "Seed-specific" includes without limitation activity in the aleurone layer, endosperm, and/or embryo of the seed.

"Sense intron suppression" refers to gene silencing that is induced by the introduction of a sense intron or fragment thereof. Sense intron suppression is described, for example by Fillatti in PCT WO 01/14538 A2.

"Simultaneous expression" of more than one agent such as an mRNA or protein refers to the expression of an agent at the same time as another agent. Such expression may only overlap in part and may also occur in different tissue or at different levels.

"Total oil level" refers to the total aggregate amount of fatty acid without regard to the type of fatty acid. As used herein, total oil level does not include the glycerol backbone.

"Transgene" refers to a nucleic acid sequence associated with the expression of a gene introduced into an organism. A transgene includes, but is not limited to, a gene endogenous or a gene not naturally occurring in the organism. A "transgenic plant" is any plant that stably incorporates a transgene in a manner that facilitates transmission of that transgene from a plant by any sexual or asexual method.

A "zero saturate" oil composition contains less than 3.6 percent saturated fatty acids.

When referring to proteins and nucleic acids herein, the use of plain capitals, e.g., "FAD2", indicates a reference to an enzyme, protein, polypeptide, or peptide, and the use of italicized capitals, e.g., "FAD2", is used to refer to nucleic acids, including without limitation genes, cDNAs, and mRNAs. A cell or organism can have a family of more than one gene encoding a particular enzyme, and the capital letter that follows the gene terminology (A, B, C) is used to designate the family member, i.e., FAD2-1A is a different gene family member from FAD2-1B.

As used herein, any range set forth is inclusive of the end points of the range unless otherwise stated.

A. Agents

The agents of the invention will preferably be "biologically active" with respect to either a structural attribute, such as the capacity of a nucleic acid molecule to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response. The agents will preferably be "substantially purified." The term "substantially purified," as used herein, refers to a molecule separated from substantially all other molecules normally associated with it in its native environmental conditions. More preferably a substantially purified molecule is the predominant species present in a preparation. A substantially purified molecule may be greater than 60% free, greater than 75% free, preferably greater than 90% free, and most preferably greater than 95% free from the other molecules (exclusive of solvent) present in the natural mixture. The term "substantially purified" is not intended to encompass molecules present in their native environmental conditions.

The agents of the invention may also be recombinant. As used herein, the term "recombinant" means any agent (e.g., including but not limited to DNA or peptide), that is, or results, however indirectly, from human manipulation of a nucleic acid molecule. It is also understood that the agents of the invention may be labeled with reagents that facilitate detection of the agent, e.g., fluorescent labels, chemical labels, and/or modified bases.

Agents of the invention include DNA molecules that have a nucleotide sequence which is capable of being transcribed in sense- and antisense-orientations that form at least one RNA molecule that is, at least in part, double-stranded. In a preferred embodiment, an agent of the invention is a double-stranded RNA molecule having a nucleotide sequence that is a fragment of FAD2, FATB, or FAD2 and FATB. In another embodiment, an agent of the present invention is a DNA molecule capable of being transcribed to produce sense- and antisense-orientations of a nucleotide sequence in a host cell. In another embodiment, a nucleic acid molecule can have a nucleotide sequence in a sense orientation and in an antisense orientation, or in another embodiment, a nucleic acid molecule can have a nucleotide sequence in a sense orientation or an antisense orientation. Such nucleotide sequences can be operably linking to the same promoter, different promoters, a single promoter, or more than one promoter. Such nucleotide sequences can be on a single DNA molecule or more than one DNA molecule.

Agents of the invention include nucleic acid molecules that comprise a DNA sequence which is at least 50%, 60%, or 70% identical over their entire length to a plant coding region or non-coding region, or to a nucleic acid sequence that is complementary to a plant coding or non-coding region. More preferable are DNA sequences that are, over their entire length, at least 80% identical; at least 85% identical; at least 90% identical; at least 95% identical; at least 97% identical; at least 98% identical; at least 99% identical; or 100% identical to a plant coding region or non-coding region, or to a nucleic acid sequence that is complementary to a plant coding or non-coding region.

"Identity," as is well understood in the art, is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" can be readily calculated by known methods including, but not limited to, those described in *Computational Molecular Biology*, Lesk, ed., Oxford University Press, New York 1988; *Biocomputing: Informatics and Genome Projects*, Smith, ed., Academic Press, New York 1993; *Computer Analysis of Sequence Data, Part I*, Griffin and Griffin, eds., Humana Press, New Jersey 1994; *Sequence Analysis in Molecular Biology*, von Heinje, Academic Press 1987; *Sequence Analysis Primer*, Gribskov and Devereux, eds., Stockton Press, New York 1991; and Carillo and Lipman, SIAM *J. Applied Math*, 48:1073 1988.

Methods to determine identity are designed to give the largest match between the sequences tested. Moreover, methods to determine identity are codified in publicly available programs. Computer programs which can be used to determine identity between two sequences include, but are not limited to, GCG; a suite of five BLAST programs, three designed for nucleotide sequences queries (BLASTN, BLASTX, and TBLASTX) and two designed for protein sequence queries (BLASTP and TBLASTN). The BLASTX program is publicly available from NCBI and other sources, e.g., *BLAST Manual*, Altschul et al., NCBI NLM NIH, Bethesda, Md. 20894; Altschul et al., *J. Mol. Biol.* 215:403-410 (1990). The well-known Smith Waterman algorithm can also be used to determine identity.

Parameters for polypeptide sequence comparison typically include the following: Algorithm: Needleman and Wunsch, *J. Mol. Biol.* 48:443-453 (1970); Comparison matrix: BLOSSUM62 from Hentikoff and Hentikoff, *Proc. Natl. Acad. Sci. USA* 89:10915-10919 (1992); Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons.

Parameters for nucleic acid molecule sequence comparison include the following: Algorithm: Needleman and Wunsch, *J. Mol. Bio.* 48:443-453 (1970); Comparison matrix: matches −+10; mismatches=0; Gap Penalty: 50; Gap Length Penalty: 3. As used herein, "% identity" is determined using the above parameters as the default parameters for nucleic acid molecule sequence comparisons and the "gap" program from GCG, version 10.2.

Subsets of the nucleic acid sequences of the present invention include fragment nucleic acid molecules. "Fragment nucleic acid molecule" refers to a piece of a larger nucleic acid molecule, and it may consist of significant portion(s) of, or indeed most of, the larger nucleic acid molecule. The fragment nucleic acid molecule may comprise a smaller oligonucleotide having from about 15 to about 400 contiguous nucleotides and more preferably, about 15 to about 45 contiguous nucleotides, about 20 to about 45 contiguous nucleotides, about 15 to about 30 contiguous nucleotides, about 21 to about 30 contiguous nucleotides, about 21 to about 25 contiguous nucleotides, about 21 to about 24 contiguous nucleotides, about 19 to about 25 contiguous nucleotides, or about 21 contiguous nucleotides. Fragment nucleic acid molecules may consist of significant portion(s) of, or indeed most of, a plant coding or non-coding region, or alternatively may comprise smaller oligonucleotides. In a preferred embodiment, a fragment shows 100% identity to the plant coding or non-coding region. In another preferred embodiment, a fragment comprises a portion of a larger nucleic acid sequence. In another aspect, a fragment nucleic acid molecule has a nucleic acid sequence that has at least 15, 25, 50, 100, 200, 300, or 400 contiguous nucleotides of a nucleic acid molecule of the present invention. In a preferred embodiment, a nucleic acid molecule has a nucleic acid sequence that has at least 15, 25, 50, 100, 200, 300, or 400 contiguous nucleotides of a plant coding or non-coding region. In a most preferred embodiment, a nucleic acid molecule has a nucleic acid sequence that has about 1, 2, 5, 10, 20, 30, 40, 50, 60, 70, 80, or 90% of the contiguous nucleotides of an entire coding or non-coding region. In a preferred embodiment, an entire coding or non-coding region can be a gene element selected from an entire gene, a single exon, a single intron, a signal sequence, or an untranslated region (UTR). A gene element that does not have the entire sequence of an entire genetic element can be a fragment of a gene element. In a preferred aspect of the present invention, a genetic element is at least 40 nucleotides in length. In an aspect of the present invention, a fragment of a gene is a portion of the entire gene element and such a fragment contains contiguous nucleotides from about 1, 2, 5, 10, 20, 30, 40, 50, 60, 70, 80, or 90% of the entire gene element. In an aspect of the present invention, a fragment nucleic acid molecule is between about 5%-about 80%, between about 10%-about 70%, between about 10%-about 60%, between about 10%-about 50%, between about 25%-about 60%, between about 25%-about 50%, between about 40%-about 60%, between about 40%-about 80%, between about 50%-about 90% of the length of an entire gene element.

In a preferred embodiment, a fragment of FAD2-1 intron is between about 20 and about 420, about 30 and about 420, between about 40 and about 320, between about 50 and about 200, between about 50 and about 400, between about 50 and about 420, between about 60 and about 320, about 70 and about 220, between about 100 and about 200, between about 100 and about 320, between about 150 and about 200, between about 150 and about 220, between about 150 and about 400, between about 200 and about 300, or between about 300 and about 400 contiguous nucleotides. In another preferred embodiment, a fragment of FAD2-1 intron is about 100, about 150, about 200, about 220, about 250, about 300, about 320, or about 350 contiguous nucleotides in length. In another preferred embodiment, a FAD2-1 intron fragment is reduced in length by about 20, about 40, about 60, about 80, about 100, about 120, about 140, about 160, about 180, about 200, about 220, about 240, about 260, about 280, about 290, about 300, about 320, about 340, about 360, about 380, about 400 contiguous nucleotides compared to the length of SEQ ID NO: 1. For all of these FAD2-1 intron fragments, the truncation or deletion can start at the 5' end, start at the 3' end, or be internal to a FAD2-1 intron. For all of these FAD2-1 intron fragments, the sequence of a FAD2-1 intron can be SEQ ID NO: 1.

In a preferred embodiment, a fragment of a FATB gene is about 80 to about 450, about 100 to about 500, about 70 to about 500, about 200 to about 400, about 150 to about 300, about 250 to about 350, about 200 to about 350 contiguous nucleotides of a FATB gene. In a preferred embodiment, a FATB fragment is derived from one-half of the total nucleotides in FATB starting at the 5' end. For all of these FATB fragments, the truncation or deletion can start at the 5' end, start at the 3' end, or be internal to FATB. In a preferred embodiment, a FATB fragment is derived from one-half of the total nucleotides in FATB starting at the 5' end of FATB, is derived from one-third of the total nucleotides in FATB that are closest to the 5' end. In a particularly preferred embodiment, a FATB fragment contains a transit peptide encoding sequence, which preferably encodes for the chloroplast transit peptide. In a particularly preferred embodiment, a FATB fragment is a fragment of a transit peptide encoding sequence, which preferably encodes for the chloroplast transit peptide. In another particularly preferred embodiment, a FATB fragment further includes about 20, about 25, about 30, about 35, 38, 39, 40, 41, 42, 43, about 45, about 50, about 55, or about 60 contiguous nucleotides of a FATB 5' UTR. In a most preferred embodiment, a fragment includes a combination of two or more discontinuous fragments or separate gene elements, such as a FATB 3' UTR fused to a FATB 5' UTR. Agents of the invention include nucleic acid molecules. For example, without limitation, in an aspect of the present invention, the nucleic acid molecule of the present invention comprises an intron sequence of SEQ ID NO: 19, 20, 21, 22, 23, 25, 32, 33, 34, 35, 44, 45, 46, or 47 or fragments thereof or complements thereof. In another aspect of the invention, the nucleic acid molecule comprises a nucleic acid sequence, which when introduced into a cell or organism, is capable of suppressing the production of an RNA or protein while simultaneously expressing, coexpressing or coordinately expressing another RNA or protein. In an aspect of the invention, the nucleic acid molecule comprises a nucleic acid sequence, which when introduced into a cell or organism is capable of suppressing, at least partially reducing, reducing, substantially reducing, or effectively eliminating the expression of endogenous FAD2, FAD3, and/or FATB RNA while at the same time coexpressing, simultaneously expressing, or coordinately expressing at least one of a beta-ketoacyl-ACP synthase I, beta-ketoacyl-ACP synthase IV, delta-9 desaturase, and/or CP4 EPSPS RNA or protein.

By suppressing, at least partially reducing, reducing, substantially reducing, or effectively eliminating the expression of at least one or more endogenous genes, the amount of FAD2 and/or FAD3 available in a plant cell is decreased, i.e. the steady-state levels of the protein are reduced, and a decreased percentage of polyunsaturated fatty acids such as linoleate (C18:2) and linolenate (C18:3) may be provided. Modifications in the pool of fatty acids available for incorporation into triacylglycerols may likewise affect the composition of oils in the plant cell. Thus, a decrease in expression of FAD2 and/or FAD3 may result in an increased proportion of mono-unsaturated fatty acids such as oleate (C18:1). When the amount of FATB is decreased in a plant cell, a decreased amount of saturated fatty acids such as palmitate and stearate may be provided. Thus, a decrease in expression of FATB may result in an increased proportion of unsaturated fatty acids such as oleate (18:1). The simultaneous suppression of FAD2, FAD3, and FATB expression thereby results in driving the FAS pathway toward an overall increase in mono-unsaturated fatty acids of 18-carbon length, such as oleate (C18:1). See U.S. Pat. No. 5,955,650.

By increasing the amount of beta-ketoacyl-ACP synthase I (KAS I) and/or beta-ketoacyl-ACP synthase IV (KAS IV) available in a plant cell, a decreased percentage of 16:0-ACP may be provided, leading to an increased percentage of 18:0-ACP. A greater amount of 18:0-ACP in combination with the simultaneous suppression of one or more of FAD2, FAD3, and FATB, thereby helps drive the oil composition toward an overall increase in oleate (C18:1). By increasing the amount of delta-9 desaturase available in a plant cell, an increased percentage of unsaturated fatty acids may be provided, resulting in an overall lowering of stearate and total saturates.

These combinations of increased and decreased enzyme expression may be manipulated to produce oil compositions, including fatty acids, having an increased oleate level, decreased linoleate, linolenate, stearate, and/or palmitate levels, and a decreased overall level of saturates. Enhancement of gene expression in plants may occur through the introduction of extra copies of coding sequences of the genes into the plant cell or, preferably, the incorporation of extra copies of coding sequences of the gene into the plant genome. Over-expression may also occur though increasing the activities of the regulatory mechanisms that regulate the expression of genes, i.e., up-regulation of the gene expression.

Production of CP4 EPSPS in a plant cell provides the plant cell with resistance or tolerance to glyphosate, thereby providing a convenient method for identification of successful transformants via glyphosate-tolerant selection.

Suppression of gene expression in plants, also known as gene silencing, occurs at both the transcriptional level and post-transcriptional level. There are various methods for the suppression of expression of endogenous sequences in a host cell, including, but not limited to, antisense suppression, co-suppression, ribozymes, combinations of sense and antisense (double-stranded RNAi), promoter silencing, and DNA binding proteins such as zinc finger proteins. (See, e.g., WO 98/53083, WO 01/14538, and U.S. Pat. No. 5,759,829 (Shewmaker). Certain of these mechanisms are associated with nucleic acid homology at the DNA or RNA level. Such homology refers to similarity in DNA or protein sequences within the same species or among different species. Gene silencing occurs if the DNA sequence introduced to a host cell is sufficiently homologous to an endogenous gene that transcription of the introduced DNA sequence will induce transcriptional or post transcriptional gene silencing of the endogenous gene. Sufficient homology for suppression of steady state expression levels may be at least 50%, about 60%, or about 70% identical over the entire length of a DNA sequence to a plant coding region or non-coding region, or to a nucleic acid sequence that is complementary to a plant coding or non-coding region. More preferable are DNA sequences that are, over their entire length, at least 80% identical; at least 85% identical; at least 90% identical; at least 95% identical; at least 97% identical; at least 98% identical; at least 99% identical; or 100% identical to a plant coding region or non-coding region, or to a nucleic acid sequence that is complementary to a plant coding or non-coding region. In plants, double-stranded RNA molecules can induce sequence-specific silencing. Gene silencing was often referred to as double-stranded RNA ("dsRNAi") in plants, as RNA interference or RNAi in *Caenorhabditis elegans* and in animals, and as quelling in fungi.

In a preferred embodiment, the nucleic acid molecule of the present invention comprises a first set of DNA sequences, each of which exhibits sufficient homology to one or more coding or non-coding sequences of a plant gene such that when it is expressed, it is capable of effectively eliminating, substantially reducing, or at least partially reducing the level of an mRNA transcript or protein encoded by the gene from which the coding or non-coding sequence was derived, or any gene which has homology to the target coding or non-coding sequence.

In a preferred embodiment, the nucleic acid molecule of the present invention comprises (a) a first set of DNA sequences, each of which exhibits sufficient homology to one or more coding or non-coding sequences of a plant gene such that when it is expressed, it is capable of effectively eliminating, substantially reducing, or at least partially reducing the level of an mRNA transcript or protein encoded by the gene from which the coding or non-coding sequence was derived, or any gene which has homology to the target non-coding sequence, and (b) a second set of DNA sequences, each of which exhibits sufficient homology to a plant gene so that when it is expressed, it is capable of at least partially enhancing, increasing, enhancing, or substantially enhancing the level of an mRNA transcript or protein encoded by the gene.

As used herein, "a set" of DNA sequences can be one or more sequences, which either code or do not code for a protein. For example, a first set of DNA sequences can be composed of only a promoter, a non-coding region, and a terminator. A second set of DNA sequences can or can not be present after or before a first set of DNA sequences.

As used herein, "a reduction" of the level or amount of an agent such as a protein or mRNA means that the level or amount is reduced relative to a cell or organism lacking a DNA sequence capable of reducing the agent. For example, "at least a partial reduction" refers to a reduction of at least 25%, "a substantial reduction" refers to a reduction of at least 75%, and "an effective elimination" refers to a reduction of greater than 95%, all of which reductions in the level or amount of the agent are relative to a cell or organism lacking a DNA sequence capable of reducing the agent.

As used herein, "an enhanced" or "increased" level or amount of an agent such as a protein or mRNA means that the level or amount is higher than the level or amount of agent present in a cell, tissue or plant with a similar genetic background but lacking an introduced nucleic acid molecule encoding the protein or mRNA. For example, an "at least partially enhanced" level refers to an increase of at least 25%, and a "substantially enhanced" level refers to an increase of at least 100%, all of which increases in the level or amount of an agent are relative to the level or amount of agent that is present in a cell, tissue or plant with a similar genetic background but lacking an introduced nucleic acid molecule encoding the protein or mRNA. In a preferred embodiment, an increase in expression may be any expression where the protein is heterologous to the system. For example, any expression of CP4 EPSPS can be an increase in expression if there was no expression in the plant prior to the introduction of a nucleic acid molecule encoding the protein.

When levels of an agent are compared, such a comparison is preferably carried out between organisms with a similar genetic background. Preferably, a similar genetic background is a background where the organisms being compared share 50% or greater, more preferably 75% or greater, and, even more preferably 90% or greater sequence identity of nuclear genetic material. In another preferred aspect, a similar genetic background is a background where the organisms being compared are plants, and the plants are isogenic except for any genetic material originally introduced using plant transformation techniques. Measurement of the level or amount of an agent may be carried out by any suitable method, non-limiting examples of which include comparison of mRNA transcript levels, protein or peptide levels, and/or phenotype, especially oil content. As used herein, mRNA transcripts include processed and non-processed mRNA transcripts, and proteins or peptides include proteins or peptides with or without any post-translational modification.

The DNA sequences of the first set of DNA sequences may be coding sequences, intron sequences, 3'UTR sequences, 5'UTR sequences, promoter sequences, other non-coding sequences, or any combination of the foregoing. The first set of DNA sequences encodes one or more sequences which, when expressed, are capable of selectively reducing either or both the protein and the transcript encoded by a gene selected from the group consisting of FAD2, FAD3, and FATB. In a preferred embodiment, the first set of DNA sequences is capable of expressing antisense RNA, in which the individual antisense sequences may be linked in one transcript, or may be in unlinked individual transcripts. In a further preferred embodiment, the first set of DNA sequences are physically linked sequences which are capable of expressing a single dsRNA molecule. In a different preferred embodiment, the first set of DNA sequences is capable of expressing sense cosuppresion RNA, in which the individual sense sequences may be linked in one transcript, or may be in unlinked individual transcripts. Exemplary embodiments of the first set of DNA sequences are described in Part B of the Detailed Description, and in the Examples.

The second set of DNA sequences encodes one or more sequences which, when expressed, are capable of increasing one or both of the protein and transcript encoded by a gene selected from the group consisting of beta-ketoacyl-ACP synthase I (KASI), beta-ketoacyl-ACP synthase IV (KASIV), delta-9 desaturase, and CP4 EPSPS. The DNA sequences of the second set of DNA sequences may be physically linked sequences. Exemplary embodiments of the second set of DNA sequences are described below in Parts C and D of the Detailed Description.

Thus, the present invention provides methods for altering the composition of fatty acids and compounds containing such fatty acids, such as oils, waxes, and fats. The present invention also provides methods for the production of particular fatty acids in host cell plants. Such methods employ the use of the expression cassettes described herein for the modification of the host plant cell's FAS pathway.

B. First Set of DNA Sequences

In an aspect of the present invention, a nucleic acid molecule comprises a first set of DNA sequences, which when introduced into a cell or organism, expresses one or more sequences capable of effectively eliminating, substantially reducing, or at least partially reducing the levels of mRNA transcripts or proteins encoded by one or more genes. Preferred aspects include as a target an endogenous gene, a plant gene, and a non-viral gene. In an aspect of the present invention, a gene is a FAD2, FAD3, or FATB gene.

In an aspect, a nucleic acid molecule of the present invention comprises a DNA sequence which exhibits sufficient homology to one or more coding or non-coding sequences from a plant gene, which when introduced into a plant cell or plant and expressed, is capable of effectively eliminating, substantially reducing, or at least partially reducing the level of an mRNA transcript or protein encoded by the gene from which the coding or non-coding sequence(s) was derived. The DNA sequences of the first set of DNA sequences transcribe RNA sequences or RNA fragments which exhibit at least 90%, preferably at least 95%, more preferably at least 98%, or most preferably 100% identity to a coding or non-coding region derived from the gene which is to be suppressed. Such percent identity may be in comparison to another nucleic acid fragment.

Preferably, the non-coding sequence is a 3' UTR, 5'UTR, a fraction of a sequence encoding a protein or an intron from a plant gene. More preferably, the non-coding sequence is a promoter sequence, 3' UTR, 5'UTR, or an intron from a plant gene. The intron may be located between exons, or located within a 5' or 3' UTR of a plant gene. The coding sequence is preferentially a fraction of a protein encoding frame.

The sequence(s) of the first set of DNA sequences may be designed to produce dsRNA, a sense suppression RNA, or an antisense RNA or any other suppressing transcript in order to achieve the desired effect when introduced into a plant cell or plant. Such DNA sequence(s) may be fragment nucleic acid molecules.

A plant intron can be any plant intron from a gene, whether endogenous or introduced. Nucleic acid sequences of such introns from organisms can be obtained or derived from a multitude of sources, including, without limitation, databases such as EMBL and Genbank which may be found on the Internet at ebi.ac.uk/swisprot/; expasy.ch/; embl-heidelberg.de/; and ncbi.nlm.nih.gov. Nucleic acid sequences of such introns can also be derived, without limitation, from sources such as the GENSCAN program which may be found on the Internet at genes.mit.edu/GENSCAN.html.

Additional introns may also be obtained by methods which include, without limitation, screening a genomic library with a probe of either known exon or intron sequences, comparing genomic sequence with its corresponding cDNA sequence, or cloning an intron such as a soybean cDNA by alignment to a genomic sequence from another organism, such as, for example, *Arabidopsis*. In addition, other nucleic acid sequences of introns will be apparent to one of ordinary skill in the art. The above-described methods may also be used to derive and obtain other non-coding sequences, including but not limited to, promoter sequences, 3'UTR sequences, and 5'UTR sequences.

A "FAD2", "Δ12 desaturase" or "omega-6 desaturase" gene encodes an enzyme (FAD2) capable of catalyzing the insertion of a double bond into a fatty acyl moiety at the twelfth position counted from the carboxyl terminus. The term "FAD2-1" is used to refer to a FAD2 gene that is naturally expressed in a specific manner in seed tissue, and the term "FAD2-2" is used to refer a FAD2 gene that is (a) a different gene from a FAD2-1 gene and (b) is naturally expressed in multiple tissues, including the seed. Representative FAD2 sequences include, without limitation, those set forth in U.S. patent application Ser. No. 10/176,149 filed on Jun. 21, 2002, now U.S. Pat. No. 7,067,722, and in SEQ ID NOs: 1-6.

A "FAD3", "Δ15 desaturase" or "omega-3 desaturase" gene encodes an enzyme (FAD3) capable of catalyzing the insertion of a double bond into a fatty acyl moiety at the fifteenth position counted from the carboxyl terminus. The terms "FAD3-1, FAD3-A, FAD3-B and FAD3-C" are used to refer to FAD3 gene family members that are naturally expressed in multiple tissues, including the seed. Representative FAD3 sequences include, without limitation, those set forth in U.S. patent application Ser. No. 10/176,149 filed on Jun. 21, 2002, now U.S. Pat. No. 7,067,722, and in SEQ ID NOs: 7-27.

A "FATB" or "palmitoyl-ACP thioesterase" gene encodes an enzyme (FATB) capable of catalyzing the hydrolytic cleavage of the carbon-sulfur thioester bond in the panthothene prosthetic group of palmitoyl-ACP as its preferred reaction. Hydrolysis of other fatty acid-ACP thioesters may also be catalyzed by this enzyme. Representative FATB-1 sequences include, without limitation, those set forth in U.S. Provisional Application No. 60/390,185 filed on Jun. 21, 2002; U.S. Pat. Nos. 5,955,329; 5,723,761; 5,955,650; and 6,331,664; and SEQ ID NOs: 28-37. Representative FATB-2 sequences include, without limitation, those set forth in SEQ ID NOs: 42-47.

C. Second Set of DNA Sequences

In an aspect of the present invention, a nucleic acid molecule comprises a second set of DNA sequences, which when introduced into a cell or organism, is capable of partially enhancing, increasing, enhancing, or substantially enhancing the levels of mRNA transcripts or proteins encoded by one or more genes. In an aspect of the present invention, a gene is an endogenous gene. In another aspect of the present invention, a gene can be a heterologous gene. In a preferred aspect, heterologous and endogenous genes can be on the same nucleic acid molecule. In an aspect of the present invention, a gene is a plant gene. In another aspect of the present invention, a gene is a truncated gene where the truncated gene is capable of catalyzing the reaction catalyzed by the full gene. In an aspect of the present invention, a gene is a beta-ketoacyl-ACP synthase I gene, beta-ketoacyl-ACP synthase IV gene, delta-9 desaturase gene, CP4 EPSPS gene, or a combination of these genes.

A gene of the present invention can be any gene, whether endogenous or introduced. Nucleic acid sequences of such genes can be derived from a multitude of sources, including, without limitation, databases such as EMBL and Genbank which may be found on the Internet at ebi.ac.uk/swisprot/; expasy.ch/; embl-heidelberg.de/; and ncbi.nlm.nih.gov. Nucleic acid sequences of such genes can also be derived, without limitation, from sources such as the GENSCAN program which may be found on the Internet at genes.mit.edu/GENSCAN.html.

Additional genes may also be obtained by methods which include, without limitation, screening a genomic library or a cDNA library with a probe of either known gene sequences, cloning a gene by alignment to a gene or probe from another organism, such as, for example, *Arabidopsis*. In addition, other nucleic acid sequences of genes will be apparent to one of ordinary skill in the art. Additional genes may, for example without limitation, be amplified by polymerase chain reaction (PCR) and used in an embodiment of the present invention. In addition, other nucleic acid sequences of genes will be apparent to one of ordinary skill in the art.

Automated nucleic acid synthesizers may be employed for this purpose, and to make a nucleic acid molecule that has a sequence also found in a cell or organism. In lieu of such synthesis, nucleic acid molecules may be used to define a pair of primers that can be used with the PCR to amplify and obtain any desired nucleic acid molecule or fragment of a first gene.

A "KAS I" or "beta-ketoacyl-ACP synthase I" gene encodes an enzyme (KAS I) capable of catalyzing the elongation of a fatty acyl moiety up to palmitoyl-ACP (C16:0). Representative KASI sequences include, without limitation, those set forth in U.S. Pat. No. 5,475,099 and PCT Publication WO 94/10189, and in SEQ ID NO: 38.

A "KAS IV" or "beta-ketoacyl-ACP synthase IV" gene encodes an enzyme (KAS IV) capable of catalyzing the condensation of medium chain acyl-ACPs and enhancing the production of 18:0-ACP. Representative KAS IV sequences include, without limitation, those set forth in PCT Publication WO 98/46776, and in SEQ ID NO: 39.

A "delta-9 desaturase" or "stearoyl-ACP desaturase" or "omega-9 desaturase" gene encodes an enzyme capable of catalyzing the insertion of a double bond into a fatty acyl moiety at the ninth position counted from the carboxyl terminus. A preferred delta-9 desaturase of the present invention is a plant or cyanobacterial delta-9 desaturase, and more preferably a delta-9 desaturase that is also found in an organism selected from the group consisting of *Cartharmus tinctorius, Ricinus communis, Simmonsia chinensis*, and *Brassica campestris*. Representative delta-9 desaturase sequences include, without limitation, those set forth in U.S. Pat. No. 5,723,595, and SEQ ID NOs: 40-41.

A "CP4 EPSPS" or "CP4 5-enolpyruvylshikimate-3-phosphate synthase" gene encodes an enzyme (CP4 EPSPS) capable of conferring a substantial degree of glyphosate resistance upon the plant cell and plants generated therefrom. The CP4 EPSPS sequence may be a CP4 EPSPS sequence derived from *Agrobacterium tumefaciens* sp. CP4 or a variant or synthetic form thereof, as described in U.S. Pat. No. 5,633,435. Representative CP4 EPSPS sequences include, without limitation, those set forth in U.S. Pat. Nos. 5,627,061 and 5,633,435.

D. Recombinant Vectors and Constructs

One or more of the nucleic acid constructs of the invention may be used in plant transformation or transfection. The levels of products such as transcripts or proteins may be increased or decreased throughout an organism such as a plant or localized in one or more specific organs or tissues of the organism. For example the levels of products may be increased or decreased in one or more of the tissues and organs of a plant including without limitation: roots, tubers, stems, leaves, stalks, fruit, berries, nuts, bark, pods, seeds and flowers. A preferred organ is a seed. For example, exogenous genetic material may be transferred into a plant cell and the plant cell regenerated into a whole, fertile or sterile plant or plant part.

"Exogenous genetic material" is any genetic material, whether naturally occurring or otherwise, from any source that is capable of being inserted into any organism. Such exogenous genetic material includes, without limitation, nucleic acid molecules and constructs of the present invention. Exogenous genetic material may be transferred into a host cell by the use of a DNA vector or construct designed for such a purpose. Similarly, a virus can transfer exogenous genetic material into a host cell. Exogenous genetic material may have a DNA sequence identical to the endogenous gene, but have been re-introduced to the host cell by the use of a DNA vector or construct for the purpose of suppressing expression of the endogenous gene. Design of such a vector is generally within the skill of the art (See, e.g., *Plant Molecular Biology: A Laboratory Manual*, Clark (ed.), Springer, New York (1997)). In a preferred embodiment, exogenous genetic material is recombinant DNA.

A construct or vector may include a promoter functional in a plant cell, or a plant promoter, to express a nucleic acid molecule of choice. A number of promoters that are active in plant cells have been described in the literature, and the CaMV 35S and FMV promoters are preferred for use in plants. Other examples of preferred promoters include bean arcelin and 7S alpha. Additional preferred promoters are enhanced or duplicated versions of the CaMV 35S and FMV 35S promoters. Odell et al., *Nature* 313: 810-812 (1985); U.S. Pat. No. 5,378,619. Additional promoters that may be utilized are described, for example, in U.S. Pat. Nos. 5,378, 619; 5,391,725; 5,428,147; 5,447,858; 5,608,144; 5,608, 144; 5,614,399; 5,633,441; 5,633,435; and 4,633,436. In addition, a tissue specific enhancer may be used.

Particularly preferred promoters can also be used to express a nucleic acid molecule of the present invention in seeds or fruits. Indeed, in a preferred embodiment, the promoter used is a seed specific promoter. Examples of such promoters include the 5' regulatory regions from such genes as napin (Kridl et al., *Seed Sci. Res.* 1:209-219 (1991)), phaseolin, stearoyl-ACP desaturase, 7Sα, 7Sα' (Chen et al., *Proc. Natl. Acad. Sci.*, 83:8560-8564 (1986)), USP, arcelin and oleosin. Preferred promoters for expression in the seed are 7Sα, 7Sα', napin, and FAD2-1A promoters.

Constructs or vectors may also include other genetic elements, including but not limited to, 3' transcriptional terminators, 3' polyadenylation signals, other untranslated nucleic acid sequences, transit or targeting sequences, selectable or screenable markers, promoters, enhancers, and operators. Constructs or vectors may also contain a promoterless gene that may utilize an endogenous promoter upon insertion.

Nucleic acid molecules that may be used in plant transformation or transfection may be any of the nucleic acid molecules of the present invention. It is not intended that the present invention be limited to the illustrated embodiments.

Exemplary nucleic acid molecules have been described in Part A of the Detailed Description, and further non-limiting exemplary nucleic acid molecules are described below and illustrated in FIGS. 1-4, and in the Examples.

Referring now to the drawings, embodiments of the nucleic acid molecule of the present invention are shown in FIGS. 1-4. As described above, the nucleic acid molecule comprises (a) a first set of DNA sequences and (b) a second set of DNA sequences, which are located on one or more T-DNA regions, each of which is flanked by a right border and a left border. Within the T-DNA regions the direction of transcription is shown by arrows. The nucleic acid molecules described may have their DNA sequences arranged in monocistronic or polycistronic configurations. Preferred configurations include a configuration in which the first set of DNA sequences and the second set of DNA sequences are located on a single T-DNA region.

In each of the illustrated embodiments, the first set of DNA sequences comprises one or more sequences which when expressed are capable of selectively reducing one, two or all of the proteins and transcripts encoded by a gene selected from the group consisting of FAD2, FAD3, and FATB. Preferably each sequence in the first set of DNA sequences is capable, when expressed, of suppressing the expression of a different gene, including without limitation different gene family members. The sequences may include coding sequences, intron sequences, 3'UTR sequences, 5'UTR sequences, other non-coding sequences, or any combination of the foregoing. The first set of DNA sequences may be expressed in any suitable form, including as a dsRNA construct, a sense cosuppression construct, or as an antisense construct. The first set of DNA sequences is operably linked to at least one promoter which drives expression of the sequences, which can be any promoter functional in a plant, or any plant promoter. Preferred promoters include, but are not limited to, a napin promoter, a 7Sα promoter, a 7Sα' promoter, an arcelin promoter, or a FAD2-1A promoter.

The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which can be any promoter functional in a plant, or any plant promoter. Preferred promoters for use in the second set of DNA sequences are an FMV promoter and/or seed-specific promoters. Particularly preferred seed-specific promoters include, but are not limited to, a napin promoter, a 7Sα promoter, a 7Sα' promoter, an arcelin promoter, a delta-9 desaturase promoter, or a FAD2-1A promoter.

Figure 2:
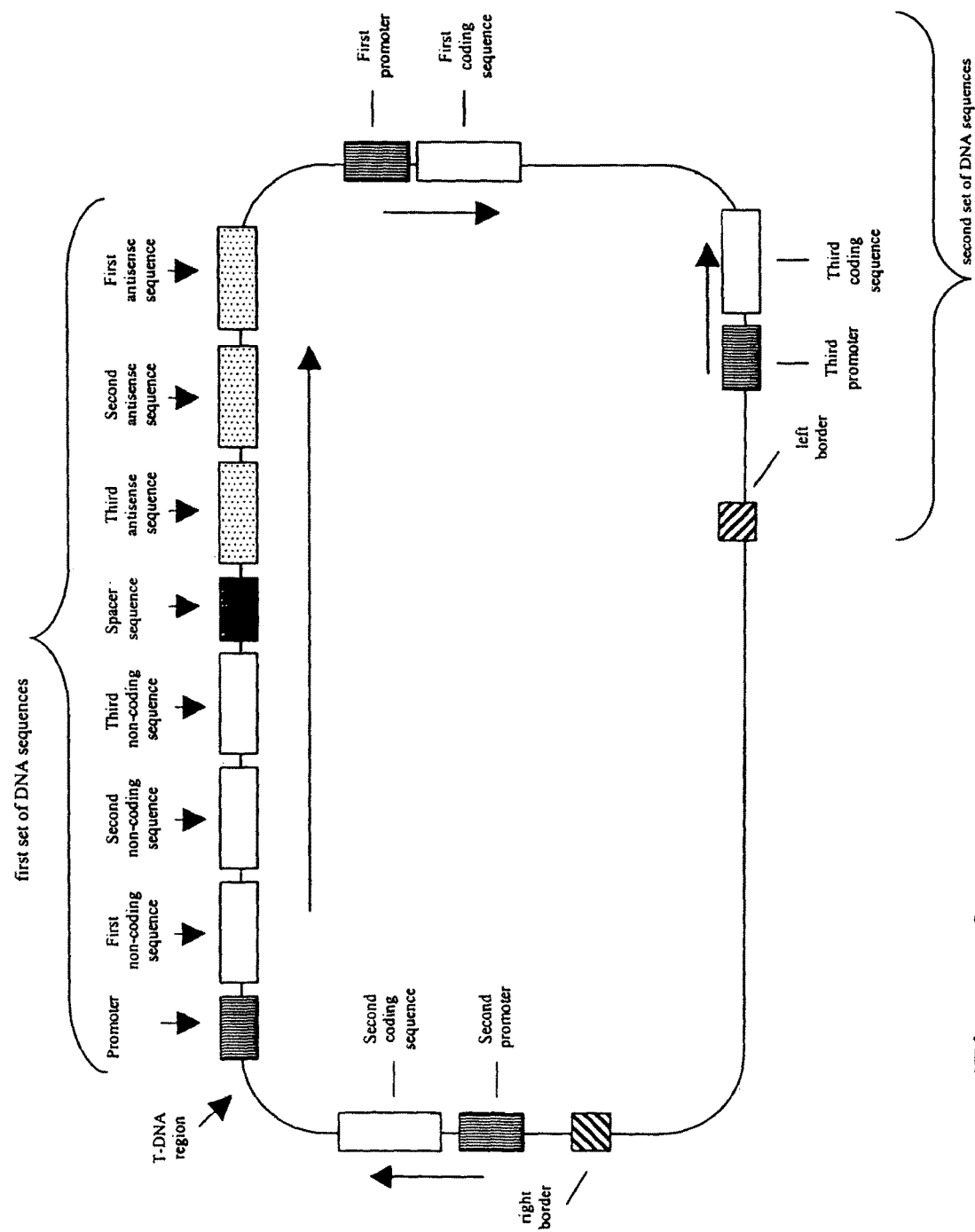

In the embodiments depicted in FIGS. 1 and 2, the first set of DNA sequences, when expressed, is capable of forming a dsRNA molecule that is capable of suppressing the expression of one or both of the protein and transcript encoded by, or transcribed from, a gene selected from the group consisting of FAD2, FAD3, and FATB. The first set of DNA sequences depicted in FIG. 1 comprises three non-coding sequences, each of which expresses an RNA sequence (not shown) that exhibits identity to a non-coding region of a gene selected from the group consisting of FAD2, FAD3, and FATB genes. The non-coding sequences each express an RNA sequence that exhibits at least 90% identity to a non-coding region of a gene selected from the group consisting of FAD2, FAD3, and FATB genes. The first set of DNA sequences also comprises three antisense sequences, each of which expresses an antisense RNA sequence (not shown) that is capable of forming a double-stranded RNA molecule with its respective corresponding RNA sequence (as expressed by the non-coding sequences).

The non-coding sequences may be separated from the antisense sequences by a spacer sequence, preferably one that promotes the formation of a dsRNA molecule. Examples of such spacer sequences include those set forth in Wesley et al., *Plant J.*, 27 (6):581-90 (2001), and Hamilton et al., *Plant J.*, 15:737-746 (1988). In a preferred aspect, the spacer sequence is capable of forming a hairpin structure as illustrated in Wesley et al., supra. Particularly preferred spacer sequences in this context are plant introns or parts thereof. A particularly preferred plant intron is a spliceable intron. Spliceable introns include, but are not limited to, an intron selected from the group consisting of PDK intron, FAD3-1A or FAD3-1B intron #5, FAD3 intron #1, FAD3 intron #3A, FAD3 intron #3B, FAD3 intron #3C, FAD3 intron #4, FAD3 intron #5, FAD2 intron #1, and FAD2-2 intron. Preferred spliceable introns include, but are not limited to, an intron selected from the group consisting of FAD3 intron #1, FAD3 intron #3A, FAD3 intron #3B, FAD3 intron #3C, and FAD3 intron #5. Other preferred spliceable introns include, but are not limited to, a spliceable intron that is about 0.75 kb to about 1.1 kb in length and is capable of facilitating an RNA hairpin structure. One non-limiting example of a particularly preferred spliceable intron is FAD3 intron #5.

The sense-oriented, non-coding molecules may be optionally separated from the corresponding antisense-oriented molecules by a spacer segment of DNA. The spacer segment can be a gene fragment or artificial DNA. The spacer segment can be short to facilitate forming hairpin dsRNA or long to facilitate dsRNA without a hairpin structure. The spacer can be provided by extending the length of one of the sense or antisense molecules as disclosed in US 2005/0176670 A1. Alternatively, a right-border-right-border ("RB-RB") sequence can be created after insertion into the plant genome as disclosed in U.S. Patent Application Publication 2005/0183170.

Referring now to FIG. 1, the nucleic acid molecule comprises two T-DNA regions, each of which is flanked by a right border and a left border. The first T-DNA region comprises the first set of DNA sequences that is operably linked to a promoter, and the first T-DNA region further comprises a first part of the second set of DNA sequences that comprises a first promoter operably linked to a first coding sequence, and a second promoter operably linked to a second coding sequence. The second T-DNA region comprises a second part of the second set of DNA sequences that comprises a third promoter operably linked to a third coding sequence. In a preferred embodiment depicted in FIG. 2, the nucleic acid molecule comprises a single T-DNA region, which is flanked by a right border and a left border. The first and second sets of DNA sequences are all located on the single T-DNA region.

In the dsRNA-expressing embodiments shown in FIGS. 1 and 2, the order of the sequences may be altered from that illustrated and described, however the non-coding sequences and the antisense sequences preferably are arranged around the spacer sequence such that, when expressed, the first non-coding sequence can hybridize to the first antisense sequence, the second non-coding sequence can hybridize to the second antisense sequence, and the third non-coding sequence can hybridize to the third antisense sequence such that a single dsRNA molecule can be formed. Preferably the non-coding sequences are in a sense orientation, and the antisense sequences are in an antisense orientation relative to the promoter. The numbers of non-coding, antisense, and coding sequences, and the various relative positions thereof on the T-DNA region(s) may also be altered in any manner suitable for achieving the goals of the present invention.

Figure 3:
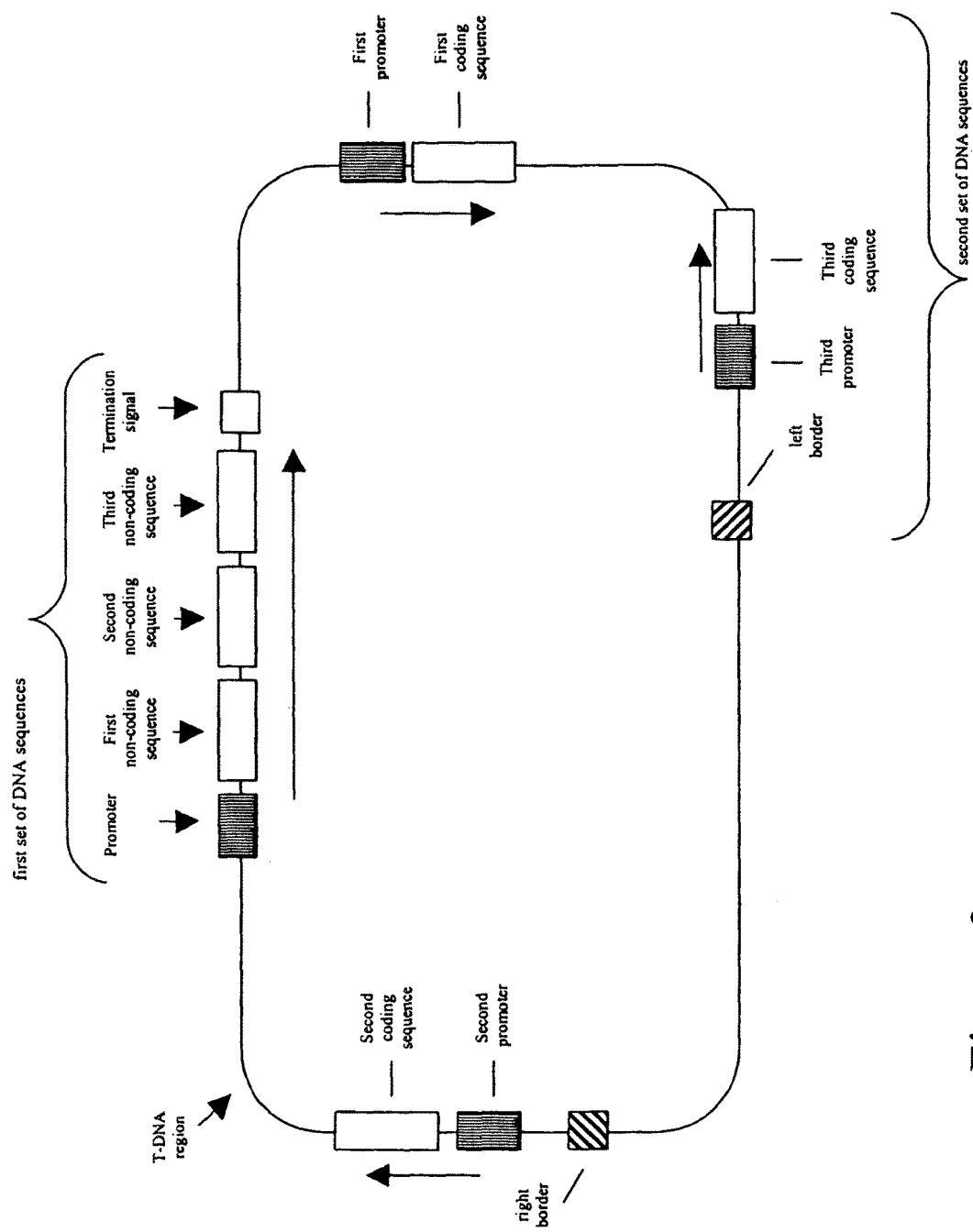
Figure 4:
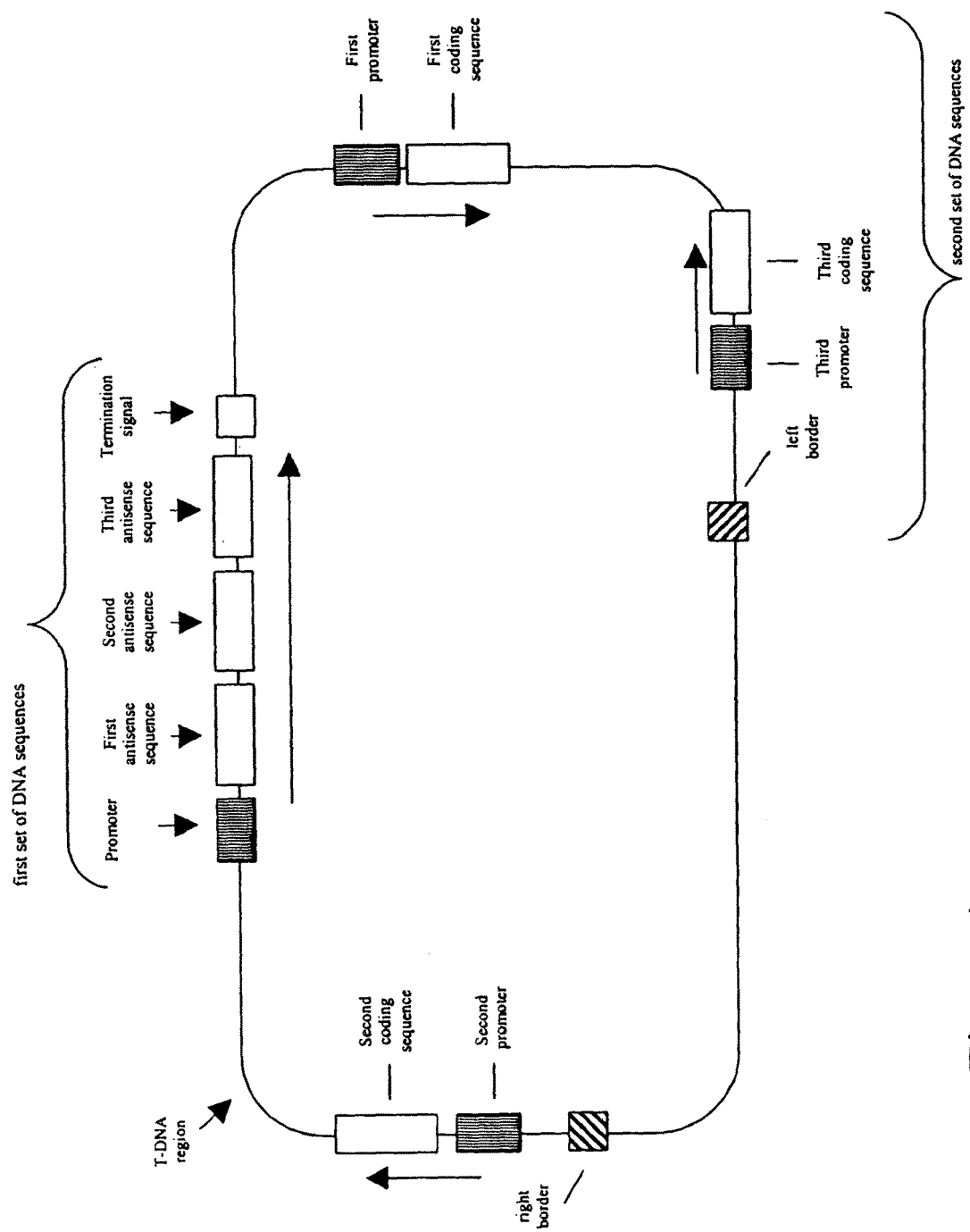

Referring now to FIGS. 3 and 4, the illustrated nucleic acid molecule comprises a T-DNA region flanked by a right border and a left border, on which are located the first and second sets of DNA sequences. The first set of DNA sequences is operably linked to a promoter and a transcriptional termination signal. The second set of DNA sequences that comprises a first promoter operably linked to a first coding sequence, a second promoter operably linked to a second coding sequence, and a third promoter operably linked to a third coding sequence. The transcriptional termination signal can be any transcriptional termination signal functional in a plant, or any plant transcriptional termination signal. Preferred transcriptional termination signals include, but are not limited to, a pea Rubisco E9 3' sequence, a *Brassica* napin 3' sequence, a tml 3' sequence, and a nos 3' sequence.

In the embodiment depicted in FIG. 3, the first set of DNA sequences, when expressed, is capable of forming a sense cosuppression construct that is capable of suppressing the expression of one or more proteins or transcripts encoded by, or derived from, a gene selected from the group consisting of FAD2, FAD3, and FATB. The first set of DNA sequences comprises three non-coding sequences, each of which expresses an RNA sequence (not shown) that exhibits sufficient identity to one or more non-coding region(s) of a gene selected from the group consisting of FAD2, FAD3, and FATB genes. The non-coding sequences each express an RNA sequence that exhibits at least 90% identity to one or more non-coding region(s) of a gene selected from the group consisting of FAD2, FAD3, and FATB genes. The order of the non-coding sequences within the first set of DNA sequences may be altered from that illustrated and described herein, but the non-coding sequences are arranged in a sense orientation relative to the promoter.

FIG. 4 depicts an embodiment in which the first set of DNA sequences, when expressed, is capable of forming an antisense construct that is capable of suppressing the expression of one or more proteins or transcripts encoded by, or derived from, a gene selected from the group consisting of FAD2, FAD3, and FATB. The first set of DNA sequences comprises three antisense sequences, each of which expresses an antisense RNA sequence (not shown) that exhibits identity to one or more non-coding region(s) of a gene selected from the group consisting of FAD2, FAD3, and FATB genes. The antisense sequences each express an antisense RNA sequence that exhibits at least 90% identity to one or more non-coding region(s) of a gene selected from the group consisting of FAD2, FAD3, and FATB genes. The order of the antisense sequences within the first set of DNA sequences may be altered from that illustrated and described herein, but the antisense sequences are arranged in an antisense orientation relative to the promoter.

The above-described nucleic acid molecules are preferred embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as described herein and illustrated in the accompanying drawings.

E. Transgenic Organisms, and Methods for Producing Same

Any of the nucleic acid molecules and constructs of the invention may be introduced into a plant or plant cell in a permanent or transient manner. Preferred nucleic acid molecules and constructs of the present invention are described above in Parts A through D of the Detailed Description, and in the Examples. Another embodiment of the invention is directed to a method of producing transgenic plants which generally comprises the steps of selecting a suitable plant or plant cell, transforming the plant or plant cell with a recombinant vector, and obtaining a transformed host cell.

In a preferred embodiment the plant or cell is, or is derived from, a plant involved in the production of vegetable oils for edible and industrial uses. Especially preferred are temperate oilseed crops. Plants of interest include, but are not limited to, rapeseed (canola and High Erucic Acid varieties), maize, soybean, crambe, mustard, castor bean, peanut, sesame, cotton, linseed, safflower, oil palm, flax, sunflower, and coconut. The invention is applicable to monocotyledonous or dicotyledonous species alike, and will be readily applicable to new and/or improved transformation and regulatory techniques.

Methods and technology for introduction of DNA into plant cells are well known to those of skill in the art, and virtually any method by which nucleic acid molecules may be introduced into a cell is suitable for use in the present invention. Non-limiting examples of suitable methods include: chemical methods; physical methods such as micro-injection, electroporation, the gene gun, microprojectile bombardment, and vacuum infiltration; viral vectors; and receptor-mediated mechanisms. Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

*Agrobacterium*-mediated transfer is a widely applicable system for introducing genes into plant cells. See, e.g., Fraley et al., *Bio/Technology* 3:629-635 (1985); Rogers et al., *Methods Enzymol.* 153:253-277 (1987). The region of DNA to be transferred is defined by the border sequences and intervening DNA is usually inserted into the plant genome. Spielmann et al., *Mol. Gen. Genet.* 205:34 (1986). Modem *Agrobacterium* transformation vectors are capable of replication in *E. coli* as well as *Agrobacterium*, allowing for convenient manipulations. Klee et al., In: *Plant DNA Infectious Agents*, Hohn and Schell (eds.), Springer-Verlag, New York, pp. 179-203 (1985).

The regeneration, development and cultivation of plants from single plant protoplast transformants or from various transformed explants is well known in the art. See generally, Maliga et al., *Methods in Plant Molecular Biology*, Cold Spring Harbor Press (1995); Weissbach and Weissbach, In: *Methods for Plant Molecular Biology*, Academic Press, San Diego, Calif. (1988). Plants of the present invention can be part of or generated from a breeding program, and may also be reproduced using apomixis. Methods for the production of apomictic plants are known in the art. See, e.g., U.S. Pat. No. 5,811,636.

In a preferred embodiment, a plant of the present invention that includes nucleic acid sequences which when expressed are capable of selectively reducing the level of a FAD2, FAD3, and/or FATB protein, and/or a FAD2, FAD3, and/or FATB transcript is crossed with another plant of the present invention that includes nucleic acid sequences which when expressed are capable of overexpressing another enzyme. Preferably the other enzyme is selected from the group consisting of beta-ketoacyl-ACP synthase I, beta-ketoacyl-ACP synthase IV, delta-9 desaturase, and CP4 EPSPS.

In another aspect, a plant of the present invention can be crossed with another plant that is transgenic or non-transgenic. A plant of the present invention can be crossed with another plant that has an oil composition containing modified levels of fatty acids, for example without limitation, a variety with an oil composition having a lower level of linolenic acid. In a preferred embodiment, a plant of the present invention is crossed with a variety with less than 3% by weight linolenic acid, or in another embodiment, a plant of the present invention is crossed with another plant having greater than 20% by weight stearic acid. Such plants having modified levels of fatty acids are known in the art and described, for example, in Hawkins and Kridl (1998) Plant Journal 13(6):743-752 and U.S. Pat. No. 6,365,802.

F. Products of the Present Invention

The plants of the present invention may be used in whole or in part. Preferred plant parts include reproductive or storage parts. The term "plant parts" as used herein includes, without limitation, seed, endosperm, ovule, pollen, roots, tubers, stems, leaves, stalks, fruit, berries, nuts, bark, pods, seeds and flowers. In a particularly preferred embodiment of the present invention, the plant part is a seed.

Any of the plants or parts thereof of the present invention may be processed to produce a feed, meal, protein, or oil preparation. In a preferred embodiment of the present invention can be a plant of the present invention having an oil with a fatty acid composition of the present invention. A particularly preferred plant part for this purpose is a seed. In a preferred embodiment the feed, meal, protein or oil preparation is designed for livestock animals, fish or humans, or any combination. Methods to produce feed, meal, protein and oil preparations are known in the art. See, e.g., U.S. Pat. Nos. 4,957,748, 5,100,679, 5,219,596, 5,936,069, 6,005,076, 6,146,669, and 6,156,227. In a preferred embodiment, the protein preparation is a high protein preparation. Such a high protein preparation preferably has a protein content of greater than 5% w/v, more preferably 10% w/v, and even more preferably 15% w/v.

In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10 or 50 liters. The present invention provides for oil produced from plants of the present invention or generated by a method of the present invention. Such an oil may exhibit enhanced oxidative stability. Also, such oil may be a minor or major component of any resultant product.

Moreover, such oil may be blended with other oils. In a preferred embodiment, the oil produced from plants of the present invention or generated by a method of the present invention constitutes greater than 0.5%, 1%, 5%, 10%, 25%, 50%, 75% or 90% by volume or weight of the oil component of any product. In another embodiment, the oil preparation may be blended and can constitute greater than 10%, 25%, 35%, 50% or 75% of the blend by volume. Oil produced from a plant of the present invention can be admixed with one or more organic solvents or petroleum distillates.

Seeds of the plants may be placed in a container. As used herein, a container is any object capable of holding such seeds. A container preferably contains greater than about 500, 1,000, 5,000, or 25,000 seeds where at least about 10%, 25%, 50%, 75% or 100% of the seeds are derived from a plant of the present invention. The present invention also provides a container of over about 10,000, more preferably about 20,000, and even more preferably about 40,000 seeds where over about 10%, more preferably about 25%, more preferably 50% and even more preferably about 75% or 90% of the seeds are seeds derived from a plant of the present invention. The present invention also provides a container of over about 10 kg, more preferably about 25 kg, and even more preferably about 50 kg seeds where over about 10%, more preferably about 25%, more preferably about 50% and even more preferably about 75% or 90% of the seeds are seeds derived from a plant of the present invention.

G. Oil Compositions

For many oil applications, saturated fatty acid levels are preferably less than 8% by weight, and more preferably about 2-3% by weight. Saturated fatty acids have high melting points which are undesirable in many applications. When used as a feedstock or fuel, saturated fatty acids cause clouding at low temperatures, and confer poor cold flow properties such as pour points and cold filter plugging points to the fuel. Oil products containing low saturated fatty acid levels may be preferred by consumers and the food industry because they are perceived as healthier and/or may be labeled as "saturated fat free" in accordance with FDA guidelines. In addition, low saturate oils reduce or eliminate the need to winterize the oil for food applications such as salad oils. In biodiesel and lubricant applications oils with low saturated fatty acid levels confer improved cold flow properties and do not cloud at low temperatures.

The factors governing the physical properties of a particular oil are complex. Palmitic, stearic and other saturated fatty acids are typically solid at room temperature, in contrast to the unsaturated fatty acids, which remain liquid. Because saturated fatty acids have no double bonds in the acyl chain, they remain stable to oxidation at elevated temperatures. Saturated fatty acids are important components in margarines and chocolate formulations, but for many food applications, reduced levels of saturated fatty acids are desired.

Oleic acid has one double bond, but is still relatively stable at high temperatures, and oils with high levels of oleic acid are suitable for cooking and other processes where heating is required. Recently, increased consumption of high oleic oils has been recommended, because oleic acid appears to lower blood levels of low density lipoproteins ("LDLs") without affecting levels of high density lipoproteins ("HDLs"). However, some limitation of oleic acid levels is desirable, because when oleic acid is degraded at high temperatures, it creates negative flavor compounds and diminishes the positive flavors created by the oxidation of linoleic acid. Neff et al., *JAOCS*, 77:1303-1313 (2000); Warner et al., *J. Agric. Food Chem.* 49:899-905 (2001). Preferred oils have oleic acid levels that are 65-85% or less by weight, in order to limit off-flavors in food applications such as frying oil and fried food. Other preferred oils have oleic acid levels that are greater than 55% by weight in order to improve oxidative stability.

Linoleic acid is a major polyunsaturated fatty acid in foods and is an essential nutrient for humans. It is a desirable component for many food applications because it is a major precursor of fried food flavor substances such as 2,4 decadienal, which make fried foods taste good. However, linoleic acid has limited stability when heated. Preferred food oils have linoleic acid levels that are 10% or greater by weight, to enhance the formation of desirable fried food flavor substances, and also are 25% or less by weight, so that the formation of off-flavors is reduced. Linoleic acid also has cholesterol-lowering properties, although dietary excess can reduce the ability of human cells to protect themselves from oxidative damage, thereby increasing the risk of cardiovascular disease. Toborek et al., *Am J. Clin. J.* 75:119-125 (2002). See generally *Flavor Chemistry of Lipid Foods*, editors D. B. Min & T. H. Smouse, Am Oil Chem. Soc., Champaign, Ill. (1989).

Linoleic acid, having a lower melting point than oleic acid, further contributes to improved cold flow properties desirable in biodiesel and biolubricant applications. Preferred oils for most applications have linoleic acid levels of 30% or less by weight, because the oxidation of linoleic acid limits the useful storage or use-time of frying oil, food, feed, fuel and lubricant products. See generally, *Physical Properties of Fats, Oils, and Emulsifiers*, ed. N. Widlak, AOCS Press (1999); Erhan & Asadauskas, *Lubricant Basestocks from Vegetable Oils, Industrial Crops and Products*, 11:277-282 (2000). In addition, high linoleic acid levels in cattle feed can lead to undesirably high levels of linoleic acid in the milk of dairy cattle, and therefore poor oxidative stability and flavor. Timmons et al., *J. Dairy Sci.* 84:2440-2449 (2001). A broadly useful oil composition has linoleic acid levels of 10-25% by weight.

Linolenic acid is also an important component of the human diet. It is used to synthesize the ω-3 family of long-chain fatty acids and the prostaglandins derived therefrom. However, its double bonds are highly susceptible to oxidation, so that oils with high levels of linolenic acid deteriorate rapidly on exposure to air, especially at high temperatures. Partial hydrogenation of such oils is often necessary before they can be used in food products to retard the formation of off-flavors and rancidity when the oil is heated, but hydrogenation creates unhealthy trans fatty acids which can contribute to cardiovascular disease. To achieve improved oxidative stability, and reduce the need to hydrogenate oil, preferred oils have linolenic acid levels that are 8% or less by weight, 6% or less, 4% or less, less than about 3%, and more preferably 0.5-2% by weight of the total fatty acids in the oil of the present invention.

Oil from soybean of the present invention can also be used as a blending source to make a blended oil product. By a blending source, it is meant that the oil from a soybean of the present invention can be mixed with other vegetable oils to improve the characteristics, such as fatty acid composition, flavor, and oxidative stability, of the other oils. The amount of oil from a soybean of the present invention which can be used will depend upon the desired properties sought to be achieved in the resulting final blended oil product. Examples of blended oil products include, but are not limited to, margarines, shortenings, frying oils, salad oils, etc. The oil from a soybean of the present invention can be a blended oil, synthesized oil or in a preferred embodiment an oil generated from an oilseed having an appropriate oil composition. An oil generated directly from an oilseed is a non-blended oil. In another aspect, an oil is directly from a mature oilseed. In this aspect, a mature seed as defined by a seed that is harvested in the field for commercial agricultural practices, such as sale for feed. In a preferred embodiment, the oil is a soybean oil. The oil can be a crude oil such as crude soybean oil, or can be a processed oil, for example the oil can be refined, bleached, deodorized, and/or winterized. As used herein, "refining" refers to a process of treating natural or processed fat or oil to remove impurities, and may be accomplished by treating fat or oil with caustic soda, followed by centrifugation, washing with water, and heating under vacuum. "Bleaching" refers to a process of treating a fat or oil to remove or reduce the levels of coloring materials in the fat or oil. Bleaching may be accomplished by treating fat or oil with activated charcoal or Fullers (diatomaceous) earth. "Deodorizing" refers to a process of removing components from a fat or oil that contribute objectionable flavors or odors to the end product, and may be accomplished by use of high vacuum and superheated steam washing. "Winterizing" refers to a process of removing saturated glycerides from an oil, and may be accomplished by chilling and removal of solidified portions of fat from an oil.

A preferred oil of the present invention has a low saturate oil composition, or a zero saturate oil composition. In other preferred embodiments, oils of the present invention have increased oleic acid levels, reduced saturated fatty acid levels, and reduced polyunsaturated fatty acid levels. In further preferred embodiments, oils of the present invention have increased oleic acid levels and reduced saturated fatty acid levels. In a preferred embodiment, the oil is a soybean oil. The percentages of fatty acid content, or fatty acid levels, used herein refer to percentages by weight.

In a first embodiment, an oil of the present invention preferably has an oil composition that is 55 to 80% oleic acid, about 12 to 43% polyunsaturates, and 2 to 8% saturated fatty acids; more preferably has an oil composition that is 55 to 80% oleic acid, about 14 to 42% polyunsaturates, and 3 to 6% saturated fatty acids; and even more preferably has an oil composition that is 55 to 80% oleic acid, about 16.5 to 43% polyunsaturates, and 2 to 3.6% saturated fatty acids.

In a second embodiment, an oil of the present invention preferably has an oil composition that is 65 to 80% oleic acid, about 12 to 33% polyunsaturates, and 2 to 8% saturated fatty acids; more preferably has an oil composition that is 65 to 80% oleic acid, about 14 to 32% polyunsaturates, and 3 to 6% saturated fatty acids; and even more preferably has an oil composition that is 65 to 80% oleic acid, about 16.5 to 33% polyunsaturates, and 2 to 3.6% saturated fatty acids.

In a third embodiment, an oil of the present invention preferably has an oil composition that is about 42 to about 85% oleic acid and about 8% to about 1.5% saturated fatty acids; more preferably the oil composition further has a combined amount of oleic acid and linolenic acid equaling about 65% to about 95% by weight of the total oil composition. Even more preferably the oil composition of the present invention has a combined amount of oleic acid and linolenic acid equaling about 75% to about 90%, about 75% to about 95%, about 75% to about 85%, about 65% to about 90%, about 70% to about 90% by weight of the total oil composition.

In a fourth embodiment, an oil of the present invention has an oil composition that is about 42 to about 85% oleic acid, about 8% to about 1.5% saturated fatty acids, about 6% to about 15% by weight linolenic acid; more preferably has an oil composition that is about 42 to about 85% oleic acid, about 8% to about 1.5% saturated fatty acids, less than 35% by weight linolenic acid; and even more preferably has an oil composition that is about 42 to about 85% oleic acid, about 8% to about 1.5% saturated fatty acids, about 9% by weight linolenic acid.

In a fifth embodiment, an oil of the present invention has an oil composition that is about 50% to about 85% oleic acid and about 8% to about 1.5% saturated fatty acids; more preferably about 50% to about 85% oleic acid, about 8% to about 1.5% saturated fatty acids, about 4% to about 14% by weight linolenic acid; more preferably has an oil composition that is about 50% to about 85% oleic acid, about 8% to about 1.5% saturated fatty acids, less than 35% by weight linolenic acid; and even more preferably has an oil composition that is about 42 to about 85% oleic acid, about 8% to about 1.5% saturated fatty acids, about 2% to about 45% by weight linolenic acid.

In another embodiment, an oil of the present invention has an oil composition that is about 65-80% oleic acid, about 3-8% saturates, and about 12-32% polyunsaturates. In another embodiment, an oil of the present invention has an oil composition that is about 65-80% oleic acid, about 2-3.5% saturates, and about 16.5-33% polyunsaturates.

In a particularly preferred embodiment, an oil of the present invention has an oil composition that is about 47-83% oleic acid and about 5% saturates; about 60-80% oleic acid and about 5% saturates; about 50-85% oleic and about 2-7% saturates; about 55-85% oleic acid and about 2.5-7% saturates; about 47-88% oleic acid and about 3-7% saturates; about 43-85% oleic acid and about 5-7% saturates; about 81-85% oleic acid and about 5% saturates; about 74-83% oleic acid and about 6% saturates; about 65-87% oleic acid and about 6% saturates; about 66-80% oleic acid and about 6% saturates; about 42-77% oleic acid and about 5-8% saturates; about 60-77% oleic acid and about 6% saturates; about 70-81% oleic acid and about 5-7% saturates; about 52-71% oleic acid and about 5-7% saturates; about 44-71% oleic acid and about 6% saturates; about 61-71% oleic acid and about 8% saturates; about 57-71% oleic acid and about 7% saturates; about 23-58% oleic acid and about 8-14% saturates; about 20-70% oleic acid and about 6% saturates; about 21-35% oleic acid and about 5-6% saturates; or about 19-28% oleic acid and about 5% saturates.

In other embodiments, the percentage of oleic acid is 50% or greater; 55% or greater; 60% or greater; 65% or greater; 70% or greater; 75% or greater; or 80% or greater; or is a range from 50 to 80%; 55 to 80%; 55 to 75%; 55 to 65%; 60 to 85%; 60 to 80%; 60 to 75%; 60 to 70%; 65 to 85%; 65 to 80%; 65 to 75%; 65 to 70%; or 69 to 73%. Suitable percentage ranges for oleic acid content in oils of the present invention also include ranges in which the lower limit is selected from the following percentages: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 percent; and the upper limit is selected from the following percentages: 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 percent.

In these other embodiments, the percentage of linoleic acid in an oil of the present invention is a range from 10 to 40%; 10 to 39%; 10 to 30%; 10 to 29%; 10 to 28%; 10 to 25%; 10 to 21%; 10 to 20%; 11 to 30%; 12 to 30%; 15 to 25%; 20 to 25%; 20 to 30%; or 21 to 24%. Suitable percentage ranges for linoleic acid content in oils of the present invention also include ranges in which the lower limit is selected from the following percentages: 10, 11, 12, 13, 14, 15, 16, 17, 18, 19, 20, 21, 22, 23, 24, 25, 26, 27, 28, 29, or 30 percent; and the upper limit is selected from the following percentages: 20, 21, 22, 23, 24, 25, 26, 27, 28, 29, 30, 31, 32, 33, 34, 35, 36, 37, 38, 39, or 40 percent.

In these other embodiments, the percentage of linolenic acid in an oil of the present invention is 10% or less; 9% or less; 8% or less; 7% or less; 6% or less; 5% or less; 4.5% or less; 4% or less; 3.5% or less; 3% or less; 3.0% or less; 2.5% or less; or 2% or less; or is a range from 0.5 to 2%; 0.5 to 3%; 0.5 to 4.5%; 0.5 to 6%; 3 to 5%; 3 to 6%; 3 to 8%; 1 to 2%; 1 to 3%; or 1 to 4%. In these other embodiments, the percentage of saturated fatty acids in an oil composition of the present invention is 15% or less; 14% or less; 13% or less; 12% or less, 11% or less; 10% or less; 9% or less; 8% or less; 7% or less; 6% or less; 5% or less; 4% or less; or 3.6% or less; or is a range from 2 to 3%; 2 to 3.6%; 2 to 4%; 2 to 8%; 3 to 15%; 3 to 10%; 3 to 8%; 3 to 6%; 3.6 to 7%; 5 to 8%; 7 to 10%; or 10 to 15%.

In other embodiments, saturated fatty acids in an oil of the present invention includes the combination of the palmitic and stearic fatty acids. In an embodiment, the percentage of saturated fatty acids ranges from about 10% or less; about 9% or less; about 8% or less; about 7% or less; about 6% or less; about 5% or less; about 4.5% or less; about 4% or less; about 3.5% or less; about 3% or less; about 3.0% or less; about 2.5% or less; or about 2% or less; or is a range from 0.5 to 2%; 0.5 to 3%; 0.5 to 4.5%; 0.5 to 6%; 0.5 to 7%; 0.5 to 8%; 0.5 to 9%; 1 to 4%; 1 to 5%; 1 to 6%; 1 to 7%; 1 to 8%; 1 to 9%; 1.5 to 5%; 1.5 to 6%; 1.5 to 7%; 1.5 to 8%; 1.5 to 9%; 2 to 5%; 2 to 6%; 2 to 7%; 2 to 8%; 2 to 9%; 3 to 5%; 3 to 6%; 3 to 7%; 3 to 8%; 3 to 9%; 4 to 7%; 4 to 8%; 4 to 9%; 5 to 7%; 5 to 8%; and 5 to 9%. In these embodiments, suitable percentage ranges for saturated fatty acid content in oils of the present invention also include ranges in which the lower limit is selected from the following percentages: 0.5, 1, 1.5, 2, 2.5, 3, 3.5, 4, 4.5, 5, 5.5, 6, or 6.5 percent; and the upper limit is selected from the following percentages: 11, 10, 9, 8, 7, 6, 5, 4.5, 4, 3.5, 3, 2.5, 2, 1.5, 1, or 0.5 percent.

In other embodiments, the percentage of palmitic fatty acid in an oil composition of the present invention ranges from 6% or less; 5% or less; 4.5% or less; 4% or less; 3.5% or less; 3% or less; 3.0% or less; 2.5% or less; or 2% or less; or is a range from 0.5 to 2%; 0.5 to 3%; 0.5 to 4.5%; 0.5 to 6%; 1 to 3%; 1 to 4%; 1 to 5%; 1 to 6%; 1.5 to 2%; 1.5 to 3%; 1.5 to 4%; 1.5 to 4.5%; 1.5 to 5%; 1.5 to 5.5%; 1.5 to 6%; 1.5 to 6.5%; 1.5 to 7%; 2 to 3%; 2 to 3.5%; 2 to 4%; 2 to 4.5%; 2 to 5%; 2 to 6%; 2 to 7%; 2 to 8%; 3 to 5%; 3 to 6%; 3 to 7%; 3 to 8%; 3 to 9%. In these embodiments, suitable percentage ranges for linoleic acid content in oils of the present invention also include ranges in which the lower limit is selected from the following percentages: 0.5, 1, 1.5, 2, 2.5, 3, 3.5, 4, 4.5, 5, 5.5, 6, 6.5, 7 or 7.5 percent; and the upper limit is selected from the following percentages: 11, 10, 9, 8, 7, 6, 5, 4.5, 4, 3.5, 3, or 2 percent.

In other embodiments, the percentage of stearic fatty acid in an oil composition of the present invention is ranges from 3% or less; 3.0% or less; 2.5% or less; or 2% or less; or is a range from 0.5 to 1%; 0.5 to 1.5%; 0.5 to 2%; 0.5 to 2.5%; 0.5 to 3%; 0.5 to 4%; 1 to 2%; 1 to 3%; 1 to 4%; 1.5 to 2%; 1.5 to 3%; or 1.5 to 4%. In these embodiments, suitable percentage ranges for linoleic acid content in oils of the present invention also include ranges in which the lower limit is selected from the following percentages: 0.5, 1, 1.5, 2, 2.5, 3, or 3.5 percent; and the upper limit is selected from the following percentages: 3.5, 3, 2.5, 2, or 1.5 percent.

An oil of the present invention is particularly suited to use as a cooking or frying oil. Because of its reduced polyunsaturated fatty acid content, the oil of the present invention does not require the extensive processing of typical oils because fewer objectionable odorous and colorant compounds are present. In addition, the low saturated fatty acid content of the present oil improves the cold flow properties of the oil, and obviates the need to heat stored oil to prevent it from crystallizing or solidifying. Improved cold flow also enhances drainage of oil from fried food material once it has been removed from frying oil, thereby resulting in a lower fat product. See Bouchon et al., *J. Food Science* 66: 918-923 (2001). The low levels of linolenic acid in the present oil are particularly advantageous in frying to reduce off-flavors.

The present oil is also well-suited for use as a salad oil (an oil that maintains clarity at refrigerator temperatures of 40-50 degrees Fahrenheit). Its improved clarity at refrigerator temperatures, due to its low saturated fatty acid and moderate linoleic acid content, reduces or eliminates the need to winterize the oil before use as a salad oil.

In addition, the moderate linoleic and low linolenic acid content of the present oil make it well-suited for the production of shortening, margarine and other semi-solid vegetable fats used in foodstuffs. Production of these fats typically involves hydrogenation of unsaturated oils such as soybean oil, corn oil, or canola oil. The increased oxidative and flavor stability of the present oil mean that it need not be hydrogenated to the extent that typical vegetable oil is for uses such as margarine and shortening, thereby reducing processing costs and the production of unhealthy trans isomers.

An oil of the present invention is also suitable for use as a feedstock to produce biodiesel, particularly because biodiesel made from such an oil has improved cold flow, improved ignition quality (cetane number), improved oxidative stability, and reduced nitric oxide emissions. Biodiesel is an alternative diesel fuel typically comprised of methyl esters of saturated, monounsaturated, and polyunsaturated $C_{16}$-$C_{22}$ fatty acids. Cetane number is a measure of ignition quality—the shorter the ignition delay time of fuel in the engine, the higher the cetane number. The ASTM standard specification for biodiesel fuel (D 6751-02) requires a minimum cetane number of 47.

The use of biodiesel in conventional diesel engines results in substantial reductions of pollutants such as sulfates, carbon monoxide, and particulates compared to petroleum diesel fuel, and use in school buses can greatly reduce children's exposure to toxic diesel exhaust. A limitation to the use of 100% conventional biodiesel as fuel is the high cloud point of conventional soy biodiesel (2 degrees C.) compared to number 2 diesel (−16 degrees C.). Dunn et al., *Recent. Res. Devel. in Oil Chem.*, 1:31-56 (1997). Biodiesel made from oil of the present invention has an improved (reduced) cloud point and cold filter plugging point, and may also be used in blends to improve the cold-temperature properties of biodiesel made from inexpensive but highly saturated sources of fat such as animal fats (tallow, lard, chicken fat) and palm oil. Biodiesel can also be blended with petroleum diesel at any level.

Biodiesel is typically obtained by extracting, filtering and refining soybean oil to remove free fats and phospholipids, and then transesterifying the oil with methanol to form methyl esters of the fatty acids. See, e.g., U.S. Pat. No. 5,891,203. The resultant soy methyl esters are commonly referred to as "biodiesel." The oil of the present invention may also be used as a diesel fuel without the formation of methyl esters, such as, for example, by mixing acetals with the oil. See, e.g., U.S. Pat. No. 6,013,114. Due to its improved cold flow and oxidative stability properties, the oil of the present invention is also useful as a lubricant, and as a diesel fuel additive. See, e.g., U.S. Pat. Nos. 5,888,947, 5,454,842 and 4,557,734.

Soybeans and oils of the present invention are also suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed as is, spray-dried, or processed to form soy yogurt, soy cheese, tofu, or yuba. The present soybean or oil may be advantageously used in these and other soyfoods because of its improved oxidative stability, the reduction of off-flavor precursors, and its low saturated fatty acid level.

G. Modulation of Suppression

Another embodiment of the invention is directed to a method of modulating gene suppression levels. Modulation of gene suppression can result in more or less gene suppression. Suppression of a gene product can be the result from insertion of a construct of the present invention into a plant genome. Similarly, modulation of gene suppression can be the result from insertion of a construct of the present invention into a plant genome. Other examples of methods to modulate gene suppression include, without limitation, antisense techniques, cosuppression, RNA interference (dsRNAi), transgenic animals, hybrids, and ribozymes using a construct of the present invention. The following examples are provided by way of illustration, and are not intended to be limiting of the present invention.

Suppression of a gene can be modulated by altering the length of the transcribable DNA used for suppression, which sequence is derived from the gene targeted for suppression. Many methods can be used for suppressing a gene using post-transcriptional gene silencing mechanisms. Without being limited to the theory, these methods are believed to have in common the expression of an RNA molecule which hybridizes to another RNA molecule. Surprisingly, there can be advantages to using a RNA molecule of particular lengths to modulate or moderate suppression of the steady state expression levels of a targeted endogenous gene.

Gene suppression of FAD2-1 leads to elevated levels of oleic acid and reduction of linoleic acid levels. When FAD2-1 is heavily suppressed, levels of oleic acid can be greater than 65%, which causes a reduction in palmitic acid and linolenic acid levels. For example, when FAD2-1 is suppressed, oleic acid levels can reach 85% and the combined palmitic and stearic acid levels are reduced to about 10%. Similarly, downregulation of FATB results in decreased levels of saturated fatty acids, primarily palmitate. When FAD2 and FATB are suppressed so that oleic levels are about 85%, saturate levels are about 10%. When FAD2 and FATB are suppressed so that oleic levels are greater than 85%, saturate levels can fall below 10%.

In light of the present invention, saturate levels can be reduced to less than 10% without enhancing oleic acids above 85%. In one embodiment, the suppression of FAD2 is modulated by reducing the length of FAD2-1 intron introduced into the plant. Less suppression of FAD2 results in moderate levels of oleic acid, approximately 40-85% oleic acid. The suppression of FAD2 is reduced as the length of the FAD2-1 intron fragment introduced is reduced. For example, a FAD2-1 intron reduced in length by at least 100 contiguous nucleotides can reduce the suppression of FAD2 and the corresponding increase in oleic acid and decrease in linoleic acid levels.

The relationship between the decrease in endogenous gene suppression and the decrease in length of homologous DNA can be determined empirically by introducing different lengths of DNA. For example, the amount of reduction in suppression obtainable by reducing the length of homologous introduced DNA can be determined by deleting increasing portions of the homologous DNA being introduced and assaying for expression of the targeted gene.

Included in the present invention is a method for moderating suppression of FAD2 while still having a strong reduction of saturate levels in a plant. In such plants, oleic acid levels can range from 40-85%. Similarly, less than full suppression of FATB occurs when the combined 3' and 5' untranslated regions are introduced as compared to when the full-length FATB gene is introduced into a host cell. In a like manner, suppression levels of FATB are reduced when the 5' part of the open reading frame, which mostly encodes the chloroplast transit peptide, is introduced into a host cell. In cells with FAD2 and FATB suppressed using methods according to the present invention, oleic acid levels can be 40-85% while saturate levels can be between 1 to 9 percent.

In one embodiment, the present invention is directed to a method of modulating gene suppression to reduce suppression relative to the suppression from a entire gene element, where a entire gene element can be an entire gene, an entire exon, an entire intron, an entire signal sequence, or an entire UTR, then constructing a recombinant nucleic acid molecule comprising a fragment of the endogenous sequence from the gene element; initiating expression of the recombinant nucleic acid molecule in a host cell; and suppressing the endogenous gene with the recombinant nucleic acid molecule. The gene being suppressed can be any gene, including FAD2 and FATB. In one embodiment, the present invention is directed to a method of modulating FAD2 or FATB suppression comprising: expressing a partial FAD2 or FATB gene element sequence in a host cell, where a FAD2 or FATB gene element is from an endogenous FAD2 or FATB gene in the host cell and a FAD2 or FATB gene element sequence can be a FAD2 or FATB gene, a FAD2 or FATB exon, a FAD2 or FATB intron, a FAD2 or FATB transit peptide coding region, or a FAD2 or FATB UTR; and the partial FAD2 or FATB gene element sequence is less than the entire FAD2 or FATB gene element sequence; and suppressing an endogenous FAD2 or FATB with the partial FAD2 or FATB gene element sequence, where suppression levels of the FAD2 or FATB endogenous gene in the host cell are less than suppression levels of the FAD2 or FATB endogenous gene in a host cell with a similar genetic background and a second FAD2 or FATB nucleic acid sequence comprising the entire FAD2 or FATB gene element sequence of the FAD2 or FATB gene element.

In another embodiment, the present invention is directed to a method of altering the oil composition of a plant cell by transforming a plant cell with a recombinant nucleic acid molecule which comprises a DNA sequence that suppresses endogenous expression of FAD2, FATB, or FAD2 and FATB where the DNA sequence comprises a nucleic acid sequence of FAD2, FATB, or FAD2 and FATB that is shorter than the entire sequence of an entire genetic element selected from a gene, an exon, an intron, a transit peptide coding region, a 3'-UTR, a 5'-UTR, and an open reading frame; and growing the plant cell under conditions where transcription of said DNA sequence is initiated, whereby the oil composition is altered relative to a plant cell with a similar genetic background but lacking the recombinant nucleic acid molecule. A gene element of FAD2 or FATB can be shortened in length by 50, 75, 100, 150, 175, 200, 250, 300, 350, 400, 450, 500, 600, 800, 1000, 2000, 3000, or 4000 nucleotides. A length of a gene element of FAD2 or FATB can be 50, 75, 100, 150, 175, 200, 220, 250, 300, 320, 350, 400, 420, 450, 500, 550 600, 800, or 1000 nucleotides.

In another embodiment, the present invention is directed to a method of enhancing oleic acid content and reducing saturated fatty acid content in a plant seed by: i) shortening the length of an exogenous FAD2 DNA sequence in a host cell until the amount of suppression of FAD2 expression from a transformed plant is at least partially reduced relative to the suppression of FAD2 expression in a host cell with a similar genetic background and an entire exogenous FAD2 gene DNA sequence; and ii) growing a plant with a nucleic acid molecule comprising the shortened FAD2 DNA sequence, where the shortened FAD2 DNA sequence at least partially suppresses endogenous expression of FAD2; and iii) cultivating a plant that produces seed with a reduced saturated fatty acid content relative to seed from a plant having a similar genetic background but lacking the shortened FAD2 DNA sequence. The amount that the exogenous FAD2 DNA sequence is shortened to at least partially reduce suppression of the endogenous FAD2 can be determined empirically by introducing different lengths of DNA. For example, the amount of reduction in suppression obtainable by reducing the length of homologous introduced DNA can be determined by deleting increasing portions of the homologous DNA being introduced and assaying for expression of the targeted gene. The amount of suppression of FAD2 expression can be obtained as an average of three or more, six or more, ten or more, fifteen or more, or twenty or more seeds from a plant.

In another embodiment, the present invention is directed to a method of producing a transformed plant having seed with a reduced saturated fatty acid content by transforming a plant cell with a recombinant nucleic acid molecule which comprises a DNA sequence that suppresses the endogenous expression of FAD2 and FATB, where the DNA sequence comprises a nucleic acid sequence of FAD2 that is shorter than the entire sequence of an entire genetic element selected from a gene, an exon, an intron, a transit peptide coding region, and a UTR; and growing the transformed plant, where the transformed plant produces seed with a reduced saturated fatty acid content relative to seed from a plant having a similar genetic background but lacking said recombinant nucleic acid molecule.

In another embodiment, the present invention is directed to a method of modulating the fatty acid composition of oil from a seed of a temperate oilseed crop by isolating a genetic element of at least 40 nucleotides in length that is capable of suppressing the expression of an endogenous gene in the fatty acid synthesis pathway; generating more than one shortened fragment of the genetic element; introducing each of the more than one shortened fragments into a plant cell of the temperate oilseed crop to produce transgenic plants; and selecting a transgenic plant comprising a shortened fragment of determined length and sequence that effects a desirable change in seed oil fatty acid composition. In a preferred embodiment, the method above also includes constructing a recombinant DNA construct having at least two shortened fragments of two different endogenous genes that effect different desirable changes in seed oil fatty acid composition; introducing the recombinant DNA construct into a plant cell of the temperate oilseed crop to produce transgenic plants; and selecting a transgenic plant comprising the at least two shortened fragments and a fatty acid composition of oil from a seed having more than one desirable change effected by the at least two shortened fragments.

In another embodiment, the present invention is directed to a soybean seed exhibiting an oil composition having a strongly reduced saturated fatty acid content and a moderately enhanced oleic acid content having a DNA sequence that suppresses the endogenous expression of FAD2 in a host cell, where the DNA sequence has a nucleic acid sequence of FAD2 that is shorter than the entire sequence of an entire genetic element selected from a gene, an exon, an intron, a transit peptide coding region, and a UTR.

The following examples are illustrative and not intended to be limiting in any way.

All publications, patents, and patent applications mentioned in this specification are herein incorporated by reference to the same extent as if each individual publication, patent, or patent application was specifically and individually indicated to be incorporated by reference.

EXAMPLES

Example 1 Isolation of FATB-2 Sequences

Leaf tissue is obtained from Asgrow soy variety A3244, ground in liquid nitrogen and stored at −80° C. until use. Six ml of SDS Extraction buffer (650 ml sterile ddH$_2$O, 100 ml 1M Tris-Cl pH 8, 100 ml 0.25M EDTA, 50 ml 20% SDS, 100 ml 5M NaCl, 4 µl beta-mercaptoethanol) is added to 2 ml of frozen/ground leaf tissue, and the mixture is incubated at 65° C. for 45 minutes. The sample is shaken every 15 minutes. 2 ml of ice-cold 5M potassium acetate is added to the sample, the sample is shaken, and then is incubated on ice for 20 minutes. 3 ml of CHCl$_3$ is added to the sample and the sample is shaken for 10 minutes.

The sample is centrifuged at 10,000 rpm for 20 minutes and the supernatant is collected. 2 ml of isopropanol is added to the supernatant and mixed. The sample is then centrifuged at 10,000 rpm for 20 minutes and the supernatant is drained. The pellet is resuspended in 200l RNase and incubated at 65° C. for 20 minutes. 300l ammonium acetate/isopropanol (1:7) is added and mixed. The sample is then centrifuged at 10,000 rpm for 15 minutes and the supernatant is discarded. The pellet is rinsed with 500 µl 80% ethanol and allowed to air dry. The pellet of genomic DNA is then resuspended in 200 µl T10E1 (10 mM Tris:1 mM EDTA).

A soy FATB-2 cDNA contig sequence (SEQ ID NO: 42) is used to design thirteen oligonucleotides that span the gene: F1 (SEQ ID NO: 48), F2 (SEQ ID NO: 49), F3 (SEQ ID NO: 50), F4 (SEQ ID NO: 51), F5 (SEQ ID NO: 52), F6 (SEQ ID NO: 53), F7 (SEQ ID NO: 54), R1 (SEQ ID NO: 55), R2 (SEQ ID NO: 56), R3 (SEQ ID NO: 57), R4 (SEQ ID NO: 58), R5 (SEQ ID NO: 59), and R6 (SEQ ID NO: 60). The oligonucleotides are used in pairs for PCR amplification from the isolated soy genomic DNA: pair 1 (F1+R1), pair 2 (F2+R1), pair 3 (F3+R2), pair 4 (F4+R3), pair 5 (F5+R4), pair 6 (F6+R5), and pair 7 (F7+R6). The PCR amplification for pair 5 is carried out as follows: 1 cycle, 95° C. for 10 minutes; 30 cycles, 95° C. for 15 sec, 43° C. for 30 sec, 72° C. for 45 sec; 1 cycle, 72° C. for 7 minutes. For all other oligo pairs, PCR amplifications are carried out as follows: 1 cycle, 95° C. for 10 minutes; 30 cycles, 95° C. for 15 sec, 48° C. for 30 sec, 72° C. for 45 sec; 1 cycle, 72° C. for 7 minutes. Positive fragments are obtained from primer pairs 1, 2, 4, 5, 6 and 7. Each fragment is cloned into vector pCR2.1 (Invitrogen). Fragments 2, 4, 5 and 6 are confirmed and sequenced. These four sequences are aligned to form a genomic sequence for the FATB-2 gene (SEQ ID NO: 43).

Four introns are identified in the soybean FATB-2 gene by comparison of the genomic sequence to the cDNA sequence: intron I (SEQ ID NO: 44) spans base 119 to base 1333 of the genomic sequence (SEQ ID NO: 43) and is 1215 bp in length; intron II (SEQ ID NO: 45) spans base 2231 to base 2568 of the genomic sequence (SEQ ID NO: 43) and is 338 bp in length; intron 111 (SEQ ID NO: 46) spans base 2702 to base 3342 of the genomic sequence (SEQ ID NO: 43) and is 641 bp in length; and intron IV (SEQ ID NO: 47) spans base 3457 to base 3823 of the genomic sequence (SEQ ID NO: 43) and is 367 bp in length.

Example 2 Suppression Constructs

2A. FAD2-1 Constructs

The FAD2-1A intron #1(SEQ ID NO: 1) is cloned into the expression cassette, pCGN3892, in sense and antisense orientations. The vector pCGN3892 contains the soybean 7S promoter and a pea rbcS 3'. Both gene fusions are then separately ligated into pCGN9372, a vector that contains the CP4 EPSPS gene regulated by the FMV promoter. The resulting expression constructs (pCGN5469 sense and pCGN5471 antisense) are used for transformation of soybean.

The FAD2-1B intron (SEQ ID NO: 2) is fused to the 3' end of the FAD2-1A intron #1 in plasmid pCGN5468 (contains the soybean 7S promoter fused to the FAD2-1A intron (sense) and a pea rbcS 3') or pCGN5470 (contains the soybean 7S promoter fused to the FAD2-1A intron (antisense) and a pea rbcS 3') in sense and antisense orientation, respectively. The resulting intron combination fusions are then ligated separately into pCGN9372, a vector that contains the CP4 EPSPS gene regulated by the FMV promoter. The resulting expression constructs (pCGN5485, FAD2-1A & FAD2-1B intron sense and pCGN5486, FAD2-1A & FAD2-1B intron antisense) are used for transformation of soybean.

2B. FAD3-1 Constructs

FAD3-1A introns #1, #2, #4 and #5 (SEQ ID NOs: 7, 8, 10 and 11, respectively), FAD3-1B introns #3C (SEQ ID NO: 23) and #4 (SEQ ID NO: 24), are all ligated separately into pCGN3892, in sense or antisense orientation. pCGN3892 contains the soybean 7S promoter and a pea rbcS 3'. These fusions are ligated into pCGN9372, a vector that contains the CP4 EPSPS gene regulated by the FMV promoter for transformation into soybean. The resulting expression constructs (pCGN5455, FAD3-1A intron #4 sense; pCGN5459, FAD3-1A intron #4 antisense; pCGN5456, FAD3 intron #5 sense; pCGN5460, FAD3-1A intron #5 antisense; pCGN5466, FAD3-1A intron #2 antisense; pCGN5473, FAD3-1A intron #1 antisense) are used for transformation of soybean.

2C. FatB Constructs

The soybean FATB-1 intron II sequence (SEQ ID NO: 30) is amplified via PCR using a FATB-1 partial genomic clone as a template. PCR amplification is carried out as follows: 1 cycle, 95° C. for 10 min; 25 cycles, 95° C. for 30 sec, 62° C. for 30 sec, 72° C. for 30 sec; 1 cycle, 72° C. for 7 min. PCR amplification results in a product that is 854 bp long, including reengineered restriction sites at both ends. The PCR product is cloned directly into the expression cassette pCGN3892 in sense orientation, by way of XhoI sites engineered onto the 5' ends of the PCR primers, to form pMON70674. Vector pCGN3892 contains the soybean 7S promoter and a pea rbcS 3'. pMON70674 is then cut with NotI and ligated into pMON41164, a vector that contains the CP4 EPSPS gene regulated by the FMV promoter. The resulting gene expression construct, pMON70678, is used for transformation of soybean using Agrobacterium methods.

Two other expression constructs containing the soybean FATB-1 intron II sequence (SEQ ID NO: 30) are created. pMON70674 is cut with NotI and ligated into pMON70675 which contains the CP4 EPSPS gene regulated by the FMV promoter and the KAS IV gene regulated by the napin promoter, resulting in pMON70680. The expression vector pMON70680 is then cut with SnaBI and ligated with a gene fusion of the jojoba delta-9 desaturase gene (SEQ ID NO: 41) in sense orientation regulated by the 7S promoter. The expression constructs pMON70680 and pMON70681 are used for transformation of soybean using Agrobacterium methods.

2D Combination Constructs

Expression constructs are made containing various permutations of a first set of DNA sequences. The first set of DNA sequences are any of those described, or illustrated in FIGS. 5 and 6, or any other set of DNA sequences that contain various combinations of sense, antisense, or sense and antisense FAD2, FAD3, and FATB non-coding or coding regions so that they are capable of forming dsRNA constructs, sense cosuppression constructs, antisense constructs, or various combinations of the foregoing.

Figure 5C:
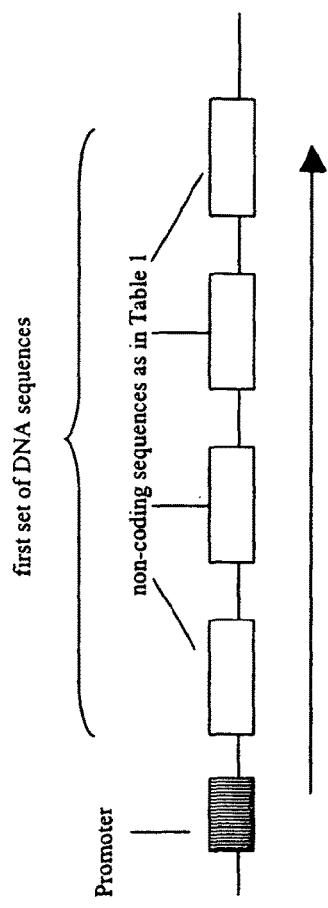
Figure 5D:
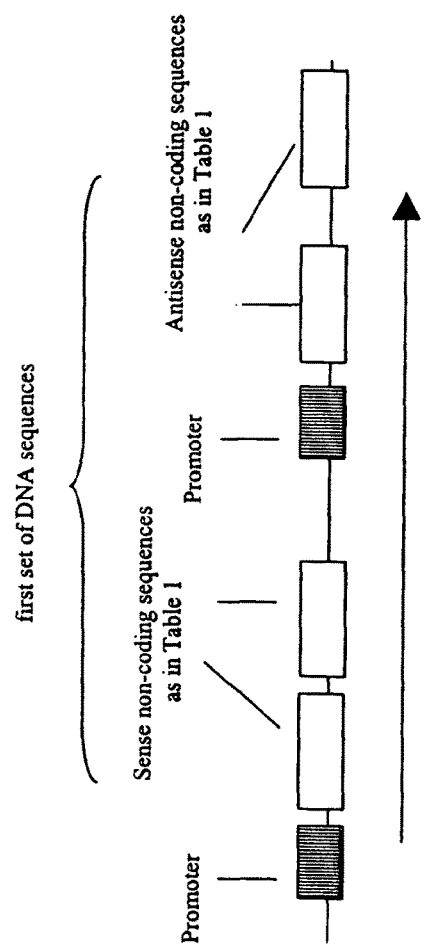

FIGS. 5(a)-(c) depict several first sets of DNA sequences which are capable of expressing sense cosuppression or antisense constructs according to the present invention, the non-coding sequences of which are described in Tables 1 and 2 below. The non-coding sequences may be single sequences, combinations of sequences (e.g., the 5'UTR linked to the 3'UTR), or any combination of the foregoing. To express a sense cosuppression construct, all of the non-coding sequences are sense sequences, and to express an antisense construct, all of the non-coding sequences are antisense sequences. FIG. 5(d) depicts a first set of DNA sequences which is capable of expressing sense and antisense constructs according to the present invention.

Figure 6A:
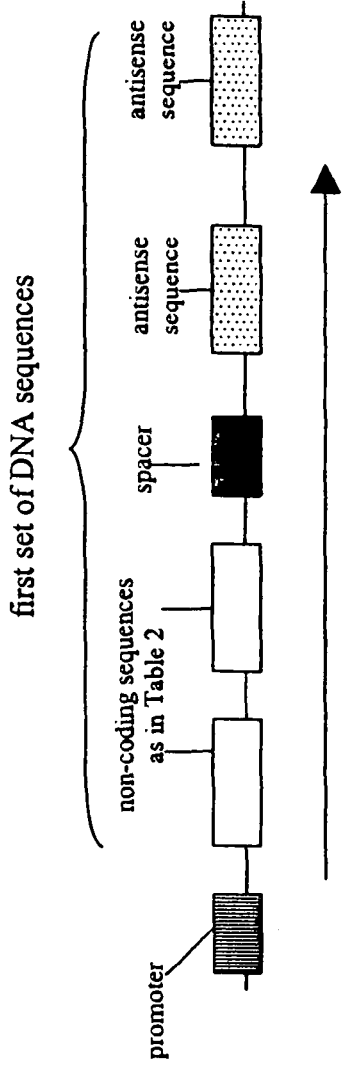
Figure 6B:
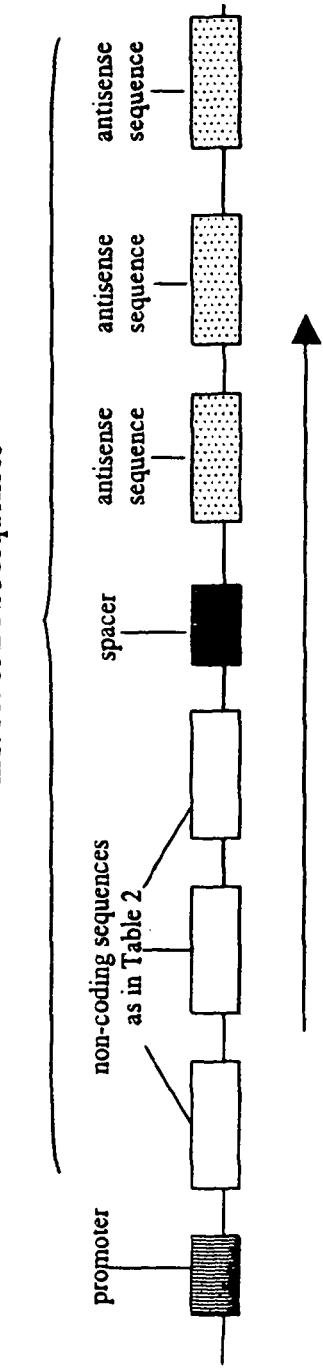
Figure 6C:
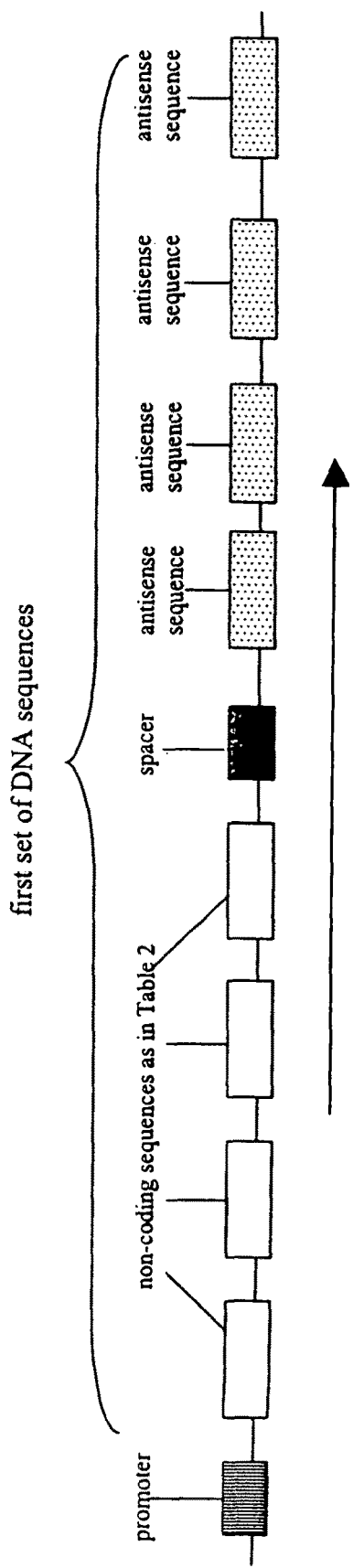

FIGS. 6(a)-(c) depict several first sets of DNA sequences which are capable of expressing dsRNA constructs according to the present invention, the non-coding sequences of which are described in Tables 1 and 2 below. The first set of DNA sequences depicted in FIG. 6 comprises pairs of related sense and antisense sequences, arranged such that, e.g., the RNA expressed by the first sense sequence is capable of forming a double-stranded RNA with the antisense RNA expressed by the first antisense sequence. For example, referring to FIG. 6(a) and illustrative combination No. 1 (of Table 1), the first set of DNA sequences comprises a sense FAD2-1 sequence, a sense FAD3-1 sequence, an antisense FAD2-1 sequence and an antisense FAD3-1 sequence. Both antisense sequences correspond to the sense sequences so that the expression products of the first set of DNA sequences are capable of forming a double-stranded RNA with each other. The sense sequences may be separated from the antisense sequences by a spacer sequence, preferably one that promotes the formation of a dsRNA molecule. Examples of such spacer sequences include those set forth in Wesley et al., supra, and Hamilton et al., Plant J., 15:737-746 (1988). The promoter is any promoter functional in a plant, or any plant promoter. Non-limiting examples of suitable promoters are described in Part D of the Detailed Description.

The first set of DNA sequences is inserted in an expression construct in either the sense or anti-sense orientation using a variety of DNA manipulation techniques. If convenient restriction sites are present in the DNA sequences, they are inserted into the expression construct by digesting with the restriction endonucleases and ligation into the construct that has been digested at one or more of the available cloning sites. If convenient restriction sites are not available in the DNA sequences, the DNA of either the construct or the DNA sequences is modified in a variety of ways to facilitate cloning of the DNA sequences into the construct. Examples of methods to modify the DNA include by PCR, synthetic linker or adapter ligation, in vitro site-directed mutagenesis, filling in or cutting back of overhanging 5' or 3' ends, and the like. These and other methods of manipulating DNA are well known to those of ordinary skill in the art.

pMON97552 contains a soybean 7Sα' promoter operably linking to a soybean FAD2-1A intron 1 (SEQ ID NO: 1), which is reduced by 140 contiguous nucleotides from the 3' end, operably linking to 42 contiguous nucleotides of a FATB-1a 5' UTR, followed by a FATB-1a CTP coding region, operably linking to 70 nucleotides from FAD3-1A intron 4 operably linking to a FATB-1a CTP coding region in the anti-sense orientation followed by 42 contiguous nucleotides of a FATB-1a 5' UTR in the antisense orientation, followed by a soybean FAD2-1A intron 1 (SEQ ID NO: 1), which is reduced by 140 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence, all of which is flanked by a RB and a LB. The resulting gene expression construct is used for transformation using methods as described herein.

pMON93758 contains a soybean 7Sα' promoter operably linking to a soybean FAD2-1A intron 1 (SEQ ID NO: 1), which is reduced by 160 contiguous nucleotides from the 5' end and ligated to a FATB-1a 3' UTR followed by a FATB-1a 5' UTR operably linking to 70 nucleotides from FAD3-1A intron 4 operably linking to a FATB-1a 5' UTR in the anti-sense orientation followed by a FATB-1a 3' UTR in the antisense orientation, followed by a soybean FAD2-1A intron 1 (SEQ ID NO: 1), which is reduced by 160 contiguous nucleotides from the 5' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON97553 contains a soybean 7Sα' promoter operably linking to a soybean FAD2-1A intron 1 (SEQ ID NO: 1), which is reduced by 200 contiguous nucleotides from the 3' end and ligated to 42 contiguous nucleotides of a FATB-1a 5' UTR followed by a FATB-1a CTP coding region operably linking to 70 nucleotides from FAD3-1A intron 4 operably linking to a FATB-1a CTP coding region in the anti-sense orientation followed by 42 contiguous nucleotides of a FATB-1a 5' UTR in the antisense orientation, followed b a soybean FAD2-1A intron 1 (SEQ ID NO: 1), which is reduced by 200 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93770 contains a soybean 7Sα' promoter operably linking to a soybean FAD2-1A intron 1 (SEQ ID NO: 1), which is reduced by 240 contiguous nucleotides from the 3' end and ligated to a FATB-1a 3' UTR and followed by a FATB-1a 5' UTR operably linking to 70 nucleotides from FAD3-1A intron 4 operably linking to a FATB-1a 5' UTR in the anti-sense orientation followed by a FATB-1a 3' UTR in the antisense orientation, followed by a soybean FAD2-1A intron 1 (SEQ ID NO: 1), which is reduced by 240 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93759 contains a soybean 7Sα' promoter operably linking to a soybean FAD2-1A intron 1 (SEQ ID NO: 1), which is reduced by 240 contiguous nucleotides from the 5' end and ligated to a FATB-1a 3' UTR followed by a FATB-1a 5' UTR operably linking to 70 nucleotides from FAD3-1A intron 4 operably linking to a FATB-1a 5' UTR in the anti-sense orientation followed by a FATB-1a 3' UTR in the antisense orientation, followed by a soybean FAD2-1A intron 1 (SEQ ID NO: 1), which is reduced by 240 contiguous nucleotides from the 5' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON97554 contains a soybean 7Sα' promoter operably linking to a soybean FAD2-1A intron 1 (SEQ ID NO: 1), which is reduced by 260 contiguous nucleotides from the 3' end and ligated to 42 contiguous nucleotides of a FATB-1a 5' UTR, followed by a FATB-1a CTP coding region, operably linking to 70 nucleotides from FAD3-1A intron 4, operably linking to a FATB-1a CTP coding region in the anti-sense orientation followed by 42 contiguous nucleotides of a FATB-1a 5' UTR in the antisense orientation, followed by a soybean FAD2-1A intron 1 (SEQ ID NO: 1), which is reduced by 260 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93771 contains a soybean 7Sα' promoter operably linking to a soybean FAD2-1A intron 1 (SEQ ID NO: 1), which is reduced by 300 contiguous nucleotides from the 3' end and ligated to a FATB-1a 3' UTR and followed by a FATB-1a 5' UTR, operably linking to 70 nucleotides from FAD3-1A intron 4 operably linking to a FATB-1a 5' UTR in the anti-sense orientation followed by a FATB-1a 3' UTR in the antisense orientation, followed by a soybean FAD2-1A intron 1 (SEQ ID NO: 1), which is reduced by 300 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON97555 contains a soybean 7Sα' promoter operably linking to a soybean FAD2-1A intron 1 (SEQ ID NO: 1), which is reduced by 320 contiguous nucleotides from the 3' end and ligated to 42 contiguous nucleotides of a FATB-1a 5' UTR followed by a FATB-1a CTP coding region operably linking to 70 nucleotides from FAD3-1A intron 4 operably linking to a FATB-1a CTP coding region in the anti-sense orientation followed by 42 contiguous nucleotides of a FATB-1a 5' UTR in the antisense orientation followed by a soybean FAD2-1A intron 1 (SEQ ID NO: 1), which is reduced by 320 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93760 contains a soybean 7Sα' promoter operably linking to a soybean FAD2-1A intron 1 (SEQ ID NO: 1), which is reduced by 320 contiguous nucleotides from the 5' end and ligated to a FATB-1a 3' UTR and followed by a FATB-1a 5' UTR operably linking to 70 nucleotides from FAD3-1A intron 4 operably linking to a FATB-1a 5' UTR in the anti-sense orientation followed by a FATB-1a 3' UTR in the antisense orientation followed by a soybean FAD2-1A intron 1 (SEQ ID NO: 1), which is reduced by 320 contiguous nucleotides from the 5' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93772 contains a soybean 7Sα' promoter operably linking to a soybean FAD2-1A intron 1 (SEQ ID NO: 1), which is reduced by 360 contiguous nucleotides from the 3' end and ligated to a FATB-1a 3' UTR and followed by a FATB-1a 5' UTR operably linking to 70 nucleotides from FAD3-1A intron 4 operably linking to a FATB-1a 5' UTR in the anti-sense orientation followed by a FATB-1a 3' UTR in the antisense orientation, followed by a soybean FAD2-1A intron 1 (SEQ ID NO: 1), which is reduced by 360 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON97556 contains a soybean 7Sα' promoter operably linking to a soybean FAD2-1A intron 1 (SEQ ID NO: 1), which is reduced by 380 contiguous nucleotides from the 3' end and ligated to 42 contiguous nucleotides of a FATB-1a 5' UTR, followed by a FATB-1a CTP coding region, operably linking to 70 nucleotides from FAD3-1A intron 4, operably linking to a FATB-1a CTP coding region in the anti-sense orientation followed by 42 contiguous nucleotides of a FATB-1a 5' UTR in the antisense orientation, operably linking to a soybean FAD2-1A intron 1 (SEQ ID NO: 1), which is reduced by 380 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

pMON93764 contains a soybean 7Sα' promoter operably linking to a soybean FAD2-1A intron 1 (SEQ ID NO: 1), which is reduced by 400 contiguous nucleotides from the 3' end and ligated to a FATB-1a CTP coding region followed by a FATB-2a CTP coding region operably linking to 70 nucleotides from FAD3-1A intron 4 operably linking to a FATB-2a CTP coding region in the anti-sense orientation followed by a FATB-1a CTP coding region in the antisense orientation, followed by a soybean FAD2-1A intron 1 (SEQ ID NO: 1), which is reduced by 400 contiguous nucleotides from the 3' end and in the anti-sense orientation, operably linked to a FATB-2a CTP coding region in the anti-sense orientation followed by 42 contiguous nucleotides of a FATB-2a 5' UTR in the antisense orientation operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for transformation using methods as described herein.

TABLE 1

| Illustrative Combinations | Non-Coding or Coding Sequences (sense or antisense) | | | |
|---|---|---|---|---|
| | First | Second | Third | Fourth |
| 1 | FAD2-1A or B | FAD3-1A or B or C | | |
| 2 | FAD3-1A or B or C | FAD2-1A or B | | |
| 3 | FAD2-1A or B | FAD3-1A or B or C | different FAD3-1A or B or C sequence | |
| 4 | FAD2-1A or B | FAD3-1A or B or C | FATB-1 | |
| 5 | FAD2-1A or B | FATB-1 | FAD3-1A or B or C | |
| 6 | FAD3-1A or B or C | FAD2-1A or B | FATB-1 | |
| 7 | FAD3-1A or B or C | FATB-1 | FAD2-1A or B | |
| 8 | FATB-1 | FAD3-1A or B or C | FAD2-1A or B | |
| 9 | FATB-1 | FAD2-1A or B | FAD3-1A or B or C | |
| 10 | FAD2-1A or B | FAD3-1A or B or C | different FAD3-1A or B or C sequence | FATB-1 |
| 11 | FAD3-1A or B or C | FAD2-1A or B | different FAD3-1A or B or C sequence | FATB-1 |
| 12 | FAD3-1A or B or C | different FAD3-1A or B or C sequence | FAD2-1A or B | FATB-1 |
| 13 | FAD2-1A or B | FAD3-1A or B or C | FATB-1 | different FAD3-1A or B or C sequence |
| 14 | FAD3-1A or B or C | FAD2-1A or B | FATB-1 | different FAD3-1A or B or C sequence |
| 15 | FAD3-1A or B or C | different FAD3-1A or B or C sequence | FATB-1 | FAD2-1A or B |
| 16 | FAD2-1A or B | FATB-1 | FAD3-1A or B or C | different FAD3-1A or B or C sequence |
| 17 | FAD3-1A or B or C | FATB-1 | FAD2-1A or B | different FAD3-1A or B or C sequence |
| 18 | FAD3-1A or B or C | FATB-1 | different FAD3-1A or B or C sequence | FAD2-1A or B |
| 19 | FATB-1 | FAD2-1A or B | FAD3-1A or B or C | different FAD3-1A or B or C sequence |

TABLE 1-continued

| Illustrative | Non-Coding or Coding Sequences (sense or antisense) | | | |
|---|---|---|---|---|
| Combinations | First | Second | Third | Fourth |
| 20 | FATB-1 | FAD3-1A or B or C | FAD2-1A or B | different FAD3-1A or B or C sequence |
| 21 | FATB-1 | FAD3-1A or B or C | different FAD3-1A or B or C sequence | FAD2-1A or B |
| 22 | FAD2-1A or B | FAD3-1A or B or C | FATB-2 | |
| 23 | FAD2-1A or B | FATB-2 | FAD3-1A or B or C | |
| 24 | FAD3-1A or B or C | FAD2-1A or B | FATB-2 | |
| 25 | FAD3-1A or B or C | FATB-2 | FAD2-1A or B | |
| 26 | FATB-2 | FAD3-1A or B or C | FAD2-1A or B | |
| 27 | FATB-2 | FAD2-1A or B | FAD3-1A or B or C | |
| 28 | FAD2-1A or B | FAD3-1A or B or C | different FAD3-1A or B or C sequence | FATB-2 |
| 29 | FAD3-1A or B or C | FAD2-1A or B | different FAD3-1A or B or C sequence | FATB-2 |
| 30 | FAD3-1A or B or C | different FAD3-1A or B or C sequence | FAD2-1A or B | FATB-2 |
| 31 | FAD2-1A or B | FAD3-1A or B or C | FATB-2 | different FAD3-1A or B or C sequence |
| 32 | FAD3-1A or B or C | FAD2-1A or B | FATB-2 | different FAD3-1A or B or C sequence |
| 33 | FAD3-1A or B or C | different FAD3-1A or B or C sequence | FATB-2 | FAD2-1A or B |
| 34 | FAD2-1A or B | FATB-2 | FAD3-1A or B or C | different FAD3-1A or B or C sequence |
| 35 | FAD3-1A or B or C | FATB-2 | FAD2-1A or B | different FAD3-1A or B or C sequence |
| 36 | FAD3-1A or B or C | FATB-2 | different FAD3-1A or B or C sequence | FAD2-1A or B |
| 37 | FATB-2 | FAD2-1A or B | FAD3-1A or B or C | different FAD3-1A or B or C sequence |
| 38 | FATB-2 | FAD3-1A or B or C | FAD2-1A or B | different FAD3-1A or B or C sequence |
| 39 | FATB-2 | FAD3-1A or B or C | different FAD3-1A or B or C sequence | FAD2-1A or B |

TABLE 2

Correlation of SEQ ID NOs with Sequences in Table 1

| | FAD2-1A | FAD2-1B | FAD3-1A | FAD3-1B | FAD3-1C | FATB-1 | FATB-2 |
|---|---|---|---|---|---|---|---|
| 3'UTR | SEQ NO: 5 | n/a | SEQ NO: 16 | SEQ NO: 26 | SEQ NO: 61 | SEQ NO: 36 | n/a |
| 5'UTR | SEQ NO: 6 | n/a | SEQ NO: 17 | SEQ NO: 27 | SEQ NO: 62 | SEQ NO: 37 | n/a |
| 5' + 3' UTR (or 3' + 5' UTR) | Linked SEQ NOs: 5 and 6 | n/a | Linked SEQ NOs: 16 and 17 | Linked SEQ NOs: 26 and 27 | n/a | Linked SEQ NOs: 36 and 37 | n/a |
| Intron #1 | SEQ NO: 1 | SEQ NO: 2 | SEQ NO: 7 | SEQ NO: 19 | n/a | SEQ NO: 29 | SEQ NO: 44 |
| Intron #2 | n/a | n/a | SEQ NO: 8 | SEQ NO: 20 | n/a | SEQ NO: 30 | SEQ NO: 45 |
| Intron #3 | n/a | n/a | n/a | n/a | n/a | SEQ NO: 31 | SEQ NO: 46 |
| Intron #3A | n/a | n/a | SEQ NO: 9 | SEQ NO: 21 | n/a | n/a | n/a |
| Intron #3B | n/a | n/a | SEQ NO: 12 | SEQ NO: 22 | n/a | n/a | n/a |
| Intron #3C | n/a | n/a | SEQ NO: 13 | SEQ NO: 23 | n/a | n/a | n/a |
| Intron #4 | n/a | n/a | SEQ NO: 10 | SEQ NO: 24 | SEQ NO: 14 | SEQ NO: 32 | SEQ NO: 47 |
| Intron #5 | n/a | n/a | SEQ NO: 11 | SEQ NO: 25 | n/a | SEQ NO: 33 | n/a |
| Intron #6 | n/a | n/a | n/a | n/a | n/a | SEQ NO: 34 | n/a |
| Intron #7 | n/a | n/a | n/a | n/a | n/a | SEQ NO: 35 | n/a |

Example 3 Combination Constructs

In FIGS. 7-15, promoters are indicated by arrows, encoding sequences (both coding and non-coding) are indicated by pentagons which point in the direction of transcription, sense sequences are labeled in normal text, and antisense sequences are labeled in upside-down text. The abbreviations used in these Figures include: 7Sa=7Sα promoter; 7Sa'=7Sα' promoter; Br napin=*Brassica* napin promoter; FMV=an FMV promoter; ARC=arcelin promoter; RBC E9 3'=Rubisco E9 termination signal; Nos 3'=nos termination signal; TML 3'=tml termination signal; napin 3'=napin termination signal; '3 (in the same box as FAD or FAT)=3' UTR; 5' (in the same box as FAD or FAT)=5'UTR; Cr=*Cuphea pulcherrima*; Gm=*Glycine max*; Rc=*Ricinus communis*; FAB2=a FAB2 allele of a delta 9 stearoyl-desaturase gene; and Intr or Int=intron.

3A. dsRNA Constructs

Figure 7:
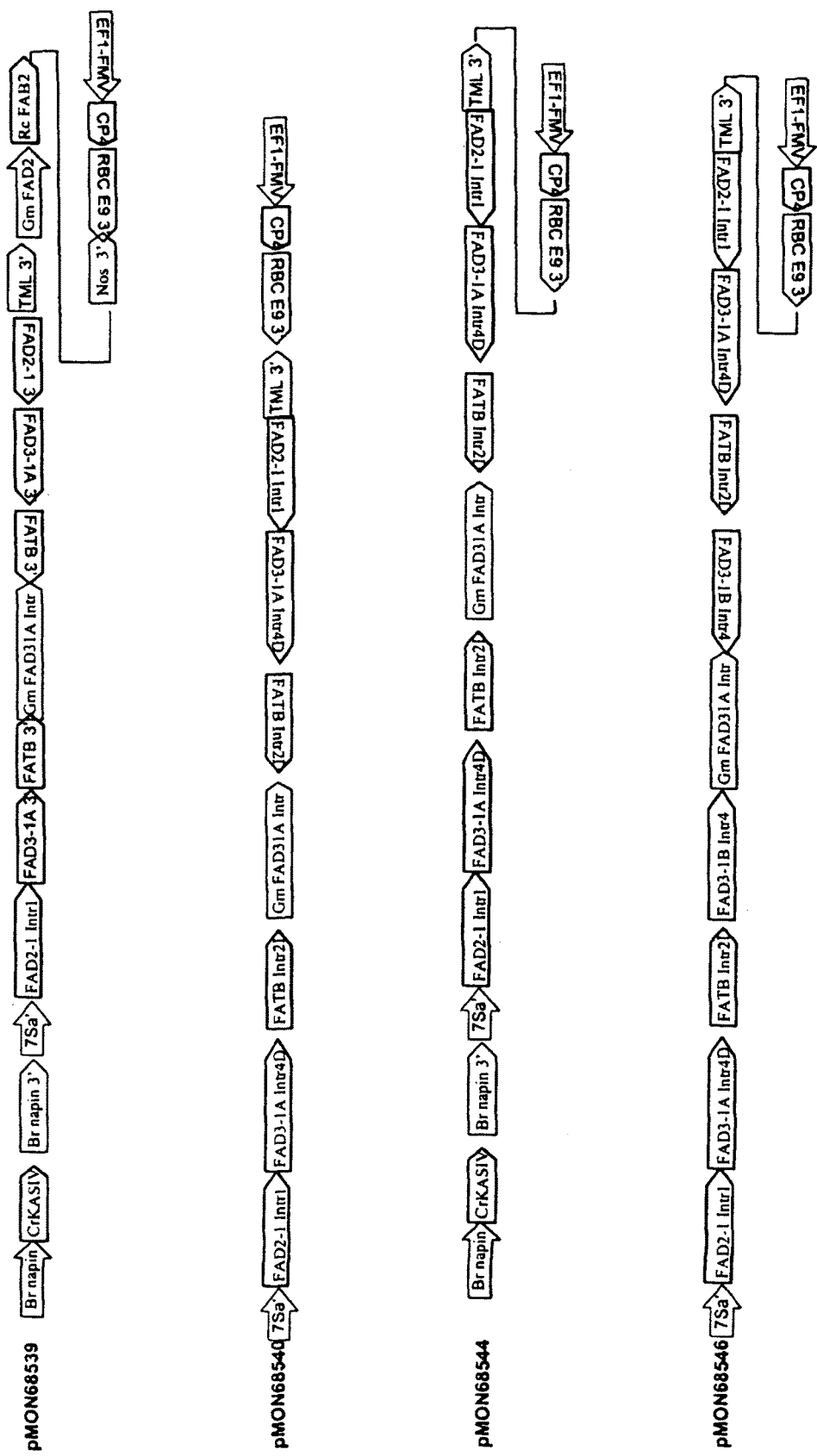
FIGS. 7-20 each depict nucleic acid molecules of the present invention.
Figure 8:
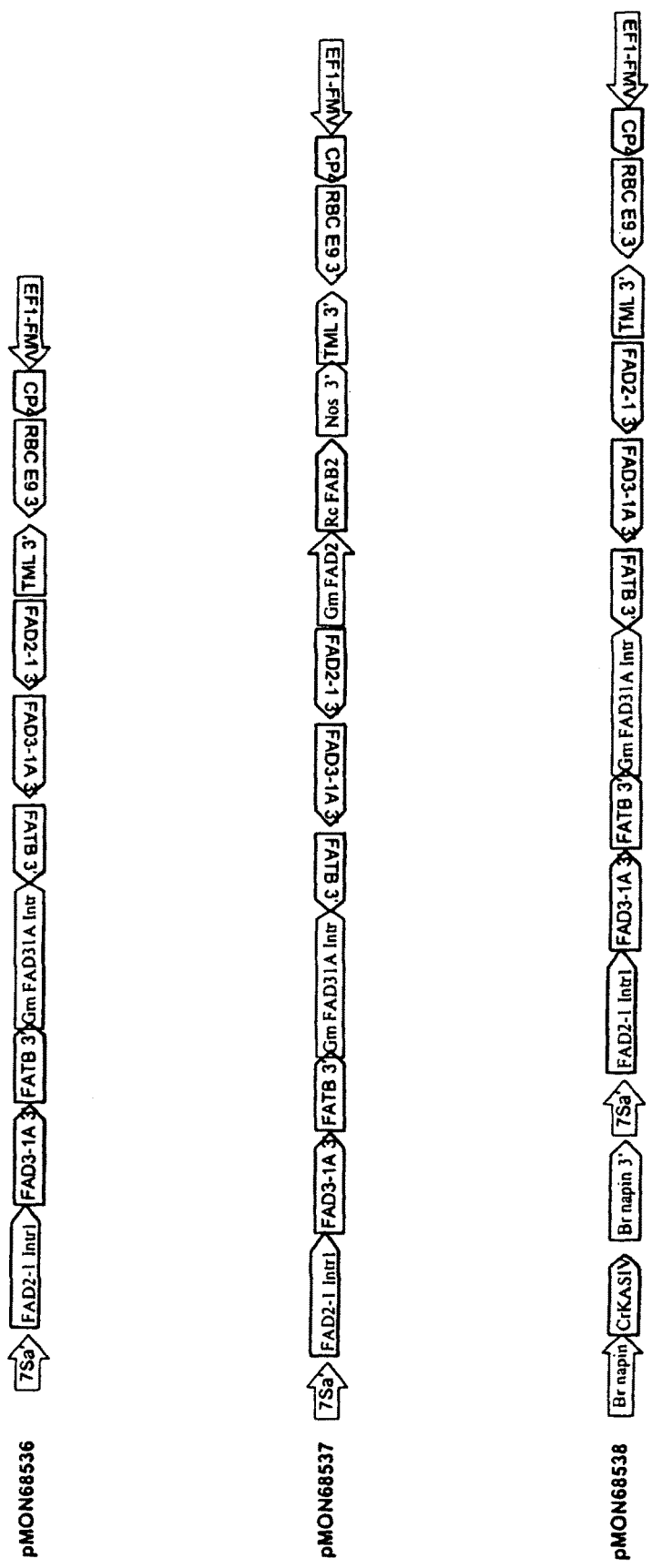
Figure 9:
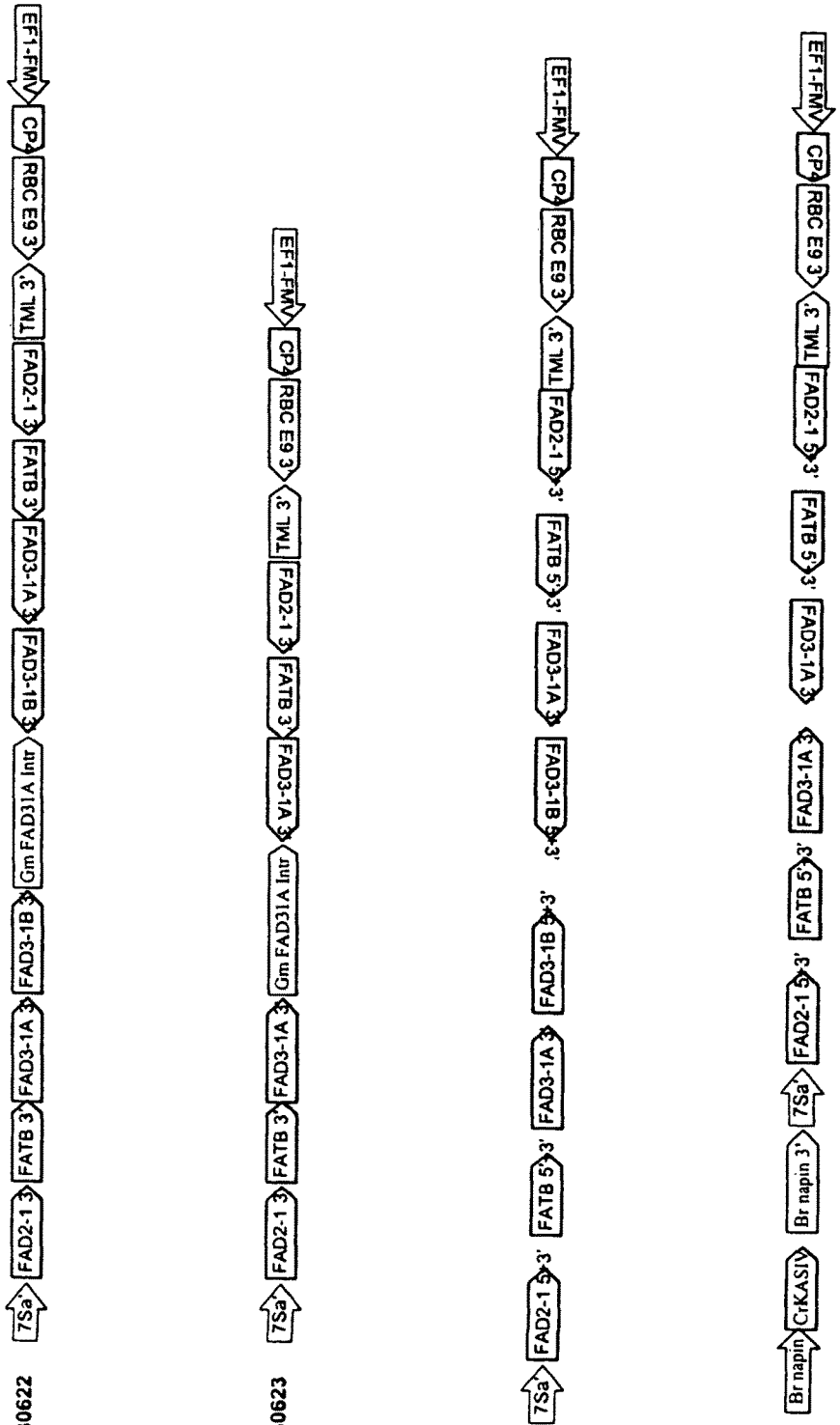

FIGS. 7-9 depict nucleic acid molecules of the present invention in which the first sets of DNA sequences are capable of expressing dsRNA constructs. The first set of DNA sequences depicted in FIGS. 7-9 comprise pairs of related sense and antisense sequences, arranged such that, e.g., the RNA expressed by the first sense sequence is capable of forming a double-stranded RNA with the antisense RNA expressed by the first antisense sequence. The sense sequences may be adjacent to the antisense sequences, or separated from the antisense sequences by a spacer sequence, as shown in FIG. 9.

The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which can be any promoter functional in a plant, or any plant promoter, and may be an FMV promoter, a napin promoter, a 7S (either 7Sα or 7Sα') promoter, an arcelin promoter, a delta-9 desaturase promoter, or a FAD2-1A promoter.

Referring now to FIG. 7, soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a *Brassica* napin promoter and a *Brassica* napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON68539, is depicted in FIG. 7 and is used for transformation using methods as described herein.

Soybean FAD2-1 intron 1 (SEQ ID NO: 1 or 2), FAD3-1A intron 4 (SEQ ID NO: 10), and FATB-1 intron II (SEQ ID NO: 30) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68540, is depicted in FIG. 7 and is used for transformation using methods as described herein.

Soybean FAD2-1 intron 1 (SEQ ID NO: 1 or 2), FAD3-1A intron 4 (SEQ ID NO: 10), and FATB-1 intron II (SEQ ID NO: 30) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, pMON68544, is depicted in FIG. 7 and is used for transformation using methods as described herein.

Soybean FAD2-1 intron 1 (SEQ ID NO: 1 or 2), FAD3-1A intron 4 (SEQ ID NO: 10), FATB-1 intron II (SEQ ID NO: 30), and FAD3-1B intron 4 (SEQ ID NO: 24) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68546, is depicted in FIG. 7 and is used for transformation using methods as described herein.

Referring now to FIG. 8, soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68536, is depicted in FIG. 8 and is used for transformation using methods as described herein.

Soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated just upstream of the tml 3' termination sequence. The vector is then cut with NotI and ligated into pMON41164, a vector that contains the CP4 EPSPS gene regulated by the FMV promoter and a pea Rubisco E9 3' termination sequence. The resulting gene expression construct, pMON68537, is depicted in FIG. 8 and is used for transformation using methods as described herein.

Soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, pMON68538, is depicted in FIG. 8 and is used for transformation using methods as described herein.

Referring now to FIG. 9, soybean FAD2-1 3'UTR (SEQ ID NO: 5), FATB-1 3'UTR (SEQ ID NO: 36), FAD3-1A 3'UTR (SEQ ID NO: 16), and FAD3-1B 3'UTR (SEQ ID NO: 26) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80622, is depicted in FIG. 9 and is used for transformation using methods as described herein.

Soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in sense and antisense orientations, separated by a spliceable soybean FAD3-1A intron 5 (SEQ ID NO: 11), into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80623, is depicted in FIG. 9 and is used for transformation using methods as described herein.

Soybean FAD2-1 5'UTR-3'UTR (SEQ ID NOs: 6 and 5, ligated together), FATB-1 5'UTR-3'UTR (SEQ ID NOs: 37 and 36, ligated together), FAD3-1A 3'UTR (SEQ ID NO: 16) and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense and antisense orientations, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, O5, is depicted in FIG. 9 and is used for transformation using methods as described herein.

Soybean FAD2-1 5'UTR-3'UTR (SEQ ID NOs: 6 and 5, ligated together), FATB-1 5'UTR-3'UTR (SEQ ID NOs: 37 and 36, ligated together) and FAD3-1A 3'UTR (SEQ ID NO: 16) sequences are amplified via PCR to result in PCR products that include reengineered restriction sites at both ends. The PCR products are cloned directly, in sense and antisense orientations, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O6, is depicted in FIG. 9 and is used for transformation using methods as described herein.

3B. Sense Cosuppression Constructs

FIGS. 10-13 and 19-20 depict nucleic acid molecules of the present invention in which the first sets of DNA sequences are capable of expressing sense cosuppression constructs. The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which is any promoter functional in a plant, or any plant promoter, and may be an FMV promoter, a napin promoter, a 7S promoter (either 7Sα or 7Sα'), an arcelin promoter, a delta-9 desaturase promoter, or a FAD2-1A promoter.

Figure 10:
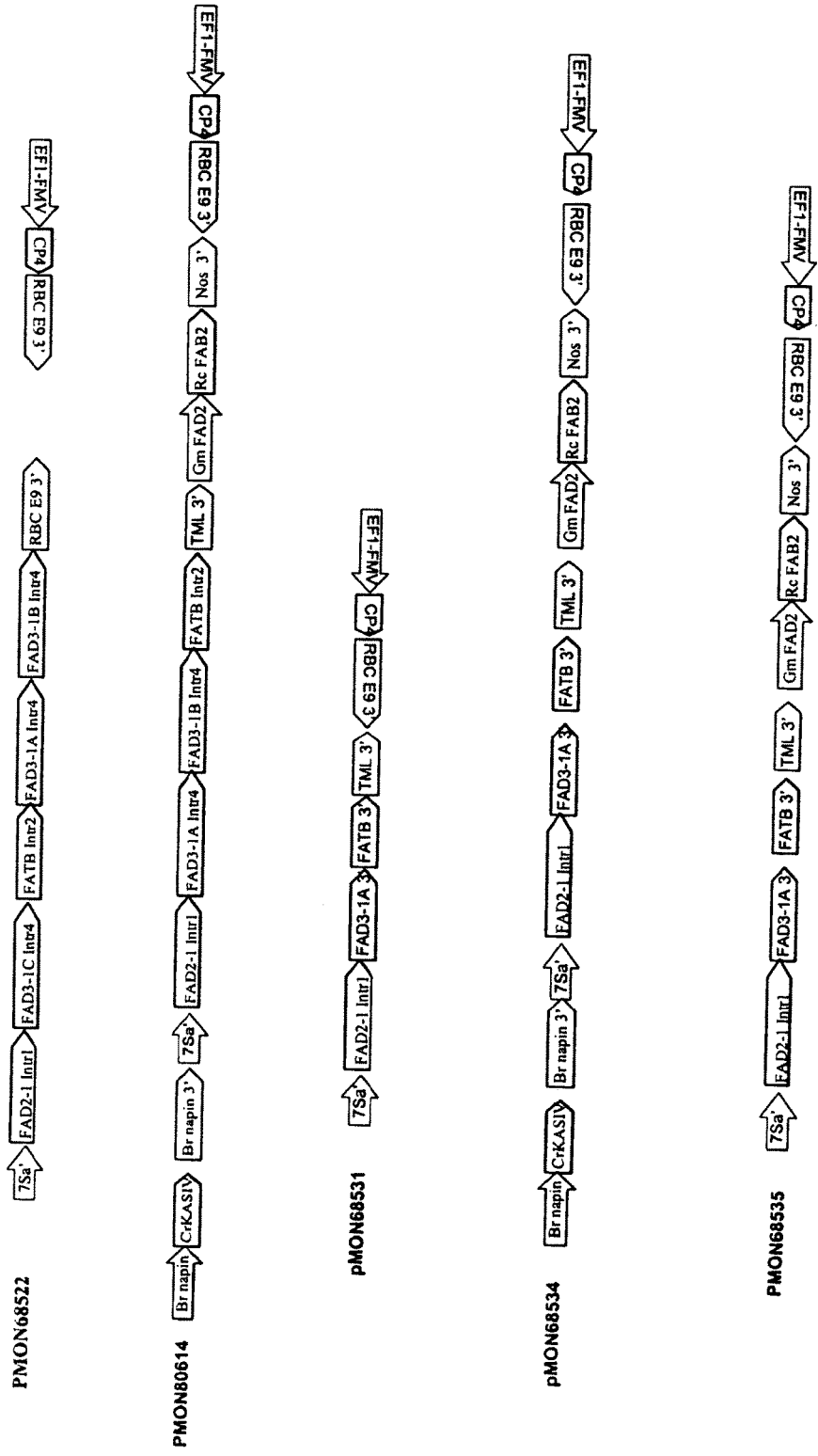

Referring now to FIG. 10, soybean FAD2-1 intron 1 (SEQ ID NO: 1 or 2), FAD3-1C intron 4 (SEQ ID NO: 14), FATB-1 intron II (SEQ ID NO: 30), FAD3-1A intron 4 (SEQ ID NO: 10), and FAD3-1B intron 4 (SEQ ID NO: 24) sequences are amplified via PCR to result in PCR products that include reengineered restriction sites at both ends. The PCR products are cloned directly, in sense orientation, into a vector containing the soybean 7Sα' promoter and a pea Rubisco E9 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68522, is depicted in FIG. 10 and is used for transformation using methods as described herein.

Soybean FAD2-1 intron 1 (SEQ ID NO: 1 or 2), FAD3-1A intron 4 (SEQ ID NO: 10), FAD3-1B intron 4 (SEQ ID NO: 24), and FATB-1 intron II (SEQ ID NO: 30) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a *Brassica* napin promoter and a *Brassica* napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON80614, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON68531, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. Vectors containing a *C. pulcherrima* KAS IV gene (SEQ ID NO: 39) regulated by a *Brassica* napin promoter and a *Brassica* napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON68534, is depicted in FIG. 10 and is used for transformation using methods as described herein.

Soybean FAD2-1 intron 1 (SEQ ID NO: 1 or 2), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated into pMON41164. The resulting gene expression construct, pMON68535, is depicted in FIG. 10 and is used for transformation using methods as described herein.

Figure 11:
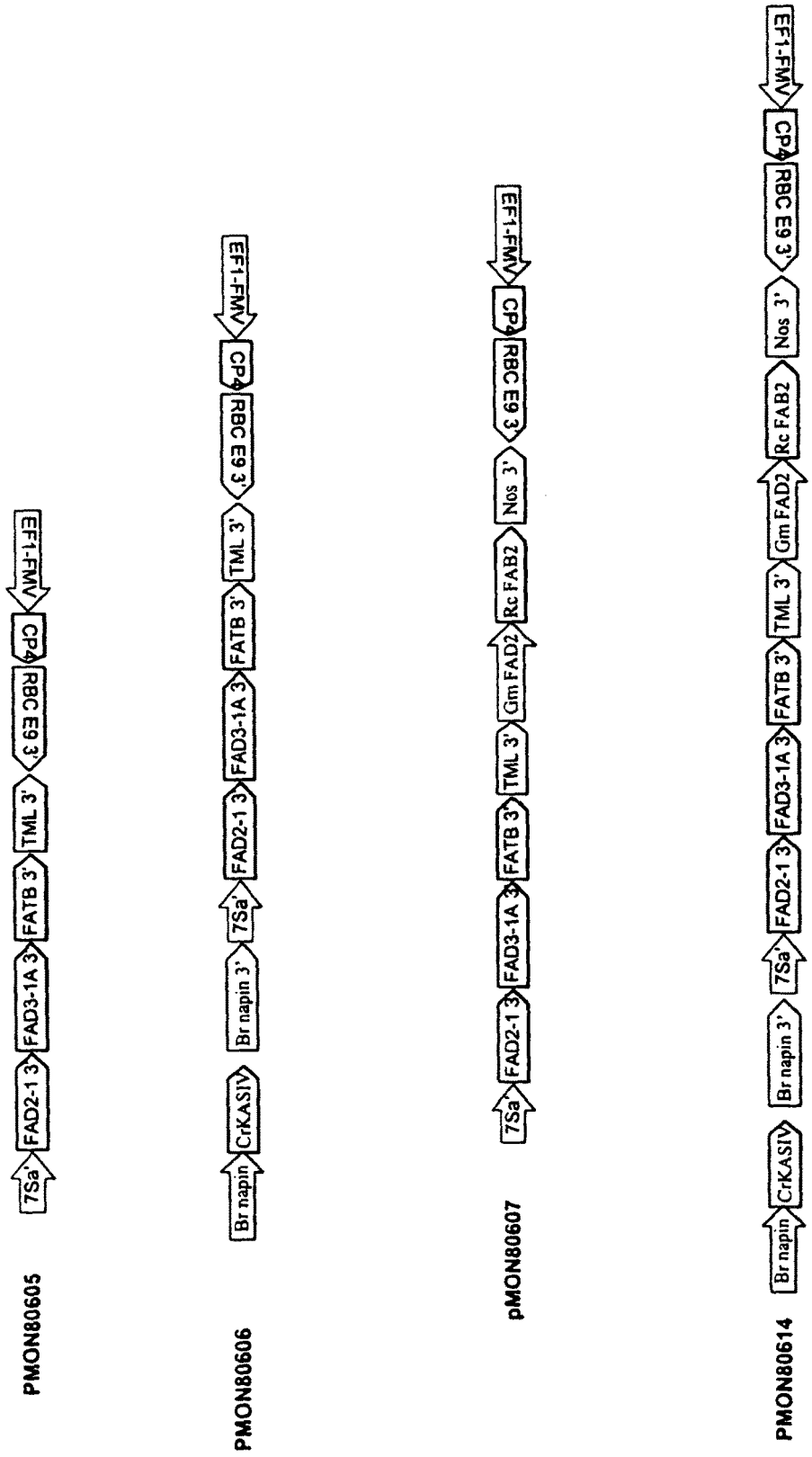

Referring now to FIG. 11, soybean FAD2-1 3'UTR (SEQ ID NO: 5), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80605, is depicted in FIG. 11 and is used for transformation using methods as described herein.

Soybean FAD2-1 3'UTR (SEQ ID NO: 5), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, pMON80606, is depicted in FIG. 11 and is used for transformation using methods as described herein.

Soybean FAD2-1 3'UTR (SEQ ID NO: 5), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence is cut with appropriate restriction enzymes, and ligated into pMON41164. The resulting gene expression construct, pMON80607, is depicted in FIG. 11 and is used for transformation using methods as described herein.

Soybean FAD2-1 3'UTR (SEQ ID NO: 5), FAD3-1A 3'UTR (SEQ ID NO: 16), and FATB-1 3'UTR (SEQ ID NO: 36) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence.

Vectors containing a *C. pulcherrima* KAS IV gene (SEQ ID NO: 39) regulated by a *Brassica* napin promoter and a *Brassica* napin 3' termination sequence, and a *R. communis* delta-9 desaturase (FAB2) gene (SEQ ID NO: 40) regulated by a soybean FAD2 promoter and a nos 3' termination sequence, are cut with appropriate restriction enzymes, and ligated into pMON41164. The resulting gene expression construct, pMON80614, is depicted in FIG. 11 and is used for transformation using methods as described herein.

Figure 12:
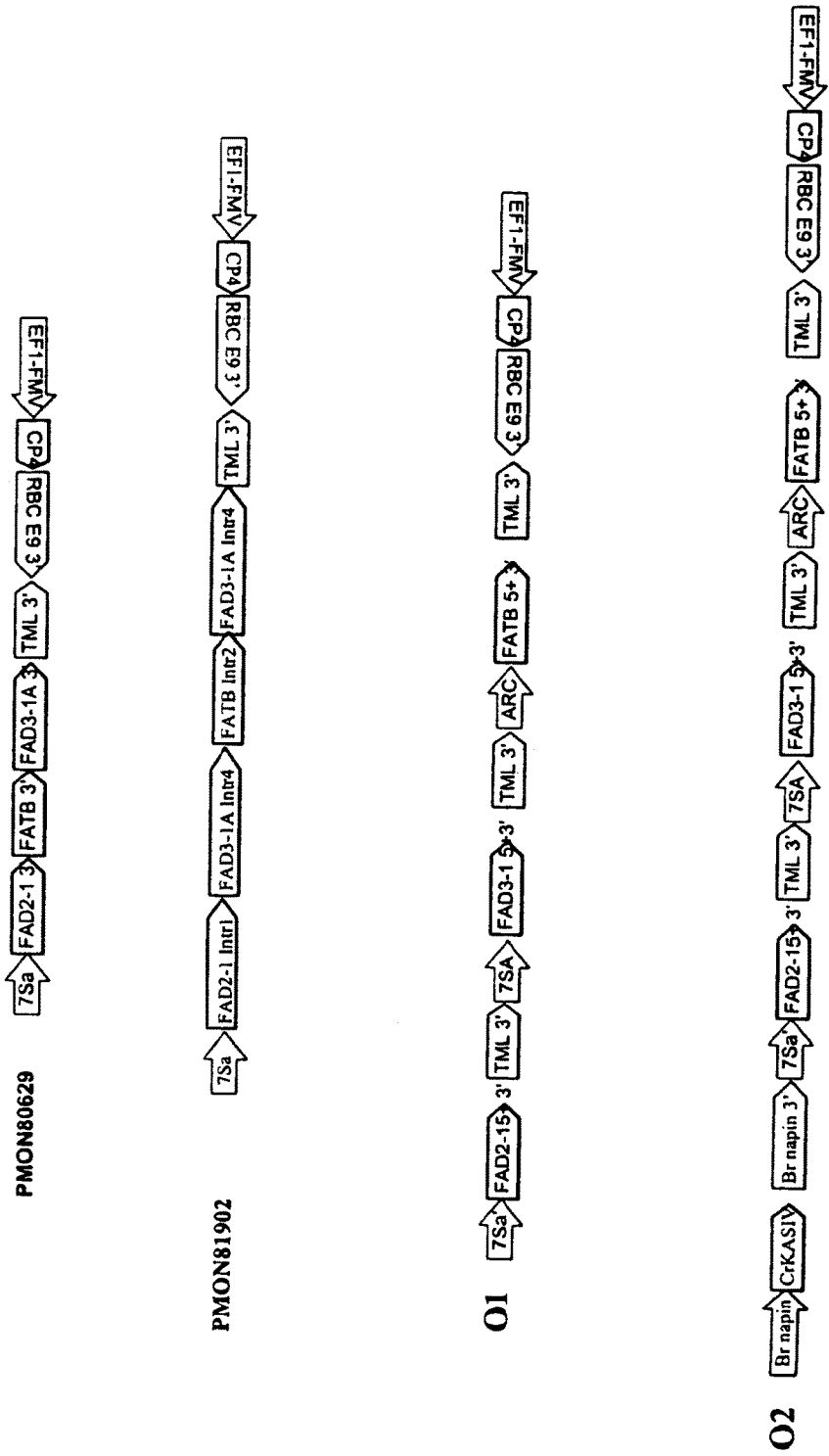

Referring now to FIG. 12, soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in sense orientation, into a vector containing the soybean 7Sα promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80629, is depicted in FIG. 12 and is used for transformation using methods as described herein.

Soybean FAD2-1 intron 1 (SEQ ID NO: 1 or 2), FAD3-1A intron 4 (SEQ ID NO: 10), FATB-1 intron II (SEQ ID NO: 30), and FAD3-1A intron 4 (SEQ ID NO: 10) sequences are amplified via PCR to result in PCR products that include reengineered restriction sites at both ends. The PCR products are cloned directly, in sense orientation, into a vector containing the soybean 7Sα promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON81902, is depicted in FIG. 12 and is used for transformation using methods as described herein.

Soybean FAD2-1 5'UTR-3'UTR (SEQ ID NOs: 6 and 5, ligated together), FAD3-1 5'UTR-3'UTR (SEQ ID NOs: 17 and 16, ligated together, or 27 and 26, ligated together), and FATB-1 5'UTR-3'UTR (SEQ ID NOs: 37 and 36, ligated together) sequences are amplified via PCR to result in PCR products that include reengineered restriction sites at both ends. The FAD2-1 PCR product is cloned directly, in sense orientation, into a vector containing the soybean 7Sα' promoter and a tml 3' termination sequence, by way of XhoI sites engineered onto the 5' ends of the PCR primers. Similarly, the FAD3-1 PCR product is cloned directly, in sense orientation, into a vector containing the soybean 7Sα promoter and a tml 3' termination sequence, by way of XhoI sites engineered onto the 5' ends of the PCR primers. The FATB-1 PCR product is cloned directly, in sense orientation, into a vector containing the arcelin promoter and a tml 3' termination sequence, by way of XhoI sites engineered onto the 5' ends of the PCR primers. These vectors are then cut with NotI and ligated into pMON41164, a vector that contains the CP4 EPSPS gene regulated by the FMV promoter and a pea Rubisco E9 3' termination sequence. The resulting gene expression construct, O1, is depicted in FIG. 12 and is used for transformation using methods as described herein.

Soybean FAD2-1 5'UTR-3'UTR (SEQ ID NOs: 6 and 5, ligated together), FAD3-1 5'UTR-3'UTR (SEQ ID NOs: 17 and 16, ligated together, or 27 and 26, ligated together), and FATB-1 5'UTR-3'UTR (SEQ ID NOs: 37 and 36, ligated together) sequences are amplified via PCR to result in PCR products that include reengineered restriction sites at both ends. The FAD2-1 PCR product is cloned directly, in sense orientation, into a vector containing the soybean 7Sα' promoter and a tml 3' termination sequence, by way of XhoI sites engineered onto the 5' ends of the PCR primers. Similarly, the FAD3-1 PCR product is cloned directly, in sense orientation, into a vector containing the soybean 7Sα promoter and a tml 3' termination sequence, by way of XhoI sites engineered onto the 5' ends of the PCR primers. The FATB-1 PCR product is cloned directly, in sense orientation, into a vector containing the arcelin promoter and a tml 3' termination sequence, by way of XhoI sites engineered onto the 5' ends of the PCR primers. These vectors are then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O2, is depicted in FIG. 12 and is used for transformation using methods as described herein.

Figure 13:
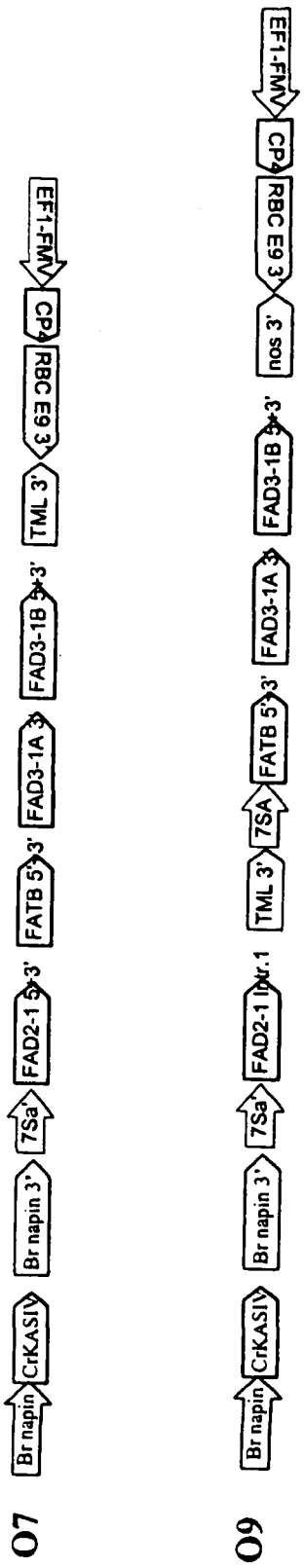

Referring now to FIG. 13, soybean FAD2-1 5'UTR-3'UTR (SEQ ID NOs: 6 and 5, ligated together), FATB-1 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vectors are then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O7, is depicted in FIG. 13 and is used for transformation using methods as described herein.

Soybean FAD2-1 intron 1 (SEQ ID NO: 1 or 2) is amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. Soybean FATB-1 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in sense orientation, into a vector containing the soybean 7Sα promoter and a nos 3' termination sequence, by way of XhoI sites engineered onto the 5' ends of the PCR primers. The vectors are then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O9, is depicted in FIG. 13 and is used for transformation using methods as described herein.

Figure 19:
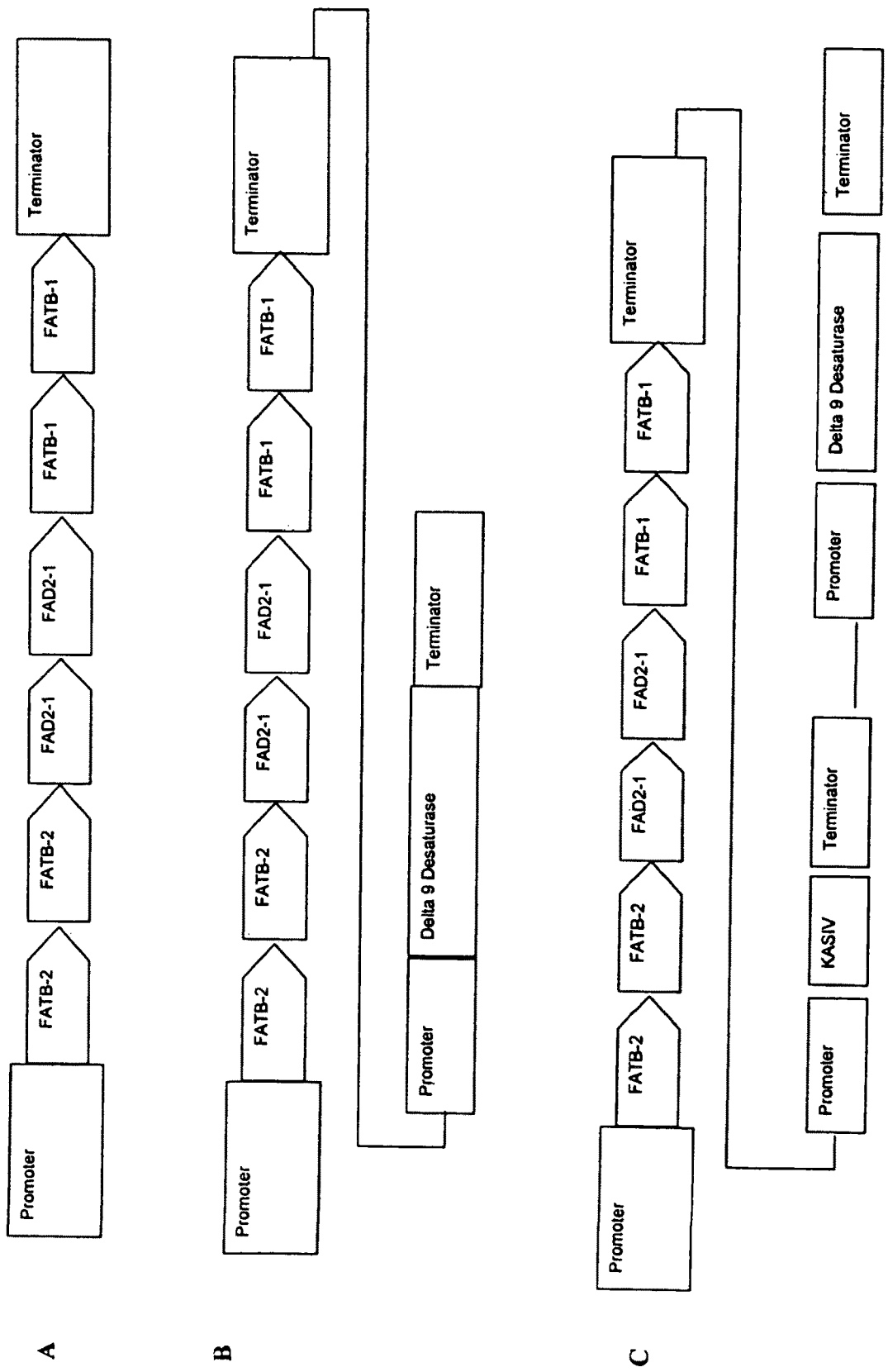

Referring now to FIG. 19, soybean FATB-2 non-coding sequences (SEQ ID NOs: 44-47), FAD2-1 non-coding sequences (SEQ ID NOs: 1 and 5-6), and FATB-1 non-coding sequences (SEQ ID NOs: 29-37) are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vectors are then cut with NotI and ligated into pMON80612, a vector that contains the CP4 EPSPS gene regulated by the FMV promoter and a pea Rubisco E9 3' termination sequence. The resulting gene expression construct is depicted in FIG. 19-A and is used for transformation using methods described herein.

A DNA sequence containing a delta-9 desaturase is regulated by a 7S alpha promoter and a TML 3' termination sequence is cut using the appropriate restriction enzymes and ligated into the above expression construct. The resulting expression construct is depicted in FIG. 19-B and is used for transformation using methods described herein.

A vector containing a *C. pulcherrima* KAS IV gene (SEQ ID NO: 39) regulated by a bean arcelin promoter and a napin 3' termination sequence is cut with appropriate restriction enzymes, and ligated into the above expression construct. The resulting gene expression construct is depicted in FIG. 19-C and is used for transformation using methods as described herein.

Figure 20:
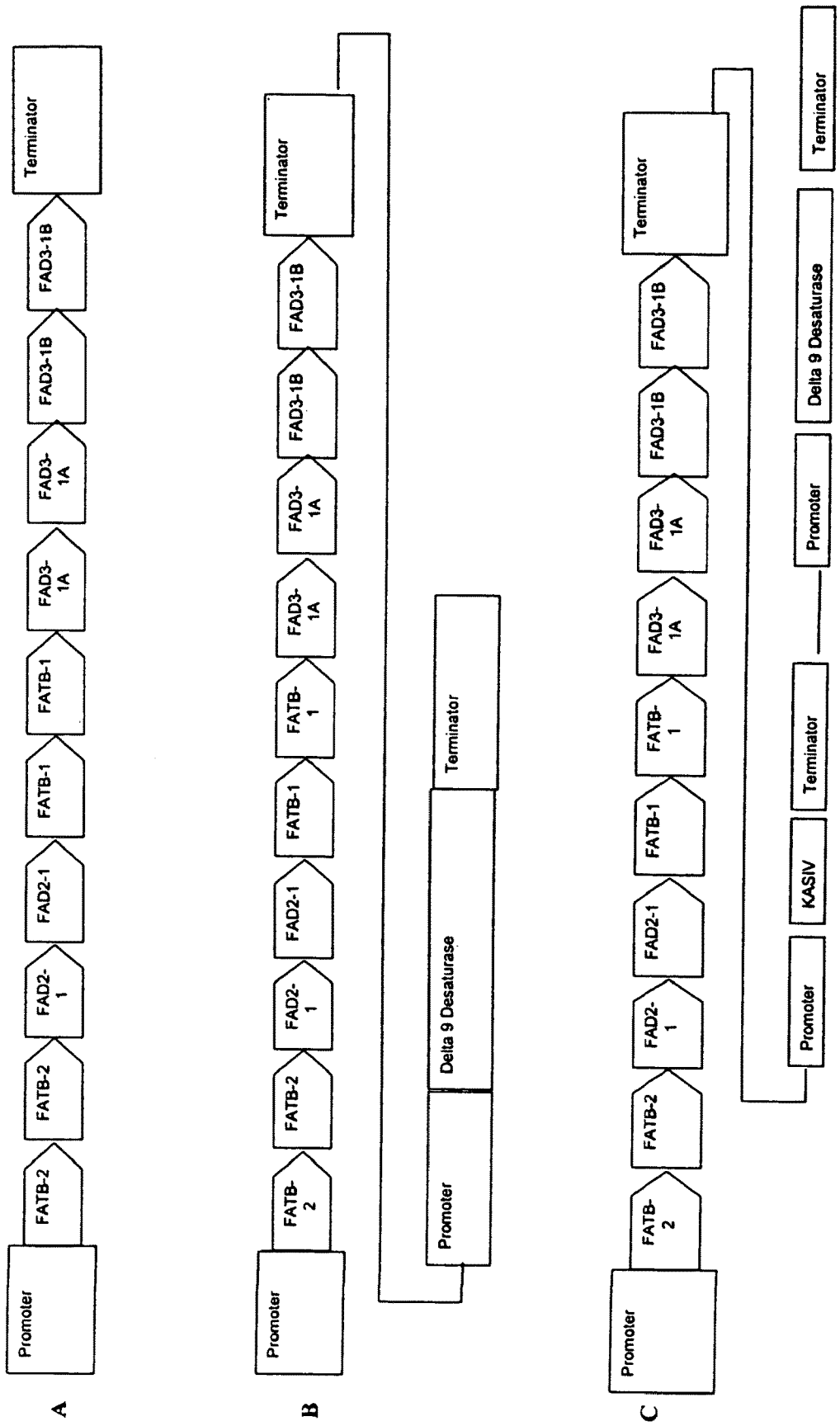
Figure 21:
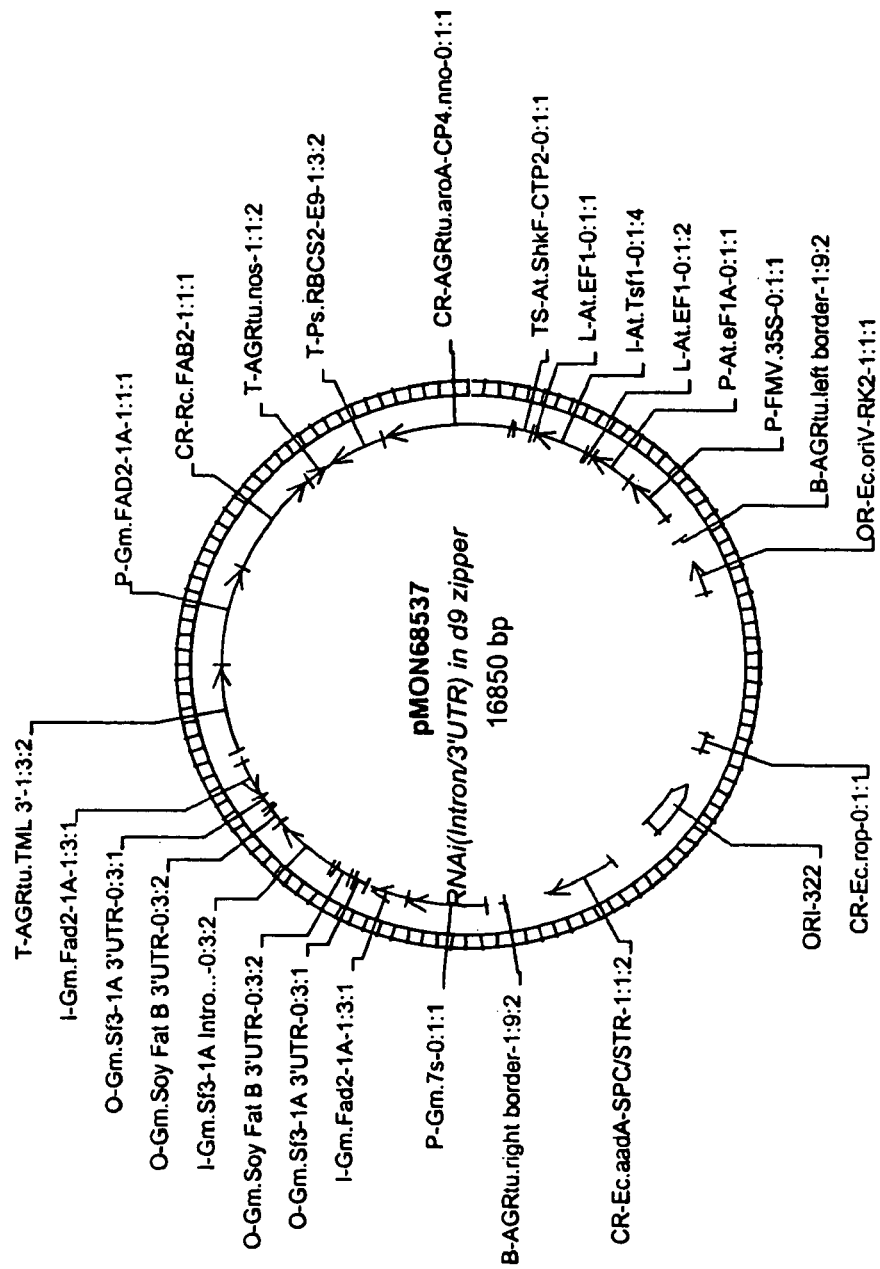
FIG. 21 depicts the construct pMON68537.

Referring now to FIG. 20 soybean FATB-2 non-coding sequences (SEQ ID NOs: 44-47), FAD2-1 non-coding sequences (SEQ ID NOs: 1 and 5-6), FATB-1 non-coding sequences (SEQ ID NOs: 29-37), FAD3-1A non-coding sequences (SEQ ID NOs: 7-13 and 16-17), and FAD3-1B non-coding sequences (SEQ ID NOs: 19-27) are amplified via PCR to result in PCR products that include reengineered restriction sites at both ends. The PCR products are cloned directly, in sense orientation, into a vector containing the soybean 7Sα' promoter and a tml 3' termination sequence, by way of XhoI sites engineered onto the 5' ends of the PCR primers. The vectors are then cut with NotI and ligated into pMON80612, a vector that contains the CP4 EPSPS gene regulated by the FMV promoter and a pea Rubisco E9 3' termination sequence. The resulting gene expression construct is depicted in FIG. 20-A and is used for transformation using methods described herein.

A DNA sequence containing a delta-9 desaturase is regulated by a 7S alpha promoter and a TML 3' termination sequence is cut using the appropriate restriction enzymes and ligated into the above expression construct. The resulting expression construct is depicted in FIG. 20-B and is used for transformation using methods described herein.

A vector containing a *C. pulcherrima* KAS IV gene (SEQ ID NO: 39) regulated by a *Brassica* bean arcelin promoter and a napin 3' termination sequence is cut with appropriate restriction enzymes, and ligated into the above expression construct. The resulting gene expression construct is depicted in FIG. 20-C and is used for transformation using methods as described herein.

pMON93501 contains a soybean FAD2-1A intron 1 (SEQ ID NO: 1) operably linking to a soybean 7Sα' promoter and a H6 3' termination sequence, a *C. pulcherrima* KAS IV gene (SEQ ID NO: 39) operably linking to a *Brassica* napin promoter and a *Brassica* napin 3' termination sequence, the *Ricinus communis* delta 9 desaturase gene (U.S. Patent Application Publication No. 2003/00229918 A1) operably linking to a soybean 7SA promoter and a nos 3' termination sequence, and a CP4 EPSPS gene operably linking to an EFMV promoter (a constitutive promoter derived from a figwort mosaic virus) promoter and a pea Rubisco E9 3' termination sequence all flanked by *Agrobacterium* T-DNA border elements, i.e. right border DNA (RB) and left border DNA (LB). The resulting gene expression construct is used for transformation using methods as described herein.

3C. Antisense Constructs

Figure 14:
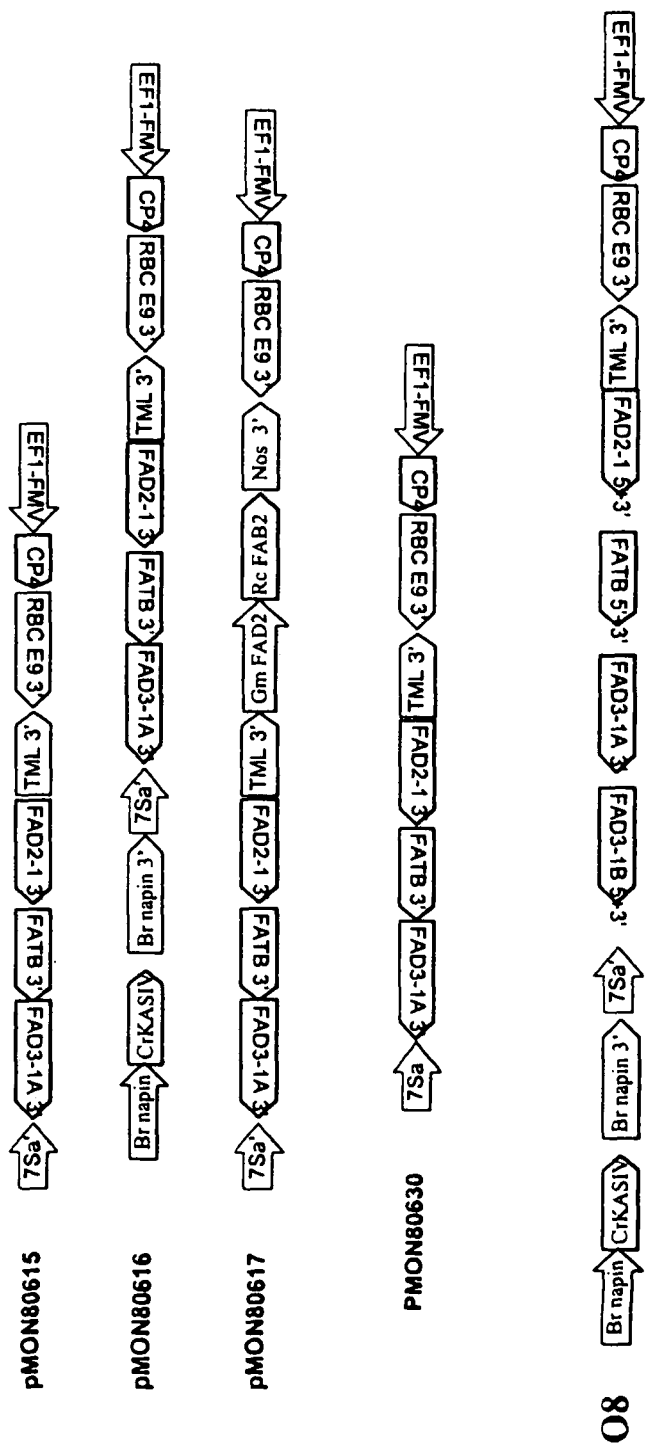

FIG. 14 depicts nucleic acid molecules of the present invention in which the first sets of DNA sequences are capable of expressing antisense constructs, and FIGS. 15 through 18 depict nucleic acid molecules of the present invention in which the first sets of DNA sequences are capable of expressing combinations of sense and antisense constructs. The second set of DNA sequences comprises coding sequences, each of which is a DNA sequence that encodes a sequence that when expressed is capable of increasing one or both of the protein and transcript encoded by a gene selected from the group consisting of KAS I, KAS IV, delta-9 desaturase, and CP4 EPSPS. Each coding sequence is associated with a promoter, which is any promoter functional in a plant, or any plant promoter, and may be an FMV promoter, a napin promoter, a 7S (either 7Sα or 7Sα') promoter, an arcelin promoter, a delta-9 desaturase promoter, or a FAD2-1A promoter.

Referring now to FIG. 14, soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80615, is depicted in FIG. 14 and is used for transformation using methods as described herein.

Soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, pMON80616, is depicted in FIG. 14 and is used for transformation using methods as described herein.

Soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *R. communis* delta-9 desaturase (FAB2) gene (SEQ ID NO: 40) regulated by a soybean FAD2 promoter and a nos 3' termination sequence, is cut with appropriate restriction enzymes, and ligated into pMON41164. The resulting gene expression construct, pMON80617, is depicted in FIG. 14 and is used for transformation using methods as described herein.

Soybean FAD2-1 3'UTR (SEQ ID NO: 5), FATB-1 3'UTR (SEQ ID NO: 36), and FAD3-1A 3'UTR (SEQ ID NO: 16) sequences are amplified via PCR to result in PCR products that include reengineered restriction sites at both ends. The PCR products are cloned directly, in antisense orientation, into a vector containing the soybean 7Sα promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, pMON80630, is depicted in FIG. 14 and is used for transformation using methods as described herein.

Soybean FAD2-1 5'UTR-3'UTR (SEQ ID NOs: 6 and 5, ligated together), FATB-1 5'UTR-3'UTR (SEQ ID NOs: 37 and 36, ligated together), FAD3-1A 3'UTR (SEQ ID NO: 16), and FAD3-1B 5'UTR-3'UTR (SEQ ID NOs: 27 and 26, ligated together) sequences are amplified via PCR to result in PCR products that include reengineered restriction sites at both ends. The PCR products are cloned directly, in antisense orientation, into a vector containing the soybean 7Sα' promoter and a tml 3' termination sequence, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O8, is depicted in FIG. 14 and is used for transformation using methods as described herein.

Figure 15:
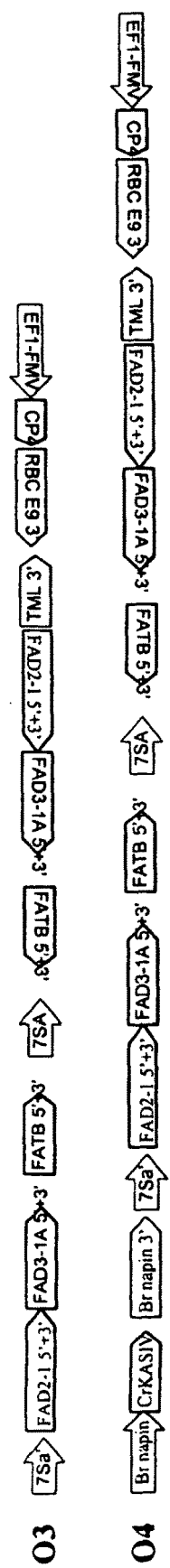

Referring now to FIG. 15, soybean FAD2-1 5'UTR-3'UTR (SEQ ID NOs: 6 and 5, ligated together), FAD3-1A 5'UTR-3'UTR (SEQ ID NOs: 17 and 16, ligated together), and FATB-1 5'UTR-3'UTR (SEQ ID NOs: 37 and 36, ligated together) sequences are amplified via PCR to result in PCR products that include reengineered restriction sites at both ends. The PCR products are cloned directly in sense and antisense orientation into a vector containing the soybean 7Sα' promoter and a tml 3' termination sequence, with an additional soybean 7Sα promoter located between the sense and antisense sequences, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. The resulting gene expression construct, O3, is depicted in FIG. 15 and is used for transformation using methods as described herein.

Soybean FAD2-1 5'UTR-3'UTR (SEQ ID NOs: 6 and 5, ligated together), FAD3-1A 5'UTR-3'UTR (SEQ ID NOs: 27 and 26, ligated together), and FATB-1 5'UTR-3'UTR (SEQ ID NOs: 37 and 36, ligated together) sequences are amplified via PCR to result in PCR products that include reengineered restriction sites at both ends. The PCR products are cloned directly in sense and antisense orientation into a vector containing the soybean 7Sα' promoter and a tml 3' termination sequence, with an additional soybean 7Sα promoter located between the sense and antisense sequences, by way of XhoI sites engineered onto the 5' ends of the PCR primers. The vector is then cut with NotI and ligated into pMON41164, a vector that contains the CP4 EPSPS gene regulated by the FMV promoter and a pea Rubisco E9 3' termination sequence. A vector containing a *C. pulcherrima* KAS IV gene (SEQ ID NO: 39) regulated by a *Brassica* napin promoter and a *Brassica* napin 3' termination sequence is cut with appropriate restriction enzymes, and ligated into pMON41164. The resulting gene expression construct, O4, is depicted in FIG. 15 and is used for transformation using methods as described herein.

Figure 16:
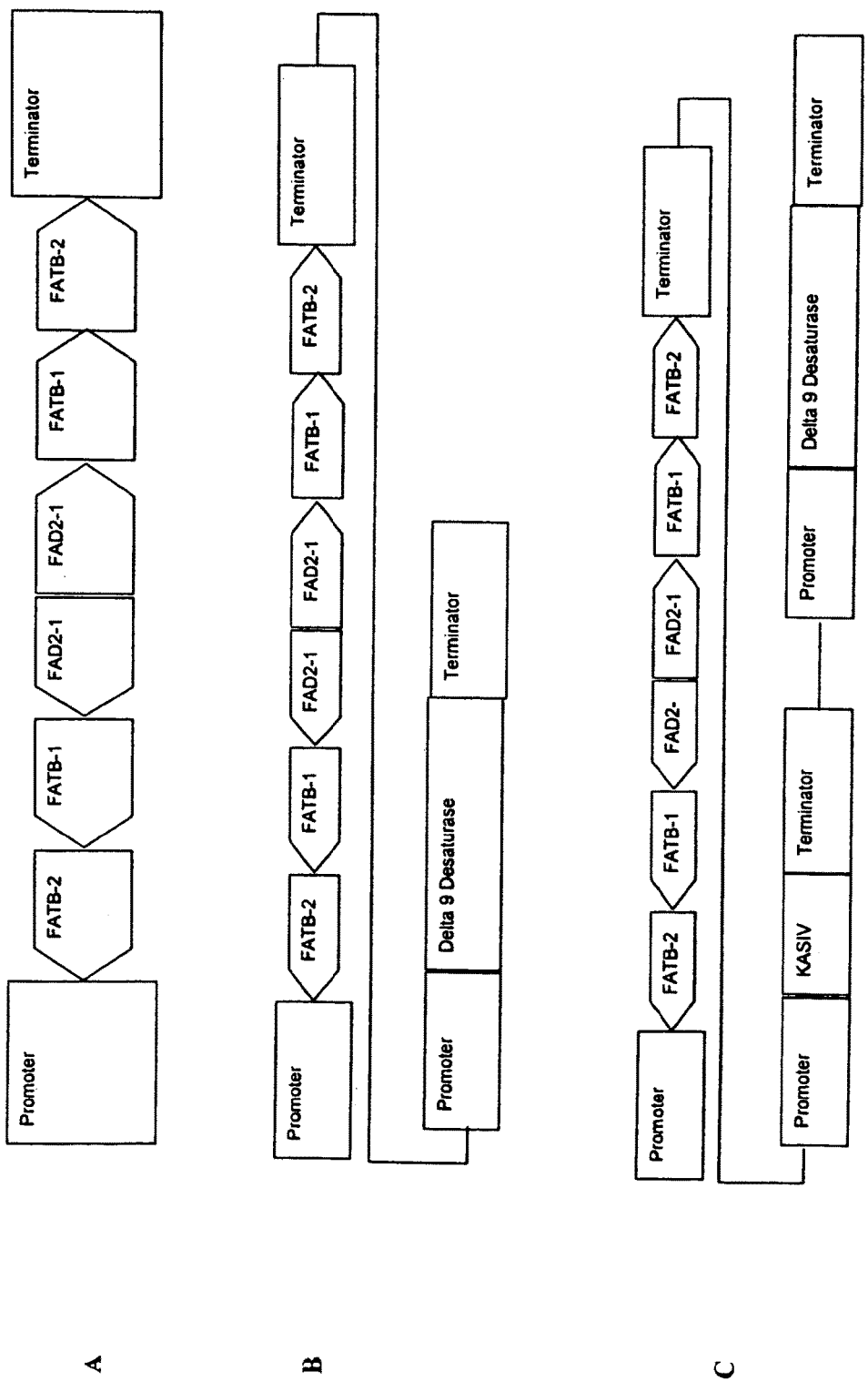

Referring now to FIG. 16, soybean FATB-2 non-coding sequences (SEQ ID NOs: 44-47), FATB-1 non-coding sequences (SEQ ID NOs: 29-37), and FAD2-1 non-coding sequences (SEQ ID NOs: 1 and 5-6) are amplified via PCR to result in PCR products that include reengineered restriction sites at both ends. The PCR products are cloned directly in sense and antisense orientation into a vector containing the soybean 7Sα' promoter and a tml 3' termination sequence. The vector is then cut with an appropriate restriction endonuclease and ligated into pMON80612 a vector that contains the CP4 EPSPS gene regulated by the FMV promoter and a pea Rubisco E9 3' termination sequence. The resulting gene expression construct is depicted in FIG. 16-A and is used for transformation using methods as described herein.

A DNA sequence containing a delta-9 desaturase is regulated by a 7S alpha promoter and a TML 3' termination sequence is cut using the appropriate restriction enzymes and ligated into the above expression construct. The resulting expression construct is depicted in FIG. 16-B and is used for transformation using methods described herein.

A vector containing a *C. pulcherrima* KAS IV gene (SEQ ID NO: 39) regulated by a bean arcelin promoter and a napin 3' termination sequence is cut with appropriate restriction enzymes, and ligated into the above expression construct. The resulting gene expression construct is depicted in FIG. 16-C and is used for transformation using methods as described herein.

Figure 17:
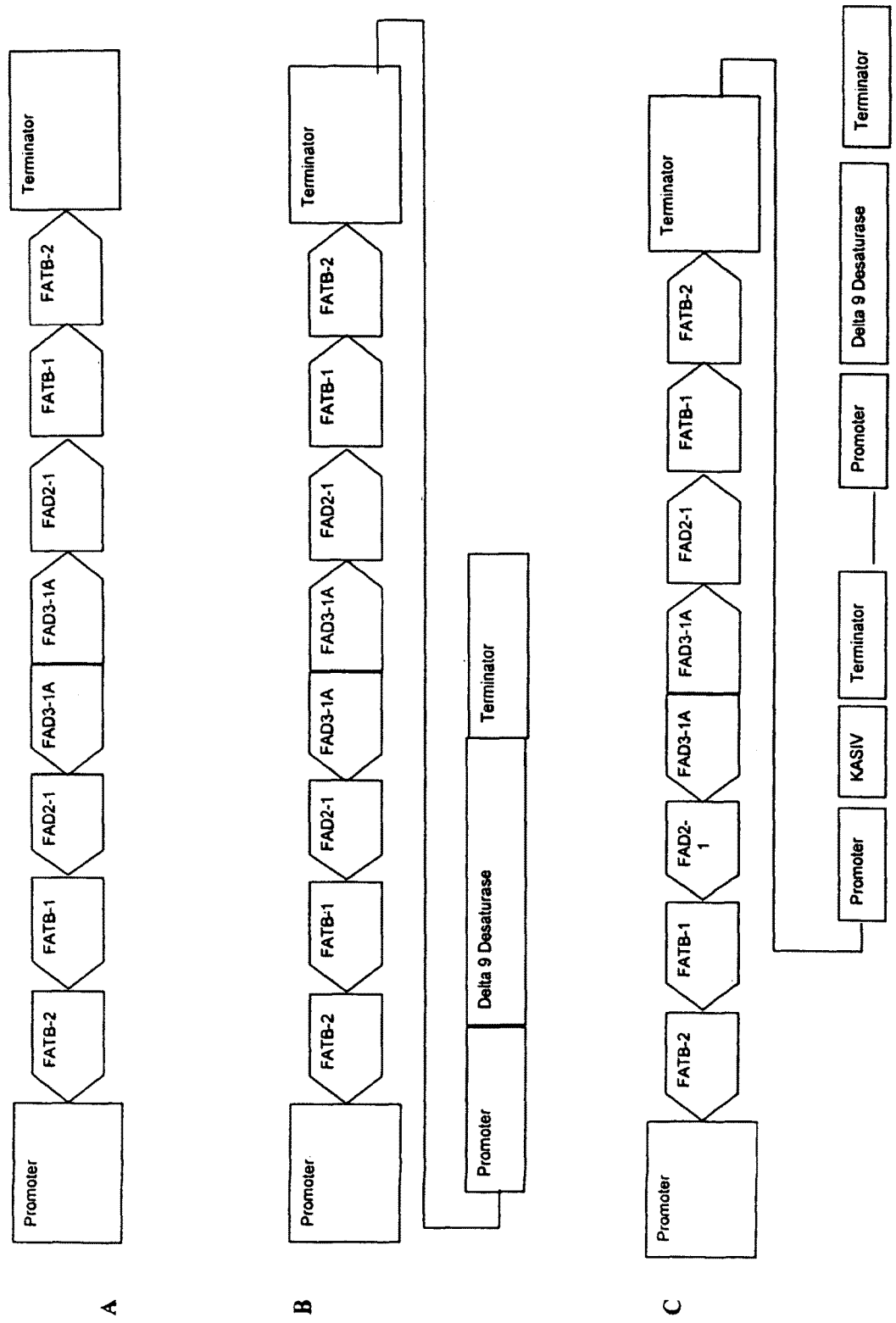

Referring now to FIG. 17, soybean FATB-2 non-coding sequences (SEQ ID NOs: 44-47), FATB-1 non-coding sequences (SEQ ID NOs: 29-37), FAD2-1 non-coding sequences (SEQ ID NOs: 1 and 5-6), and FAD3-1A non-coding sequences (SEQ ID NOs: 7-13 and 16-17) are amplified via PCR to result in PCR products that include reengineered restriction sites at both ends. The PCR products are cloned directly in sense and antisense orientation into a vector containing the soybean 7Sα' promoter and a tml 3' termination sequence. The vector is then cut with an appropriate restriction endonuclease and ligated into pMON80612, a vector that contains the CP4 EPSPS gene regulated by the FMV promoter and a pea Rubisco E9 3' termination sequence. The resulting gene expression construct is depicted in FIG. 17-A and is used for transformation using methods as described herein.

A DNA sequence containing a delta-9 desaturase is regulated by a 7S alpha promoter and a TML 3' termination sequence is cut using the appropriate restriction enzymes and ligated into the above expression construct. The resulting expression construct is depicted in FIG. 17-B and is used for transformation using methods described herein.

A vector containing a *C. pulcherrima* KAS IV gene (SEQ ID NO: 39) regulated by a bean arcelin promoter and a napin 3' termination sequence is cut with appropriate restriction enzymes, and ligated into the above expression construct. The resulting gene expression construct is depicted in FIG. 17-C and is used for transformation using methods as described herein.

Figure 18:
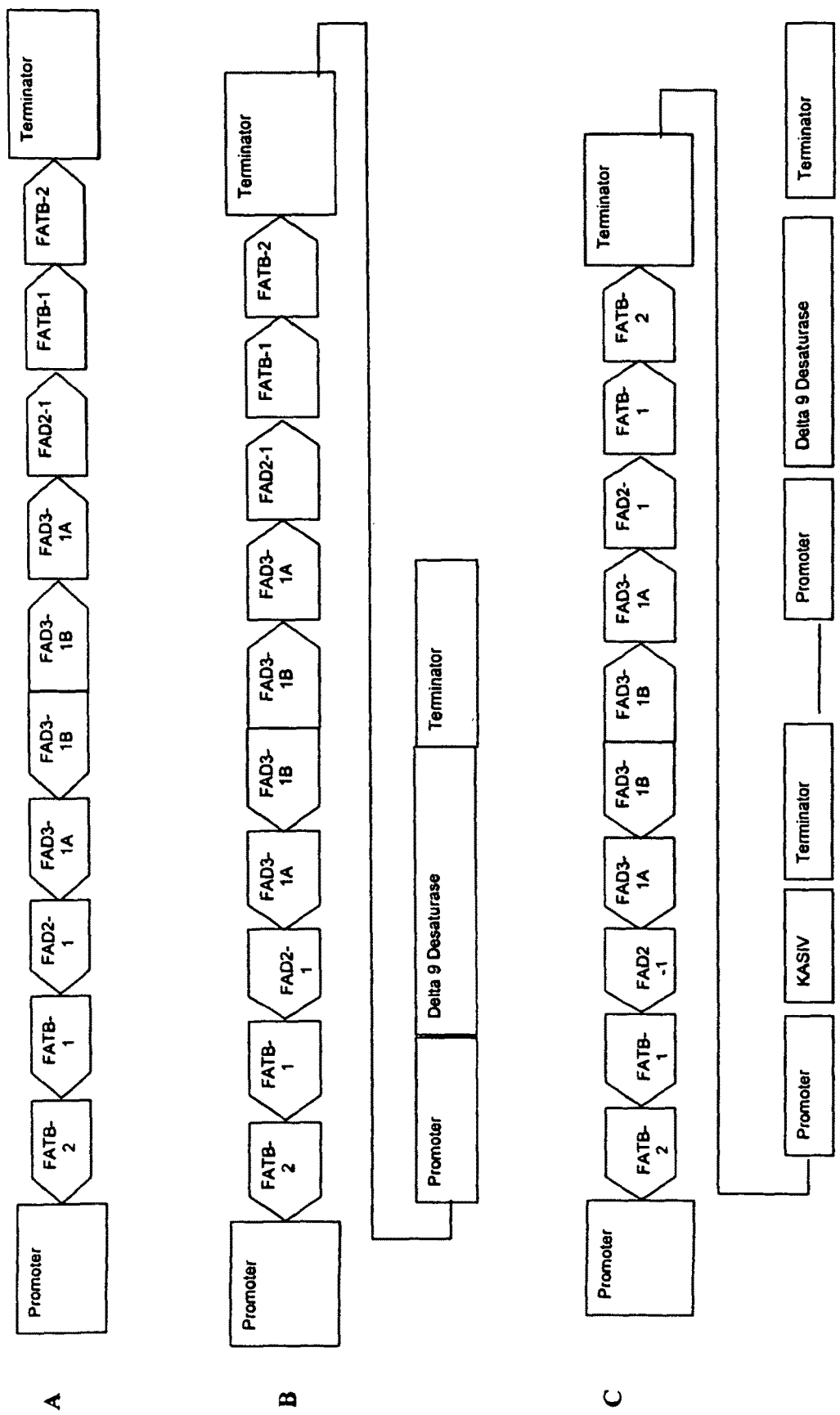

Referring now to FIG. 18, soybean FATB-2 non-coding sequences (SEQ ID NOs: 44-47), FATB-1 non-coding sequences (SEQ ID NOs: 29-37), FAD2-1 non-coding sequences (SEQ ID NOs: 1 and 5-6), FAD3-1A non-coding sequences (SEQ ID NOs: 7-13 and 16-17) and FAD3-1B non-coding sequences (SEQ ID NOs: 19-27) are amplified via PCR to result in PCR products that include reengineered restriction sites at both ends. The PCR products are cloned directly in sense and antisense orientation into a vector containing the soybean 7Sα' promoter and a tml 3' termination sequence. The vector is then cut with an appropriate restriction endonuclease and ligated into pMON80612, a vector that contains the CP4 EPSPS gene regulated by the FMV promoter and a pea Rubisco E9 3' termination sequence. The resulting gene expression construct is depicted in FIG. 18-A and is used for transformation using methods as described herein.

A DNA sequence containing a delta-9 desaturase is regulated by a 7S alpha promoter and a TML 3' termination sequence is cut using the appropriate restriction enzymes and ligated into the above expression construct. The resulting expression construct is depicted in FIG. 18-B and is used for transformation using methods described herein.

A vector containing a *C. pulcherrima* KAS IV gene (SEQ ID NO: 39) regulated by a bean arcelin promoter and a napin 3' termination sequence is cut with appropriate restriction enzymes, and ligated into the above expression construct. The resulting gene expression construct is depicted in FIG. 18-C and is used for transformation using methods as described herein. The above-described nucleic acid molecules are preferred embodiments which achieve the objects, features and advantages of the present invention. It is not intended that the present invention be limited to the illustrated embodiments. The arrangement of the sequences in the first and second sets of DNA sequences within the nucleic acid molecule is not limited to the illustrated and described arrangements, and may be altered in any manner suitable for achieving the objects, features and advantages of the present invention as described herein, illustrated in the accompanying drawings, and encompassed within the claims.

3D. In Vivo Assembly

An aspect of the present invention includes a DNA construct that assembles into a recombinant transcription unit on a plant chromosome in planta capable of forming double-stranded RNA. The assembly of such constructs and the methods for assembling in vivo a recombinant transcription unit for gene suppression are described in International Application No. PCT/US2005/00681, hereby incorporated by reference in its entirety.

pMON93505 is a construct used for in vivo assembly and has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 100 contiguous nucleotides from the 3' end and ligated to the FATB-1a3' UTR followed by a FATB-1a5' UTR, a *C. pulcherrima* KAS IV gene (SEQ ID NO: 39) operably linking to a *Brassica* napin promoter and a *Brassica* napin 3' termination sequence, a *Ricinus communis* delta 9 desaturase gene (U.S. Patent Application Publication No. 2003/00229918 A1) operably linking to a soybean 7SA promoter and a nos 3' termination sequence, and a CP4 EPSPS gene operably linking to a eFMV promoter and a pea Rubisco E9 3' termination sequence all flanked by *Agrobacterium* T-DNA border elements, i.e. right border DNA (RB) and left border DNA (LB). On the same construct, in the second T-DNA segment, flanked by another RB and LB, is a H6 3' termination sequence operably linking to a soybean FAD2-1A intron 1 (SEQ ID NO: 1), which is reduced by 100 contiguous nucleotides from the 3' end and ligated to the FATB-1a3' UTR followed by a FATB-1a5' UTR. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON93506 is a construct used for in vivo assembly that has two T-DNA segments, each flanked by *Agrobacterium* T-DNA border elements, i.e. right border DNA (RB) and left border DNA (LB). The first T-DNA contains a soybean 7Sα' promoter operably linking to a soybean FAD2-1A intron 1 (SEQ ID NO: 1), which is reduced by 100 contiguous nucleotides from the 3' end and ligated to the FATB-1a3' UTR followed by a FATB-1a5' UTR, a *Ricinus communis* delta 9 desaturase gene (U.S. Patent Application Publication No. 2003/00229918 A1) operably linking to a soybean 7SA promoter and a nos 3' termination sequence, and a CP4 EPSPS gene operably linking to an eFMV promoter and a pea Rubisco E9 3' termination sequence all flanked by LB and RB. On the same vector, in the second T-DNA segment, is a H6 3' termination sequence operably linked to the soybean FAD2-1A intron 1 (SEQ ID NO: 1), which is reduced by 100 contiguous nucleotides from the 3' end and ligated to the FATB-1a3' UTR followed by a FATB-1a5' UTR, flanked by another RB and LB. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON95829 is a construct used for in vivo assembly that has two T-DNA segments, each flanked by *Agrobacterium* T-DNA border elements, i.e. right border DNA (RB) and left border DNA (LB). The first T-DNA contains a soybean 7Sα' promoter operably linking to a soybean FAD2-1A intron 1 (SEQ ID NO: 1), which is reduced by 100 contiguous nucleotides from the 3' end and ligated to 42 contiguous nucleotides of a FATB-1a 5' UTR, followed by the FATB-1a chloroplast transit peptide ("CTP") coding region, and a CP4 EPSPS gene operably linking to an EFMV promoter and a pea Rubisco E9 3' termination sequence all flanked by *Agrobacterium* T-DNA border elements, i.e. right border DNA (RB) and left border DNA (LB). On the same vector in the second T-DNA segment, flanked by another RB and LB, is a H6 3' termination sequence operably linking to a soybean FAD2-1A intron 1 (SEQ ID NO: 1), which is reduced by 100 contiguous nucleotides from the 3' end and ligated to 42 contiguous nucleotides of a FATB-1a 5' UTR, followed by the FATB-1a chloroplast transit peptide ("CTP") coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON97595 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to 42 contiguous nucleotides of a FATB-1a5' UTR followed by the FATB-1achloroplast transit peptide ("CTP") coding region, and a CP4 EPSPS gene operably linking to an EFMV promoter and a pea rubisco E9 3' termination sequence, all flanked by *Agrobacterium* T-DNA border elements, i.e. right border DNA (RB) and left border DNA (LB). On the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to 42 contiguous nucleotides of a FATB-1a5' UTR followed by the FATB-1aCTP coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON97581 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the FATB-1achloroplast transit peptide ("CTP") coding region, and a CP4 EPSPS gene operably linking to an EFMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the FATB-1aCTP coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON97596 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the 5' 180 bp of the FATB-1achloroplast transit peptide ("CTP") coding region, and a CP4 EPSPS gene operably linking to an EFMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the 5' 180 bp of the FATB-1aCTP coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON97597 is a construct used for in vivo assembly that has two T-DNA segments, each flanked by *Agrobacterium* T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 320 contiguous nucleotides from the 3' end and ligated to the 5' 120 bp of the FATB-1achloroplast transit peptide ("CTP") coding region, and a CP4 EPSPS gene operably linking to an EFMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 320 contiguous nucleotides from the 3' end and ligated to the 5' 120 bp of the FATB-1aCTP coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

pMON97598 is a construct used for in vivo assembly that has two T-DNA segments, each flanked by *Agrobacterium*

T-DNA border elements, i.e. right border DNA (RB) and left border DNA (LB). The first T-DNA segment contains a soybean 7Sα' promoter operably linking to a soybean FAD2-1A intron 1 (SEQ ID NO: 1), which is reduced by 340 contiguous nucleotides from the 3' end and ligated to the FATB-1achloroplast transit peptide ("CTP") coding region, and a CP4 EPSPS gene operably linking to an EFMV promoter and a pea Rubisco E9 3' termination sequence, all flanked by *Agrobacterium* T-DNA border elements, i.e. right border DNA (RB) and left border DNA (LB). On the same construct, in the second T-DNA segment, flanked by another RB and LB, is a H6 3' termination sequence operably linked to a soybean FAD2-1A intron 1 (SEQ ID NO: 1), which is reduced by 340 contiguous nucleotides from the 3' end and ligated to the FATB-1aCTP coding region. The resulting gene expression construct is used for transformation using methods as described herein.

When the two T-DNA segments of the above construct are inserted into a single locus of the chromosome of a host organism in a RB to RB orientation, the assembled transcription unit has a soybean 7Sα' promoter operably linking sense and anti-sense-oriented soybean FAD2-1A intron 1 and FATB-1a DNA fragments. When transcribed, the operably linked sense and anti-sense oriented RNA sequences are capable of forming double-stranded RNA effective for suppression of FAD2-1A and FATB.

Example 4 Plant Transformation and Analysis

The constructs of Examples 2 and 3 are stably introduced into soybean (for example, Asgrow variety A4922 or Asgrow variety A3244 or Asgrow variety A3525) by the methods described earlier, including the methods of McCabe et al., *Bio/Technology*, 6:923-926 (1988), or *Agrobacterium*-mediated transformation. Transformed soybean plants are identified by selection on media containing glyphosate. Fatty acid compositions are analyzed from seed of soybean lines transformed with the constructs using gas chromatography. In addition, any of the constructs may contain other sequences of interest, as well as different combinations of promoters.

For some applications, modified fatty acid compositions are detected in developing seeds, whereas in other instances, such as for analysis of oil profile, detection of fatty acid modifications occurring later in the FAS pathway, or for detection of minor modifications to the fatty acid composition, analysis of fatty acid or oil from mature seeds is preferred. Furthermore, analysis of oil and/or fatty acid content of individual seeds may be desirable, especially in detection of oil modification in the segregating $R_1$ seed populations. As used herein, $R_0$ generation indicates the plant arising from transformation/regeneration protocols described herein, the R1 generation indicates seeds grown on the selfed transgenic $R_0$ plant. R1 plants are grown from the R1 seeds.

Fatty acid compositions are determined for the seed of soybean lines transformed with the constructs of Example 3. One to ten seeds of each of the transgenic and control soybean lines are ground individually using a tissue homogenizer (Pro Scientific) for oil extraction. Oil from ground soybean seed is extracted overnight in 1.5 ml heptane containing triheptadecanoin (0.50 mg/ml). Aliquots of 200 µl of the extracted oil are derivatized to methyl esters with the addition of 500 µl sodium methoxide in absolute methanol. The derivatization reaction is allowed to progress for 20 minutes at 50° C. The reaction is stopped by the simultaneous addition of 500 µl 10% (w/v) sodium chloride and 400 µl heptane. The resulting fatty acid methyl esters extracted in hexane are resolved by gas chromatography (GC) on a Hewlett-Packard model 6890 GC (Palo Alto, Calif.). The GC was fitted with a Supelcowax 250 column (30 m, 0.25 mm id, 0.25 micron film thickness) (Supelco, Bellefonte, Pa.). Column temperature is 175° C. at injection and the temperature programmed from 175° C. to 245° C. to 175° C. at 40° C./min. Injector and detector temperatures are 250° C. and 270° C., respectively.

Example 5 Synthesized Fuel Oil with Improved Biodiesel Properties

A synthesized fuel oil fatty acid composition is prepared having the following mixtures of fatty acid methyl esters: 73.3% oleic acid, 21.4% linoleic acid, 2.2% palmitic acid, 2.1% linolenic acid and 1.0% stearic acid (all by weight). Purified fatty acid methyl esters are obtained from Nu-Chek Prep, Inc., Elysian, Minn., USA. The cetane number and ignition delay of this composition is determined by the Southwest Research Institute using an Ignition Quality Tester ("IQT") 613 (Southwest Research Institute, San Antonio, Tex., USA).

An IQT consists of a constant volume combustion chamber that is electrically heated, a fuel injection system, and a computer that is used to control the experiment, record the data and provide interpretation of the data. The fuel injection system includes a fuel injector nozzle that forms an entrance to the combustion chamber. A needle lift sensor in the fuel injector nozzle detects fuel flow into the combustion chamber. A pressure transducer attached to the combustion chamber measures cylinder pressure, the pressure within the combustion chamber. The basic concept of an IQT is measurement of the time from the start of fuel injection into the combustion chamber to the start of combustion. The thermodynamic conditions in the combustion chamber are precisely controlled to provide consistent measurement of the ignition delay time.

For a cetane number and ignition delay test, the test fuel is filtered using a 5-micron filter. The fuel reservoir, injection line, and nozzle are purged with pressurized nitrogen. The fuel reservoir is then cleaned with a lint free cloth. A portion of the test fuel is used to flush the fuel reservoir, injection line, and nozzle. The reservoir is filled with the test fuel and all air is bled from the system. The reservoir is pressurized to 50 psig. The method basically consists of injecting at high pressure a precisely metered quantity of the test fuel into the combustion chamber that is charged with air to the desired pressure and temperature. The measurement consists of determining the time from the start of injection to the onset of combustion, often referred to as the ignition delay time. This determination is based on the measured needle lift and combustion chamber pressures. The normal cetane rating procedure calls for setting the skin temperature at 567.5° C. and the air pressure at 2.1 MPa.

A fuel with a known injection delay is run in the IQT combustion bomb at the beginning of the day to make sure the unit is operating within normal parameters. The test synthetic is then run. The known fuel is run again to verify that the system has not changed. Once the fuel reservoir is reconnected to the fuel injection pump, the test procedure is initiated on the PC controller. The computer controls all the procedure, including the air charging, fuel injection, and exhaust events. 32 repeat combustion events are undertaken.

The ignition delay is the time from the start of injection to the start of ignition. It is determined from the needle lift and cylinder pressure data. The rise of the injection needle signals start of injection. The cylinder pressure drops slightly due to the cooling effect of the vaporization of the fuel. Start of combustion is defined as the recovery time of the cylinder pressure—increases due to combustion to the pressure it was just prior to fuel injection.

The measured ignition delay times are then used to determine the cetane number based on a calibration curve that is incorporated into the data acquisition and reduction software. The calibration curve, consisting of cetane number as a function of ignition delay time, is generated using blends of the primary reference fuels and NEG check fuels. In the case of test fuels that are liquid at ambient conditions, the calibration curve is checked on a daily basis using at least one check fuel of known cetane number (Ryan, "Correlation of Physical and Chemical Ignition Delay to Cetane Number", SAE Paper 852103 (1985); Ryan, "Diesel Fuel Ignition Quality as Determined in a Constant Volume Combustion Bomb", SAE Paper 870586 (1986); Ryan, "Development of a Portable Fuel Cetane Quality Monitor", Belvoir Fuels and Lubricants Research Facility Report No. 277, May (1992); Ryan, "Engine and Constant Volume Bomb Studies of Diesel Ignition and Combustion", SAE Paper 881616 (1988); and Allard et al., "Diesel Fuel Ignition Quality as Determined in the Ignition Quality Tester ("IQT")", SAE Paper 961182 (1996)). As shown in Table 3, the synthesized oil composition exhibits cetane numbers and ignition delays that are suitable for use for example, without limitation, as a biodiesel oil.

TABLE 3

| Fuel Name | Test Number | Cetane Number | Std. Dev. Cetane No. | Ignition Delay (ms) | Std. Dev. Ign. Delay |
|---|---|---|---|---|---|
| Check-High[1] | 1777 | 49.55 | 0.534 | 4.009 | 0.044 |
| Check-High | 1778 | 49.33 | 0.611 | 4.028 | 0.051 |
| Average | | 49.4 | | 4.02 | |
| Synthesized Oil | 1779 | 55.02 | 1.897 | 3.622 | 0.116 |
| Synthesized Oil | 1780 | 55.65 | 1.807 | 3.583 | 0.109 |
| Synthesized Oil | 1781 | 55.63 | 1.649 | 3.583 | 0.098 |
| Average | | 55.4 | | 3.60 | |
| Check-High | 1786 | 49.2 | 0.727 | 4.04 | 0.061 |

[1] The fuel called "Check-High" is a calibration fuel. It should have a cetane number of 49.3 ± 0.5. The unit is checked with the calibration before and after running the synthetic test fuel.

The density (ASTM D-4052) cloud point (ASTM D-2500), pour point (ASTM D-97), and cold filter plugging point (IP 309/ASTM D-6371) are determined for the synthesized oil using ASTM D protocols. ASTM D protocols are obtained from ASTM, 100 Barr Harbor Drive, West Conshohocken, Pa., USA. The results of these tests are set forth in Table 4. As shown in Table 4, the synthesized oil composition exhibits numbers that are suitable for use as, for example without limitation, as a biodiesel oil.

TABLE 4

| TEST | METHOD | RESULTS |
|---|---|---|
| Density | ASTM D-4052 | 0.8791 g/mL |
| Cloud Point | ASTM D-2500 | −18 deg. C. |
| Pour Point | ASTM D-97 | −21 deg. C. |
| Cold Filter Plugging Point | IP 309 (same as ASTM D-6371) | −21 deg. C. |

Levels of nitric oxide emissions are estimated by evaluating the unsaturation levels of a biologically-based fuel, by measuring the fuel density and indirectly calculating the estimated emissions levels, or by directly measuring. There are also standard protocols available for directly measuring levels of nitric oxide emissions. The synthesized oil is estimated to have lower nitric oxide emissions levels than methyl esters of fatty acids made from conventional soybean oil based on an evaluation of the overall level of unsaturation in the synthesized oil. Oils containing larger numbers of double bonds, i.e., having a higher degree of unsaturation, tend to produce higher nitric oxide emissions. The oil has a total of 123 double bonds, as compared to conventional soybean oil's total of 153 double bonds, as shown in Table 5.

TABLE 5

| SYNTHETIC OIL | |
|---|---|
| 73% oleic acid (18:1) × 1 double bond = | 73 |
| 22% linoleic acid (18:2) × 2 double bonds = | 44 |
| 2% linolenic acid (18:3) × 3 double bonds = | 6 |
| TOTAL double bonds | 123 |
| CONVENTIONAL SOYBEAN OIL | |
| 23% oleic acid (18:1) × 1 double bond = | 23 |
| 53% linoleic acid (18:2) × 2 double bonds = | 106 |
| 8% linolenic acid (18:3) × 3 double bonds = | 24 |
| TOTAL double bonds | 153 |

As reported by the National Renewable Energy Laboratory, Contract No. ACG-8-17106-02 Final Report, *The Effect Of Biodiesel Composition On Engine Emissions From A DDC Series 60 Diesel Engine*, (June 2000), nitric acid emissions of biodiesel compositions are predicted by the formula $y=46.959x-36.388$ where y is the oxide emissions in grams/brake horse power hours; and x is the density of biodiesel. The formula is based on a regression analysis of nitric acid emission data in a test involving 16 biodiesel fuels. The test makes use of a 1991 calibration, production series 60 model Detroit Diesel Corporation engine.

The density of the synthesized oil is determined by Southwest Research Institute using the method ASTM D4052. The result shown in Table 4 is used in the above equation to predict a nitric oxide emission value of 4.89 g/bhp-h. This result is compared to a control soybean product. The National Renewable Energy Laboratory report gives the density and nitric oxide emissions of a control soy based biodiesel (methyl soy ester IGT). The density of the control biodiesel is 0.8877 g/mL, giving a calculated nitric oxide emission of 5.30 g/bhp-h. This calculated emission value is similar to the experimental value for nitric oxide emission of 5.32 g/bhp-h. The synthesized oil composition exhibits improved numbers compared to the control and is suitable for use, for example without limitation, as a biodiesel oil.

Example 6 Optimum Fatty Acid Composition for Healthy Serum Lipid Levels

The cholesterol lowering properties of vegetable compositions are determined to identify fatty acid compositions that have a more favorable effect on serum lipid levels than conventional soybean oil (i.e., lower LDL-cholesterol and higher HDL-cholesterol). Published equations based on 27 clinical trials (Mensink, R. P. and Katan, M. B. Arteriosclerosis and Thrombosis, 12:911-919 (1992)) are used to compare the effects on serum lipid levels in humans of new oilseed compositions with that of normal soybean oil.

Table 6 below presents the results of the change in serum lipid levels where 30% of dietary energy from carbohydrate is substituted by lipids. The results show that soybean oil already has favorable effects on serum lipids when it replaces carbohydrates in the diet. Improvements on this composition are possible by lowering saturated fat levels and by obtaining a linoleic acid level between 10-30% of the total fatty acids, preferably about 15-25% of the total fatty acids. When the proportion of linoleic acid is less than 10% of the total fatty acids, the new composition raises LDL-cholesterol compared to control soybean oil, even though the saturated fat content is lowered to 5% of the total fatty acids. When the proportion of linoleic acid is increased, the ability of the composition to raise serum HDL levels is reduced. Therefore, the preferred linoleic acid composition is determined to be about 15-25% of the total fatty acids.

Step 1—The soybean FAD3-1A intron #5, which serves as the spliceable intron portion of the dsRNAi construct, is PCR amplified using soybean genomic DNA as template, with the following primers:

```
5' primer = 19037 =
ACTAGTATATTGAGCTCATATTCCACTGCAGTGGATATT

GTTTAAACATAGCTAGCATATTACGCGTATATTATACAA

GCTTATATTCCCGGGATATTGTCGACATATTAGCGGTAC

ATTTTATTGCTTATTCAC
```

TABLE 6

| | Fatty acids | | | | | | Serum |
|---|---|---|---|---|---|---|---|
| | C16:0 | C18:0 | C18:1 | C18:2 | C18:3 | Other (C20:1) | Lipids |
| Soy control (%) | 11.000 | 4.000 | 23.400 | 53.200 | 7.800 | 0.600 | |
| Proportion of 30% fat E (%) | 3.300 | 1.200 | 7.020 | 15.960 | 2.340 | 0.180 | |
| LDL Calculation (mg/dl) | 4.224 | 1.536 | 1.685 | 8.778 | 1.287 | 0.043 | −6.033 |
| HDL Calc (mg/dl) | 1.551 | 0.564 | 2.387 | 4.469 | 0.655 | 0.061 | 9.687 |
| 3% 18:2, <6% sat (%) | 3.000 | 2.000 | 85.000 | 3.000 | 3.000 | 4.000 | |
| Proportion of 30% fat E (%) | 0.900 | 0.600 | 25.500 | 0.900 | 0.900 | 1.200 | |
| LDL Calculation (mg/dl) vs. control (mg/dl) | 1.152 | 0.768 | 6.120 | 0.495 | 0.495 | 0.288 | −5.478 0.555 |
| HDL calculation (mg/dl) vs. control (mg/dl) | 0.423 | 0.282 | 8.670 | 0.252 | 0.252 | 0.408 | 10.287 0.600 |
| 10% 18:2, <6% sat (%) | 3.000 | 2.000 | 72.000 | 10.000 | 3.000 | 10.000 | |
| Proportion of 30% fat E (%) | 0.900 | 0.600 | 21.600 | 3.000 | 0.900 | 3.000 | |
| LDL Calculation (mg/dl) vs. control (mg/dl) | 1.152 | 0.768 | 5.184 | 1.650 | 0.495 | 0.720 | −6.129 −0.096 |
| HDL calculation (mg/dl) vs. control (mg/dl) | 0.423 | 0.282 | 7.344 | 0.840 | 0.252 | 1.020 | 10.161 0.474 |
| 20% 18:2, <6% sat (%) | 3.000 | 2.000 | 65.000 | 20.000 | 3.000 | 7.000 | |
| Proportion of 30% fat E (%) | 0.900 | 0.600 | 19.500 | 6.000 | 0.900 | 2.100 | |
| LDL Calculation (mg/dl) vs. control (mg/dl) | 1.152 | 0.768 | 4.680 | 3.300 | 0.495 | 0.504 | −7.059 −1.026 |
| HDL calculation (mg/dl) vs. control (mg/dl) | 0.423 | 0.282 | 6.630 | 1.680 | 0.252 | 0.714 | 9.981 0.294 |
| 21% 18:2, <3.2% sat (%) | 2.000 | 1.000 | 72.000 | 21.000 | 1.000 | 3.000 | |
| Proportion of 30% fat E (%) | 0.600 | 0.300 | 21.600 | 6.300 | 0.300 | 0.900 | |
| LDL Calculation (mg/dl) vs. control (mg/dl) | 0.768 | 0.384 | 5.184 | 3.465 | 0.165 | 0.216 | −7.878 −1.845 |
| HDL calculation (mg/dl) vs. control (mg/dl) | 0.282 | 0.141 | 7.344 | 1.764 | 0.084 | 0.306 | 9.921 0.234 |
| 30% 18:2, <6% sat (%) | 3.000 | 2.000 | 57.000 | 30.000 | 3.000 | 5.000 | |
| Proportion of 30% fat E (%) | 0.900 | 0.600 | 17.100 | 9.000 | 0.900 | 1.500 | |
| LDL Calculation (mg/dl) vs. control (mg/dl) | 1.152 | 0.768 | 4.104 | 4.950 | 0.495 | 0.360 | −7.989 −1.956 |
| HDL calculation (mg/dl) vs. control (mg/dl) | 0.423 | 0.282 | 5.814 | 2.520 | 0.252 | 0.510 | 9.801 0.114 |

Example 7

The following fourteen steps illustrate the construction of vector pMON68537 designed for plant transformation to suppress FAD2, FAD3, and FATB genes and overexpress delta-9 desaturase in soybean. In particular, the construct comprises a 7S alpha promoter operably linked to soybean sense-oriented intron and 3'UTRs, i.e., a FAD2-1A intron #1, a FAD3-1A 3'UTR, a FATB-1 3'UTR, a hairpin loop-forming spliceable intron, and a complementary series of soybean anti-sense-oriented intron and 3'UTR's, i.e., a FATB-1 3'UTR, a FAD3-1A 3'UTR and a FAD2-1A intron #1 and the soybean FAD2 promoter driving the delta-9 desaturase.

```
3' primer = 19045 =
ACTAGTATATTGAGCTCATATTCCTGCAGGATATTCTCG

AGATATTCACGGTAGTAATCTCCAAGAACTGGTTTTGCT

GCTTGTGTCTGCAGTGAATC.
```

These primers add cloning sites to the 5' and 3' ends. To 5' end: SpeI, SacI, BstXI, PmeI, NheI, MluI, HindIII, XmaI, SmaI, SalI. To 3' end: SpeI, SacI, Sse8387I, XhoI. The soybean FAD3-1A intron #5 PCR product is cloned into pCR2.1, resulting in KAWHIT03.0065. KAWHIT03.0065 is then digested with SpeI and the ends are filled with Pfu polymerase and pMON68526 (empty chloramphenicol (hereinafter CM) resistant vector) is digested with HindIII and the ends are filled with Pfu polymerase. KAWHIT03.0065 and pMON68526 are then ligated to create pMON68541 (soybean FAD3-1A intron #5 with multiple cloning sites in Amp resistant vector).

Step 2—The soybean FATB-1 3'UTR is amplified with the following primers: 18662=TTTTAATTACAAT-GAGAATGAGATTTACTGC (adding Bsp120I to the 5' end) and 18661=GGGCCCGATTTGAAATGGTTAACG. The PCR product is then ligated into pCR2.1 to make KAWHIT03.0036.

Step 3—KAWHIT03.0036 is then digested with Bsp120I and EcoRI and then cloned into KAWHIT03.0032 (empty CM resistant vector with a multiple cloning site) to make KAWHIT03.0037 (FATB-1 3'UTR in empty CM resistant vector).

Step 4—The soybean FAD3-1A 3'UTR is amplified with the following primers: 18639=GGGCCCGTTTCAAA CTTTTTGG (adding Bsp120I to the 5' end) and 18549=TGAAACTGACAATTCAA. The PCR product is then ligated into pCR2.1 to make KAWHIT03.0034.

Step 5—KAWHIT03.0034 is digested with Bsp120I and EcoRI and then ligated into KAWHIT03.0032 (empty CM resistant vector with a multiple cloning site) to make KAWHIT03.0035 (FAD3-1A 3'UTR in empty CM resistant vector).

Step 6—The soybean FAD 2-1A intron #1 is PCR amplified using soybean genomic DNA as template, with the following primers: 5' primer=18663=GGGCCCGG TAAATTAAATTGTGC (Adding Bsp120I site to 5' end); and 3' primer=18664=CTGTGTCAAAGTATAAACAAGT-TCAG. The resulting PCR product is cloned into pCR 2.1 creating KAWHIT03.0038.

Step 7—Soybean FAD 2-1A intron #1 PCR product in KAWHIT03.0038 is cloned into KAWHIT03.0032 (empty CM resistant vector with a multiple cloning site) using the restriction sites Bsp120I and EcoRI. The resulting plasmid is KAWHIT03.0039 (soybean FAD 2-1A intron #1 in empty CM resistant vector).

Step 8—KAWHIT03.0039 is digested with AscI and HindIII and pMON68541 (FAD3-1A intron #5 dsRNAi AMP resistant base vector) is digested with MluI and HindIII. The soybean FAD 2-1A intron #1 is then directionally cloned into pMON68541 to generate KAWHIT03.0071 (soybean FAD2-1A intron #1 with soybean FAD3-1A intron #5).

Step 9—KAWHIT03.0035 (FAD3-1A 3'UTR in CM resistant vector) is digested with AscI and HindIII and KAWHIT03.0071 (FAD2-1A intron and FAD3-1A intron #5 dsRNAi AMP resistant base vector) is digested with MluI and HindIII. The soybean FAD 3-1A 3'UTR is then directionally cloned into KAWHIT03.0071 to generate KAWHIT03.0072 (soybean FAD2-1A intron #1 and FAD3-1A 3'UTR with soybean FAD3-1A intron #5).

Step 10—KAWHIT03.0037 (FATB-1 3'UTR in CM resistant vector) is digested with AscI and HindIII and KAWHIT03.0072 is digested with MluI and HindIII. The FATB-1 3'UTR is then directionally cloned into KAWHIT03.0072 to make KAWHIT03.0073 (soybean FAD2-1A intron, FAD3-1A 3'UTR, FATB-1 3'UTR with FAD3-1A intron #5).

Step 11—KAWHIT03.0073 is digested with BstXI and SalI and the fragment containing FAD2-1A intron, FAD3-1A 3'UTR and FATB-1 3'UTR is gel purified. In a different tube KAWHIT03.0073 is digested with XhoI and Sse8387I. The intron/3'UTR fragment is then cloned back into KAWHIT03.0073 in the opposite orientation on the other site of soybean FAD3-1A intron #5 to create KAWHIT03.0074 (soybean FAD2-1A intron #1 sense, soybean FAD3-1A 3'UTR sense, soybean FATB-1 3'UTR sense, soybean, spliceable soybean FAD3-1A intron #5, soybean FATB-1 3'UTR anti-sense, soybean FAD3-1A 3'UTR anti-sense, soybean FAD2-1A intron #1 anti-sense).

Step 12—To link the dsRNAi construct to the 7S alpha' promoter and the TML 3', KAWHIT03.0074 and pMON68527 (7Sa'/TML3' cassette) are digested with SacI and ligated together to make pMON68563 (7S alpha' promoter—FAD2-1A intron #1 sense, soybean FAD3-1A 3'UTR sense, soybean FATB-1 3'UTR sense, spliceable soybean soybean FATB-1 3'UTR anti-sense, soybean FAD3-1A 3'UTR anti-sense, soybean FAD2-1A intron #1 anti-sense—TML3').

Step 13—To introduce the assembled dsRNAi construct into pMON70682, pMON68563 and pMON70682 are digested with NotI and ligated together to form pMON68536 comprising a 7S alpha' promoter operably linked to the double-stranded-RNA-forming construct of FAD2-1A intron #1 sense, soybean FAD3-1A 3'UTR sense, soybean FATB-1 3'UTR sense, spliceable soybean FAD3-1A intron #5, soybean FATB-1 3'UTR anti-sense, soybean FAD3-1A 3'UTR anti-sense, soybean FAD2-1A intron #1 anti-sense and TML3' terminator).

Step 14—pMON68536 is then digested with AscI and RsrII and pMON68529 (which contains the selectable marker CP4 fused to the FMV promoter and the RBCS 3' and the soybean FAD2 promoter driving the delta 9 desaturase) is digested with SanDI and AscI. The dsRNAi portion of pMON68536 is then directionally cloned into pMON68529 to create pMON68537 (7S alpha' promoter operably linked to the double-stranded-RNA-forming construct of FAD2-1A intron #1 sense, soybean FAD3-1A 3'UTR sense, soybean FATB-1 3'UTR sense, spliceable soybean FAD3-1A intron #5, soybean FATB-1 3'UTR anti-sense, soybean FAD3-1A 3'UTR anti-sense, soybean FAD2-1A intron #1 anti-sense and TML3' terminator and soybean FAD2 promoter driving the delta 9 desaturase).

Example 8

Figure 22:
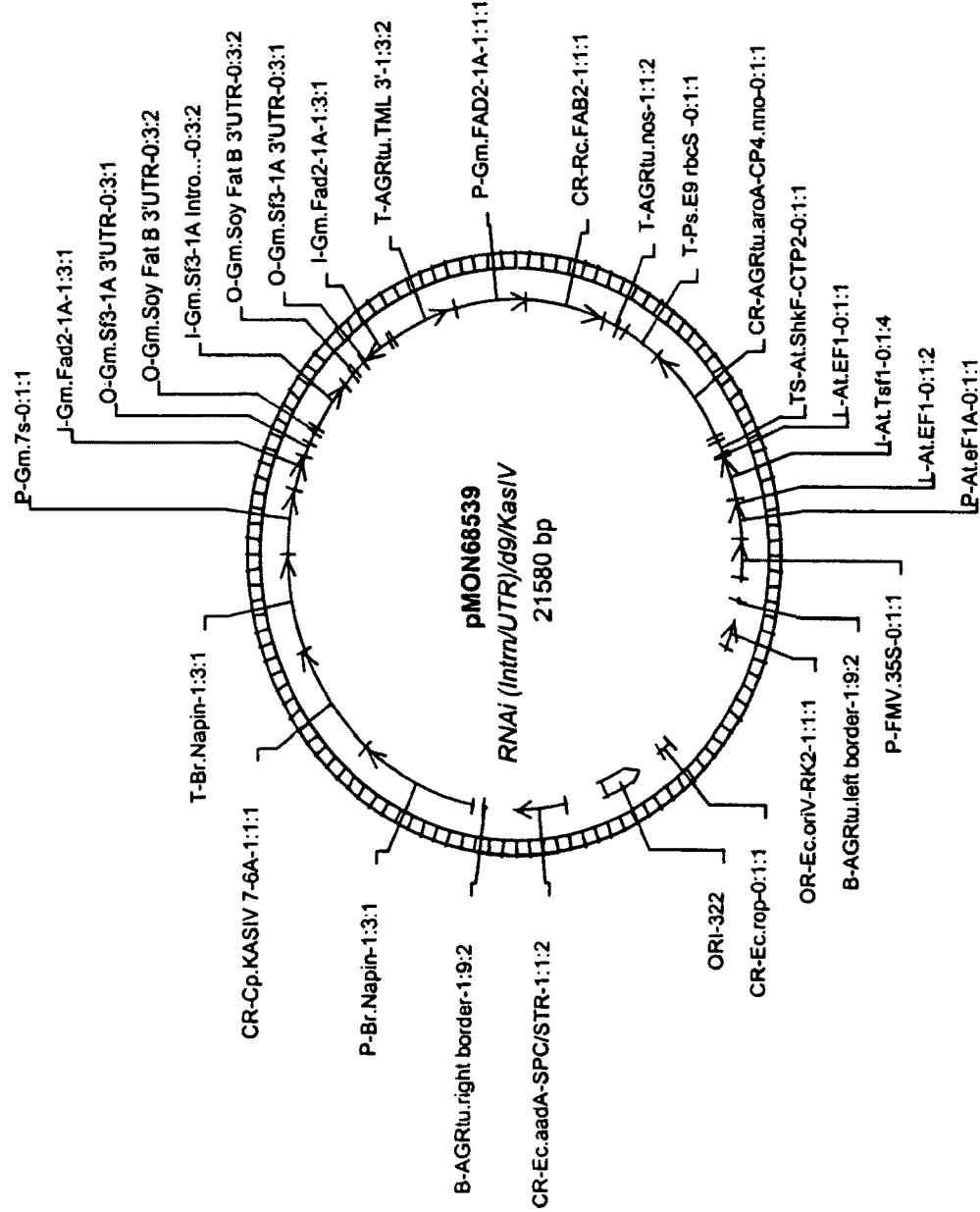
FIG. 22 depicts the construct pMON68539.

The following fifteen steps illustrate the construction of vector pMON68539 (FIG. 22) designed for plant transformation to suppress FAD2, FAD3, and FATB genes and over-express delta-9 desaturase and the KASIV enzyme in soybean. In particular, the construct comprises a 7S alpha promoter operably linked to soybean sense-oriented intron and 3'UTRs, i.e., a FAD2-1A intron #1, a FAD3-1A 3'UTR, a FATB-1 3'UTR, a hairpin loop-forming spliceable intron, and a complementary series of soybean anti-sense-oriented intron and 3'UTR's, i.e., a FATB-1 3'UTR, a FAD3-1A 3'UTR and a FAD2-1A intron #1, the soybean FAD2 promoter driving the delta-9 desaturase, and the Napin promoter driving KASIV.

Step 1—The soybean FAD3-1A intron #5, which serves as the spliceable intron portion of the dsRNAi construct, is PCR amplified using soybean genomic DNA as template, with the following primers:

```
5' primer = 19037 =
ACTAGTATATTGAGCTCATATTCCACTGCAGTGGATATT

GTTTAAACATAGCTAGCATATTACGCGTATATTATACAA

GCTTATATTCCCGGGATATTGTCGACATATTAGCGGTAC

ATTTTATTGCTTATTCAC
```

-continued

```
3' primer = 19045 =
ACTAGTATATTGAGCTCATATTCCTGCAGGATATTCTCG

AGATATTCACGGTAGTAATCTCCAAGAACTGGTTTTGCT

GCTTGTGTCTGCAGTGAATC.
```

These primers add cloning sites to the 5' and 3' ends. To 5' end: SpeI, SacI, BstXI, PmeI, NheI, MluI, HindIII, XmaI, SmaI, SalI. To 3' end: SpeI, SacI, Sse8387I, XhoI. The soybean FAD3-1A intron #5 PCR product is cloned into pCR2.1, resulting in KAWHIT03.0065. KAWHIT03.0065 is then digested with SpeI and the ends are filled with Pfu polymerase and pMON68526 (empty CM resistant vector) is digested with HindIII and the ends are filled with Pfu polymerase. KAWHIT03.0065 and pMON68526 are ligated to create pMON68541 (soybean FAD3-1A intron #5 with multiple cloning sites in Amp resistant vector).

Step 2—The soybean FATB-1 3'UTR is amplified with the following primers: 18662=TTTTAATTACAAT-GAGAATGAGATTTACTGC (adding Bsp120I to the 5' end) and 18661=GGGCCCGATTTGAAATGGTTAACG. The PCR product is then ligated into pCR2.1 to make KAWHIT03.0036.

Step 3—KAWHIT03.0036 is then digested with Bsp120I and EcoRI and then cloned into the KAWHIT03.0032 (empty CM resistant vector with a multiple cloning site) to make KAWHIT03.0037 (FATB-1 3'UTR in empty CM resistant vector).

Step 4—The soybean FAD3-1A 3'UTR is amplified with the following primers: 18639=GGGCCCGTTTCAAA CTTTTTGG (adding Bsp120I to the 5' end) and 18549=TGAAACTGACAATTCAA. The PCR product is then ligated into pCR2.1 to make KAWHIT03.0034.

Step 5—KAWHIT03.0034 is digested with Bsp120I and EcoRI and then ligated into KAWHIT03.0032 (empty CM resistant vector with a multiple cloning site) to make KAWHIT03.0035 (FAD3-1A 3'UTR in empty CM resistant vector).

Step 6—The soybean FAD 2-1A intron #1 is PCR amplified using soybean genomic DNA as template, with the following primers: 5' primer=18663=GGGCCCGGT AAATTAAATTGTGC (Adding Bsp120I site to 5' end); and 3' primer=18664=CTGTGTCAAAGTATAAA CAAGT-TCAG. The resulting PCR product is cloned into pCR 2.1 creating KAWHIT03.0038.

Step 7—Soybean FAD 2-1A intron #1 PCR product in KAWHIT03.0038 is cloned into KAWHIT03.0032 (empty CM resistant vector with a multiple cloning site) using the restriction sites Bsp120I and EcoRI. The resulting plasmid is KAWHIT03.0039 (soybean FAD 2-1A intron #1 in empty CM resistant vector).

Step 8—KAWHIT03.0039 is digested with AscI and HindIII and pMON68541 (FAD3-JA intron #5 dsRNAi AMP resistant base vector) is digested with MluI and HindIII. The soybean FAD 2-1A intron #1 is then directionally cloned into pMON68541 (FAD3-1A intron #5 in Amp resistant vector with multiple cloning sites) to generate KAWHIT03.0071 (soybean FAD2-1A intron #1 with soybean FAD3-1A intron #5).

Step 9—KAWHIT03.0035 (FAD3-1A 3'UTR in CM resistant vector) is digested with AscI and HindIII and KAWHIT03.0071 (FAD2-1A intron and FAD3-1A intron #5 dsRNAi AMP resistant base vector) is digested with MluI and HindIII. The soybean FAD 3-1A 3'UTR is then directionally cloned into KAWHIT03.0071 to generate KAWHIT03.0072 (soybean FAD2-1A intron #1 and FAD3-1A 3'UTR with soybean FAD3-1A intron #5).

Step 10—KAWHIT03.0037 (FATB-1 3'UTR in CM resistant vector) is digested with AscI and HindIII and KAWHIT03.0072 is digested with MluI and HindIII. The FATB-1 3'UTR is then directionally cloned into KAWHIT03.0072 to make KAWHIT03.0073 (soybean FAD2-1A intron, FAD3-1A 3'UTR, FATB-1 3'UTR with FAD3-1A intron #5).

Step 11—KAWHIT03.0073 is digested with BstXI and SalI and the fragment containing FAD2-1A intron, FAD3-1A 3'UTR and FATB-1 3'UTR is gel purified. In a different tube KAWHIT03.0073 is digested with XhoI and Sse8387I. The Intron/3'UTR fragment is then cloned back into KAWHIT03.0073 in the opposite orientation on the other site of soybean FAD3-1A intron #5 to create KAWHIT03.0074 (soybean FAD2-1A intron #1 sense, soybean FAD3-1A 3'UTR sense, soybean FATB-1 3'UTR sense, soybean, spliceable soybean FAD3-1A intron #5, soybean FATB-1 3'UTR anti-sense, soybean FAD3-1A 3'UTR anti-sense, soybean FAD2-1A intron #1 anti-sense).

Step 12—To link the dsRNAi construct to the 7S alpha' promoter and the TML 3', KAWHIT03.0074 and pMON68527 (7Sa'/TML3' cassette) are digested with SacI and ligated together to make pMON68563 (7S alpha' promoter—FAD2-1A intron #1 sense, soybean FAD3-1A 3'UTR sense, soybean FATB-1 3'UTR sense, spliceable soybean soybean FATB-1 3'UTR anti-sense, soybean FAD3-1A 3'UTR anti-sense, soybean FAD2-1A intron #1 anti-sense—TML3').

Step 13—To introduce the assembled dsRNAi construct into pMON70682, pMON68563 and pMON70682 are digested with NotI and ligated together to form pMON68536 comprising a 7S alpha' promoter operably linked to the double-stranded-RNA-forming construct of FAD2-1A intron #1 sense, soybean FAD3-1A 3'UTR sense, soybean FATB-1 3'UTRsense, spliceable soybean FAD3-1A intron #5, soybean FATB-1 3'UTR anti-sense, soybean FAD3-1A 3'UTR anti-sense, soybean FAD2-1A intron #1 anti-sense and TML3' terminator).

Step 14—pMON68536 is then digested with AscI and RsrII and pMON68529 (which contains the selectable marker CP4 fused to the FMV promoter and the RBCS 3' and the soybean FAD2 promoter driving the delta 9 desaturase) is digested with SanDI and AscI. The dsRNAi portion of pMON68536 is then directionally cloned into pMON68529 to create pMON68537 (7S alpha' promoter operably linked to the double-stranded-RNA-forming construct of FAD2-1A intron #1 sense, soybean FAD3-1A 3'UTR sense, soybean FATB-1 3'UTR sense, spliceable soybean FAD3-1A intron #5, soybean FATB-1 3'UTR anti-sense, soybean FAD3-1A 3'UTR anti-sense, soybean FAD2-1A intron #1 anti-sense and TML3' terminator and soybean FAD2 promoter driving the delta 9 desaturase.

Step 15—pMON68537 is then digested with SanDI and AscI and pMON70683 (Napin driving KasIV) is digested with AscI and RsrII. The Napin/KasIV fragment is directionally cloned into pMON68537 to create pMON68539 (7S alpha' promoter operably linked to the double-stranded-RNA-forming construct of FAD2-1A intron #1 sense, soybean FAD3-1A 3'UTR sense, soybean FATB-1 3'UTRsense, spliceable soybean FAD3-1A intron #5, soybean FATB-1 3'UTR anti-sense, soybean FAD3-1A 3'UTR anti-sense, soybean FAD2-1A intron #1 anti-sense and TML3' terminator, soybean FAD2 promoter driving the delta 9 desaturase and Napin promoter driving KasIV.

Example 9

This example illustrates plant transformation to produce soybean plants with suppressed genes.

A transformation vector pMON68537 as prepared in Example 7 is used to introduce an intron/3'UTR double-stranded RNA-forming construct into soybean for suppressing the Δ12 desaturase, Δ15 desaturase, and FATB genes. Vector pMON68537 also contains the delta-9 desaturase (FAB2) and the CP4 genes. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with the intron/3'UTR dsRNAi expression constructs using gas chromatography. $R_1$ pooled seed and $R_1$ single seed oil compositions demonstrate that the mono- and polyunsaturated fatty acid compositions are altered in the oil of seeds from transgenic soybean lines as compared to that of the seed from non-transformed soybean, (See Table 7). For instance, FAD2 suppression provides plants with increased amount of oleic acid ester compounds; FAD3 suppression provides plants with decreased linolenic acid ester compounds; and FATB suppression provides plants with reduced saturated fatty ester compounds, e.g. palmitates and stearates. Selections can be made from such lines depending on the desired relative fatty acid composition. Fatty acid compositions are analyzed from seed of soybean lines transformed with constructs using gas chromatography.

Example 10

This example illustrates plant transformation to produce soybean plants with suppressed genes.

A transformation vector pMON68539 as prepared in Example 3 is used to introduce an intron/3'UTR double-stranded RNA-forming construct into soybean for suppressing the Δ12 desaturase, A15 desaturase, and FATB genes. Vector pMON68539 also contains the KasIV and the CP4 genes. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with the intron/3'UTR dsRNAi expression constructs using gas chromatography. $R_1$ pooled seed and $R_1$ single seed oil compositions demonstrate that the mono- and polyunsaturated fatty acid compositions were altered in the oil of seeds from transgenic soybean lines as compared to that of the seed from non-transformed soybean (See Table 8). For example, FAD2 suppression provides plants with increased oleic acid ester compounds; FAD3 suppression provides plants with decreased linolenic acid ester compounds; and FATB suppression provides plants with reduced saturated fatty ester compounds, e.g. palmitates and stearates. Selections can be made from such lines depending on the desired relative fatty acid composition. Fatty acid compositions are analyzed from seed of soybean lines transformed with constructs using gas chromatography.

TABLE 7

Fatty acid composition of R1 single seeds from pMON68537 Events

| Construct | Event | 18:1 | 18:3 | 16:0 | 18:0 | 18:2 |
|---|---|---|---|---|---|---|
| PMON68537 | GM_A36305 | 74.92 | 4.42 | 6.35 | 2.93 | 10.24 |
| PMON68537 | GM_A36305 | 74.8 | 4.33 | 6.57 | 2.93 | 10.23 |
| PMON68537 | GM_A36305 | 74.43 | 3.95 | 5.98 | 2.82 | 11.81 |
| PMON68537 | GM_A36305 | 73.32 | 3.99 | 6.79 | 3.24 | 11.48 |
| PMON68537 | GM_A36305 | 72.87 | 4.33 | 7.06 | 3.08 | 11.7 |
| PMON68537 | GM_A36305 | 16.63 | 9.53 | 13.5 | 4.06 | 55.31 |
| PMON68537 | GM_A36305 | 16.52 | 9.61 | 13.92 | 4.24 | 54.79 |
| PMON68537 | GM_A36305 | 15.67 | 9.66 | 13.64 | 4.19 | 55.89 |
| PMON68537 | GM_A36306 | 77.45 | 3.93 | 6.76 | 2.47 | 8.4 |
| PMON68537 | GM_A36306 | 74.51 | 4.38 | 6.58 | 2.47 | 10.94 |
| PMON68537 | GM_A36306 | 73.21 | 4.64 | 7.04 | 3.08 | 11.04 |
| PMON68537 | GM_A36306 | 72.78 | 4.4 | 6.97 | 2.55 | 12.21 |
| PMON68537 | GM_A36306 | 71.67 | 4.76 | 6.94 | 3.25 | 12.2 |
| PMON68537 | GM_A36306 | 71.01 | 4.86 | 7.64 | 3.05 | 12.41 |
| PMON68537 | GM_A36306 | 69.72 | 4.76 | 7.66 | 2.95 | 13.75 |
| PMON68537 | GM_A36306 | 17.41 | 8.88 | 13.35 | 3.85 | 55.63 |
| PMON68537 | GM_A36307 | 77.22 | 3.71 | 6.8 | 2.77 | 8.5 |
| PMON68537 | GM_A36307 | 76.79 | 3.65 | 6.76 | 2.85 | 8.75 |
| PMON68537 | GM_A36307 | 71.44 | 4.54 | 7.2 | 3.58 | 12.17 |
| PMON68537 | GM_A36307 | 18.83 | 8.62 | 13.94 | 4.02 | 53.61 |
| PMON68537 | GM_A36307 | 18.81 | 8.38 | 13.27 | 3.7 | 54.97 |
| PMON68537 | GM_A36307 | 15.68 | 9.97 | 14.06 | 4.55 | 54.79 |
| PMON68537 | GM_A36307 | 15.28 | 10.64 | 14.68 | 4.43 | 53.97 |
| PMON68537 | GM_A36307 | 14.08 | 9.36 | 14.39 | 4.31 | 56.89 |
| PMON68537 | GM_A36309 | 78.67 | 3.53 | 6.09 | 2.5 | 8.18 |
| PMON68537 | GM_A36309 | 75.43 | 3.96 | 6.7 | 2.53 | 10.3 |
| PMON68537 | GM_A36309 | 71.41 | 4.19 | 6.92 | 2.74 | 13.67 |
| PMON68537 | GM_A36309 | 70.51 | 4.14 | 6.85 | 3.16 | 14.33 |
| PMON68537 | GM_A36309 | 67.51 | 5.01 | 7.45 | 3.15 | 15.69 |
| PMON68537 | GM_A36309 | 66.99 | 4.92 | 7.15 | 3.9 | 15.79 |
| PMON68537 | GM_A36309 | 20.09 | 8.46 | 12.41 | 5 | 52.97 |
| PMON68537 | GM_A36309 | 15.15 | 9.73 | 14.61 | 3.85 | 55.79 |
| PMON68537 | GM_A36310 | 74.28 | 4.77 | 7.31 | 1.85 | 10.9 |
| PMON68537 | GM_A36310 | 74.03 | 5.43 | 8.23 | 1.63 | 9.66 |
| PMON68537 | GM_A36310 | 73.07 | 5.09 | 7.37 | 1.76 | 11.75 |
| PMON68537 | GM_A36310 | 71.83 | 5.04 | 7.78 | 1.86 | 12.54 |
| PMON68537 | GM_A36310 | 68.01 | 6.26 | 9.8 | 1.97 | 13.13 |
| PMON68537 | GM_A36310 | 67.22 | 6.28 | 8.71 | 3.28 | 13.45 |
| PMON68537 | GM_A36310 | 65.37 | 6.87 | 10.01 | 1.94 | 14.9 |
| PMON68537 | GM_A36310 | 15.76 | 10.09 | 13.4 | 4.28 | 55.52 |
| PMON68537 | GM_A36311 | 77.87 | 3.56 | 5.9 | 2.46 | 9.05 |
| PMON68537 | GM_A36311 | 75.8 | 3.87 | 5.91 | 2.93 | 10.22 |
| PMON68537 | GM_A36311 | 75.61 | 3.71 | 6.21 | 2.56 | 10.75 |
| PMON68537 | GM_A36311 | 73.68 | 4.06 | 6 | 3.09 | 11.98 |
| PMON68537 | GM_A36311 | 72.66 | 4.11 | 6.41 | 3.14 | 12.48 |
| PMON68537 | GM_A36311 | 70.89 | 4.39 | 6.52 | 3.11 | 13.93 |
| PMON68537 | GM_A36311 | 70.82 | 3.97 | 6.52 | 3.18 | 14.29 |
| PMON68537 | GM_A36311 | 16.67 | 9.39 | 13.65 | 4.44 | 54.77 |
| PMON68537 | GM_A36312 | 78.32 | 4.3 | 6.36 | 1.79 | 8.16 |
| PMON68537 | GM_A36312 | 77.55 | 4.46 | 6.51 | 2.13 | 8.23 |
| PMON68537 | GM_A36312 | 77.43 | 4.17 | 6.31 | 1.81 | 9.24 |
| PMON68537 | GM_A36312 | 76.98 | 4.29 | 6.25 | 2.27 | 9.05 |
| PMON68537 | GM_A36312 | 76.43 | 4.55 | 6.82 | 2.16 | 8.96 |
| PMON68537 | GM_A36312 | 76.38 | 4.5 | 6.46 | 2.04 | 9.54 |
| PMON68537 | GM_A36312 | 75.25 | 4.27 | 6.41 | 1.97 | 11.06 |
| PMON68537 | GM_A36312 | 18.24 | 9.43 | 13.6 | 3.07 | 54.75 |
| PMON68537 | GM_A36313 | 80.18 | 4.07 | 6.17 | 2.59 | 5.85 |
| PMON68537 | GM_A36313 | 79.96 | 4.16 | 6.03 | 2.59 | 6.11 |
| PMON68537 | GM_A36313 | 78.88 | 3.9 | 5.6 | 2.8 | 7.65 |
| PMON68537 | GM_A36313 | 78.76 | 3.92 | 5.44 | 2.91 | 7.82 |
| PMON68537 | GM_A36313 | 77.64 | 4.22 | 5.88 | 2.9 | 8.25 |
| PMON68537 | GM_A36313 | 76.15 | 4.14 | 6.06 | 3.13 | 9.42 |
| PMON68537 | GM_A36313 | 19.05 | 8.87 | 13.45 | 3.71 | 54.03 |
| PMON68537 | GM_A36313 | 18.47 | 8.46 | 13.13 | 3.63 | 55.41 |
| PMON68537 | GM_A36314 | 80.27 | 3.17 | 5.77 | 3.4 | 6.03 |
| PMON68537 | GM_A36314 | 79.66 | 3.24 | 5.72 | 3.19 | 6.91 |
| PMON68537 | GM_A36314 | 79.5 | 3.45 | 5.83 | 3.23 | 6.74 |
| PMON68537 | GM_A36314 | 77.42 | 3.52 | 5.76 | 3.57 | 8.42 |
| PMON68537 | GM_A36314 | 77.33 | 3.71 | 6.36 | 3.34 | 8.01 |
| PMON68537 | GM_A36314 | 76.83 | 3.71 | 6.38 | 3.24 | 8.59 |
| PMON68537 | GM_A36314 | 16.6 | 9.3 | 12.63 | 4.43 | 55.99 |
| PMON68537 | GM_A36314 | 15.26 | 8.59 | 13.71 | 4.54 | 56.84 |
| PMON68537 | GM_A36315 | 20.21 | 8.25 | 13.61 | 3.59 | 53.37 |
| PMON68537 | GM_A36315 | 17.47 | 9.22 | 13.46 | 3.35 | 55.57 |
| PMON68537 | GM_A36315 | 16.75 | 9.3 | 13.61 | 3.66 | 55.75 |

TABLE 7-continued

Fatty acid composition of R1 single seeds from pMON68537 Events

| Construct | Event | 18:1 | 18:3 | 16:0 | 18:0 | 18:2 |
|---|---|---|---|---|---|---|
| PMON68537 | GM_A36315 | 16.54 | 9.18 | 13.54 | 3.88 | 55.9 |
| PMON68537 | GM_A36315 | 16.06 | 10.07 | 13.44 | 4.01 | 55.42 |
| PMON68537 | GM_A36315 | 16.05 | 9.58 | 12.82 | 4.25 | 56.29 |
| PMON68537 | GM_A36315 | 15.95 | 10.42 | 13.12 | 3.63 | 55.91 |
| PMON68537 | GM_A36315 | 15.5 | 10.22 | 13.25 | 3.78 | 56.3 |
| PMON68537 | GM_A36316 | 79.61 | 3.56 | 5.79 | 2.94 | 6.87 |
| PMON68537 | GM_A36316 | 75.11 | 4.01 | 6.45 | 3.44 | 9.76 |
| PMON68537 | GM_A36316 | 75.07 | 4.25 | 6.74 | 3.09 | 9.64 |
| PMON68537 | GM_A36316 | 73.92 | 3.97 | 6.53 | 3.56 | 10.75 |
| PMON68537 | GM_A36316 | 17.26 | 9.59 | 13.1 | 4.26 | 54.78 |
| PMON68537 | GM_A36316 | 17.15 | 9.03 | 12.81 | 4.04 | 55.97 |
| PMON68537 | GM_A36316 | 16.62 | 9.2 | 13.15 | 3.99 | 56.03 |
| PMON68537 | GM_A36316 | 16.6 | 9.44 | 13.19 | 3.95 | 55.84 |
| PMON68537 | GM_A36317 | 18.96 | 7.55 | 13.2 | 3.75 | 55.51 |
| PMON68537 | GM_A36317 | 16.19 | 9.43 | 13.33 | 3.96 | 56.04 |
| PMON68537 | GM_A36317 | 16.05 | 9.1 | 14.02 | 3.94 | 55.91 |
| PMON68537 | GM_A36317 | 15.33 | 9.4 | 13.91 | 4.22 | 56.11 |
| PMON68537 | GM_A36317 | 15.28 | 9.2 | 13.87 | 4.27 | 56.36 |
| PMON68537 | GM_A36317 | 14.58 | 10.15 | 13.74 | 4.38 | 56.15 |
| PMON68537 | GM_A36317 | 13.95 | 9.47 | 13.98 | 4.76 | 56.79 |
| PMON68537 | GM_A36317 | 13.91 | 9.88 | 14.26 | 4.62 | 56.25 |
| PMON68537 | GM_A36318 | 78.82 | 3.64 | 5.7 | 2.77 | 7.87 |
| PMON68537 | GM_A36318 | 77.94 | 3.73 | 5.9 | 2.94 | 8.29 |
| PMON68537 | GM_A36318 | 75.18 | 4.11 | 6.08 | 3.48 | 9.95 |
| PMON68537 | GM_A36318 | 75.1 | 3.93 | 6.02 | 3.04 | 10.75 |
| PMON68537 | GM_A36318 | 75.01 | 4.22 | 6.57 | 3.29 | 9.72 |
| PMON68537 | GM_A36318 | 74.17 | 4.2 | 6.51 | 3.27 | 10.68 |
| PMON68537 | GM_A36318 | 73.47 | 4.27 | 6.7 | 3.22 | 11.16 |
| PMON68537 | GM_A36318 | 30.57 | 10.54 | 14.83 | 5.55 | 36.92 |
| PMON68537 | GM_A36319 | 80 | 3.65 | 5.83 | 2.31 | 7.02 |
| PMON68537 | GM_A36319 | 79.89 | 3.65 | 5.64 | 2.35 | 7.26 |
| PMON68537 | GM_A36319 | 79.4 | 3.59 | 5.73 | 1.76 | 8.46 |
| PMON68537 | GM_A36319 | 78 | 3.87 | 6.11 | 2.35 | 8.5 |
| PMON68537 | GM_A36319 | 76.08 | 4.22 | 6.5 | 2.35 | 9.74 |
| PMON68537 | GM_A36319 | 75.56 | 3.89 | 6.41 | 1.78 | 11.3 |
| PMON68537 | GM_A36319 | 75.26 | 4.27 | 6.47 | 2.37 | 10.5 |
| PMON68537 | GM_A36319 | 75.16 | 4.1 | 6.48 | 2.49 | 10.66 |
| PMON68537 | GM_A36320 | 81.27 | 3.19 | 5.84 | 2.4 | 6.09 |
| PMON68537 | GM_A36320 | 80.21 | 3.27 | 5.18 | 2.44 | 7.76 |
| PMON68537 | GM_A36320 | 79.64 | 3.38 | 5.5 | 2.67 | 7.63 |
| PMON68537 | GM_A36320 | 79.46 | 3.38 | 5.82 | 2.67 | 7.42 |
| PMON68537 | GM_A36320 | 78.5 | 3.59 | 6.24 | 2.49 | 8 |
| PMON68537 | GM_A36320 | 73.83 | 3.79 | 6.72 | 2.78 | 11.74 |
| PMON68537 | GM_A36320 | 73.1 | 3.95 | 6.9 | 2.39 | 12.48 |
| PMON68537 | GM_A36320 | 22.99 | 8.03 | 12.19 | 4.81 | 50.89 |
| PMON68537 | GM_A36324 | 75.93 | 3.77 | 6.58 | 2.76 | 9.76 |
| PMON68537 | GM_A36324 | 75.1 | 4.05 | 7.01 | 2.83 | 9.8 |
| PMON68537 | GM_A36324 | 17.83 | 8.79 | 12.78 | 4.11 | 55.49 |
| PMON68537 | GM_A36324 | 16.46 | 8.88 | 12.84 | 4.48 | 56.29 |
| PMON68537 | GM_A36324 | 16.35 | 9.25 | 13.51 | 4.17 | 55.66 |
| PMON68537 | GM_A36324 | 15.25 | 8.99 | 13.73 | 4.28 | 56.69 |
| PMON68537 | GM_A36324 | 14.16 | 10.17 | 13.95 | 4.11 | 56.58 |
| PMON68537 | GM_A36324 | 13.59 | 9.87 | 14.61 | 4.5 | 56.33 |
| PMON68537 | GM_A36357 | 80.19 | 3.03 | 5.59 | 3.2 | 6.62 |
| PMON68537 | GM_A36357 | 79.78 | 3.19 | 5.51 | 3.24 | 6.89 |
| PMON68537 | GM_A36357 | 78.5 | 3.55 | 5.75 | 3.17 | 7.71 |
| PMON68537 | GM_A36357 | 77.48 | 3.68 | 5.71 | 3.55 | 8.23 |
| PMON68537 | GM_A36357 | 77.28 | 3.79 | 5.66 | 3.48 | 8.46 |
| PMON68537 | GM_A36357 | 77.1 | 3.51 | 5.43 | 3.65 | 8.99 |
| PMON68537 | GM_A36357 | 71.9 | 4.24 | 6.47 | 3.67 | 12.39 |
| PMON68537 | GM_A36357 | 17.66 | 9.32 | 13.26 | 4.21 | 54.51 |
| PMON68537 | GM_A36359 | 77.91 | 3.35 | 5.67 | 3.24 | 8.53 |
| PMON68537 | GM_A36359 | 77.85 | 3.29 | 5.42 | 3.29 | 8.87 |
| PMON68537 | GM_A36359 | 76.71 | 3.65 | 6.07 | 3.35 | 8.95 |
| PMON68537 | GM_A36359 | 71.73 | 4.01 | 6.79 | 3.49 | 12.68 |
| PMON68537 | GM_A36359 | 69.32 | 4.51 | 6.99 | 3.66 | 14.13 |
| PMON68537 | GM_A36359 | 68.63 | 4.44 | 6.91 | 3.76 | 14.89 |
| PMON68537 | GM_A36359 | 18.87 | 8.03 | 13.38 | 3.86 | 54.81 |
| PMON68537 | GM_A36359 | 16.81 | 9.83 | 13.08 | 4.68 | 54.55 |
| PMON68537 | GM_A36360 | 79.34 | 3.29 | 5.99 | 3.15 | 6.88 |
| PMON68537 | GM_A36360 | 75.42 | 3.47 | 6.47 | 3.08 | 10.26 |
| PMON68537 | GM_A36360 | 75.3 | 3.86 | 6.69 | 3.2 | 9.64 |
| PMON68537 | GM_A36360 | 74.51 | 3.8 | 6.39 | 3.32 | 10.67 |
| PMON68537 | GM_A36360 | 21.49 | 6.95 | 13.07 | 3.92 | 53.46 |
| PMON68537 | GM_A36360 | 20.05 | 7.4 | 13.09 | 3.83 | 54.57 |
| PMON68537 | GM_A36360 | 16.08 | 9.14 | 13.02 | 4.64 | 56.03 |
| PMON68537 | GM_A36360 | 15.86 | 9.07 | 13.44 | 4.49 | 56.04 |
| PMON68537 | GM_A36361 | 82.13 | 2.83 | 5.67 | 3.13 | 4.81 |
| PMON68537 | GM_A36361 | 80.99 | 3.2 | 5.79 | 3.01 | 5.64 |
| PMON68537 | GM_A36361 | 74.39 | 3.85 | 6.33 | 3.5 | 10.59 |
| PMON68537 | GM_A36361 | 18.01 | 8.46 | 13.18 | 3.92 | 55.41 |
| PMON68537 | GM_A36361 | 17.99 | 8.11 | 13.05 | 4.09 | 55.7 |
| PMON68537 | GM_A36361 | 17.35 | 8.31 | 13.4 | 4 | 55.88 |
| PMON68537 | GM_A36361 | 16.81 | 10.2 | 12.9 | 4.32 | 54.87 |
| PMON68537 | GM_A36361 | 16.55 | 8.5 | 13.21 | 4.22 | 56.45 |
| PMON68537 | GM_A36362 | 78.05 | 3.89 | 6.29 | 2.81 | 7.76 |
| PMON68537 | GM_A36362 | 76.89 | 3.69 | 6.32 | 3.12 | 8.76 |
| PMON68537 | GM_A36362 | 76.1 | 4 | 6.57 | 3.02 | 9.24 |
| PMON68537 | GM_A36362 | 76.01 | 4.08 | 6.24 | 3.03 | 9.48 |
| PMON68537 | GM_A36362 | 75.86 | 3.76 | 5.68 | 3.56 | 9.95 |
| PMON68537 | GM_A36362 | 75.79 | 4.07 | 6.43 | 3.15 | 9.34 |
| PMON68537 | GM_A36362 | 74.89 | 4.14 | 6.63 | 3.11 | 10.07 |
| PMON68537 | GM_A36362 | 17.22 | 8.8 | 13.75 | 3.77 | 55.54 |
| PMON68537 | GM_A36363 | 79.15 | 3.57 | 6.2 | 3.03 | 6.84 |
| PMON68537 | GM_A36363 | 75.69 | 3.83 | 7.07 | 2.73 | 9.53 |
| PMON68537 | GM_A36363 | 73.97 | 4.22 | 6.82 | 3.39 | 10.33 |
| PMON68537 | GM_A36363 | 72.53 | 4.31 | 6.64 | 3.7 | 11.59 |
| PMON68537 | GM_A36363 | 68.42 | 4.5 | 7.05 | 3.95 | 14.79 |
| PMON68537 | GM_A36363 | 18.39 | 8.7 | 13.61 | 4.1 | 54.28 |
| PMON68537 | GM_A36363 | 17.54 | 8.87 | 14.08 | 4.07 | 54.56 |
| PMON68537 | GM_A36363 | 15.87 | 9.66 | 14.56 | 4.2 | 54.69 |
| PMON68537 | GM_A36365 | 78.79 | 3.11 | 5.87 | 1.27 | 9.9 |
| PMON68537 | GM_A36365 | 76.76 | 3.86 | 5.79 | 1.66 | 10.91 |
| PMON68537 | GM_A36365 | 75.41 | 3.49 | 6.06 | 1.83 | 12.15 |
| PMON68537 | GM_A36365 | 73.57 | 3.65 | 6.11 | 1.5 | 14.19 |
| PMON68537 | GM_A36365 | 71.55 | 3.56 | 6.62 | 1.24 | 16.08 |
| PMON68537 | GM_A36365 | 70.41 | 4 | 6.07 | 2.15 | 16.33 |
| PMON68537 | GM_A36365 | 66.66 | 3.9 | 6.84 | 1.5 | 20.21 |
| PMON68537 | GM_A36365 | 63.96 | 4.22 | 7.08 | 2.27 | 21.52 |
| PMON68537 | GM_A36366 | 75.44 | 4.33 | 6.49 | 3.21 | 9.32 |
| PMON68537 | GM_A36366 | 74.75 | 4.21 | 6.87 | 2.71 | 10.33 |
| PMON68537 | GM_A36366 | 74.69 | 4.65 | 6.91 | 3.06 | 9.65 |
| PMON68537 | GM_A36366 | 73.23 | 4.89 | 7.23 | 2.99 | 10.52 |
| PMON68537 | GM_A36366 | 72.53 | 4.76 | 7.42 | 3.26 | 10.85 |
| PMON68537 | GM_A36366 | 67.15 | 5.05 | 7.47 | 3.33 | 15.87 |
| PMON68537 | GM_A36366 | 65.81 | 5.6 | 7.9 | 3.37 | 16.09 |
| PMON68537 | GM_A36366 | 62.31 | 6.19 | 8.71 | 3.22 | 18.55 |
| PMON68537 | GM_A36367 | 80.56 | 3.3 | 6.07 | 2.58 | 6.34 |
| PMON68537 | GM_A36367 | 77.78 | 3.58 | 6.47 | 2.66 | 8.45 |
| PMON68537 | GM_A36367 | 77.78 | 3.46 | 6.25 | 2.84 | 8.51 |
| PMON68537 | GM_A36367 | 77.39 | 3.81 | 6.71 | 2.86 | 8.11 |
| PMON68537 | GM_A36367 | 77.32 | 3.74 | 6.17 | 3.12 | 8.47 |
| PMON68537 | GM_A36367 | 75.93 | 3.97 | 6.23 | 3.43 | 9.29 |
| PMON68537 | GM_A36367 | 72.82 | 4.09 | 6.85 | 3.25 | 11.88 |
| PMON68537 | GM_A36367 | 19.31 | 7.58 | 13.7 | 3.59 | 55 |
| PMON68537 | GM_se36410 | 21.67 | 7.62 | 13.38 | 3.43 | 53.1 |
| PMON68537 | GM_A36410 | 20.9 | 8.33 | 12.93 | 3.64 | 53.33 |
| PMON68537 | GM_A36410 | 20.21 | 8.04 | 13.28 | 3.86 | 53.66 |
| PMON68537 | GM_A36410 | 20.02 | 8.71 | 12.79 | 3.71 | 53.87 |
| PMON68537 | GM_A36410 | 18.96 | 8.95 | 13.3 | 3.77 | 54.15 |
| PMON68537 | GM_A36410 | 18.18 | 8.98 | 13.56 | 3.74 | 54.66 |
| PMON68537 | GM_A36410 | 17.61 | 9.29 | 12.93 | 4.12 | 55.13 |
| PMON68537 | GM_A36410 | 16.78 | 9.8 | 13.78 | 3.92 | 54.83 |
| PMON68537 | GM_A36411 | 75.06 | 4.33 | 6.49 | 2.93 | 10.08 |
| PMON68537 | GM_A36411 | 74.32 | 4.46 | 6.76 | 2.96 | 10.38 |
| PMON68537 | GM_A36411 | 73.41 | 4.76 | 6.91 | 3.11 | 10.78 |
| PMON68537 | GM_A36411 | 73.24 | 4.87 | 7.28 | 2.89 | 10.67 |
| PMON68537 | GM_A36411 | 22.38 | 8.17 | 13.47 | 3.6 | 51.51 |
| PMON68537 | GM_A36411 | 18.26 | 9.07 | 14.14 | 3.81 | 54.02 |
| PMON68537 | GM_A36411 | 17.52 | 10.1 | 13.1 | 4.03 | 54.36 |
| PMON68537 | GM_A36411 | 17.02 | 9.71 | 13.45 | 4.02 | 54.89 |
| A3244 | A3244 | 18.29 | 7.79 | 13.69 | 4.15 | 55.08 |
| A3244 | A3244 | 17.54 | 8.19 | 13.32 | 4.32 | 55.57 |
| A3244 | A3244 | 17.13 | 8.13 | 13.21 | 4.46 | 56.04 |
| A3244 | A3244 | 15.47 | 9.56 | 13.04 | 4.43 | 56.46 |
| A3244 | A3244 | 15.17 | 8.95 | 13.79 | 4.3 | 56.78 |
| A3244 | A3244 | 15.05 | 9.03 | 14.16 | 4.01 | 56.8 |
| A3244 | A3244 | 13.51 | 10.07 | 12.95 | 5.07 | 57.3 |
| A3244 | A3244 | 13.49 | 9.91 | 13.31 | 4.56 | 57.67 |

TABLE 8

Fatty acid composition of R1 single seeds from pMON68539 Events

| Construct | Event | 16:0 | 18:0 | 18:1 | 18:2 | 18:3 |
|---|---|---|---|---|---|---|
| PMON68539 | GM_A36448 | 4.51 | 2.65 | 79.64 | 8.66 | 3.55 |
| PMON68539 | GM_A36448 | 4.62 | 2.64 | 78.35 | 9.99 | 3.77 |
| PMON68539 | GM_A36448 | 5.89 | 2.65 | 76.86 | 9.79 | 3.84 |
| PMON68539 | GM_A36448 | 4.92 | 2.62 | 72.61 | 14.61 | 4.01 |
| PMON68539 | GM_A36448 | 5.48 | 2.86 | 71.07 | 15.63 | 4.16 |
| PMON68539 | GM_A36448 | 13.5 | 4.2 | 16.28 | 56.86 | 8.29 |
| PMON68539 | GM_A36448 | 14.49 | 4.67 | 14.88 | 56.56 | 9.07 |
| PMON68539 | GM_A36449 | 5.16 | 2.42 | 81.91 | 6.54 | 3.12 |
| PMON68539 | GM_A36449 | 4.26 | 2.41 | 79.99 | 8.4 | 3.94 |
| PMON68539 | GM_A36449 | 4.26 | 2.72 | 79.07 | 9.32 | 3.38 |
| PMON68539 | GM_A36449 | 5.01 | 2.54 | 75.71 | 11.94 | 3.9 |
| PMON68539 | GM_A36449 | 4.34 | 2.76 | 75.07 | 12.75 | 4.16 |
| PMON68539 | GM_A36449 | 11.57 | 3.52 | 44.08 | 35.22 | 4.98 |
| PMON68539 | GM_A36449 | 13.42 | 3.84 | 21.35 | 52.38 | 8.17 |
| PMON68539 | GM_A36449 | 13.25 | 3.99 | 15.3 | 57.6 | 9.04 |
| PMON68539 | GM_A36450 | 3.28 | 2.6 | 82.21 | 7.26 | 3.95 |
| PMON68539 | GM_A36450 | 4.16 | 2.51 | 80.93 | 7.72 | 3.76 |
| PMON68539 | GM_A36450 | 4.3 | 3.42 | 78.78 | 8.43 | 4.22 |
| PMON68539 | GM_A36450 | 4.84 | 3.16 | 77.07 | 9.6 | 4.22 |
| PMON68539 | GM_A36450 | 5.11 | 3.1 | 75.21 | 10.98 | 4.49 |
| PMON68539 | GM_A36450 | 13.74 | 4.26 | 17.31 | 54.32 | 10.11 |
| PMON68539 | GM_A36450 | 13.82 | 4.34 | 17.13 | 54.96 | 9.47 |
| PMON68539 | GM_A36450 | 13.56 | 3.83 | 17.06 | 56.7 | 8.6 |
| PMON68539 | GM_A36705 | 9.73 | 1.83 | 75.04 | 8.23 | 4.27 |
| PMON68539 | GM_A36705 | 10.85 | 1.74 | 72.89 | 9.29 | 4.53 |
| PMON68539 | GM_A36705 | 10.05 | 1.78 | 72.68 | 9.83 | 4.48 |
| PMON68539 | GM_A36705 | 10.02 | 1.77 | 72.57 | 10.04 | 4.36 |
| PMON68539 | GM_A36705 | 10.75 | 1.75 | 72.37 | 9.68 | 4.77 |
| PMON68539 | GM_A36705 | 10.58 | 1.78 | 70.35 | 11.64 | 4.43 |
| PMON68539 | GM_A36705 | 7.69 | 5.63 | 16.21 | 60.39 | 8.85 |
| PMON68539 | GM_A36705 | 8.02 | 5.69 | 15.58 | 60.65 | 8.86 |
| | A3244 | 13.03 | 4.31 | 21.23 | 52.61 | 7.77 |
| | A3244 | 12.69 | 3.98 | 20.71 | 55.12 | 6.53 |
| | A3244 | 15.2 | 5.02 | 19.83 | 49.96 | 8.83 |
| | A3244 | 12.63 | 4.84 | 19.55 | 53.18 | 8.66 |
| | A3244 | 13.27 | 4.48 | 18.28 | 54.4 | 8.5 |
| | A3244 | 13.22 | 4.91 | 17.38 | 54.73 | 8.63 |
| | A3244 | 13.44 | 4.81 | 15.46 | 56.49 | 8.91 |

Example 11

Construct pMON95829 as described in Example 3D is used to introduce a FAD2-1 intron, double-stranded RNA-forming construct into soybean for suppressing the Fad2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide. Subsequently, the genomes of transformed plants are screened for concurrent tandem insertion of the first T-DNA and the second T-DNA, i.e. in the "right border to right border" assembly. Screening is done with Southern hybridization mapping methods. Transformed soybean plants containing the preferred configuration in their genome are transferred to a green house for seed production.

For example, leaf tissue was taken from the $R_0$ plants transformed with construct pMON95829 and Southern analysis is performed. Probes and restriction enzyme digests are chosen in order to identify events containing a right-border-right-border ("RB-RB") assembly of both T-DNAs. Typically, approximately 25% of all transformants have properly assembled RB-RB T-DNAs.

Fatty acid compositions are analyzed from seed of soybean lines transformed with a pMON95829 construct using gas chromatography as described in Example 4 to identify methyl esters of fatty acid compounds extracted from seeds. First, six $R_1$ seeds taken from soybean plants transformed with construct pMON95829 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 9). For example, FAD2 suppression provides plants with increased amount of oleic acid ester compounds.

TABLE 9

Fatty acid composition of R1 single seeds from pMON95829 events

| Construct | Event # | 16:0 | 18:0 | 18:1 | 18:2 | 18:3 |
|---|---|---|---|---|---|---|
| PMON95829 | GM_A94247 | 2.1 | 2.8 | 83.0 | 6.0 | 5.5 |
| PMON95829 | GM_A94296 | 2.6 | 2.9 | 80.6 | 7.1 | 5.8 |
| PMON95829 | GM_A93590 | 2.5 | 2.8 | 80.4 | 7.4 | 5.8 |
| PMON95829 | GM_A93437 | 2.6 | 2.8 | 79.8 | 7.9 | 6.0 |
| PMON95829 | GM_A93517 | 2.9 | 2.8 | 79.5 | 7.7 | 6.0 |
| PMON95829 | GM_A93647 | 2.3 | 3.0 | 78.6 | 9.0 | 6.5 |
| PMON95829 | GM_A93670 | 3.1 | 2.9 | 77.3 | 10.1 | 6.2 |
| PMON95829 | GM_A92396 | 2.9 | 2.6 | 76.0 | 11.1 | 7.0 |
| PMON95829 | GM_A92455 | 3.6 | 3.1 | 74.9 | 12.0 | 5.5 |
| PMON95829 | GM_A93678 | 2.8 | 3.4 | 74.0 | 11.9 | 7.4 |
| PMON95829 | GM_A93640 | 2.5 | 2.7 | 71.6 | 14.6 | 7.6 |
| PMON95829 | GM_A94937 | 4.5 | 3.3 | 67.2 | 17.7 | 7.1 |
| PMON95829 | GM_A92481 | 4.9 | 2.8 | 58.1 | 25.3 | 8.1 |
| PMON95829 | GM_A94306 | 3.1 | 3.2 | 55.9 | 29.0 | 7.9 |
| PMON95829 | GM_A94211 | 3.0 | 2.7 | 47.0 | 38.3 | 8.7 |

Example 12

Construct pMON93505 as described in Example 3D is used to introduce a FAD2-1A intron, double-stranded RNA-forming construct into soybean for suppressing the Fad2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide. Subsequently, the genomes of transformed plants are screened for concurrent tandem insertion of the first T-DNA and the second T-DNA, i.e. in the "right border to right border" assembly. Screening is done with Southern hybridization mapping methods. Transformed soybean plants containing the preferred configuration in their genome are transferred to a green house for seed production.

For example, leaf tissue was taken from the $R_0$ plants transformed with construct pMON93505 and Southern analysis is performed. Probes and restriction enzyme digests are chosen in order to identify events containing a right-border-right-border ("RB-RB") assembly of both T-DNAs. Typically, approximately 25% of all transformants have properly assembled RB-RB T-DNAs.

Fatty acid compositions are analyzed from seed of soybean lines transformed with a pMON93505 construct using gas chromatography as described in Example 4 to identify methyl esters of fatty acid compounds extracted from seeds. First, six $R_1$ seeds taken from soybean plants transformed with construct pMON93505 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 10). For example, FAD2 suppression provides plants with increased amount of oleic acid ester compounds.

TABLE 10

Fatty acid composition of R1 single seeds from pMON93505 events

| Construct | Event # | 16:0 | 18:0 | 18:1 | 18:2 | 18:3 |
|---|---|---|---|---|---|---|
| PMON93505 | GM_A87814 | 1.3 | 1.0 | 84.9 | 5.5 | 6.3 |
| PMON93505 | GM_A86449 | 1.5 | 0.9 | 84.9 | 4.9 | 6.8 |
| PMON93505 | GM_A86032 | 1.5 | 1.1 | 83.5 | 6.3 | 7.0 |
| PMON93505 | GM_A86159 | 1.5 | 0.9 | 82.8 | 6.7 | 7.5 |
| PMON93505 | GM_A86178 | 1.7 | 1.0 | 82.5 | 6.7 | 7.3 |
| PMON93505 | GM_A86075 | 1.4 | 0.9 | 81.4 | 6.6 | 8.5 |
| PMON93505 | GM_A86303 | 1.0 | 0.6 | 81.4 | 7.4 | 8.8 |
| PMON93505 | GM_A86454 | 1.4 | 0.9 | 79.9 | 7.4 | 8.8 |
| PMON93505 | GM_A86799 | 1.4 | 1.1 | 79.4 | 9.6 | 7.7 |
| PMON93505 | GM_A85997 | 2.2 | 2.5 | 79.3 | 7.7 | 7.4 |
| PMON93505 | GM_A86058 | 1.8 | 1.0 | 76.8 | 11.3 | 8.3 |
| PMON93505 | GM_A86274 | 1.2 | 0.7 | 74.6 | 10.2 | 11.9 |
| PMON93505 | GM_A86325 | 1.1 | 0.7 | 72.8 | 15.4 | 9.2 |
| PMON93505 | GM_A85969 | 2.0 | 0.7 | 70.7 | 13.6 | 12.1 |
| PMON93505 | GM_A86033 | 1.7 | 0.9 | 69.1 | 18.2 | 9.5 |
| PMON93505 | GM_A86372 | 1.7 | 1.0 | 65.7 | 12.6 | 17.6 |
| PMON93505 | GM_A86403 | 1.5 | 0.9 | 64.6 | 16.8 | 15.4 |
| PMON93505 | GM_A87803 | 1.1 | 0.6 | 57.7 | 26.0 | 13.8 |
| PMON93505 | GM_A86036 | 3.1 | 1.5 | 54.8 | 30.4 | 9.7 |
| PMON93505 | GM_A86269 | 4.9 | 1.8 | 51.4 | 31.9 | 9.5 |

Example 13

Construct pMON93506 as described in Example 3D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide. Subsequently, the genomes of transformed plants are screened for concurrent tandem insertion of the first T-DNA and the second T-DNA, i.e. in the "right border to right border" assembly. Screening is done with Southern hybridization mapping methods. Transformed soybean plants containing the preferred configuration in their genome are transferred to a green house for seed production.

For example, leaf tissue was taken from the R₀ plants transformed with construct pMON93506 and Southern analysis is performed. Probes and restriction enzyme digests are chosen in order to identify events containing a right-border-right-border ("RB-RB") assembly of both T-DNAs. Typically, approximately 25% of all transformants have properly assembled RB-RB T-DNAs.

Fatty acid compositions are analyzed from seed of soybean lines transformed with a pMON93506 construct using gas chromatography as described in Example 4 to identify methyl esters of fatty acid compounds extracted from seeds. First, six R₁ seeds taken from soybean plants transformed with construct pMON93506 are harvested, and the fatty acid composition of each single seed is determined. Since R₁ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 11). For example, FAD2 suppression provides plants with increased amount of oleic acid ester compounds.

TABLE 11

Fatty acid composition of R1 single seeds from pMON93506 events

| Construct | Event # | 16:0 | 18:0 | 18:1 | 18:2 | 18:3 |
|---|---|---|---|---|---|---|
| PMON93506 | GM_A87174 | 2.2 | 0.8 | 88.1 | 2.3 | 5.1 |
| PMON93506 | GM_A86998 | 2.1 | 0.6 | 87.1 | 3.4 | 5.5 |
| PMON93506 | GM_A87075 | 2.7 | 1.2 | 85.9 | 4.8 | 4.2 |
| PMON93506 | GM_A87255 | 2.9 | 0.8 | 84.8 | 5.5 | 5.4 |
| PMON93506 | GM_A91253 | 2.7 | 0.9 | 84.5 | 5.9 | 5.1 |
| PMON93506 | GM_A86561 | 2.8 | 0.7 | 83.8 | 5.9 | 6.0 |
| PMON93506 | GM_A86875 | 3.1 | 1.0 | 83.6 | 6.2 | 5.5 |
| PMON93506 | GM_A89967 | 1.8 | 1.3 | 83.2 | 4.1 | 7.9 |
| PMON93506 | GM_A86927 | 2.1 | 0.8 | 82.6 | 4.8 | 8.5 |
| PMON93506 | GM_A87883 | 2.7 | 0.7 | 82.4 | 6.5 | 7.2 |
| PMON93506 | GM_A87133 | 3.0 | 3.1 | 81.5 | 5.2 | 6.3 |
| PMON93506 | GM_A88072 | 2.8 | 0.7 | 80.6 | 8.2 | 7.1 |
| PMON93506 | GM_A87069 | 3.8 | 0.7 | 80.4 | 8.2 | 6.4 |
| PMON93506 | GM_A86835 | 2.7 | 3.0 | 80.3 | 6.4 | 6.4 |
| PMON93506 | GM_A87929 | 2.7 | 1.0 | 76.3 | 7.8 | 11.5 |
| PMON93506 | GM_A87298 | 3.0 | 1.2 | 72.9 | 13.0 | 9.1 |
| PMON93506 | GM_A91226 | 3.4 | 1.0 | 69.3 | 18.0 | 7.7 |
| PMON93506 | GM_A88076 | 3.7 | 3.9 | 68.0 | 15.4 | 8.1 |
| PMON93506 | GM_A86530 | 2.9 | 1.0 | 59.3 | 25.0 | 11.5 |
| PMON93506 | GM_A87292 | 4.6 | 4.3 | 54.2 | 27.6 | 8.3 |
| PMON93506 | GM_A87076 | 5.5 | 0.9 | 46.7 | 38.0 | 8.4 |

Example 14

Construct pMON93501 as described in Example 3B is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93501 construct using gas chromatography as described in Example 4 to identify methyl esters of fatty acid compounds extracted from seeds. First, six R₁ seeds taken from soybean plants transformed with construct pMON93501 are harvested, and the fatty acid composition of each single seed is determined. Since R₁ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 12). For example, FAD2 suppression provides plants with increased amount of oleic acid ester compounds.

TABLE 12

Fatty acid composition of R1 single seeds from pMON93501 events

| Construct | Event # | 16:0 | 18:0 | 18:1 | 18:2 | 18:3 |
|---|---|---|---|---|---|---|
| PMON93501 | GM_A85435 | 4.4 | 1.1 | 85.8 | 2.5 | 5.1 |
| PMON93501 | GM_A85439 | 4.6 | 0.9 | 84.8 | 3.7 | 5.1 |
| PMON93501 | GM_A85276 | 4.8 | 1.4 | 84.3 | 3.0 | 4.9 |
| PMON93501 | GM_A85697 | 4.8 | 1.3 | 83.6 | 3.8 | 5.6 |
| PMON93501 | GM_A85777 | 6.6 | 1.8 | 80.0 | 4.5 | 6.4 |
| PMON93501 | GM_A84790 | 7.2 | 5.7 | 78.3 | 2.9 | 4.7 |
| PMON93501 | GM_A85910 | 4.2 | 1.1 | 77.8 | 6.9 | 9.3 |
| PMON93501 | GM_A86186 | 5.3 | 1.1 | 77.4 | 7.4 | 7.7 |
| PMON93501 | GM_A85065 | 7.3 | 2.2 | 76.8 | 5.7 | 6.9 |
| PMON93501 | GM_A85744 | 4.1 | 0.9 | 76.0 | 7.4 | 10.6 |
| PMON93501 | GM_A85261 | 4.7 | 1.0 | 75.8 | 4.9 | 11.9 |
| PMON93501 | GM_A85479 | 3.7 | 1.1 | 75.8 | 8.6 | 9.8 |
| PMON93501 | GM_A85819 | 4.5 | 1.7 | 74.9 | 6.9 | 11.1 |
| PMON93501 | GM_A85945 | 4.6 | 1.2 | 74.6 | 8.7 | 10.0 |
| PMON93501 | GM_A85301 | 6.9 | 1.2 | 73.1 | 9.5 | 8.4 |
| PMON93501 | GM_A85929 | 6.1 | 1.4 | 72.4 | 10.8 | 8.7 |
| PMON93501 | GM_A85908 | 6.9 | 1.3 | 70.0 | 8.0 | 13.6 |
| PMON93501 | GM_A85393 | 4.8 | 1.3 | 67.0 | 13.3 | 12.2 |
| PMON93501 | GM_A85756 | 4.8 | 1.8 | 57.3 | 17.6 | 17.8 |
| PMON93501 | GM_A85415 | 5.0 | 1.3 | 52.9 | 26.0 | 12.1 |
| PMON93501 | GM_A85950 | 5.5 | 1.8 | 47.5 | 38.6 | 6.1 |
| PMON93501 | GM_A84705 | 5.7 | 2.3 | 46.0 | 37.7 | 7.4 |
| PMON93501 | GM_A85787 | 4.5 | 1.6 | 43.4 | 37.0 | 13.1 |

Example 15

Construct pMON97552 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON97552 construct using gas chromatography as described in Example 4 to identify methyl esters of fatty acid compounds extracted from seeds. First, six $R_1$ seeds taken from soybean plants transformed with construct pMON97552 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 13). For example, FAD2 suppression provides plants with increased amount of oleic acid ester compounds.

TABLE 13

Fatty acid composition of R1 single seeds from pMON97552 events

| Construct | Event # | 16:0 | 18:0 | 18:1 | 18:2 | 18:3 |
|---|---|---|---|---|---|---|
| PMON97552 | GM_A98359 | 2.1 | 2.7 | 84.4 | 4.7 | 5.3 |
| PMON97552 | GM_A98361 | 2.3 | 2.7 | 84.0 | 5.3 | 4.8 |
| PMON97552 | GM_A98358 | 2.3 | 2.7 | 81.6 | 6.8 | 6.2 |

Example 16

Construct pMON93758 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93758 construct using gas chromatography as described in Example 4 to identify methyl esters of fatty acid compounds extracted from seeds. First, six $R_1$ seeds taken from soybean plants transformed with construct pMON93758 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 14). For example, FAD2 suppression provides plants with increased amount of oleic acid ester compounds.

TABLE 14

Fatty acid composition of R1 single seeds from pMON93758 events

| Construct | Event # | 16:0 | 18:0 | 18:1 | 18:2 | 18:3 |
|---|---|---|---|---|---|---|
| PMON93758 | GM_A89686 | 2.7 | 2.9 | 82.7 | 5.3 | 5.5 |
| PMON93758 | GM_A89678 | 2.9 | 2.9 | 81.8 | 5.5 | 6.0 |
| PMON93758 | GM_A89670 | 2.8 | 3.0 | 81.7 | 5.6 | 6.1 |
| PMON93758 | GM_A89688 | 2.7 | 3.2 | 81.6 | 5.8 | 5.9 |
| PMON93758 | GM_A89683 | 2.9 | 2.9 | 81.5 | 5.8 | 6.1 |
| PMON93758 | GM_A89699 | 2.7 | 3.1 | 81.4 | 5.8 | 6.1 |
| PMON93758 | GM_A89675 | 2.9 | 3.0 | 81.4 | 5.6 | 6.2 |
| PMON93758 | GM_A89690 | 3.0 | 2.8 | 81.3 | 5.7 | 6.3 |
| PMON93758 | GM_A89680 | 3.0 | 2.8 | 81.3 | 5.9 | 6.0 |
| PMON93758 | GM_A89674 | 2.9 | 2.9 | 80.4 | 6.3 | 6.7 |
| PMON93758 | GM_A89677 | 3.0 | 2.8 | 79.7 | 7.0 | 6.8 |
| PMON93758 | GM_A89676 | 3.0 | 2.9 | 78.7 | 7.6 | 7.4 |
| PMON93758 | GM_A89694 | 3.2 | 2.8 | 76.7 | 8.8 | 8.0 |
| PMON93758 | GM_A89696 | 3.0 | 2.6 | 74.7 | 10.4 | 8.9 |

Example 17

Construct pMON97553 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON97553 construct using gas chromatography as described in Example 4 to identify methyl esters of fatty acid compounds extracted from seeds. First, six $R_1$ seeds taken from soybean plants transformed with construct pMON97553 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 15). For example, FAD2 suppression provides plants with increased amount of oleic acid ester compounds.

TABLE 15

Fatty acid composition of R1 single seeds from pMON97553 events

| Construct | Event # | 16:0 | 18:0 | 18:1 | 18:2 | 18:3 |
|---|---|---|---|---|---|---|
| PMON97553 | GM__A98670 | 2.1 | 2.6 | 86.7 | 2.9 | 4.3 |
| PMON97553 | GM__A98595 | 2.3 | 2.7 | 86.3 | 3.5 | 4.7 |
| PMON97553 | GM__A98649 | 2.2 | 2.9 | 86.3 | 3.6 | 4.7 |
| PMON97553 | GM__A98669 | 2.1 | 3.0 | 85.5 | 3.3 | 4.6 |
| PMON97553 | GM__A98656 | 2.4 | 2.8 | 85.5 | 4.2 | 4.6 |
| PMON97553 | GM__A98643 | 2.3 | 2.8 | 85.0 | 3.8 | 4.9 |
| PMON97553 | GM__A98647 | 2.2 | 2.8 | 84.2 | 5.1 | 5.6 |
| PMON97553 | GM__A98582 | 2.6 | 2.8 | 84.0 | 4.1 | 5.6 |
| PMON97553 | GM__A98674 | 2.1 | 2.3 | 83.9 | 5.8 | 5.3 |
| PMON97553 | GM__A98663 | 2.2 | 2.8 | 83.3 | 5.5 | 5.1 |
| PMON97553 | GM__A98587 | 2.8 | 2.8 | 83.0 | 5.5 | 5.3 |
| PMON97553 | GM__A98592 | 2.9 | 2.9 | 82.9 | 4.6 | 5.8 |
| PMON97553 | GM__A98677 | 2.2 | 3.0 | 82.4 | 5.9 | 5.4 |
| PMON97553 | GM__A98594 | 2.2 | 2.9 | 82.3 | 6.5 | 5.4 |
| PMON97553 | GM__A98659 | 2.5 | 3.0 | 82.2 | 5.4 | 6.1 |
| PMON97553 | GM__A98622 | 2.8 | 3.0 | 81.6 | 6.0 | 6.1 |
| PMON97553 | GM__A98589 | 2.9 | 3.0 | 81.3 | 6.2 | 6.1 |
| PMON97553 | GM__A98679 | 2.2 | 3.1 | 81.2 | 6.7 | 5.7 |
| PMON97553 | GM__A98642 | 2.3 | 3.1 | 80.0 | 7.4 | 6.1 |
| PMON97553 | GM__A98639 | 2.7 | 3.0 | 78.4 | 8.0 | 6.8 |
| PMON97553 | GM__A98563 | 3.3 | 2.9 | 78.1 | 9.9 | 5.6 |
| PMON97553 | GM__A98618 | 2.9 | 2.8 | 78.0 | 8.8 | 6.9 |
| PMON97553 | GM__A98567 | 2.7 | 3.2 | 77.5 | 9.1 | 6.3 |
| PMON97553 | GM__A98625 | 2.3 | 2.9 | 77.4 | 9.5 | 6.9 |
| PMON97553 | GM__A98660 | 3.3 | 2.9 | 77.1 | 10.7 | 5.6 |
| PMON97553 | GM__A98615 | 2.7 | 3.2 | 76.4 | 9.9 | 7.1 |
| PMON97553 | GM__A98561 | 3.3 | 3.1 | 75.3 | 10.9 | 6.7 |
| PMON97553 | GM__A98603 | 2.9 | 3.6 | 73.5 | 11.0 | 7.8 |
| PMON97553 | GM__A98648 | 2.7 | 3.3 | 70.2 | 14.4 | 8.3 |
| PMON97553 | GM__A98565 | 3.2 | 2.8 | 67.9 | 17.9 | 7.2 |
| PMON97553 | GM__A98681 | 3.1 | 3.0 | 65.9 | 19.3 | 7.7 |

Example 18

Construct pMON93770 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93770 construct using gas chromatography as described in Example 4 to identify methyl esters of fatty acid compounds extracted from seeds. First, six R$_1$ seeds taken from soybean plants transformed with construct pMON93770 are harvested, and the fatty acid composition of each single seed is determined. Since R$_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 16). For example, FAD2 suppression provides plants with increased amount of oleic acid ester compounds.

TABLE 16

Fatty acid composition of R1 single seeds from pMON93770 events

| Construct | Event # | 16:0 | 18:0 | 18:1 | 18:2 | 18:3 |
|---|---|---|---|---|---|---|
| PMON93770 | GM__A97973 | 2.8 | 2.7 | 80.0 | 7.3 | 6.2 |
| PMON93770 | GM__A97996 | 2.5 | 3.5 | 76.6 | 9.5 | 6.8 |
| PMON93770 | GM__A97977 | 2.7 | 3.1 | 75.8 | 9.8 | 7.5 |
| PMON93770 | GM__A97981 | 3.1 | 3.0 | 71.8 | 13.2 | 8.0 |
| PMON93770 | GM__A97971 | 3.4 | 3.1 | 70.3 | 14.8 | 7.5 |
| PMON93770 | GM__A97985 | 2.9 | 2.7 | 67.9 | 15.9 | 9.6 |
| PMON93770 | GM__A97991 | 3.2 | 2.9 | 66.4 | 19.0 | 7.6 |

Example 19

Construct pMON93759 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93759 construct using gas chromatography as described in Example 4 to identify methyl esters of fatty acid compounds extracted from seeds. First, six R$_1$ seeds taken from soybean plants transformed with construct pMON93759 are harvested, and the fatty acid composition of each single seed is determined. Since R$_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 17). For example, FAD2 suppression provides plants with increased amount of oleic acid ester compounds.

TABLE 17

Fatty acid composition of R1 single seeds from pMON93759 events

| Construct | Event # | 16:0 | 18:0 | 18:1 | 18:2 | 18:3 |
|---|---|---|---|---|---|---|
| PMON93759 | GM__A88219 | 3.0 | 2.7 | 77.0 | 9.1 | 7.4 |
| PMON93759 | GM__A88212 | 3.1 | 2.7 | 76.6 | 9.1 | 7.6 |
| PMON93759 | GM__A88205 | 3.1 | 2.8 | 73.9 | 11.5 | 7.8 |
| PMON93759 | GM__A88209 | 2.9 | 2.7 | 73.9 | 11.6 | 8.2 |
| PMON93759 | GM__A88222 | 3.1 | 2.6 | 73.7 | 11.9 | 8.0 |
| PMON93759 | GM__A88223 | 2.7 | 2.6 | 73.5 | 12.4 | 8.3 |
| PMON93759 | GM__A88215 | 2.9 | 2.9 | 73.3 | 12.1 | 7.9 |
| PMON93759 | GM__A88202 | 3.4 | 2.8 | 72.9 | 12.6 | 7.7 |
| PMON93759 | GM__A88220 | 3.0 | 3.0 | 72.1 | 13.3 | 7.7 |
| PMON93759 | GM__A88213 | 2.9 | 3.0 | 71.8 | 13.1 | 8.3 |
| PMON93759 | GM__A88210 | 3.3 | 2.8 | 71.6 | 13.5 | 8.3 |
| PMON93759 | GM__A88217 | 2.5 | 2.7 | 71.5 | 14.9 | 7.8 |
| PMON93759 | GM__A88206 | 2.9 | 2.9 | 71.3 | 13.3 | 8.8 |
| PMON93759 | GM__A88211 | 3.1 | 3.0 | 71.3 | 13.8 | 7.9 |
| PMON93759 | GM__A88204 | 3.1 | 2.8 | 70.5 | 14.3 | 8.8 |
| PMON93759 | GM__A88201 | 3.2 | 2.7 | 69.4 | 15.5 | 8.4 |
| PMON93759 | GM__A88200 | 3.3 | 3.0 | 67.3 | 17.1 | 8.5 |
| PMON93759 | GM__A88214 | 3.3 | 2.9 | 60.6 | 23.7 | 8.7 |

TABLE 17-continued

Fatty acid composition of R1 single seeds from pMON93759 events

| Construct | Event # | 16:0 | 18:0 | 18:1 | 18:2 | 18:3 |
|---|---|---|---|---|---|---|
| PMON93759 | GM__A88203 | 3.5 | 3.1 | 60.6 | 23.3 | 8.9 |
| PMON93759 | GM__A88226 | 3.0 | 2.8 | 60.5 | 23.7 | 9.5 |
| PMON93759 | GM__A88198 | 4.7 | 3.1 | 42.7 | 39.6 | 9.1 |

Example 20

Construct pMON97554 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON97554 construct using gas chromatography as described in Example 4 to identify methyl esters of fatty acid compounds extracted from seeds. First, six $R_1$ seeds taken from soybean plants transformed with construct pMON97554 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 18). For example, FAD2 suppression provides plants with increased amount of oleic acid ester compounds.

TABLE 18

Fatty acid composition of R1 single seeds from pMON97554 events

| Construct | Event # | 16:0 | 18:0 | 18:1 | 18:2 | 18:3 |
|---|---|---|---|---|---|---|
| PMON97554 | GM__A98420 | 2.3 | 2.6 | 80.4 | 8.0 | 5.7 |
| PMON97554 | GM__A98445 | 2.1 | 3.0 | 77.4 | 10.1 | 6.3 |
| PMON97554 | GM__A98423 | 2.7 | 2.9 | 77.0 | 10.3 | 6.1 |
| PMON97554 | GM__A98440 | 2.7 | 2.8 | 76.0 | 10.8 | 6.6 |
| PMON97554 | GM__A98438 | 2.8 | 3.0 | 70.6 | 15.2 | 7.3 |
| PMON97554 | GM__A98435 | 3.6 | 3.0 | 69.6 | 16.5 | 6.3 |

Example 21

Construct pMON93771 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93771 construct using gas chromatography as described in Example 4 to identify methyl esters of fatty acid compounds extracted from seeds. First, six $R_1$ seeds taken from soybean plants transformed with construct pMON93771 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 19). For example, FAD2 suppression provides plants with increased amount of oleic acid ester compounds.

TABLE 19

Fatty acid composition of R1 single seeds from pMON93771 events

| Construct | Event # | 16:0 | 18:0 | 18:1 | 18:2 | 18:3 |
|---|---|---|---|---|---|---|
| PMON93771 | GM__A97841 | 2.5 | 2.3 | 70.8 | 17.0 | 6.6 |
| PMON93771 | GM__A97839 | 3.8 | 3.0 | 65.8 | 18.3 | 8.1 |
| PMON93771 | GM__A97836 | 4.1 | 2.9 | 65.5 | 19.3 | 7.1 |
| PMON93771 | GM__A97844 | 2.6 | 2.7 | 65.2 | 20.9 | 8.0 |
| PMON93771 | GM__A97835 | 4.4 | 2.9 | 62.9 | 21.0 | 7.8 |
| PMON93771 | GM__A97852 | 3.3 | 3.1 | 62.9 | 21.0 | 8.9 |
| PMON93771 | GM__A97857 | 3.4 | 2.7 | 61.7 | 22.6 | 8.7 |
| PMON93771 | GM__A97846 | 4.2 | 2.7 | 52.0 | 30.8 | 9.6 |

Example 22

Construct pMON97555 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON97555 construct using gas chromatography as described in Example 4 to identify methyl esters of fatty acid compounds extracted from seeds. First, six $R_1$ seeds taken from soybean plants transformed with construct pMON97555 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 20). For example, FAD2 suppression provides plants with increased amount of oleic acid ester compounds.

TABLE 20

Fatty acid composition of R1 single seeds from pMON97555 events

| Construct | Event # | 16:0 | 18:0 | 18:1 | 18:2 | 18:3 |
|---|---|---|---|---|---|---|
| PMON97555 | GM__A98913 | 2.7 | 2.9 | 71.0 | 14.5 | 7.8 |
| PMON97555 | GM__A98912 | 2.1 | 2.2 | 70.5 | 18.0 | 6.4 |
| PMON97555 | GM__A98905 | 2.7 | 3.1 | 65.9 | 19.0 | 8.2 |
| PMON97555 | GM__A98909 | 2.4 | 2.8 | 63.5 | 21.5 | 9.1 |
| PMON97555 | GM__A98936 | 4.9 | 2.4 | 61.9 | 24.9 | 5.3 |

TABLE 20-continued

Fatty acid composition of R1 single
seeds from pMON97555 events

| Construct | Event # | 16:0 | 18:0 | 18:1 | 18:2 | 18:3 |
|---|---|---|---|---|---|---|
| PMON97555 | GM__A98893 | 2.5 | 2.8 | 61.5 | 23.7 | 8.6 |
| PMON97555 | GM__A98924 | 3.0 | 3.0 | 61.4 | 23.5 | 8.1 |
| PMON97555 | GM__A98904 | 3.1 | 2.9 | 60.6 | 24.0 | 8.3 |
| PMON97555 | GM__A98938 | 2.3 | 2.9 | 58.3 | 28.1 | 7.6 |
| PMON97555 | GM__A98900 | 3.2 | 2.8 | 56.7 | 28.4 | 8.0 |
| PMON97555 | GM__A98906 | 2.7 | 2.9 | 56.7 | 27.8 | 8.8 |
| PMON97555 | GM__A98917 | 2.7 | 3.1 | 53.0 | 32.1 | 8.4 |
| PMON97555 | GM__A98939 | 3.0 | 3.1 | 52.9 | 31.4 | 8.9 |
| PMON97555 | GM__A98935 | 4.5 | 3.2 | 48.2 | 35.4 | 7.8 |
| PMON97555 | GM__A98919 | 3.1 | 3.4 | 44.2 | 40.3 | 8.0 |

Example 23

Construct pMON93760 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93760 construct using gas chromatography as described in Example 4 to identify methyl esters of fatty acid compounds extracted from seeds. First, six $R_1$ seeds taken from soybean plants transformed with construct pMON93760 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 21). For example, FAD2-1 intron, reduced in length by 320 contiguous nucleotides from the 5' end of (SEQ ID NO:1) and capable of forming dsRNA, does at least partially suppress FAD2.

TABLE 21

Fatty acid composition of R1 single
seeds from pMON93760 events

| Construct | Event # | 16:0 | 18:0 | 18:1 | 18:2 | 18:3 |
|---|---|---|---|---|---|---|
| PMON93760 | GM__A88236 | 10.0 | 3.6 | 58.3 | 23.4 | 4.4 |
| PMON93760 | GM__A88240 | 2.9 | 2.6 | 56.0 | 28.4 | 9.5 |
| PMON93760 | GM__A88245 | 3.3 | 3.2 | 54.8 | 28.7 | 9.6 |
| PMON93760 | GM__A88231 | 3.2 | 2.7 | 48.8 | 35.0 | 9.6 |
| PMON93760 | GM__A88234 | 3.8 | 2.7 | 47.7 | 36.1 | 9.1 |
| PMON93760 | GM__A88252 | 3.1 | 2.5 | 45.3 | 40.9 | 7.5 |
| PMON93760 | GM__A88244 | 3.4 | 3.0 | 41.6 | 42.2 | 9.2 |
| PMON93760 | GM__A88256 | 2.7 | 2.7 | 41.3 | 44.6 | 8.5 |
| PMON93760 | GM__A88243 | 2.8 | 2.7 | 36.6 | 50.4 | 7.1 |
| PMON93760 | GM__A88254 | 3.7 | 2.6 | 27.5 | 58.1 | 7.6 |
| PMON93760 | GM__A88253 | 3.7 | 2.8 | 25.4 | 60.6 | 6.9 |
| PMON93760 | GM__A88239 | 7.2 | 2.8 | 25.0 | 58.6 | 6.2 |
| PMON93760 | GM__A88250 | 4.7 | 2.9 | 24.4 | 59.2 | 8.4 |
| PMON93760 | GM__A88251 | 5.5 | 3.0 | 22.7 | 60.0 | 8.6 |

Example 24

Construct pMON93772 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93772 construct using gas chromatography as described in Example 4 to identify methyl esters of fatty acid compounds extracted from seeds. First, six $R_1$ seeds taken from soybean plants transformed with construct pMON93772 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 22). For example, FAD2-1 intron, reduced in length by 360 contiguous nucleotides from the 3' end of (SEQ ID NO:1) and capable of forming dsRNA, does at least partially suppress FAD2 for some events.

TABLE 22

Fatty acid composition of R1 single
seeds from pMON93772 events

| Construct | Event # | 16:0 | 18:0 | 18:1 | 18:2 | 18:3 |
|---|---|---|---|---|---|---|
| PMON93772 | GM__A97768 | 3.4 | 2.3 | 69.6 | 17.6 | 6.3 |
| PMON93772 | GM__A97781 | 3.3 | 2.6 | 55.1 | 30.9 | 7.3 |
| PMON93772 | GM__A97763 | 3.7 | 2.6 | 45.2 | 38.2 | 9.6 |
| PMON93772 | GM__A97796 | 2.3 | 2.9 | 35.1 | 50.3 | 8.7 |
| PMON93772 | GM__A97798 | 3.3 | 2.6 | 33.5 | 51.2 | 8.6 |
| PMON93772 | GM__A97782 | 2.6 | 2.7 | 33.4 | 52.0 | 8.5 |
| PMON93772 | GM__A97819 | 3.8 | 3.1 | 30.1 | 53.8 | 8.7 |
| PMON93772 | GM__A97777 | 3.3 | 2.7 | 28.1 | 56.7 | 8.6 |
| PMON93772 | GM__A97767 | 2.9 | 2.8 | 26.3 | 57.9 | 9.6 |
| PMON93772 | GM__A97792 | 3.7 | 2.6 | 26.2 | 57.8 | 9.1 |
| PMON93772 | GM__A97808 | 3.0 | 3.0 | 25.7 | 58.4 | 9.2 |
| PMON93772 | GM__A97790 | 2.8 | 2.7 | 25.1 | 59.7 | 9.2 |
| PMON93772 | GM__A97805 | 3.5 | 2.8 | 24.6 | 59.7 | 8.7 |
| PMON93772 | GM__A97817 | 3.5 | 2.9 | 24.0 | 59.4 | 9.5 |
| PMON93772 | GM__A97828 | 3.2 | 2.9 | 23.4 | 60.3 | 9.8 |
| PMON93772 | GM__A97812 | 2.5 | 2.9 | 23.0 | 61.3 | 9.8 |
| PMON93772 | GM__A97765 | 2.8 | 3.0 | 20.7 | 63.0 | 10.1 |

Example 25

Construct pMON97556 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON97556 construct using gas chromatography as described in Example 4 to identify methyl esters of fatty acid compounds extracted from seeds. First, six $R_1$ seeds taken from soybean plants transformed with construct pMON97556 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the mono- and polyunsaturated fatty acid compositions are altered in the oil of seeds from transgenic soybean lines as compared to that of the seed from non-transformed soybean (See Table 23). For example, FAD2-1 intron, reduced in length by 200 contiguous nucleotides from the 3' end of (SEQ ID NO:1) and capable of forming dsRNA, does at least partially suppress FAD2.

TABLE 23

Fatty acid composition of R1 single seeds from pMON97556 events

| Construct | Event # | 16:0 | 18:0 | 18:1 | 18:2 | 18:3 |
|---|---|---|---|---|---|---|
| PMON97556 | GM_A98772 | 3.6 | 2.8 | 34.3 | 51.0 | 7.4 |
| PMON97556 | GM_A98744 | 2.4 | 2.6 | 26.6 | 60.3 | 7.4 |
| PMON97556 | GM_A98787 | 2.5 | 2.8 | 26.4 | 58.9 | 8.7 |
| PMON97556 | GM_A98745 | 2.2 | 2.5 | 26.3 | 60.2 | 8.0 |
| PMON97556 | GM_A98758 | 2.5 | 2.9 | 25.6 | 59.6 | 8.7 |
| PMON97556 | GM_A98789 | 2.1 | 2.5 | 22.3 | 64.9 | 7.7 |
| PMON97556 | GM_A98790 | 2.2 | 3.0 | 22.1 | 62.8 | 9.4 |
| PMON97556 | GM_A98783 | 2.5 | 2.6 | 21.5 | 64.0 | 8.7 |
| PMON97556 | GM_A98761 | 2.3 | 2.3 | 20.9 | 65.2 | 8.7 |

Example 26

Construct pMON93764 as described in Example 2D is used to introduce a FAD2-1A intron, double-stranded RNA-forming construct into soybean for suppressing the FAD2 gene. The vector is stably introduced into soybean (Asgrow variety A4922) via *Agrobacterium tumefaciens* strain ABI (Martinell, U.S. Pat. No. 6,384,301). The CP4 selectable marker allows transformed soybean plants to be identified by selection on media containing glyphosate herbicide.

Fatty acid compositions are analyzed from seed of soybean lines transformed with a pMON93764 construct using gas chromatography as described in Example 4 to identify methyl esters of fatty acid compounds extracted from seeds. First, six $R_1$ seeds taken from soybean plants transformed with construct pMON93764 are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the saturated fatty acid compositions are altered in the oil of seeds from transgenic soybean lines as compared to that of the seed from non-transformed soybean (See Table 24). Also, FAD2-1 intron, reduced in length by 400 contiguous nucleotides from the 3' end of (SEQ ID NO:1) and capable of forming dsRNA, does not substantially reduce FAD2 expression.

TABLE 24

Fatty acid composition of R1 single seeds from pMON93764 events

| Construct | Event # | 16:0 | 18:0 | 18:1 | 18:2 | 18:3 |
|---|---|---|---|---|---|---|
| PMON93764 | GM_A98489 | 2.1 | 2.2 | 28.1 | 60.5 | 6.5 |
| PMON93764 | GM_A98452 | 2.2 | 2.2 | 27.4 | 61.3 | 6.8 |
| PMON93764 | GM_A98451 | 2.3 | 2.5 | 26.2 | 60.7 | 7.8 |
| PMON93764 | GM_A98467 | 2.5 | 2.8 | 25.4 | 60.9 | 8.2 |
| PMON93764 | GM_A98455 | 1.8 | 2.3 | 24.4 | 63.5 | 7.8 |
| PMON93764 | GM_A98499 | 1.8 | 2.5 | 24.1 | 63.5 | 7.8 |
| PMON93764 | GM_A98453 | 2.5 | 2.6 | 23.7 | 63.2 | 7.5 |

TABLE 24-continued

Fatty acid composition of R1 single seeds from pMON93764 events

| Construct | Event # | 16:0 | 18:0 | 18:1 | 18:2 | 18:3 |
|---|---|---|---|---|---|---|
| PMON93764 | GM_A98492 | 1.6 | 2.7 | 23.7 | 63.6 | 7.7 |
| PMON93764 | GM_A98456 | 1.8 | 2.4 | 23.4 | 64.2 | 8.0 |
| PMON93764 | GM_A98471 | 2.2 | 2.7 | 23.4 | 64.2 | 7.4 |
| PMON93764 | GM_A98500 | 2.5 | 2.3 | 22.9 | 64.1 | 7.9 |
| PMON93764 | GM_A98482 | 2.3 | 2.5 | 22.9 | 64.6 | 7.3 |
| PMON93764 | GM_A98485 | 2.5 | 2.7 | 22.8 | 63.8 | 8.0 |
| PMON93764 | GM_A98463 | 1.9 | 2.2 | 22.6 | 64.7 | 8.3 |
| PMON93764 | GM_A98469 | 3.4 | 2.5 | 22.1 | 63.3 | 8.5 |
| PMON93764 | GM_A98474 | 1.6 | 2.3 | 21.5 | 65.7 | 8.4 |
| PMON93764 | GM_A98483 | 2.0 | 2.5 | 21.4 | 65.4 | 8.5 |
| PMON93764 | GM_A98476 | 2.7 | 2.6 | 21.2 | 64.4 | 8.8 |
| PMON93764 | GM_A98498 | 2.5 | 2.5 | 21.1 | 64.8 | 8.9 |
| PMON93764 | GM_A98496 | 2.5 | 2.3 | 20.6 | 65.2 | 8.9 |
| PMON93764 | GM_A98468 | 1.9 | 2.7 | 19.3 | 66.0 | 9.7 |

Example 27

TaqMan is an assay that quantifies nucleic acids via a selective amplification and real-time fluorescence measurements (also called real-time PCR). This procedure is used to determine the extent of target transcript suppression in transgenic developing seeds. To determine the absolute transcript levels of target mRNA in a sample, a standard curve is established for each TaqMan experiment. For this purpose, different amounts of cloned soy target gene sequence, diluted in 20 ng total RNA from canola, are amplified in parallel with the samples of unknown target amounts. Precision of the transcript copy number determined in this way has an error margin of 25%.

For template material, total RNA is extracted using an ABI 6100 Nucleic Acid Prep Station, and 20 ng is used per TaqMan sample. The samples are analyzed on an ABI 700 Sequence Detection instrument using ABI Prism-One Step RT-PCR Master Mix Chemistry. TaqMan Count (Ct) values from the end of the TaqMan PCR reaction are plotted against the known quantity of synthetic target sequence to calculate a linear regression so that the amount of FAD2-1 target DNA in an unknown sample can be determined from the TaqMan Ct values created at the end of each TaqMan PCR reaction.

Plants were transformed with either pMON68540, pMON68546, or pMON80623, all of which suppress FAD2-1A (see Section 3A and FIG. 7 for descriptions of the constructs).

Total RNA is obtained from null and transformed plants using an ABI 6100 Nucleic Acid Prep Station. Transformed plants are third generation homozygous and have levels of oleic acid greater than 50%. FAD2-1A primers, FAD2-1B primers, or FAD2-2A primers are added in separate TaqMan samples to the total RNA from each plant to be tested. The samples are analyzed on an ABI 700 Sequence Detection instrument using ABI Prism-One Step RT-PCR Master Mix Chemistry.

All transgenic plants substantially suppress FAD2-1A and FAD2-1B transcript levels. None of the transgenic plants even partially reduced FAD2-2A or FAD2-2B levels.

Plant to plant comparisons of FAD2-1A transcript levels in null plants determine natural variation between plants. FAD2-1A mRNA from developing seeds is assayed using PCR primers, which produce the Probe sequence in multiple plants. Seeds at size 0.2 g fresh weight are taken from four different $R_2$ null segregant plants, each plant from a different line. $R_2$ seed pools of same size class and from four different null segregants are tested. PCR reactions are done in triplicate and the results are normalized in comparison to the amount of 18S RNA in each sample. Plant to plant biological variability in FAD2-1A transcripts is low. Three of the four samples have a normalized TaqMan Count (Ct) value of about 65 and one of the samples has a normalized TaqMan Ct value of about 50.

Example 28

A 200 contiguous fragment of soybean FAD2-1 intron 1 (SEQ ID NO: 1) sequence is amplified via PCR to result in PCR products that include the first 200 nucleotides of SEQ ID NO: 1, starting at the 5' end of SEQ ID NO: 1. The PCR products are cloned directly, in sense orientation, into a vector containing the soybean 7Sα' promoter and a tml 3' termination sequence, by way of restriction sites engineered onto the 5' ends of the PCR primers. The vector is then cut with a restriction enzyme and ligated into a vector that contains the CP4 EPSPS gene regulated by the FMV promoter and a pea Rubisco E9 3' termination sequence. The resulting gene expression construct is used for transformation using methods as described herein.

Fatty acid compositions are analyzed from seed of soybean lines transformed with this construct using gas chromatography as described in Example 4 to identify methyl esters of fatty acid compounds extracted from seeds. First, six $R_1$ seeds taken from soybean plants transformed with this construct are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the saturated fatty acid compositions are altered in the oil of seeds from transgenic soybean lines as compared to that of the seed from non-transformed soybean.

Example 29

A 180 contiguous fragment of soybean FAD2-1 intron 1 (SEQ ID NO: 1) sequence is amplified via PCR to result in PCR products that include the first 180 nucleotides of SEQ ID NO: 1, starting at the 3' end of SEQ ID NO: 1. The PCR products are cloned directly, in sense orientation, into a vector containing the soybean 7Sα' promoter and a tml 3' termination sequence, by way of restriction sites engineered onto the 5' ends of the PCR primers. The vector is then cut with a restriction enzyme and ligated into a vector that contains the CP4 EPSPS gene regulated by the FMV promoter and a pea Rubisco E9 3' termination sequence. The resulting gene expression construct is used for transformation using methods as described herein.

Fatty acid compositions are analyzed from seed of soybean lines transformed with this construct using gas chromatography as described in Example 4 to identify methyl esters of fatty acid compounds extracted from seeds. First, six $R_1$ seeds taken from soybean plants transformed with this construct are harvested, and the fatty acid composition of each single seed is determined. Since $R_1$ plants of each event are segregating for the transgenes and, therefore, yield seeds with conventional soybean composition, as well as modified versions. The positive seeds are pooled and averaged for each event. The pooled positive averages demonstrate that the saturated fatty acid compositions are altered in the oil of seeds from transgenic soybean lines as compared to that of the seed from non-transformed soybean.

Example 30 pMON97562 contains a soybean 7Sα' promoter operably linked to a soybean FAD2-1A intron 1 (SEQ ID NO: 1), which is reduced by 100 contiguous nucleotides from the 3' end and linked to a FAD3-1A 5'UTR, followed by a FAD3-1A 3'UTR, linked to a FAD3-1B 5'UTR, followed by a FAD3-1B 3'UTR, followed by a FATB-1a 5'UTR, followed by a FATB-1a 3'UTR, operably linking to 70 nucleotides from FAD3-1A intron 4, operably linking to a FATB-1a 3'UTR in the anti-sense orientation followed by a FATB-1a 5'UTR in the antisense orientation, linked to a FAD3-1B 3'UTR in antisense, followed by a FAD3-1B 5'UTR in antisense, linked to a FAD3-1A 3'UTR in antisense, followed by a FAD3-1A 5'UTR in antisense, followed by a soybean FAD2-1A intron 1 (SEQ ID NO: 1), which is reduced by 100 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for soy transformation using methods as described herein. Fatty acid compositions are determined from seed of soybean lines transformed with this construct using gas chromatography as described in Example 4. Table 25 gives the compositions of representative seeds. The level of 18:3 is reduced to approximately 1%.

TABLE 25

| Fatty acid composition of R1 single seeds from pMON97562 events | | | | | | |
|---|---|---|---|---|---|---|
| Construct | Event | 16:0 | 18:0 | 18:1 | 18:2 | 18:3 |
| PMON97562 | GM__A103478 | 2.82 | 3.17 | 82.88 | 9.18 | 1.15 |
| PMON97562 | GM__A103481 | 2.99 | 2.75 | 82.7 | 9.39 | 1.13 |
| PMON97562 | GM__A103476 | 3.13 | 3.11 | 81.35 | 10.25 | 1.12 |

Example 31 pMON97563 contains a soybean 7Sα' promoter operably linked to a soybean FAD2-1A intron 1 (SEQ ID NO: 1), which is reduced by 100 contiguous nucleotides from the 3' end and linked to a FAD3-1A 5'UTR, followed by a FAD3-1A 3'UTR, linked to a FAD3-1B 5'UTR, followed by a FAD3-1B 3'UTR, linked to a FAD3-1C 5'UTR, followed by a FAD3-1C 3'UTR, followed by a FATB-1a CTP coding region, followed by a FATB-2a CTP coding region operably linking to 70 nucleotides from FAD3-1A intron 4, operably linking to a FATB-2a CTP coding region in the anti-sense orientation followed by a FATB-1a CTP coding region in the antisense orientation, linked to a FAD3-1C 3'UTR in antisense, followed by a FAD3-1C 5'UTR in antisense, linked to a FAD3-1B 3'UTR in antisense, followed by a FAD3-1B 5'UTR in antisense, linked to a FAD3-1A 3'UTR in antisense, followed by a FAD3-1A 5'UTR in antisense, followed by a soybean FAD2-1A intron 1 (SEQ ID NO: 1), which is reduced by 100 contiguous nucleotides from the 3' end and in the anti-sense orientation, operably linked to a H6 3' polyadenylation segment with a CP4 EPSPS gene operably linking to an EFMV promoter and a pea Rubisco E9 3' termination sequence all flanked by RB and LB on the same DNA molecule. The resulting gene expression construct is used for plant transformation using methods as described herein. Fatty acid compositions are determined from seed of soybean lines transformed with this construct using gas chromatography as described in Example 4. Table 26 gives the compositions of representative seeds. The level of 18:3 is reduced to approximately 1%.

TABLE 26

Fatty acid composition of R1 single seeds from pMON97563 events

| Construct | Event | 16:0 | 18:0 | 18:1 | 18:2 | 18:3 |
|---|---|---|---|---|---|---|
| PMON97563 | GM_A109156 | 2.21 | 2.78 | 85.05 | 8.48 | 0.69 |
| PMON97563 | GM_A109196 | 2.07 | 2.31 | 84.4 | 9.42 | 0.97 |
| PMON97563 | GM_A109207 | 2.24 | 2.78 | 83.98 | 9.36 | 0.82 |
| PMON97563 | GM_A103543 | 2.21 | 2.63 | 83.94 | 10.28 | 0.95 |
| PMON97563 | GM_A103547 | 2.06 | 2.47 | 83.67 | 10.47 | 0.89 |
| PMON97563 | GM_A109146 | 1.71 | 2.34 | 81.14 | 13.71 | 0.91 |
| PMON97563 | GM_A109155 | 2.33 | 2.7 | 80.76 | 12.28 | 1.11 |
| PMON97563 | GM_A109164 | 2.07 | 2.61 | 78.8 | 14.6 | 1 |
| PMON97563 | GM_A109170 | 2.68 | 1.95 | 78.78 | 14.14 | 1.55 |
| PMON97563 | GM_A109277 | 2.49 | 3.19 | 78.19 | 14.51 | 0.93 |
| PMON97563 | GM_A109194 | 2.46 | 2.81 | 76.62 | 16.26 | 0.92 |
| PMON97563 | GM_A109177 | 2.56 | 2.49 | 72.64 | 20.14 | 1.44 |
| PMON97563 | GM_A109201 | 2.46 | 2.9 | 72.21 | 20.13 | 1.11 |
| PMON97563 | GM_A103550 | 2.18 | 2.67 | 70.84 | 22.25 | 1.17 |
| PMON97563 | GM_A109203 | 2.18 | 2.81 | 69.93 | 22.91 | 0.98 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of modulating the fatty acid composition of a temperate oilseed comprising:
   transforming a temperate oilseed crop cell with a recombinant nucleic acid molecule comprising a first nucleic acid sequence that is a fragment of a FAD2-1 intron and the reverse complement thereof, wherein said recombinant nucleic acid molecule is capable of forming double stranded RNA of said fragment of FAD2-1 intron when transcribed in said transformed temperate oilseed crop cell,
   producing a transgenic plant from said transformed temperate oilseed crop cell, and
   obtaining a transgenic plant seed comprising said recombinant nucleic acid molecule,
   wherein said fragment of an intron is at least 40 nucleotides in length and up to 90% of the full length of said intron and said recombinant nucleic acid molecule does not include a full length FAD2-1 intron, and
   said transgenic plant seed has a modulated FAD2-1 activity which is between that of a seed from a plant having an identical genetic background containing no recombinant nucleic acid molecule, and that of a seed from a plant having an identical genetic background having a recombinant nucleic acid molecule comprising a nucleic acid sequence that is a full length FAD2-1 intron.

2. The method of claim 1, wherein said FAD2-1 intron is a FAD2-1A intron or a FAD2-1B intron.

3. The method of claim 2, wherein said fragment of a FAD2-1 intron shares between 100% and 90% sequence identity to a nucleic acid sequence selected from the group consisting of SEQ ID NO: 1, 2, and complements thereof.

4. The method of claim 1, further comprising selecting a transgenic plant seed having a modulated fatty acid composition.

5. The method of claim 3, wherein said first nucleic acid sequence comprises a 5' deletion, a 3' deletion, a 5' and 3' deletion, or an internal deletion relative to said full length intron.

6. The method of claim 5, wherein said first nucleic acid sequence is further reduced in length compared to the nucleic acid sequence of said full length intron by about 60 or more contiguous nucleotides.

7. The method of claim 6, wherein said recombinant nucleic acid molecule further comprises a nucleic acid sequence of one or more promoters functional in a plant cell.

8. The method of claim 1, wherein said recombinant nucleic acid molecule further comprises a second nucleic acid sequence and the reverse complement thereof, wherein said second nucleic acid sequence comprises a coding sequence, a non-coding sequence, or a combination thereof that is not a full length FAD2-1 intron, and wherein said recombinant nucleic acid molecule is capable of forming double stranded RNA of said fragment of said second nucleic acid sequence when transcribed in said transformed temperate oilseed crop cell.

9. The method of claim 8, wherein said second nucleic acid sequence is a fragment of a second gene that is at least 40 nucleotides in length and is capable of decreasing the expression of said second gene.

10. The method of claim 8 wherein said second nucleic acid sequence is about 50, 75, 100, 150, 175, 200, 220, 250, 300, 320, 350, 400, 420, 450, 500, 550, 600, 800, or 1000 nucleotides in length.

11. The method of claim 9, wherein said second nucleic acid sequence comprises between 5% to 80% of the length of said second gene.

12. The method of claim 8, wherein said second gene is selected from the group consisting of FATA, FATB-1, FATB-2, beta-ketoacyl-ACP synthase I, beta-ketoacyl-ACP synthase IV, delta-9 desaturase, CP4 EPSPS, and combinations thereof.

13. The method of claim 12, wherein said second nucleic acid sequence shares between 100% and 90% sequence identity to a nucleic acid sequence selected from the group consisting of SEQ ID NO: 28, 29, 30, 31, 32, 33, 34, 35, 36, 37, 38, 39, 40, 41, 42, 43, 44, 45, 46, 47, fragments thereof, and complements thereof.

14. The method of claim 9, wherein said second nucleic acid sequence is a non-coding sequence selected from the group consisting of a 5'UTR sequence, a 3'UTR sequence, an intron sequence, and combinations thereof.

15. The method of claim 8, wherein said first nucleic acid sequence and said second nucleic acid sequence are assembled as a functional transcription unit upon insertion into a temperate oilseed crop chromosome.

16. The method of claim 8, wherein said second nucleic acid sequence further comprises a sequence encoding a chloroplast transit peptide, or the reverse complement thereof.

17. The method of claim 8, wherein said recombinant nucleic acid molecule further comprises one or more spacer sequences.

18. The method of claim 8, wherein said second nucleic acid sequence is a fragment of a FATB gene.

19. The method of claim 1, wherein said temperate oilseed crop is selected from the group consisting of soybean, canola, sunflower, peanut, maize, and cotton.

* * * * *